United States Patent
Konishi

(10) Patent No.: US 7,864,129 B2
(45) Date of Patent: Jan. 4, 2011

(54) RADIO FREQUENCY MEDICAL TREATMENT DEVICE AND SYSTEM AND USAGE METHOD THEREOF

(75) Inventor: Satoshi Konishi, Tokyo (JP)

(73) Assignee: Namiki Seimitsu Houseki Kabushiki Kaisha (JP)

( * ) Notice: Subject to any disclaimer, the term of this patent is extended or adjusted under 35 U.S.C. 154(b) by 951 days.

(21) Appl. No.: 11/727,662

(22) Filed: Mar. 28, 2007

(65) Prior Publication Data
US 2007/0233057 A1    Oct. 4, 2007

(30) Foreign Application Priority Data
Apr. 4, 2006    (JP) ............... 2006-103652
Aug. 29, 2006    (JP) ............... 2006-231559

(51) Int. Cl.
H01Q 9/16    (2006.01)
H01Q 1/42    (2006.01)
A61B 18/18    (2006.01)

(52) U.S. Cl. ............ 343/793; 343/872; 606/33
(58) Field of Classification Search ............ 343/793, 343/872, 893; 606/33
See application file for complete search history.

(56) References Cited

U.S. PATENT DOCUMENTS

| | | | |
|---|---|---|---|
| 4,980,021 A | | 12/1990 | Kitamura et al. |
| 6,233,490 B1 | * | 5/2001 | Kasevich ............ 607/101 |
| 7,494,467 B2 | * | 2/2009 | Makin et al. ............ 600/439 |
| 2006/0018600 A1 | | 1/2006 | Noguchi et al. |

FOREIGN PATENT DOCUMENTS

| | | |
|---|---|---|
| JP | 3111062 | 5/1991 |
| JP | 7116274 | 5/1995 |
| JP | 2004187703 | 7/2004 |
| JP | 2004187704 | 7/2004 |
| WO | WO 93/17756 | 9/1993 |

OTHER PUBLICATIONS

Saito et al., "Clinical Trials of Interstitial Microwave Hyperthermia by Use of Coaxial-Slot Antenna with Two Slots", IEEE Transactions on Microwave Theory and Techniques, pp. 1987-1991, vol. 52, No. 8, Aug. 2004.
"Microtaze AZM 520—Microwave Surgical Device", Innovation for Minimally Invasive Surgery, pp. 1-7.
Copy of International Search Report Application No. PCT/JP2007/000345 dated Jul. 7, 2007.

* cited by examiner

*Primary Examiner*—Shih-Chao Chen
(74) *Attorney, Agent, or Firm*—Studebaker & Brackett PC; Donald R. Studebaker

(57) ABSTRACT

Advanced RF therapeutic antenna probes, their systems and usage methods are disclosed. The therapeutic antenna probe comprising an RF power transmitting cable by which a dipole antenna assembly is formed and a sheath that includes the dipole antenna assembly therein. The RF power transmitting means comprises at least a central conductor, a cylindrical dielectric insulator formed around the central conductor and an outer conductor all of which are formed to be the dipole antenna assembly. A dipole antenna which is a member of the dipole antenna assembly is composed of the first and second electrodes which are formed by a part and another part of the outer conductor, respectively, and electrically connected to the one central conductor and an isolating means which is formed between the first and the second electrodes. The sheath is made of a hard material for at least a head element having a sharp edge.

37 Claims, 121 Drawing Sheets

RADIO FREQUENCY MEDICAL TREATMENT DEVICE AND SYSTEM AND USAGE METHOD THEREOF

REFERENCE

Ref. 1: "Microtaze" (Trade Mark), a corporate booklet of Alfresa Pharma (www.alfresa-pharma.co.jp/microtaze/520e.pdf)

Ref. 2: "Clinical Trials of Interstitial Microwave Hyperthermia by Use of Coaxial-Slot Antenna With Two Slots", Kazuyuki Saito, Hiroyuki Yoshimura, koichi Ito, Yutaka Aoyagi and Hirotoshi Horita, IEEE Transaction on Microwave Theory and Techniques, Vol. 52, No. 8, August 2004

FIELD OF THE INVENTION

The present invention relates generally to the structure and use of radio frequency (called "RF", hereinafter) medical treatment devices and the system thereof. More particularly, the invention relates to RF medical treatment devices such as therapeutic antenna probes having an RF antenna assembly and a sheath which at least consists of a hard material cutting tip, RF medical treatment system including the RF medical treatment devices and the method thereof.

BACKGROUND OF THE INVENTION

RF surgical devices have been widely used for removing the tumors or the pathological tissues. One of the features of the RF surgical devices is less invasive due to the particular use of the devices such that the devices are inserted into the specific region of the pathological tumors or the tissues which are close to the pathological tumors. The RF surgical devices induce the heat in the tumors or the pathological tissues which suffer the pathology or cancers in a manner that the RF power is absorbed in the right tissue regions which suffer the pathology so that the tissue regions cauterized by the thermal heating. The treatment by the RF surgical devices is percutaneous but less laparotomy and therefore the treat is less invasive so that the patient can be discharged from the hospital in a short time.

There are two categories of RF surgical devices. The first one is an RF ablation device that can make an induced current flow in the tissue to which the device is inserted and then the tissue is coagulated by the thermal heat generated by the induced current flow. This has been proposed by LeVeen as described in the reference 1. The second category is an RF surgical device that radiates microwave power which is absorbed by the water included in the tissue to which the RF surgical device is inserted. The power absorption in the cell water heats the tissue up above the temperature at which protein of the tissue decomposes and the cells of the tissue die. The microwave frequency as 945 MHz or 2.45 GHz has been used. The therapy that uses such RF surgical device is called RF hyperthermia oncology or percutaneous microwave coagulation.

A therapeutic product called as "Microtaze" (a trade mark of " " Alfresa Pharma, Co. Ltd., Ref. 1) is well-known. This product exploits the above two therapeutic effects. The electric probe (abbreviated as "probe", hereinafter) used for Microtaze has a coaxial structure similar to coaxial cables. More specifically, as illustrated in FIG. 1 and FIG. 2, it consists of a central conducting wire 102 (abbreviated as "a central conductor"), a cylindrical dielectric insulator 103 therearound, an outer conducting cylinder 104 (as abbreviated as "an outer conductor") and a jacket 105 covering thereof. The outer conductor 104 is formed into an electrode and the central conductor 102 the other electrode. For the purpose of easy surgical operation, the tip of the probe is formed into a needle tip as illustrated in FIG. 1 and FIG. 2 or a bullet head 106 in FIG. 3 and FIG. 4. The overall structures are called a thermo-therapeutic probe, especially, thermo-therapeutic monopole probe (abbreviated as a TTMP) in accordance with the electrical characteristics of this electric probe.

A new thermo-therapeutic probe, which is dedicated for heating by microwave absorption in the water, has been announced in addition to the thermo-therapeutic probe described in the above second category (Ref. 2). The probe is made from a semi-rigid coaxial cable of which coaxial structure is formed for the purpose thereof. More concretely, as illustrated in FIG. 5 and FIG. 6, the outer conductor 104 is segregated into certain segments between which an electrically isolating gap 107 is made for every two adjacent segments. A first electrode 108 which is a part of the outer conductor 104 and one of the adjacent segments is connected to the central conductor 102 is formed for the outer conductor 104. A second electrode 109 which is the other part of the outer conductor 104 and the other adjacent segments and which is isolated from the first electrode 108 is formed from the outer conductor 104. The outer conductor is covered by a jacket 105. Accordingly, the electrodes of this thermo-therapeutic probe have a structure of an antenna assembly, especially, a dipole antenna. The whole antenna assembly is covered by an insulating material or put into an insulating case made of insulating material. This structure is called thermo-therapeutic dipole probe (abbreviated as a TTDP, hereinafter).

An insulating case 117 or 117A of the TTDP described in Ref. 1, as illustrated in FIG. 5 and FIG. 6, is made of hard polyvinyl chloride (or PVC) or polytetrafluoroethylene (or PTFE). The insulating case 117 covers the whole part of the dipole antenna and insulating case 117A encloses the whole part of the dipole antenna therein. Another part of the structure of the outer conductor, in which the part of the first electrode is electrically connected to the central conductor by means of disc conductive piece 110, so that cylindrical symmetry is realized for the probe structure, is known. Such TTDPs are illustrated in FIGS. 7 and 8, which are particularly covered by the insulating case 117.

By comparing the therapeutic effects obtained by the TTMP and the TTDP, the actual phenomenon of the usage shows that the pathological tissue into which the TTMP is inserted is heated in the region in a manner that the region between the central conductor and the surrounding outer conductor near by is heated by the electric induction current flowing thereof (FIG. 9). Therefore the cauterized (heated but not burned) region by the TTMP is localized in the distance form the central conductor 102 (which is at t0) to r1. On the other hand, the first electrode and the second one of the TTDP construct a dipole antenna The water of the pathological tissue region which surrounds the position where the TTDP is inserted absorbs the microwave radiated from such position and is heated to be higher than the temperature at which the protein of the pathological tissue decomposes. Therefore the "cauterized" region cured by the TTDP is larger than that by TTMP (as illustrated in FIG. 10) due to the physical property of microwave radiation which is horizontal microwave propagation after converted from the TEM mode existing in the coaxial cable from which the dipole antenna comprising the first and the second electrodes is formed. The cauterized region is from r=ts which is the surface of the insulating case 117 or 117A to r=r2. Especially, tumors such as cancer tissues easily become necrotic in such low temperature as slightly higher than the protein decomposition one. Therefore the TTDP can provide very little burden against sound tissues but cauterize tumors to become necrotic. This is the same therapeutic effect against tumors as that of hyperthermia oncology. The detailed structures of the TTMP and the TTDP illustrated in FIG. 11 and FIG. 12 are same as those illustrated in FIG. 2 and FIG. 6, respectively.

SUMMARY OF THE INVENTION

The surface of the TTMP is formed from the outer conductor which is made of copper. Due to the medical regulation, copper is not allowed to directly contact tissues. Therefore the head portion of the TTDP described in Ref. 2 is covered or enclosed by an insulating case made of hard PVC (Polyvinyl Chloride) or PTFE. However, the hardness of these materials is not enough to percutaneously insert the TTDPs into tissues. Surgeons need to cut holes reaching to and inserting TTDPs into tumors by using scalpels or surgical blades before inserting the TTDPs for RF thermo-therapy. Therefore, surgeons need pre-treatment before the therapeutic operations. The "pre-cutting" skins tissues to make a guiding channel that guide TTDPs but may be induce bleeding therefrom afterwards and a single action treatment such that the TTDPs percutaneously invade into the tumors and heat them for the purpose of RF thermo-therapy. This single action enables surgeons to shorten the operation time and improve the safety of the surgical operation.

The first object of the present invention is to provide a means to make such pre-treatment unnecessary and enables to perform quick RF thermo-therapy. For this purpose, sharpness at the front heads of the insulating cases of TTDPs is necessary. The sharp heads of the TTDPs can percutaneously cut the tissues and surgeons can be inserted the TTDPs into tumors in a single action.

Another problem of the TTDPs in Ref. 2 is that the insulating case to cover the antenna assembly is not strong or cannot hold it mechanically stable. Therefore, RF power radiation from the dipole antenna especially from the electrically isolating gap between the first electrode and the second electrode deviates in the direction of the radiation when the electrically isolating gap is slightly deformed when the TTDPs are bended by the forces of human muscles when the patient moves on the surgical operating table. Due to the deviation of the radiation power, the tumors are not homogeneously heated and the RF thermo-therapy is not sufficiently or completely performed. To solve this problem, we need insulating case that tightly holds antenna assembly and keeps rigidness of the TTDP as a whole with the insulating case. In order to obtain such insulating case, a sheath combined with a sharp head and tight antenna-holding pipe can be used so that the deviation of RF power radiation during operation can be suppressed. The sharp head is made of a hard material. Therefore the first object of the present invention can be solved by using the insulating cases of which head portions have sharpness and tight pipe that satisfies rigidity or tightness of antenna assembly.

The TTMPs and the TTDPs illustrated in Ref. 1 and Ref. 2 radiate RF power from the electrically isolating gaps between the central conductors and the outer conductors and the electrically isolating gaps between the first electrodes and the second electrodes, respectively. Therefore the induced current and RF power tend to be localized at these electrically isolating gaps so that the temperature of the tissues close to the probes is higher than those being peripheral to the probes. The problem of such temperature localization does not make serious troubles for the use of the TTMP since it is used to coagulate the tumors in high temperature. However, the temperature localization results into the high temperature at the tissues which are close to the probes when TTDPs are used since they need to keep the tumors only over the temperature to decompose the proteins of the tumors. High temperature makes tissue burning and not cauteries for protein decomposition. Another problem remains for TTDP, that is, the tissues which are close to the electrically isolating gaps between the first electrodes and the second electrodes of the TTDPs are easily heated in higher temperature than the other tissues in the regions far from the electrically isolating gaps since the microwave radiation power density decrease from such electrically isolating gaps.

It is possible to suppress the temperature rising by reducing RF power supplied to the TTDPs. Such lower RF power can keep the temperature of the tissue close to the TTDPs at that of protein decomposition, however the tissues peripheral to the TTDPs are maintained in the lower temperature than that of protein decomposition. This reduces the merit of TTDPs that are to provide necrosis to tumors grown in a large region.

The second object of the present invention is to solve this temperature localization. For solving this problem, a sheath of which material is electrically non-conductive but has highly thermal conductivity are used for the insulating case. The material of the sheath can be a hard material. The properties such as electrically non-conductiveness and highly thermal conductivity support RF radiation from the sheath and the heat of the localized temperature close to the sheath easily spreads therethrough. It is further preferable that the permittivity of the sheath is large because the dielectric constant ratio of the air to the tumor can be relaxed by such permittivity of the sheath and the effective electrical length from a TTDP can be long so that the surface of the sheath is not over heated.

The TTDPs in Ref. 2 has only one electrically isolating gap through which RF power radiates and heats the pathological tissues to become necrotic. Therefore, these TTDPs have another problem such that homogenous heating of the tumors along the insulating cases of TTDPs is limited due to this single radiation gap.

The third object of the present invention is to solve this single radiation gap problem. We provide a new antenna configuration such that plurality of electrically isolating gaps is formed onto the antenna assembly used for TTDPs. The gaps are formed along the longitudinal direction of the antenna assembly.

More specifically, the antennas have plurality of electrically isolating gaps and the interval of the electrically isolating gaps is shortened, which further contributes better homogeneity in heating. For such shortening, the structure of the dipole antennas such that the effective wavelength of the microwave that propagates the antenna can be shortened is invented. By this new antenna structure, the vertical RF power distribution along the antennas can be kept long and homogenous. Then, it is possible to homogenously heat the tumors in longitudinal direction of the TTDP.

The RF power is radiated from an electrically isolating gap formed in the antenna. The electrically isolating gap is formed between the second electrode made from the outer conductor and the first electrode connected to the central conductor. Therefore the electrically isolating gap is apart from the front tip of the antenna so that the RF power radiation is not supplied enough to the front region of a TTDP. This is called "a lighthouse effect" since the RF power is not radiated from the front tip of the antenna like as light is not emitted from the top roof of the lighthouse.

The fourth object of the present invention is to solve the lighthouse effect, the length of the first electrode is shortened and RF power is diffracted to the front of the antenna, or the front tip of the antenna has a different radiation gap from those provided in the inventions of the first to the third object. The structure of such an antenna can be additionally adopted to the above new antenna assembly which has a plurality of electrically isolating gaps. Then more homogenous RF power distribution to the tumors can be obtained.

The fifth object of the present invention is to provide a drug delivery capability to the TTDP by which the drug is injected into the pathological tissues to which the TTDP is inserted. After injection, the drug can spread or be activated (so-called drug conversion) by heating by the RF power radiated from the TTDP. The TTDP has a channel for such drug delivery. Then the use of TTDPs can be effective for oncology therapies since a single action operation to percutaneously insert the TTDPs into tissues sequentially or simultaneously provides pathological tissue heating treatment, drug conversion and medicine injection. Drug delivery of the anti-cancer medicines is worth for tumor therapy.

The sixth object of the present invention is to provide a control system for the surgeons to safely use the TTDPs disclosed in the present invention as explained in the first to the fifth object of the present invention. The operation of the control system is served with the drug delivery by using the TTDPs which have fundamental structure described in the first to the fifth object of the present invention.

BRIEF DESCRIPTION OF THE DRAWINGS

For a further understanding of the objects and advantages of the present invention, reference should be had to the following detailed description, taken in conjunction with the accompanying drawing, in which like parts are given like reference numerals and wherein.

DETAILED DESCRIPTION OF THE INVENTION

Figure 1:
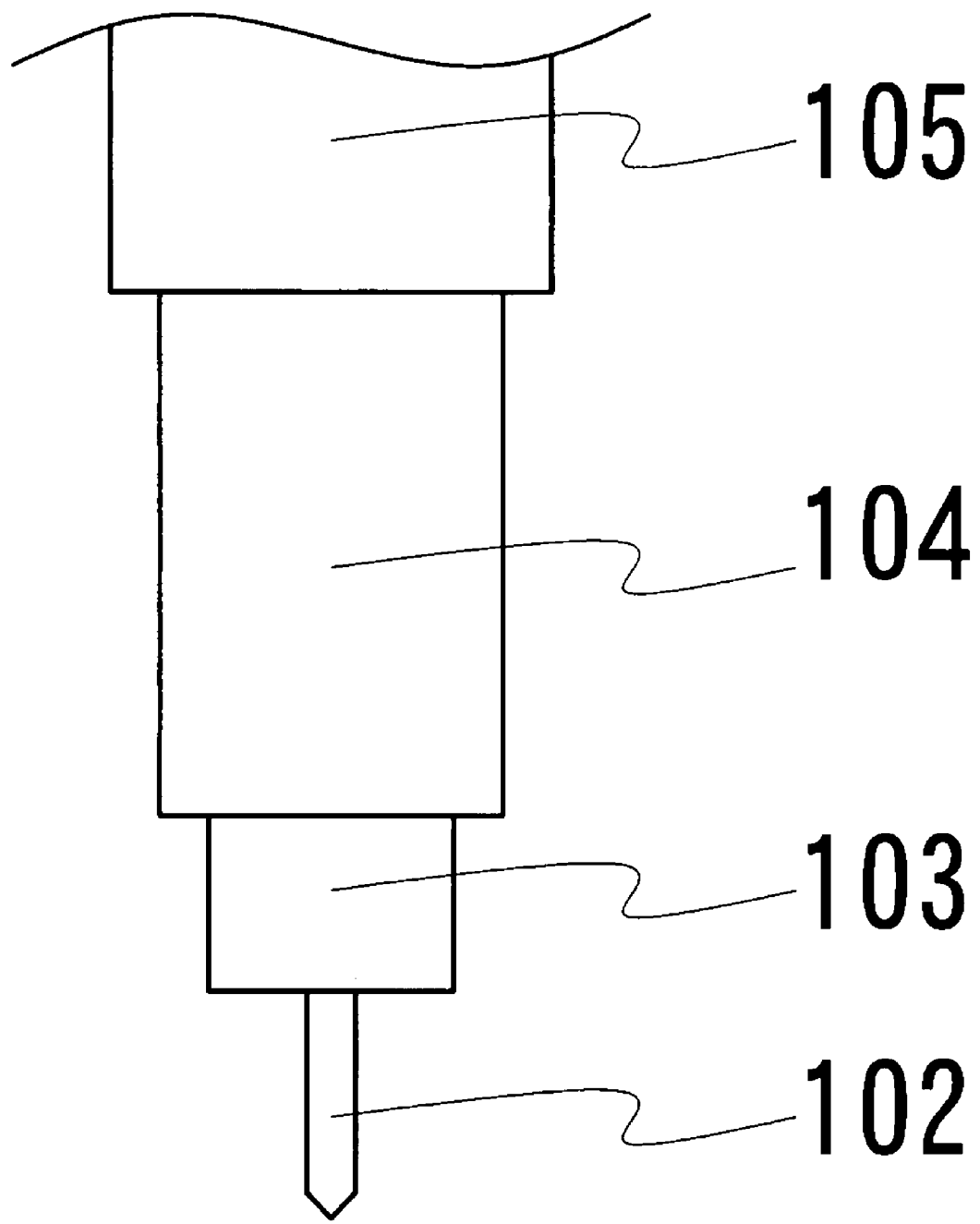
FIG. 1 is a side view of the electric probe used for Microtaze.
Figure 2:
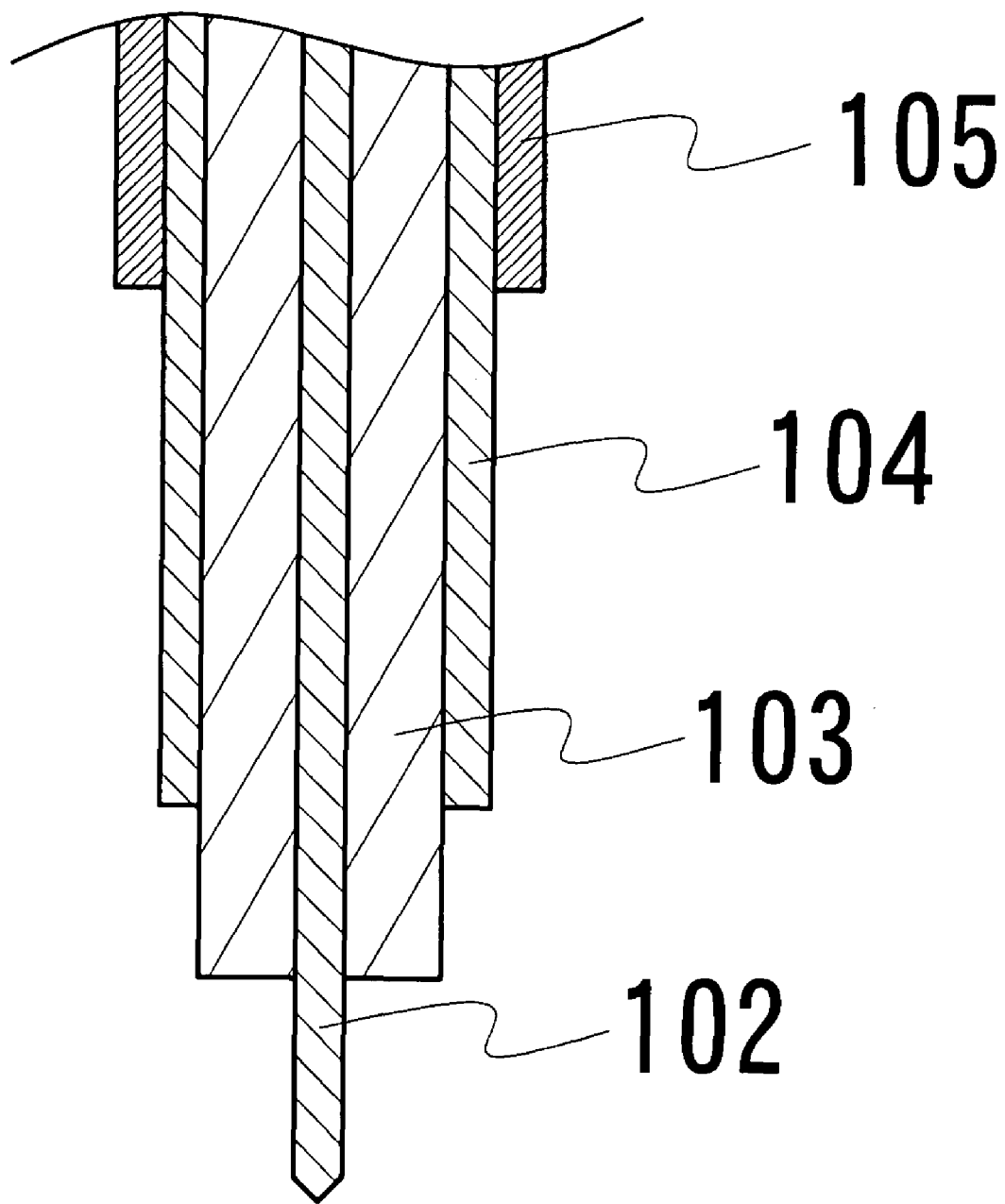
FIG. 2 is a cross-sectional view of the electric probe used for Microtaze.
Figure 3:
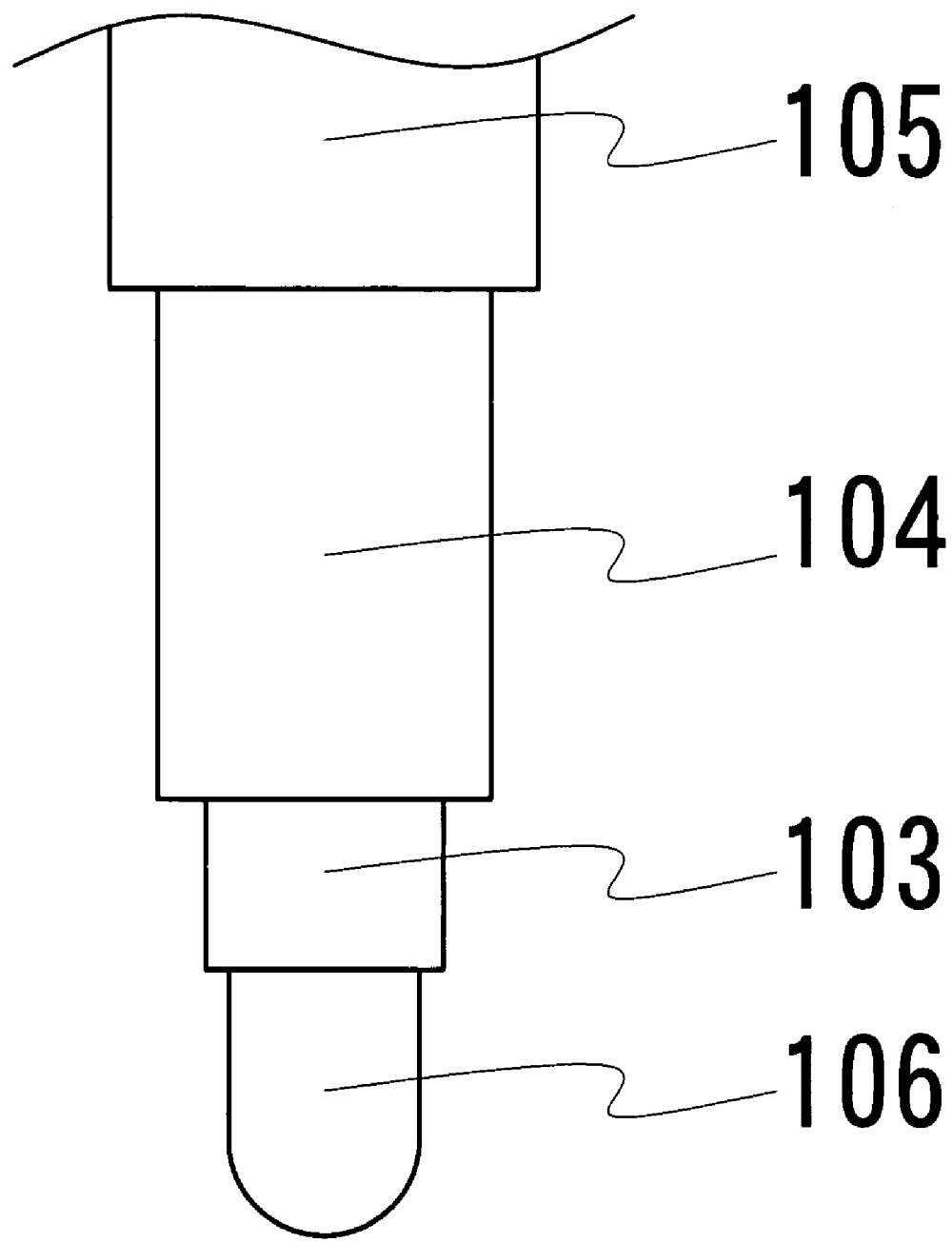
FIGS. 3 and 4 are a view of a cross-sectional view of the electric probe used for Microtaze with a bullet head.
Figure 4:
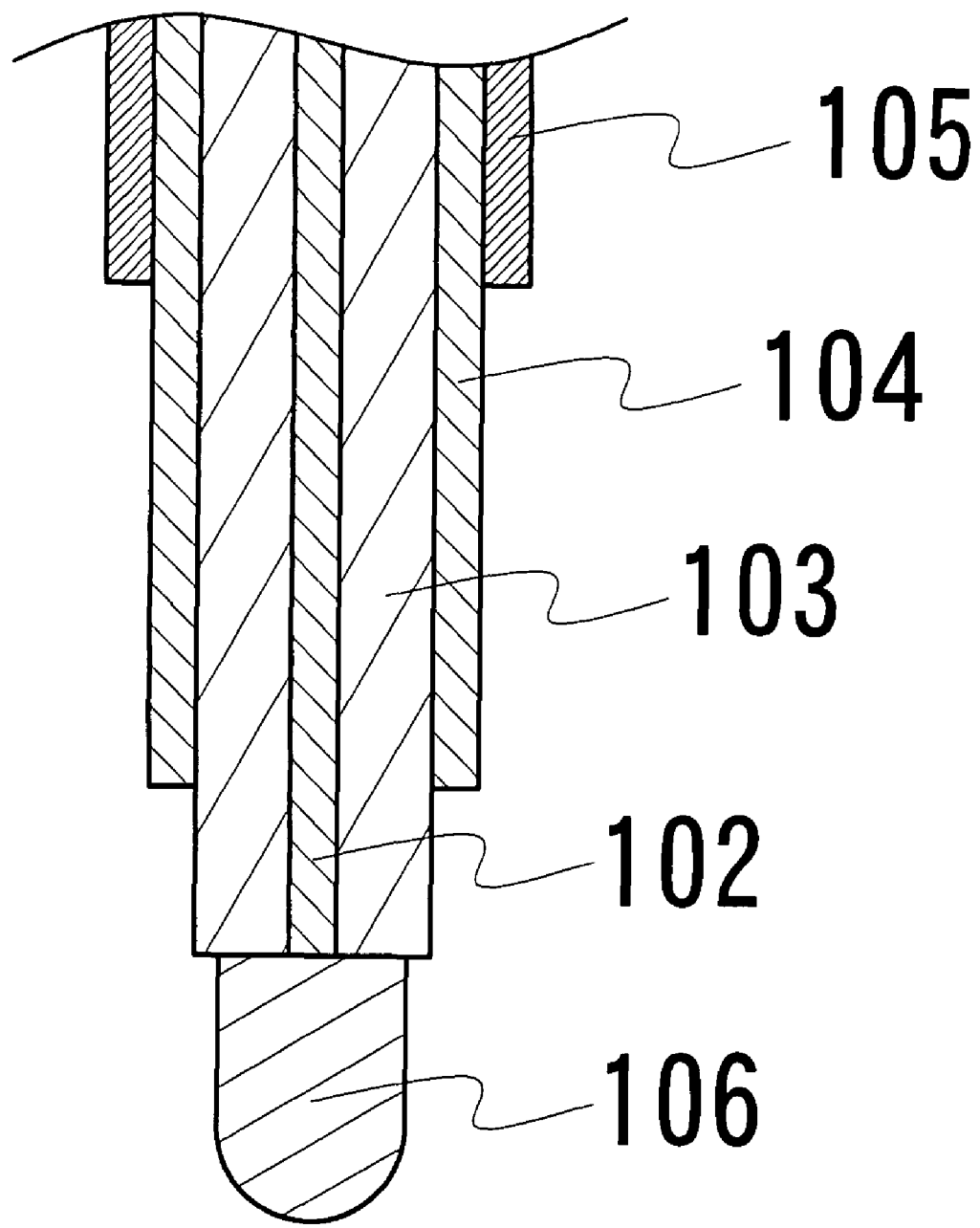
Figure 5:
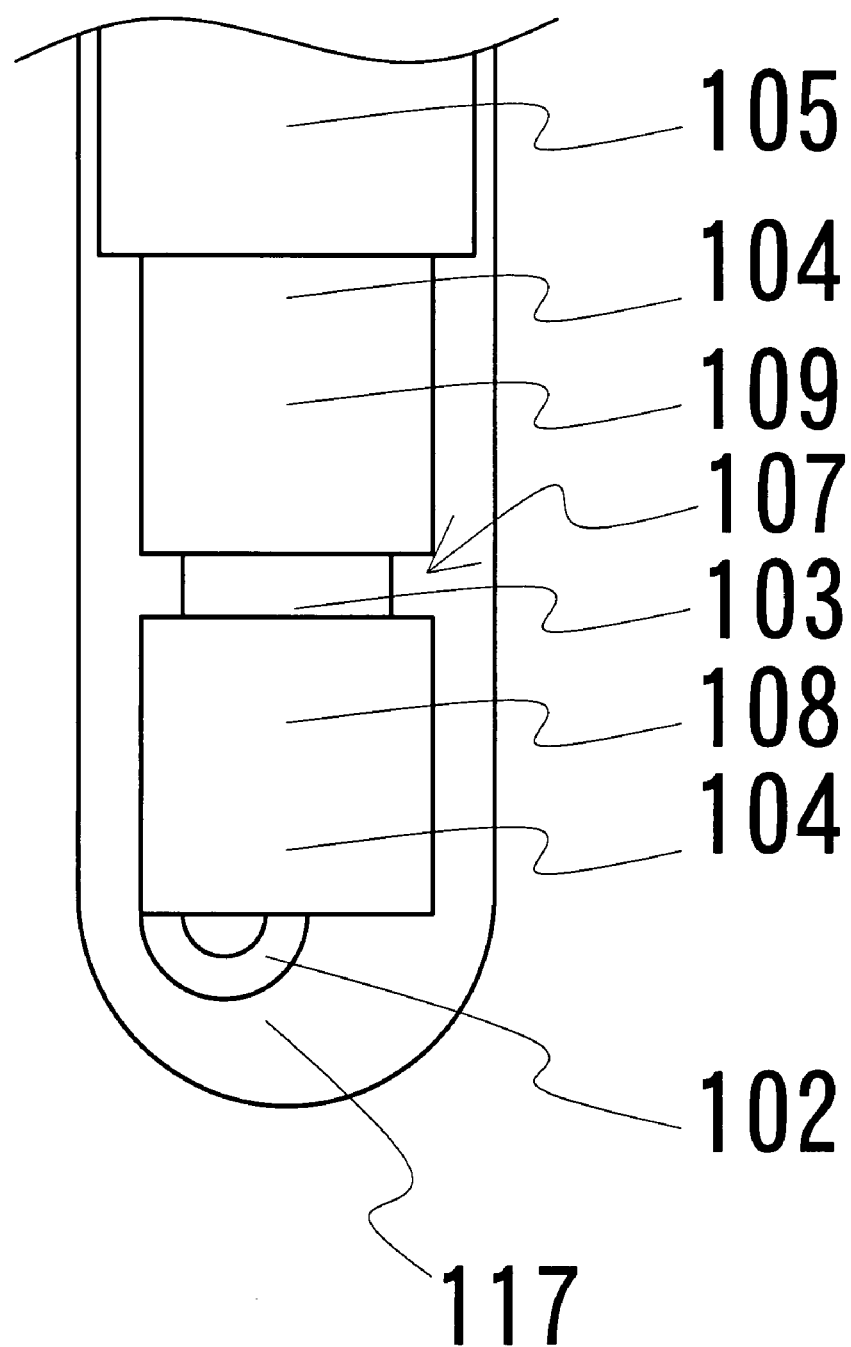
FIGS. 5 to 8 are views of new thermo-therapeutic probe studied in the reference 2.
Figure 6:
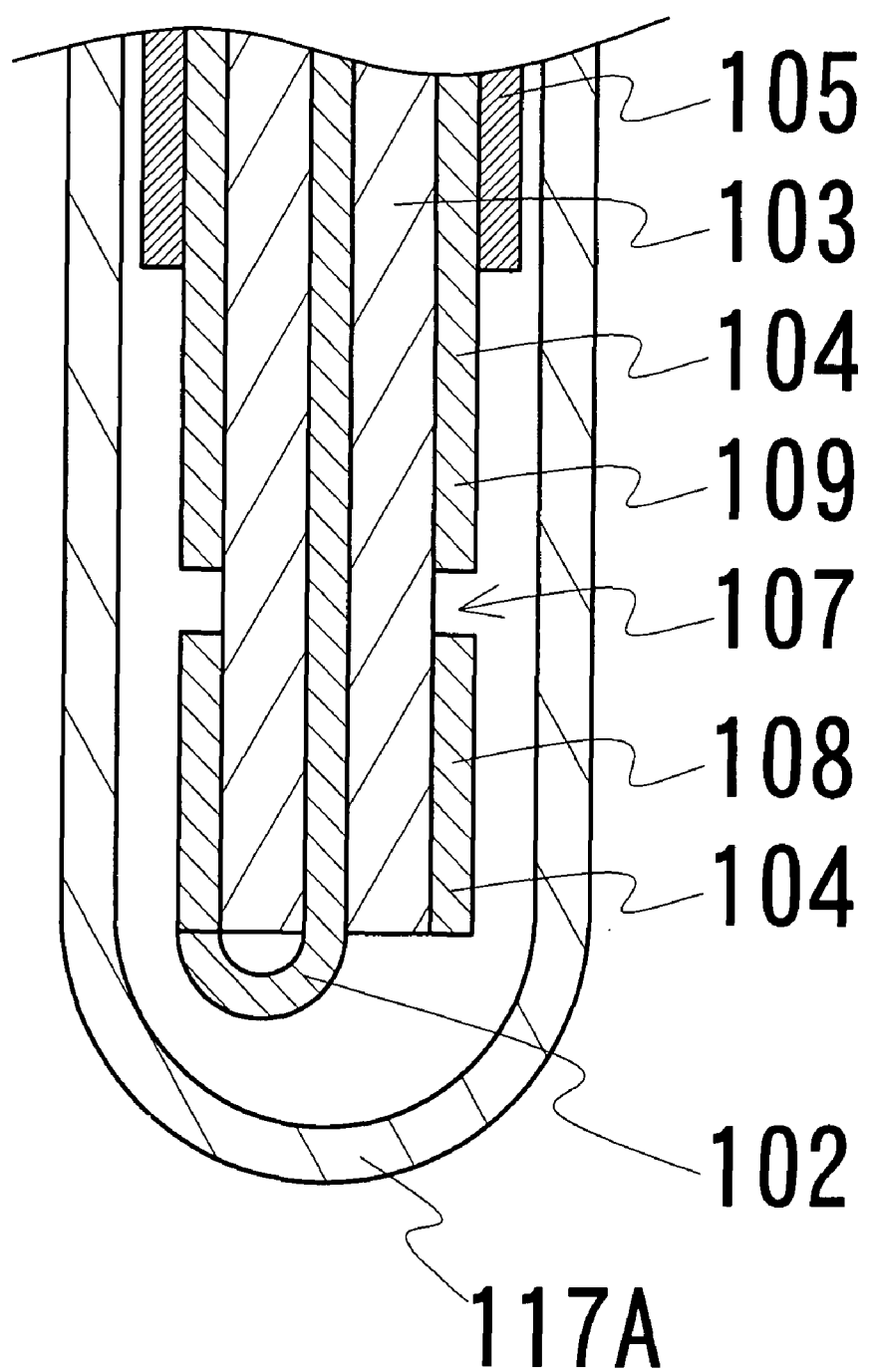
Figure 7:
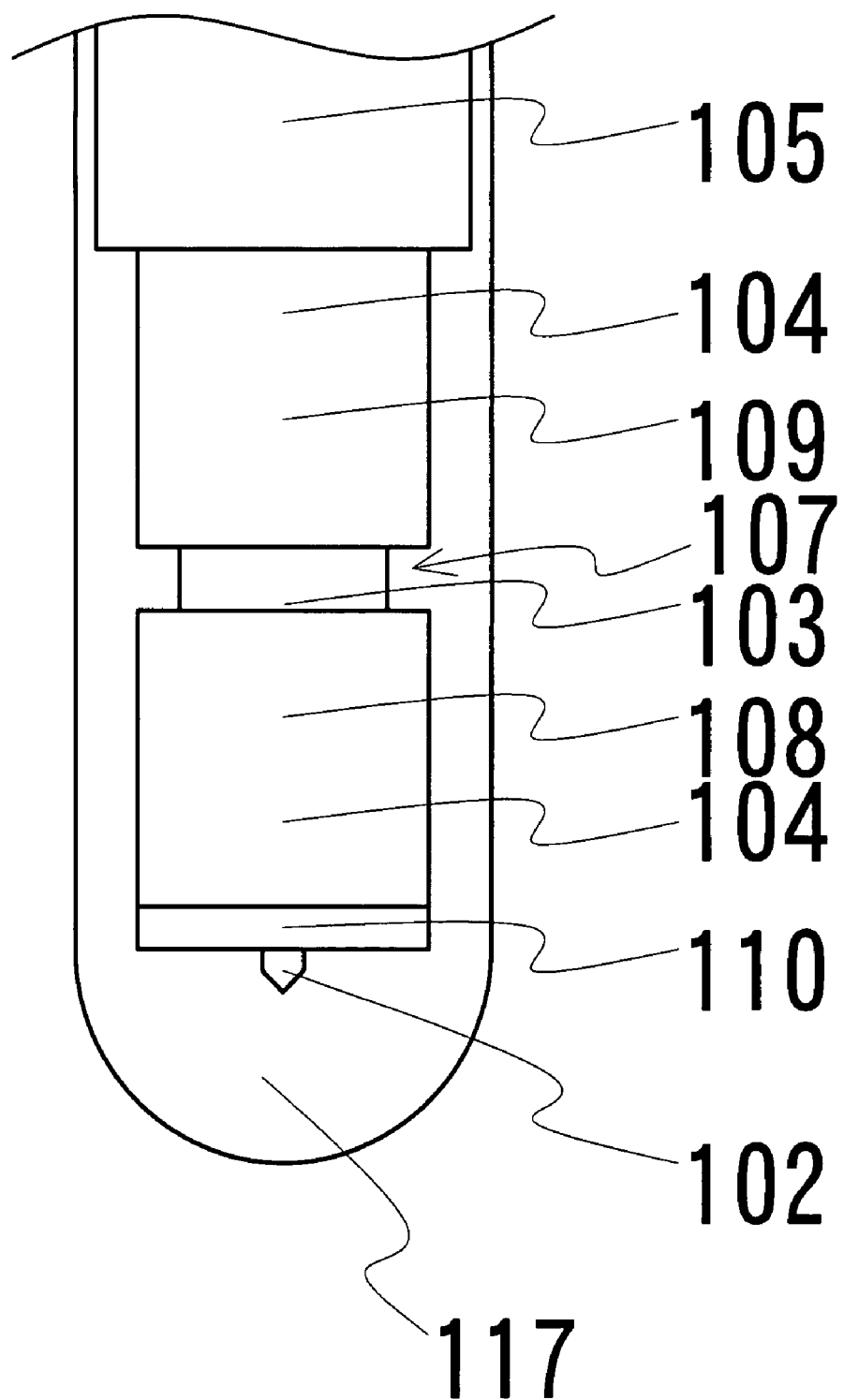
Figure 8:
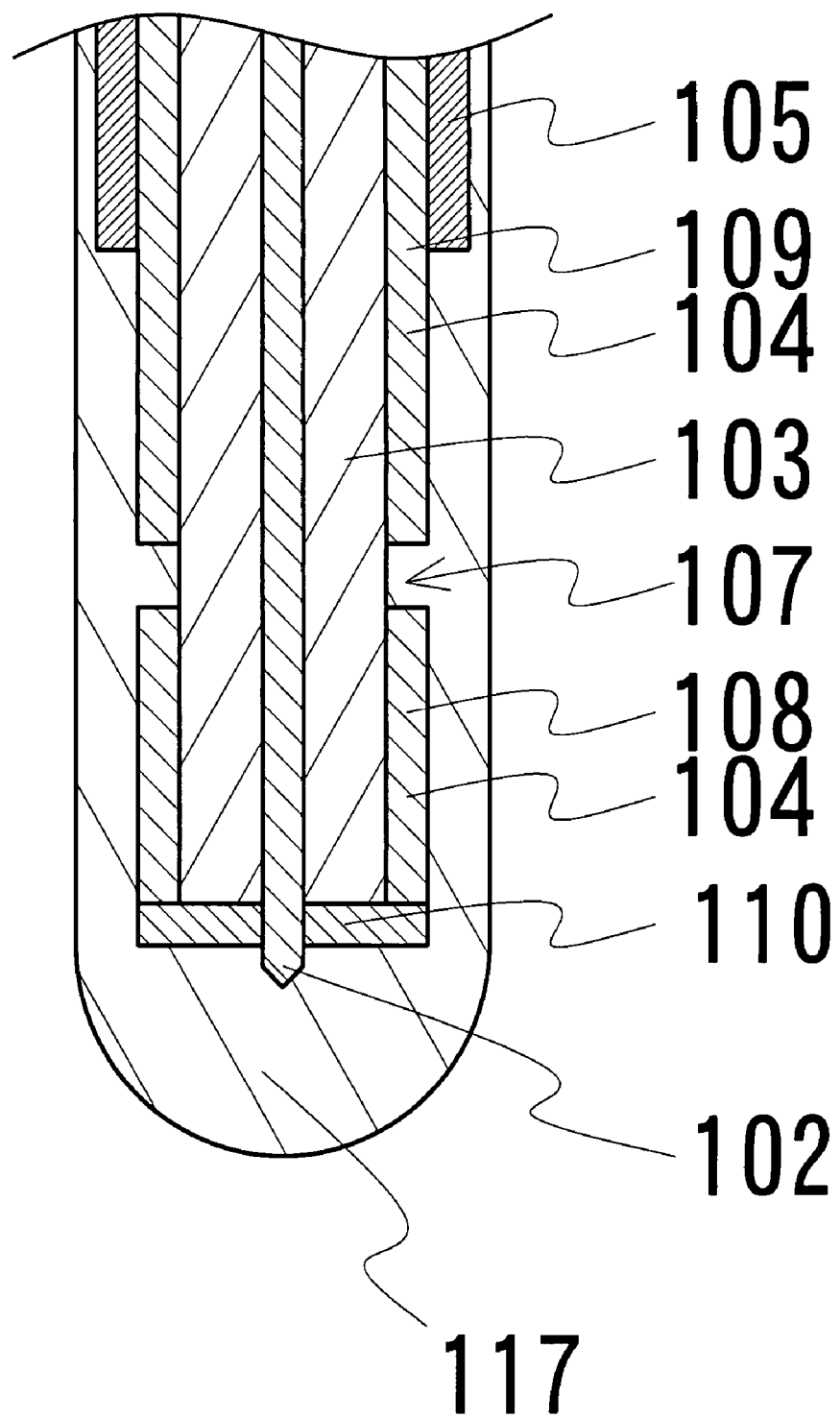

The present invention provides improved TTDP for RF thermo-therapy to achieve the first object.

The improved TTDP (simply called as "a TTDP", hereinafter) comprises an RF power transmitting means (such as a coaxial cable) by which antenna assembly is formed and a sheath, being made of a hard material for at least a head portion which has a sharp edge, that includes the dipole antenna assembly (simply called as "an antenna assembly", hereinafter) therein. The RF power transmitting means comprises one central conductor, a cylindrical dielectric insulator formed around the central conductor and an outer conductor all of which are formed to be the antenna assembly of which an dipole antenna is composed of a first electrode which is formed by a part of the outer conductor and electrically connected to the at least one central conductor, a second electrode which is formed by another part of the out conductor and an isolating means which is formed between the first electrode and the second electrode. The head portion is a head element comprising an edge portion and a flexible pipe that is coupled to a coupling portion formed in the head element.

More concretely, the TTDP includes an insulating case which is a sheath comprising a head portion of which specific portion is a head element made of a hard material such as sapphire. The head element of the sheath has a sharp edge at the front end of the sheath and a flexible pipe that tightly clings to the head element. The head portion of the sheath is composed with the head element and the flexible pipe. The head element of the sheath is called a sharp edge head hereinafter and one of the function of the sharp edge head is to work as a blade that allows a surgeon to percutaneously stab the TTDP into the tumors or pathological tissues. No pretreatment to make a probe insertion hole in the tissues is required for the therapy so that quick therapy can be performed. The sapphire is not electrically conductive and therefore the fields of the microwave radiated from the antenna do not seriously decay. Therefore, the cauterization by the TTDP is not degraded in comparison to the conventional TTDP which uses PVC or PTFE as described in Ref. 2.

For the tight antenna-holding pipe, an insulating flexible pipe, being made of FEP (Fluorinated Ethylene Propylene copolymer), PTFE (Poly Tetra Fluoro Ethylene), ETFE (Ethylene TetrafluoroEthylene), PFA (Tetra Fluoro Ethylene-Perfluoro Alkylvinyl Ether Copolymer), thermal shrinkable Crosslinked Polyethylene or thermal shrinkable Ethylene-Propylene which mechanically contact to an antenna assembly in a tight force can be used. The tight contact against the antenna assembly is realized by the effect of the thermal shrinking of these materials (as called as "thermal shrinkable tubes", hereinafter) such that the insulating pipe is made once in molding process and formed into the sheath with a sharp edge head. The heating process is carried for the preassembly including the sharp edge heads, the antennas assembly and an insulating pipe that covers thereof. In these processes, the insulating flexible pipe of which material has the thermal shrinkability shrinks and tightly holds the antenna assembly. Therefore, the RF power radiation from the electrically isolating gap of this TTDP can be mechanically stable against the bending force of the patient muscles during the operation.

Figure 13:
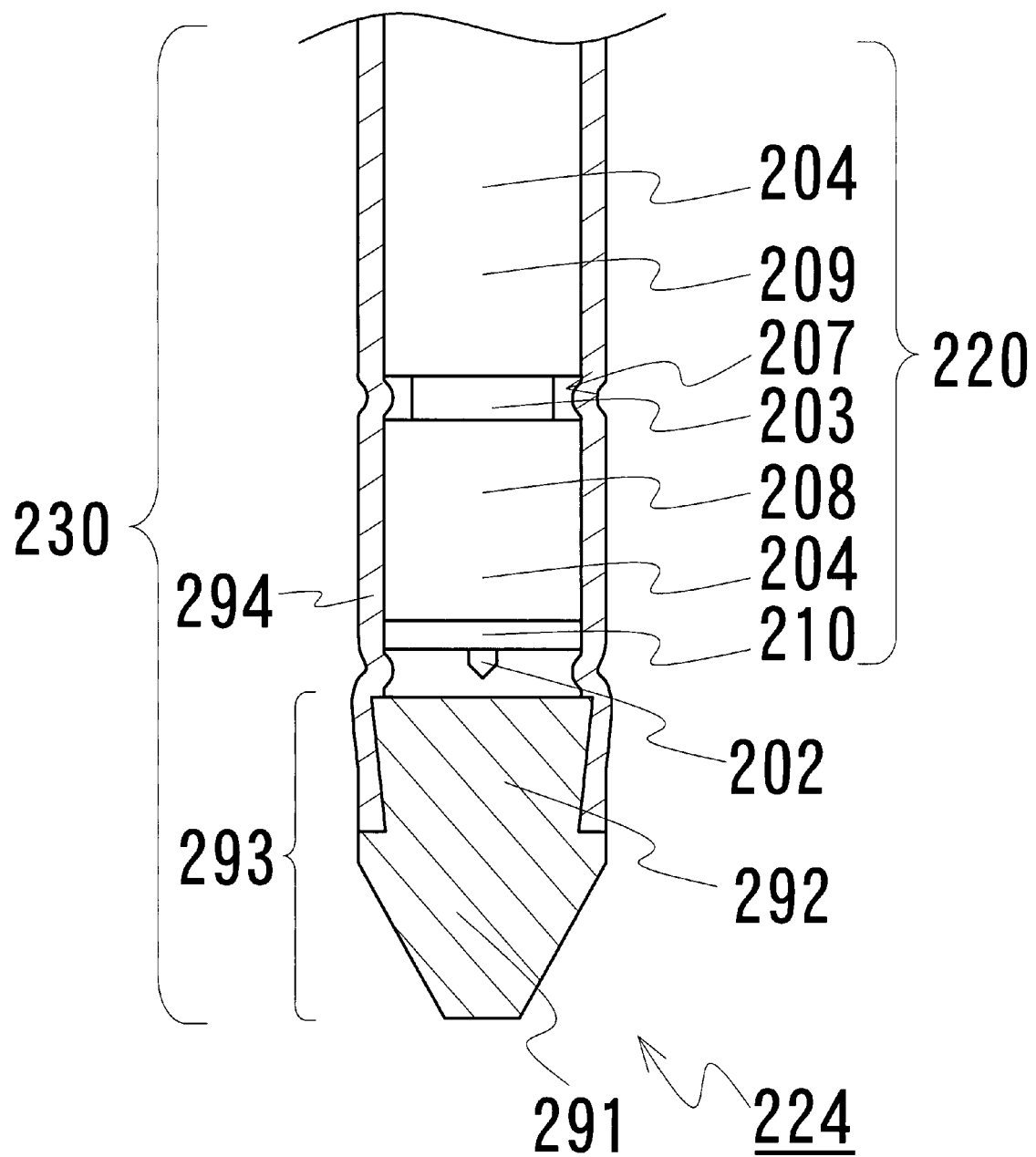
FIGS. 13 to 15 are cut views of TTDPs regarding the first object of the present invention.
Figure 14:
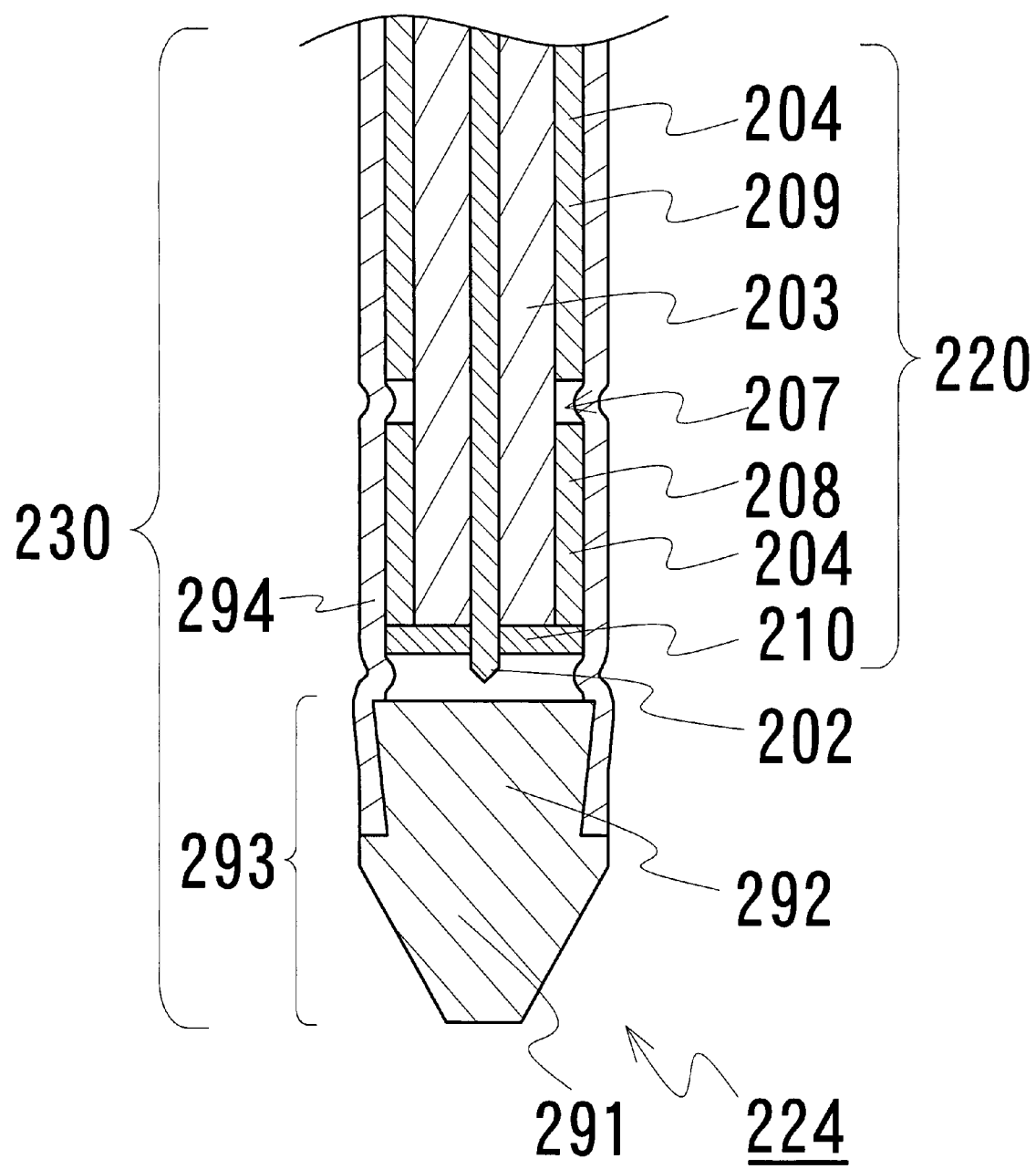
Figure 15:
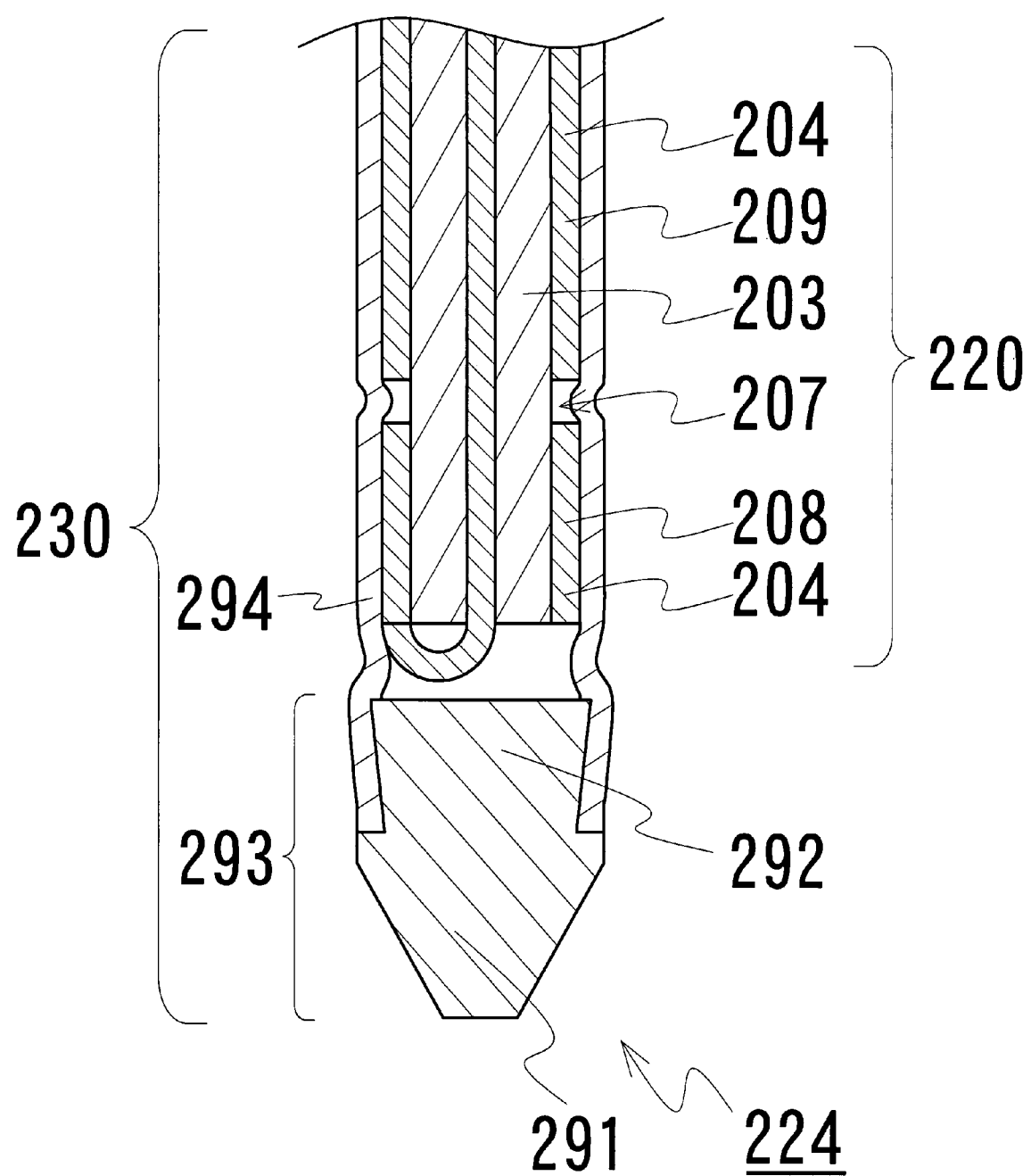

The TTDP for this object has a configuration as illustrated in FIGS. 13-15. The antenna assembly 220 comprises a central conductor 202, a cylindrical dielectric insulator 203 around the central conductor 202 and an outer conductor 204 which is partly formed into a first electrode 208 which is electrically connected to the central conductor 202 and partly formed into a second electrode 209 which is electrically isolated from the first electrode 208. The TTDP 224 consists of the antenna assembly 220 and a sheath 230 which has a head portion therein. The head portion includes i) a head element (called "a sharp edge head" hereinafter) 293 which consists of a sharp edge portion and a coupling portion 292 and ii) thermal shrinkable tube 294 coupled to the coupling portion 292. The sharp edge head 293 is made of a non-conductive and hard material such as sapphire and is formed into an edge portion 291 and a coupling portion 292 to which the thermal shrinkable tube 294 is coupled. The first electrode 208 and the second electrode 209 are electrically isolated with via electrically isolating gap 207, all of which construct a dipole antenna which is a member of an antenna assembly 220. The electrically insolating gap 207 is formed by removing the outer conductor 204. The central conductor 202 is connected to the first electrode 208 by means of a conductive disc 210 for the antenna assembly 220 illustrated in FIG. 13 and 14. For another kind of TTDP 224 illustrated in FIG. 15, the central conductor 202 is directly connected to the first electrode 208. FIG. 13 shows the out view of the first electrode 208 and the second electrode 209 but the cut view of the sheath 230. The thermal shrinkable tube 294 can tightly hold the antenna assembly 220 after being exposed to heated environment. Therefore the antennas assembly is not easily bended. The edge portion 291 of the sharp edge head 293 can easily cut the tissues so that the TTDP 224 is possible to percutaneously invade into the tumor with ease in a single action treatment. In such invasion, surgeons push the TTDP 224 but it can invade straight forward to the tumors without bending. The tightness of the shrinkable tube 294 keeps the antenna assembly 220 stable so that shaking of the TTDP does not lead the instability of RF power radiation from the dipole antenna configuration formed by the first electrode 208, the second electrode 209 and the electrically insulating gap 207.

The TTDP 224 of the first object of the present invention has many advantages other than explained above and further advantages will be explained in the description of the specific embodiments.

The second object of the present invention is to solve temperature localization.

More specifically, it is 1) to keep the temperature difference between the surface of the TTDP (therefore the surface of the sheath) and the tissues therearound small, 2) to effectively suppress the temperature of the surface of the TTDP particularly at the high-temperature portion of which back surface faces to the electrically isolating gap between the first electrode and the second electrode, 3) to keep the difference of the temperature which is on the surface of the TTDP and in the tissues nearby against the temperature at which the protein of the pathological tissue decomposes small and 4) to provide a rigid sheath so that the TTDP can percutaneously invade into the tumor with ease in a single action treatment.

For the second object of the present invention, the TTDP comprises an RF power transmitting means (such as a coaxial cable) by which an antenna assembly is formed and a sheath, being formed in a single-body that has a sharp edge and made of a hard material such as sapphire, that includes the antenna assembly therein. The RF power transmitting means comprises one central conductor, a cylindrical dielectric insulator formed around the central conductor and an outer conductor all of which are formed to be the antenna assembly of which an dipole antenna is composed of a first electrode which is formed by a part of the outer conductor and electrically connected to the at least one central conductor, a second electrode which is formed by another part of the out conductor and an isolating means which is formed between the first electrode and the second electrode.

Figure 16:
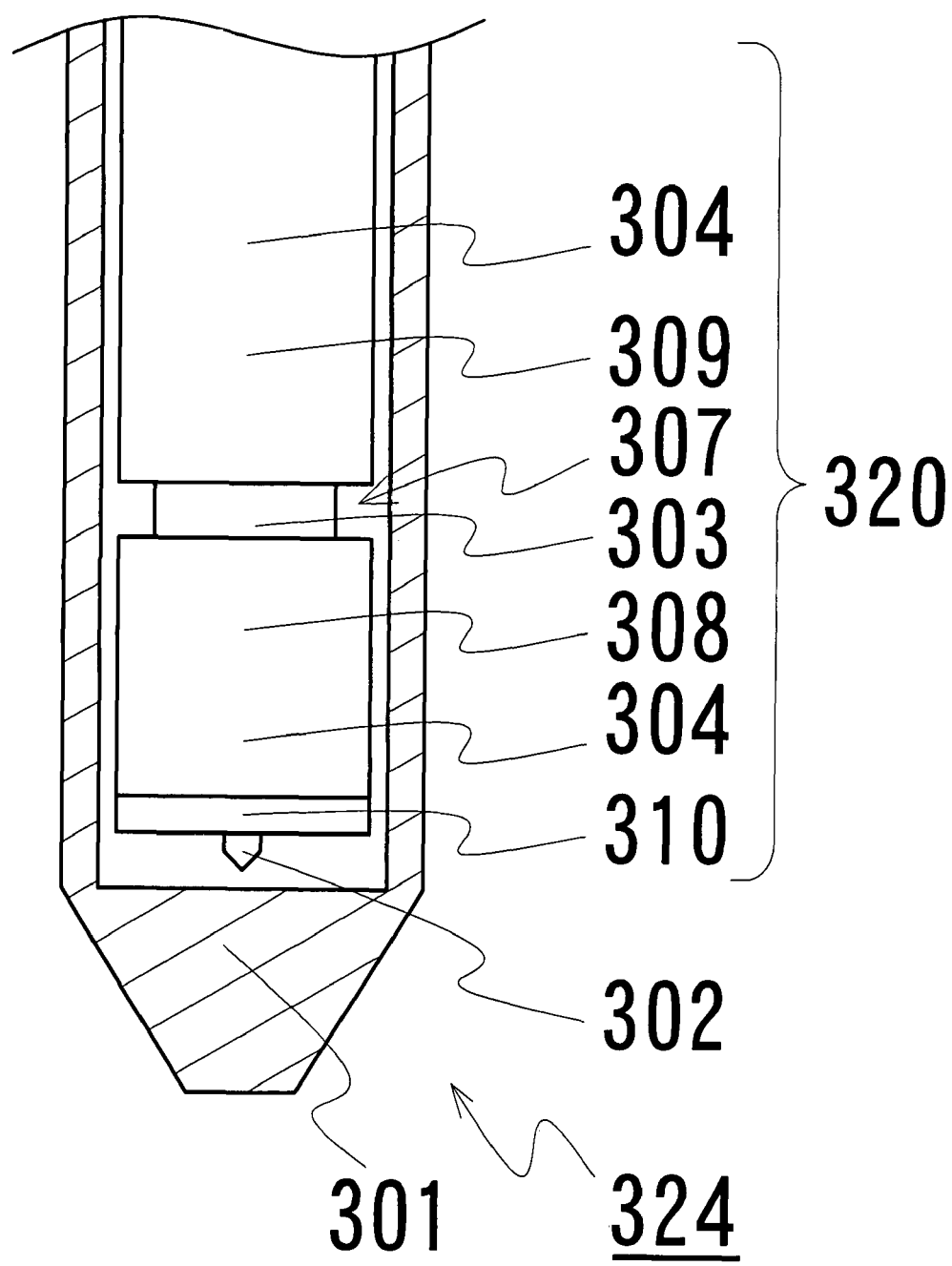
FIGS. 16 to 18 are cut views of TTDPs regarding the second object of the present invention.
Figure 17:
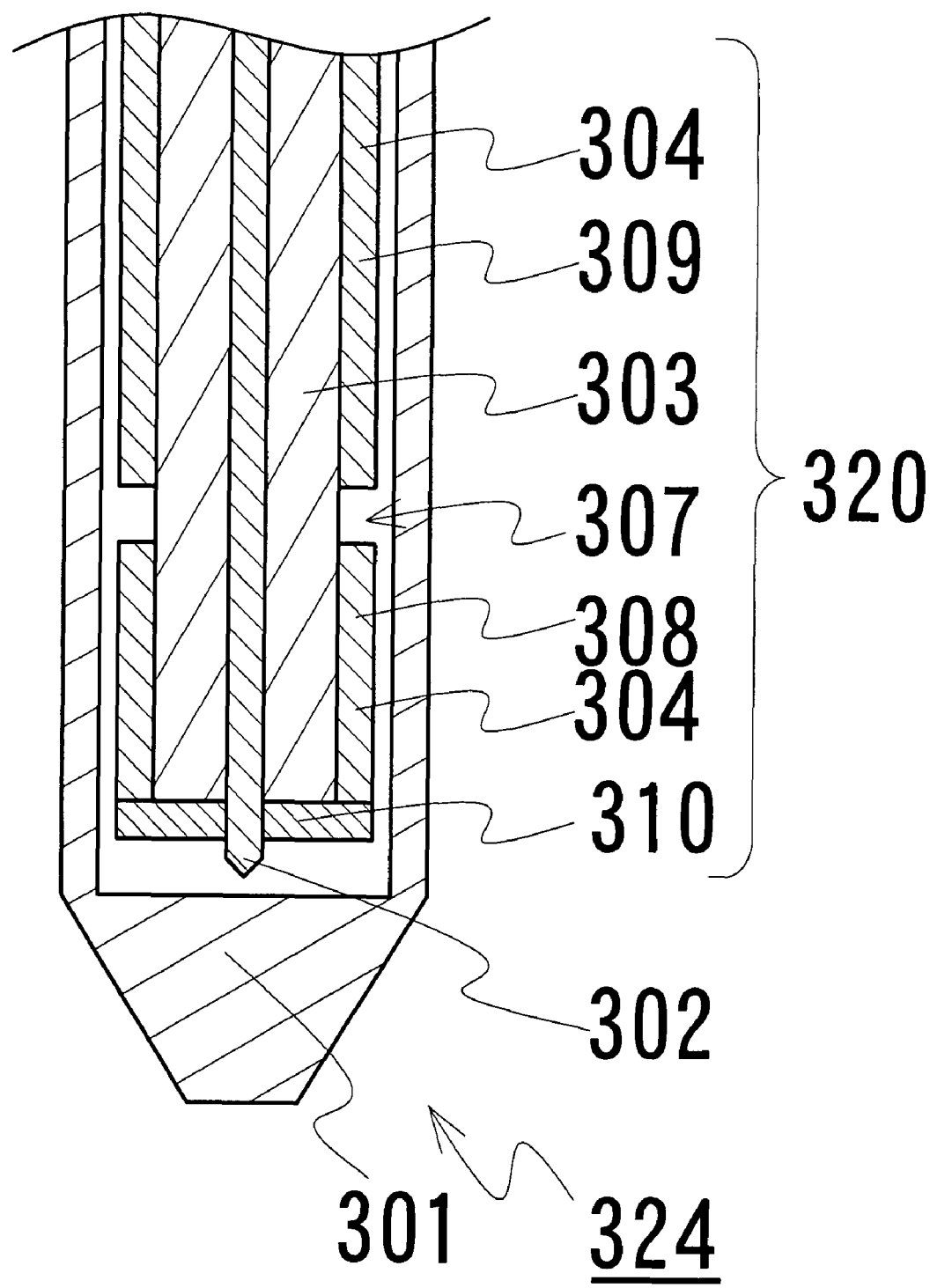
Figure 18:
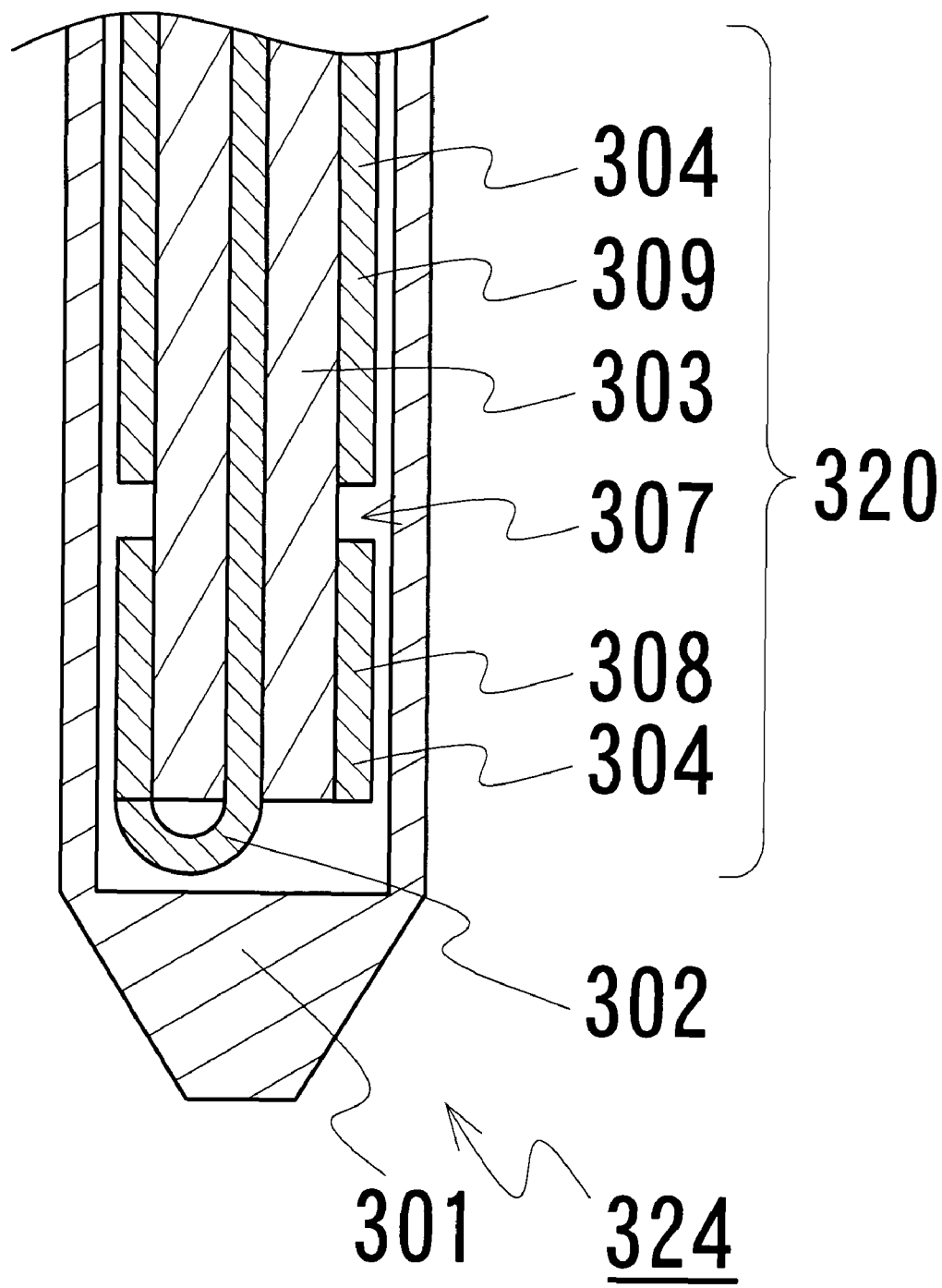

More concretely, the TTDP for this object has a configuration as illustrated in FIGS. 16-18. The antenna assembly 320 comprises a central conductor 302, a cylindrical dielectric insulator 303 around the central conductor 302 and an outer conductor 304 which is partly formed into a first electrode 308 which is electrically connected to the central conductor 302 and partly into a second electrode 309 which is electrically isolated from the first electrode 308. The TTDP 324 consists of the antenna assembly 320 and a single-body sheath 301 of which material is a dielectric single material such as sapphire. The first electrode 308 and the second electrode 309 are electrically isolated via an electrically isolating gap 307, all of which construct a dipole antenna which is a member of the antenna assembly 320. The central conductor 302 is connected to the first electrode 308 by means of a conductive disc 310 for the antenna assembly 320 illustrated in FIG. 16 and 17 and directly connected to the first electrode 308 for another kind of TTDP 324 illustrated in FIG. 18. FIG. 16 shows the out view of the first electrode 308 and the second electrode 309 but the cut view of the single-body sheath 301

Figure 10:
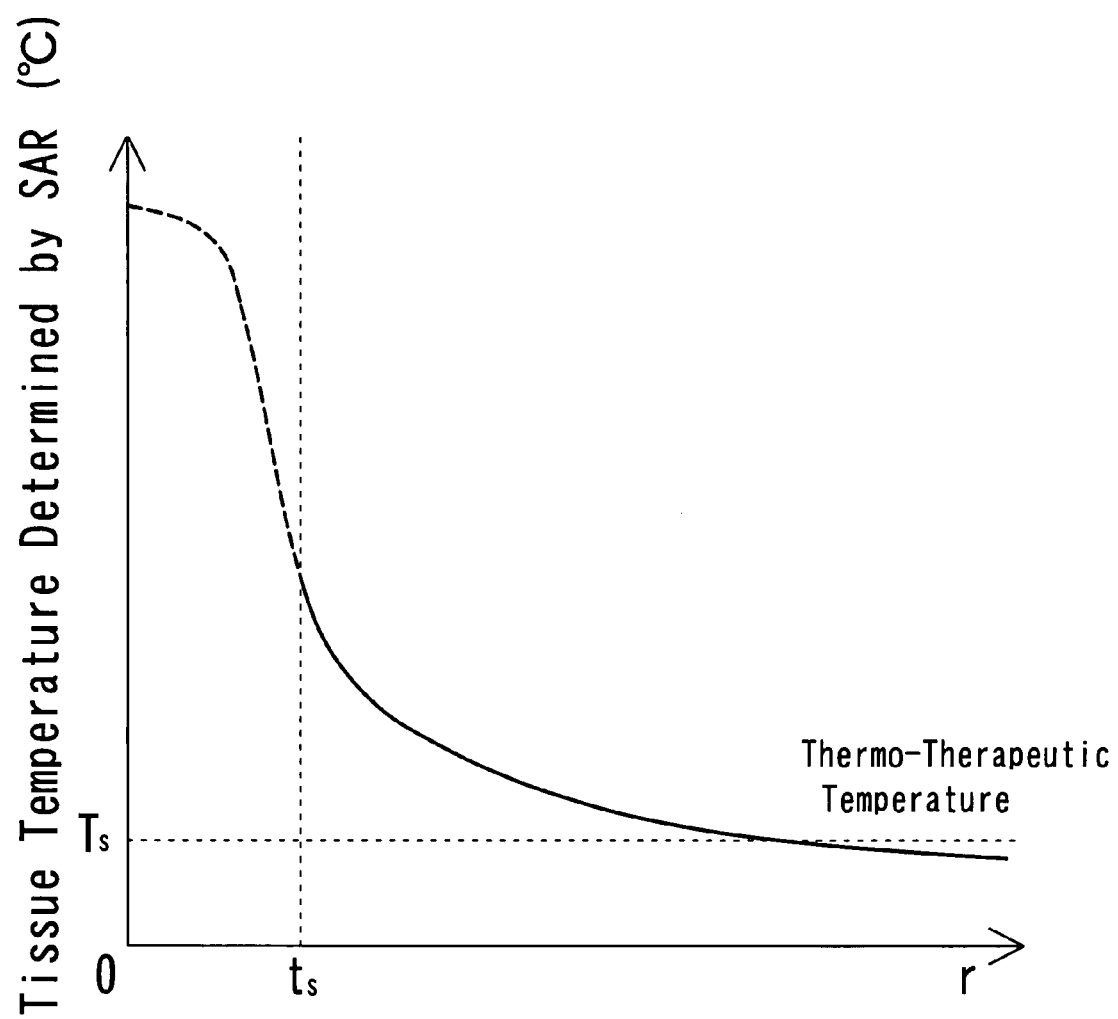
Figure 11:
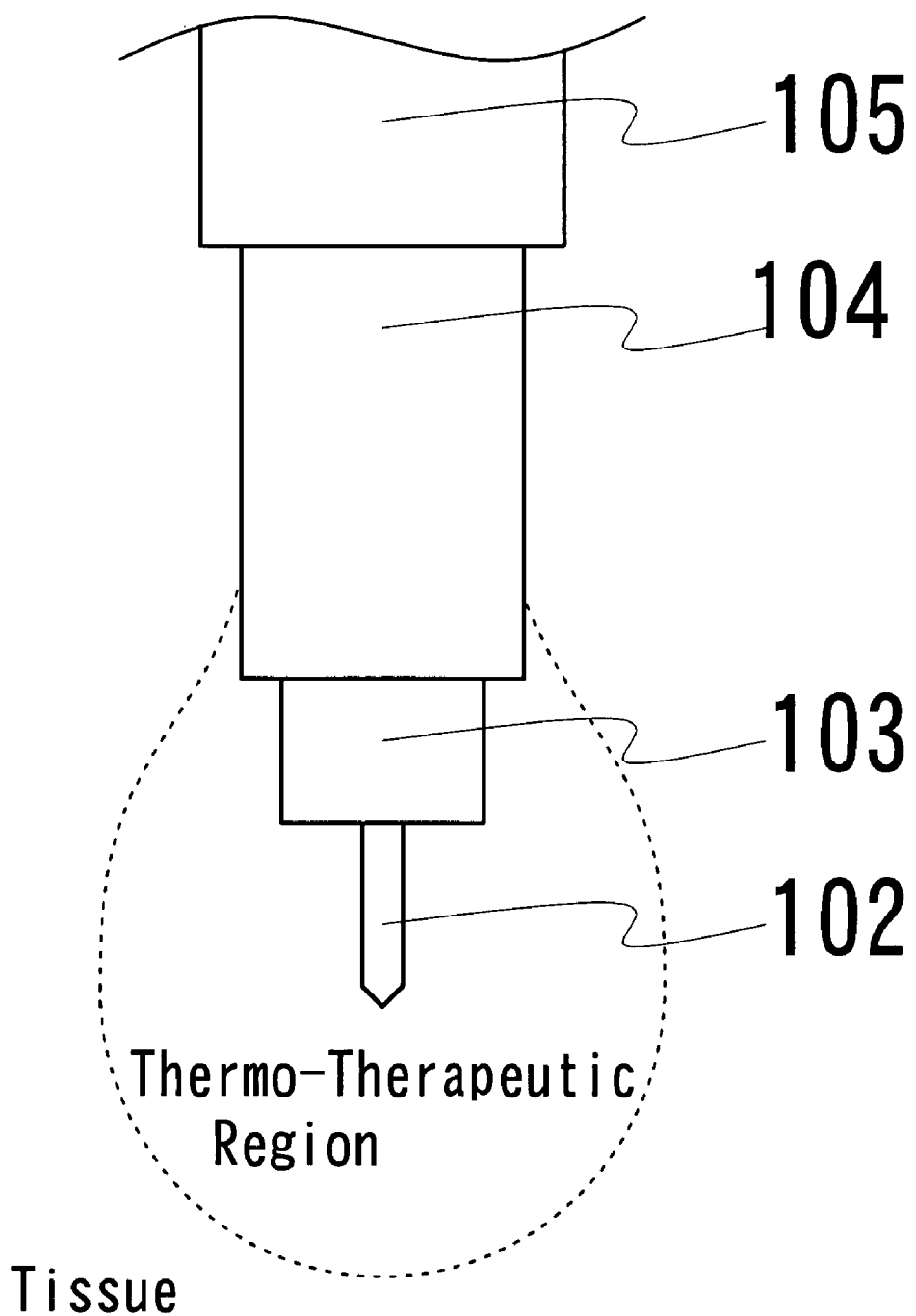
FIGS. 11 and 12 are the schematics showing the effective region obtained by thermo-therapeutic operation using the thermo-therapeutic probe of the prior art.
Figure 12:
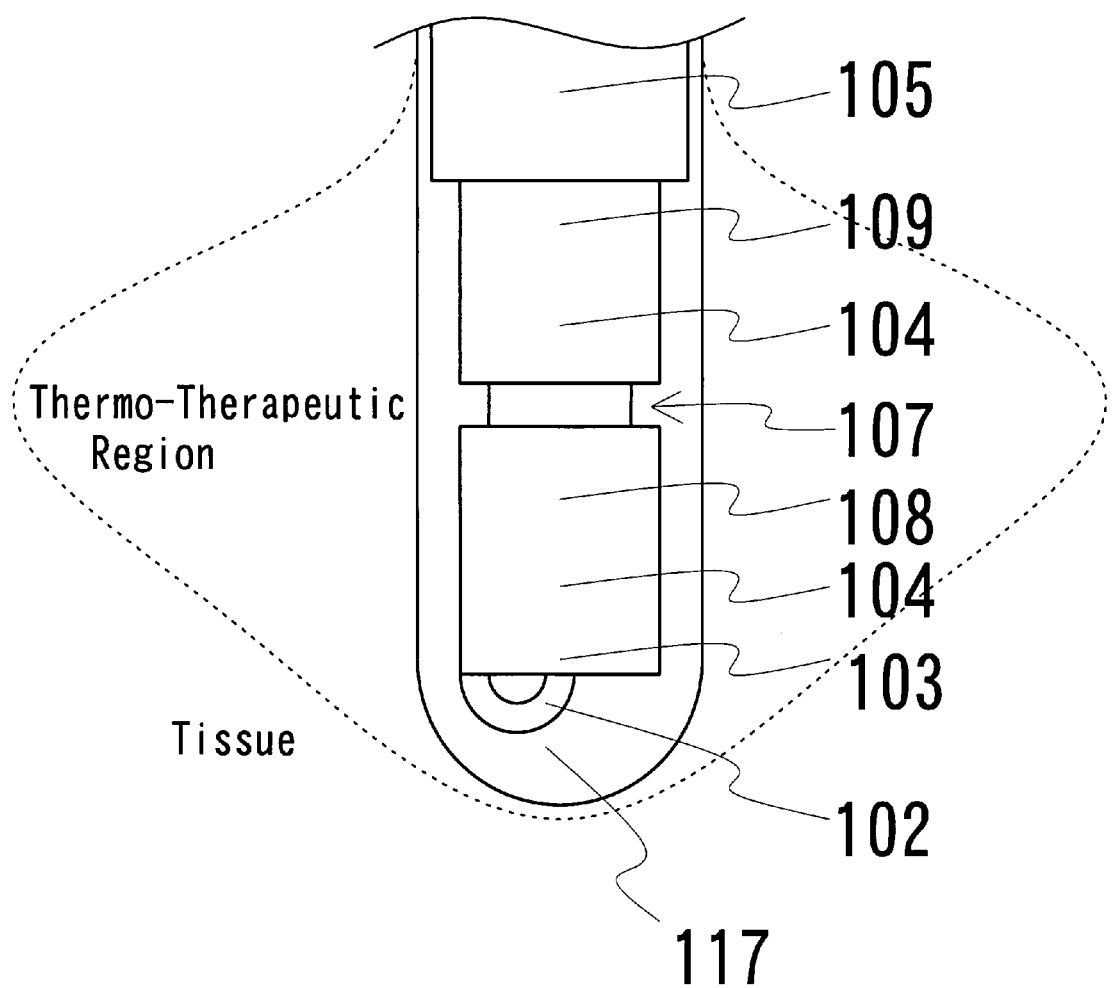

In the radial plane at the origin which corresponds to the rotation axis of the TTDP 324, distribution of the temperature prescribed by SAR (Specific Absorption Rate) is shown in FIG. 10 where the sheath 301 is made of sapphire. The solid line shows the temperature in the tissues and the broken line the temperature in the sheath 301. The zero point corresponds to the surface of the outer conductor 304 (therefore the surfaces of the first electrode 308 and the second electrode 309). The temperature Ts shows 42 deg C. in which protein starts to decompose. The material of the sheath 201 has rather high permittivity as 9.4-11.6 depending on the crystal orientation of sapphire. This is much larger than that of glasses.

Figure 9:
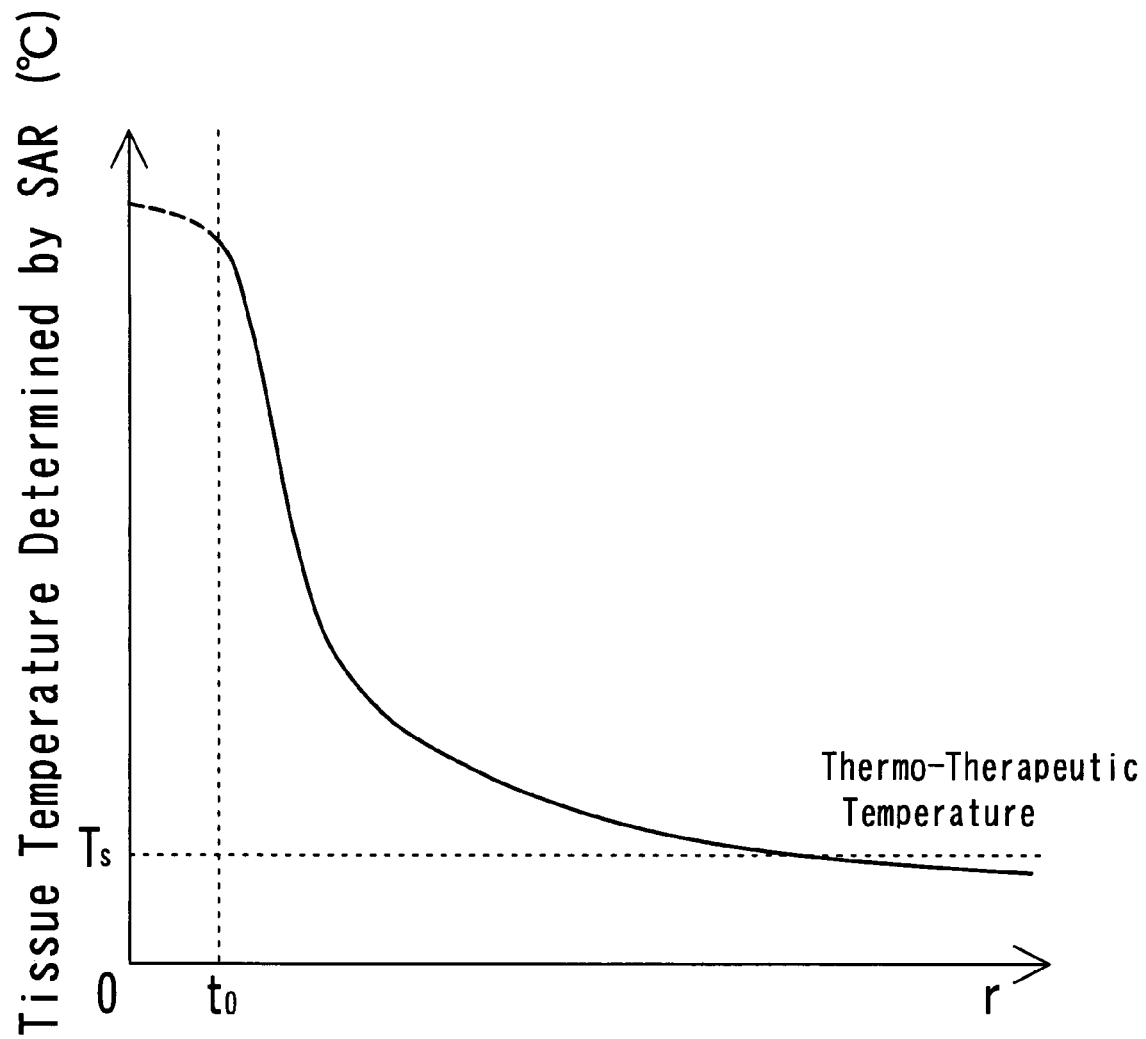
FIGS. 9 and 10 are the temperature distribution determined by SAR in the tissues.

For the purpose of comparison, distribution of the temperature prescribed by SAR for the conventional TTDP illustrated in FIGS. 5, 6, 7, and 8 is shown in FIG. 9. The solid line shows the temperature in the tissues and broken line the temperature in the insulating case 117 of the TTDP.

The specific permittivity of the insulating case 117 or 117A depends on the materials such as hard PVC and PTFE used for the insulating case 117 or 117A. The former is 2.3-3.1 and the latter 2.2-2.9. Either of the permittivity is much smaller than that (about 80 at the body temperature) of water in the tissues. Therefore the electric path determined by the electric field path penetrating the insulating case 117 or 117A multiplied with the square root of permittivity is rather short and the decay of the RF power radiated from the TTMP is small. Due to the water permittivity of the pathological tissues, the electric path is longer than the physical length. Therefore, the temperature steeply decreases from the surface of the insulating case 117 or 117A (which is r=t0 in FIG. 9) to the pathological tissues. In order to keep the temperature in the pathological tissues higher than Ts which is protein decomposing temperature, the surface temperature at r=t0 of the insulating case 117 becomes high enough.

The TTDP of the present invention has a sheath surface at ts which is electrically farther (see FIG. 10) from the origin r=0 in comparison to the TTDP with the case 117 or 117A (called conventional TTDP, hereinafter) which is illustrated in FIG. 9 because the dielectric constant of the single-body sheath 301 which is made of sapphire is larger than the conventional sheath 117. Since the sheath surface of the TTDP 324 is electrically far from the surface of the antenna assembly TTDP 320, the surface temperature of the TTDP 324 can be suppressed even the temperature generated by the RF power at the surface of the antenna assembly TTDP 324 is highly raised. In other words, the temperature of the tissues close to the TTDP surface can be suppressed not to be remarkably higher than the protein decomposing temperature Ts so that the tissues are not burned by the RF power heating.

Since the position of the single-body sheath 301 is at r=ts, the RF absorption region where the temperature of the tissues is higher than Ts is smaller than that when the conventional TTDP is used. However, by increasing RF power supplied to TTDP with single-body sheath 301, the RF absorption region which has the temperature higher than Ts can be extensively larger than that for the insulating case of using the conventional TTDP. For example, 20% increase in the RF power can produce 60% increase in RF absorption region.

Figure 19:
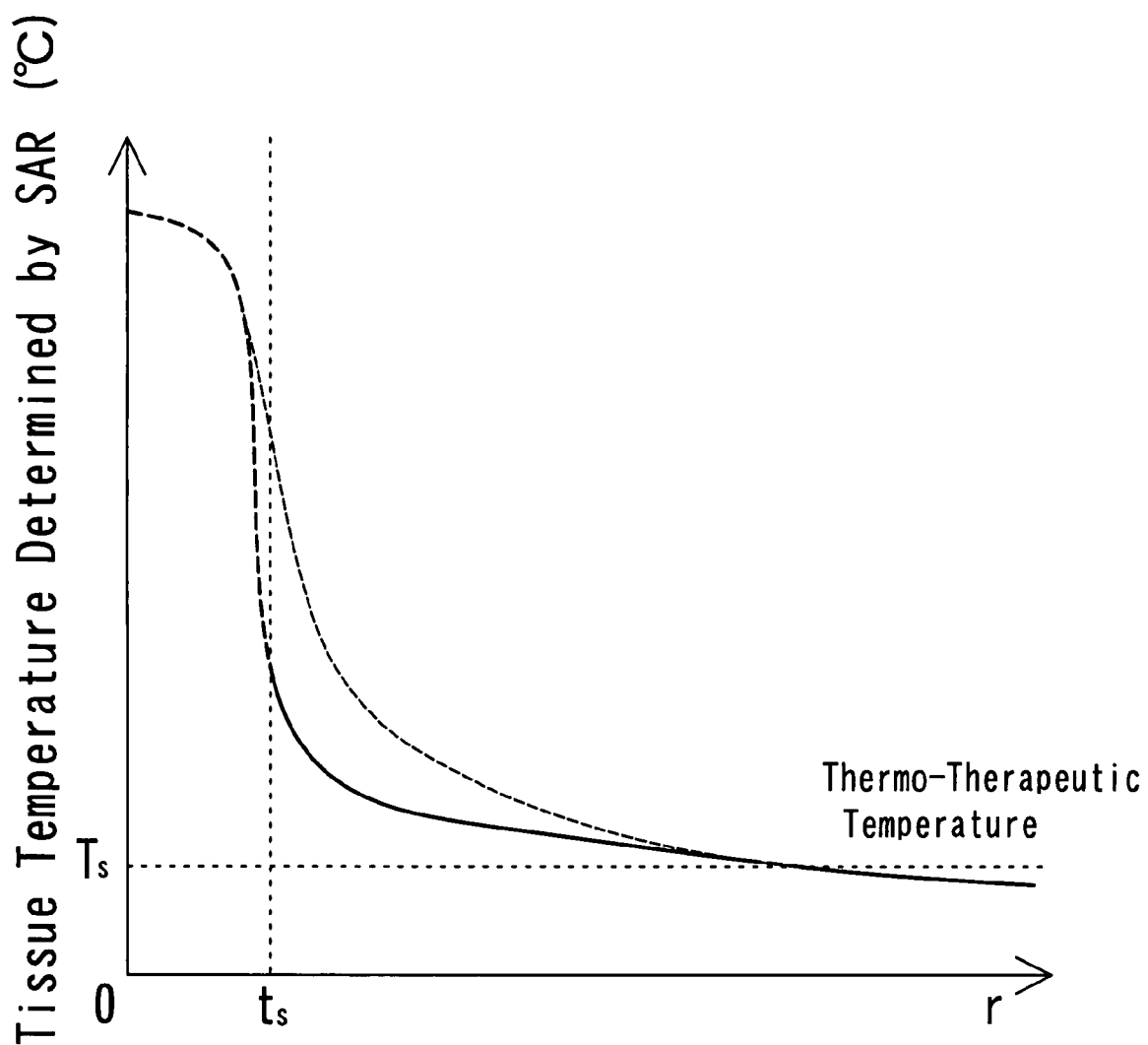
FIG. 19 is the temperature distribution determined by SAR in the tissues using the TTDPs regarding the second object of the present invention.

The heat generation of the TTDP of the present invention is originated from the electrically isolating gap 307 between the first electrode 308 and the second electrode 309. The thermal conductivity of sapphire used for the single-body sheath 301 is 25 W/m/K which is much larger than the PVC used for the conventional TTDP. Therefore, such heat generated at the area close to the electrically isolating gap 307 can be suppressed by the large thermal conduction through the single-body sheath 301 in the axial direction. Therefore, the temperature T prescribed by SAR has a distribution shown in a solid line illustrated by FIG. 19. The dotted line in FIG. 19 is same as the temperature distribution in the thermal absorption of the tissues as illustrated in FIG. 9. High conduction effect of temperature regarding sapphire can be easily notified. The heat generated in the single-body sheath 301 at the position close to the electrically isolating gap 307 expands to the axial direction of the TTDP along the single-body sheath 301 and longitudinally homogeneous heating along the sheath direction can be obtained.

The TTDP 324 regarding the second object of the present invention is enclosed in a single-body sheath 301 which is made of sapphire that has Mohs hardness 9. This value is much larger than the materials of the conventional sheath 117 which is, for example, made of PTFE and therefore has 1-2 for Mohs hardness. The rigidity of sapphire is so high that the single-body sheath 301 is not deformed or does not loose cutting ability in the high temperature environment even when the RF power is supplied to the TTDP 324. Therefore, the surgical operation is quickly performed and the recovery after treatment is rather quick.

For the purpose of quantitative analysis of the size of the TTDP 324, we discuss the dipole antenna structure in an aspect of an electrical structure in the followings. We consider that the TTDP 324 has a dipole antenna formed from an RF power transmitting means such as a coaxial cable. The dipole antenna is a member of an antenna assembly, which is called an antenna assembly (320), hereinafter. In order to obtain the maximum field intensity at the electrically isolating gaps 307 (as illustrated in FIGS. 16-18), the effective length of the first and the second electrodes 308 and 309 have to be quarter wave lengths. Assuming that "L" is the physical length of the first electrodes and "a" the physical length of the gaps 307 in the longitudinal direction of the coaxial cable and "d" the diameter of the cylindrical dielectric insulator 303, the following equation can be obtained.

$$\lambda/4 = a + d/2 + 2/k \cdot L \quad (1)$$

where, $\lambda$ is the wave length of the microwave ($\lambda$=122.4 mm when 2.45 GHz microwave is used), k shortening coefficient of the transmitting wave traveling through the coaxial cable. The maximum power radiation from the TTDP is, by taking the dielectric constant of side wall of the insulating case $\epsilon_s$ (if the insulating case is made of sapphire, the value of $\epsilon_s$ is about 11.6) into account, obtained in the range of, $$\left(\frac{1}{k} + \sqrt{\varepsilon_s}\right) L \geq \frac{\lambda}{4} - a - \frac{d}{2} \geq \frac{2}{k} L \quad (2)$$

According to the equation (2), the maximum power can be exited from the TTDP 324 for the insulating case made of sapphire for which the length of the electrodes is L=4.9~9.7 mm. This length can much shorter than the quarter wave length (30.6 mm) of the microwave. Therefore the antenna assembly can be fabricated in a short size so that small size probes can be realized. Therefore TTDP 324 are usable for a smaller tumor operation than the conventional TTMPs.

The TTDP 324 of the present invention has many advantages other than explained above and further advantages will be explained in the description of the specific embodiments.

The third object of the present invention is to solve this single radiation gap problem. An arrayed antenna assembly which has a plurality of electrically isolating gaps is used for this solution. The electrically isolating gaps are formed along the longitudinal direction of the antenna assembly.

For the third object of the present invention, the TTDP comprises an RF power transmitting means (such as a coupler-line) by which an antenna assembly is formed and a sheath, being made of a hard material for at least a head portion which has a sharp edge, that includes the antenna assembly therein. The RF power transmitting means comprises at least one central conductor, a cylindrical dielectric insulator formed around the central conductor and an outer conductor all of which are formed to be the antenna assembly of which at least one dipole antenna is composed of a first electrode which is formed by a part of the outer conductor and electrically connected to the at least one central conductor, a second electrode which is formed by another part of the out conductor and an isolating means which is formed between the first electrode and the second electrode. The head portion is a head element comprising an edge portion and a flexible pipe that is coupled to a coupling portion formed in the head element. The sheath can be made of a hard material such as sapphire and formed in a single-body.

A modification of the TTDP may be possible in a structure that a first dipole antenna and a second dipole antenna are constructed in such a manner that the first dipole antenna is formed in such a structure that the first and second central conductors are respectively connected to the first electrodes and the second electrodes via power supplied points in an arrangement that the first electrodes and the second electrodes are adjacently facing at the power supply points and the second dipole antenna is formed in such a structure that the first and second central conductors are respectively connected to the second electrodes and the first electrodes via power supplied points in an arrangement that the first electrodes and the second electrodes are adjacently facing at the power supply points. The first electrode pair and the second electrode pair are alternatively formed in the antenna assembly.

The TTDP may further have a dipole antenna formed at an end of the coupler-line. The dipole antenna has a configuration such that it has a folded first electrode and a folded second electrode which have outer electrodes electrically connected to the first and second electrodes formed from the outer conductor, respectively.

Figure 20:
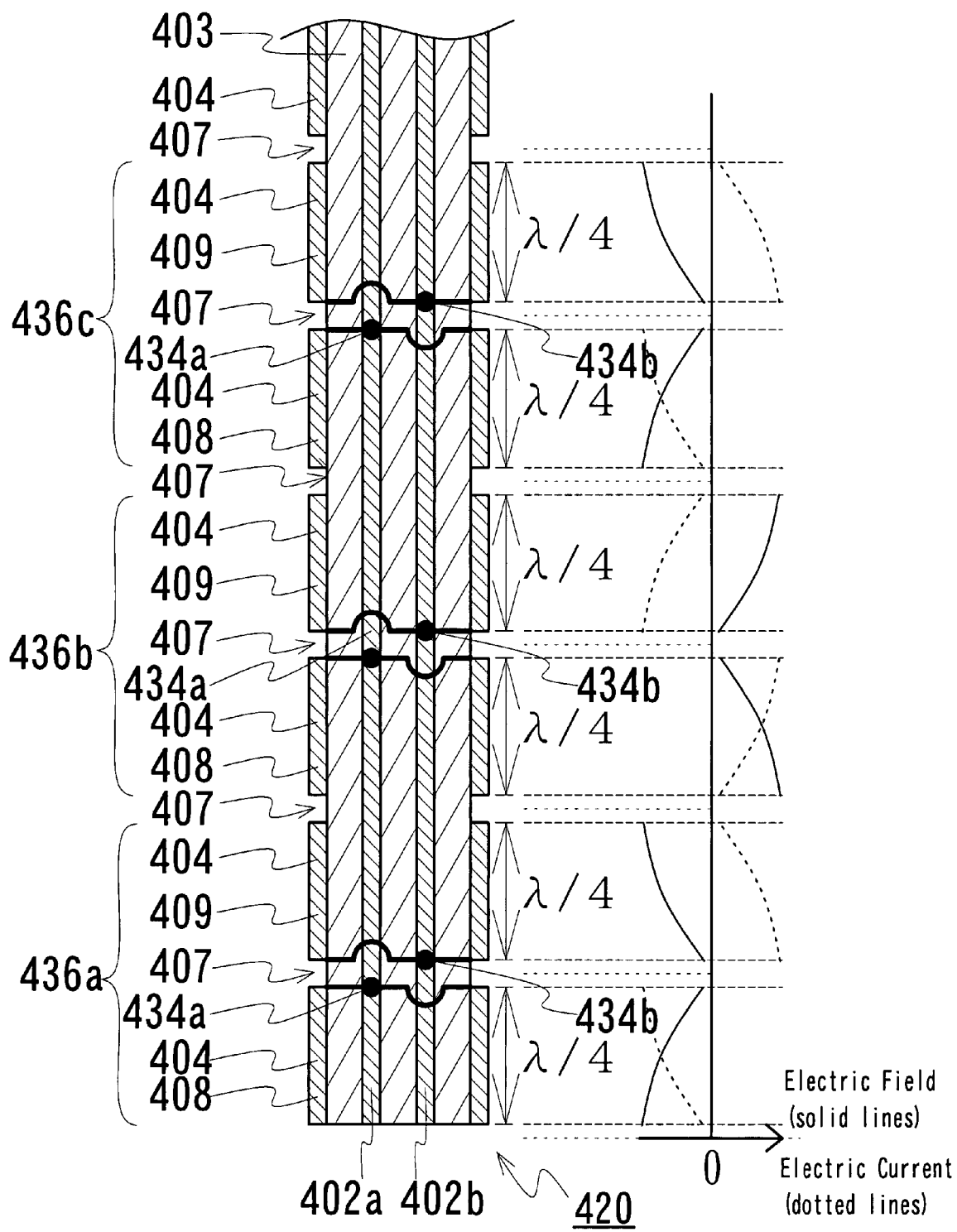
FIGS. 20 to 21 are cut views of the antenna assemblies of the TTDPs regarding the third object of the present invention.
Figure 21:
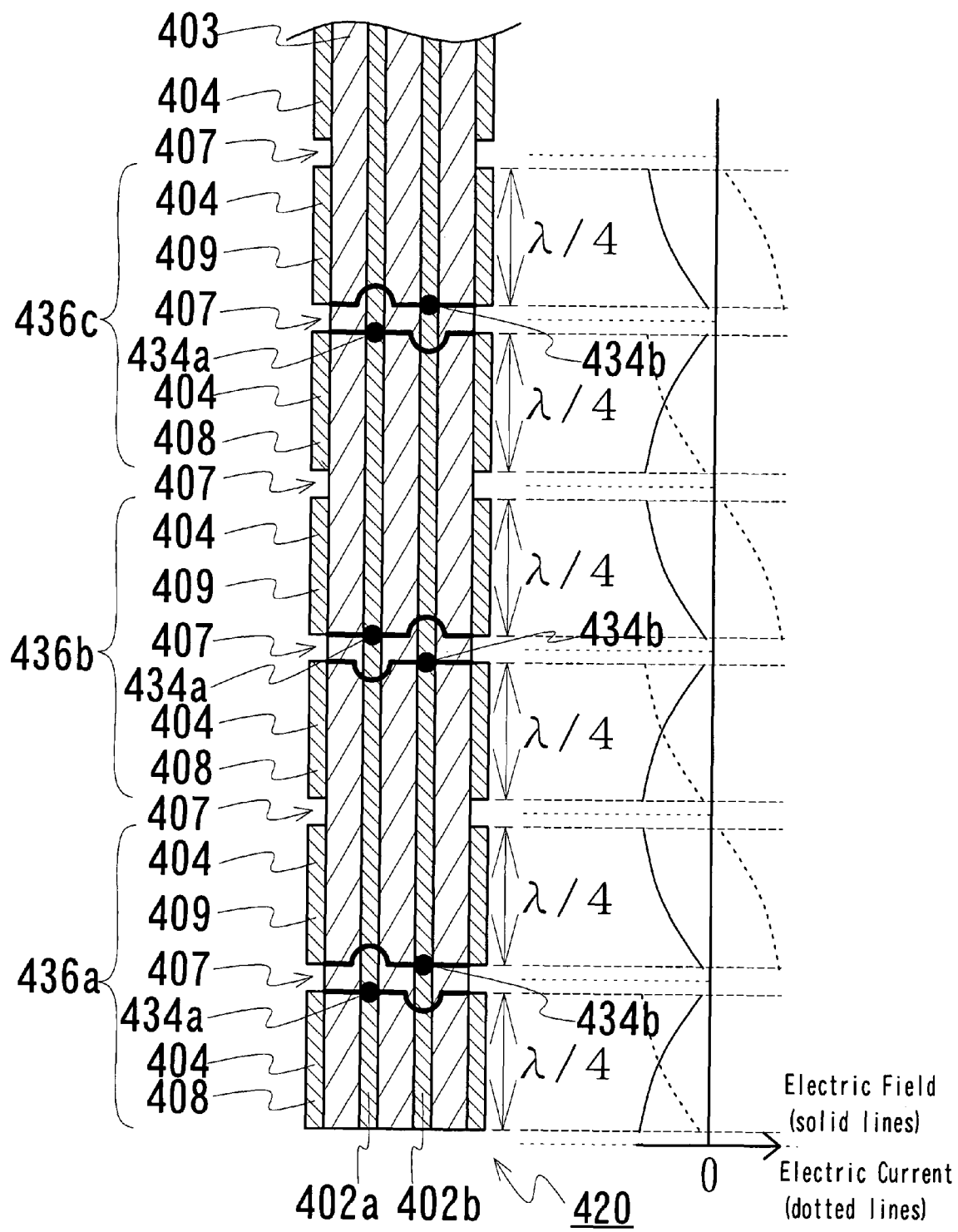
Figure 22:
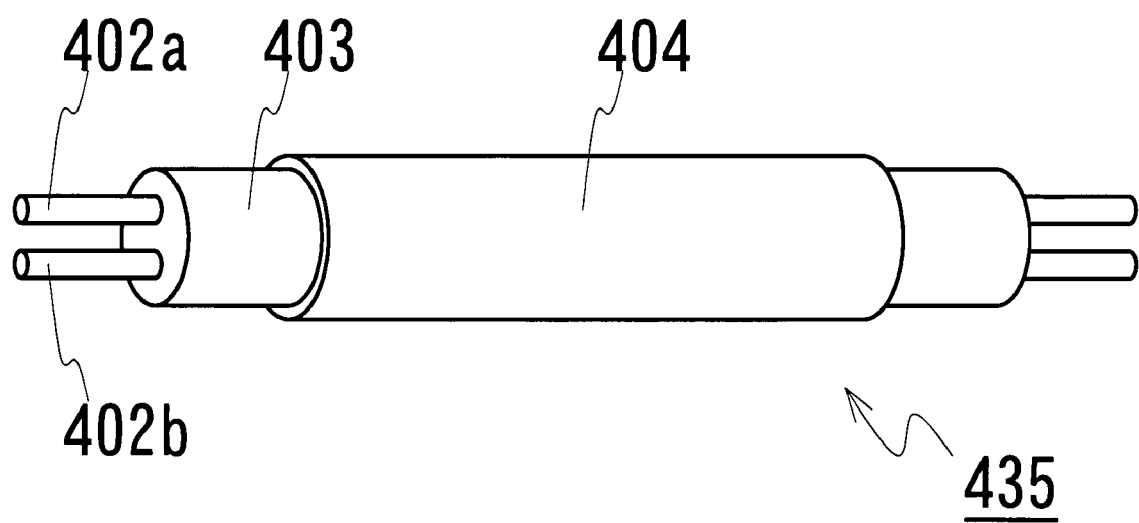
FIGS. 22 and 23 are a perspective view and a cut view of coupler-lines used the third object of the present invention, respectively.
Figure 23:
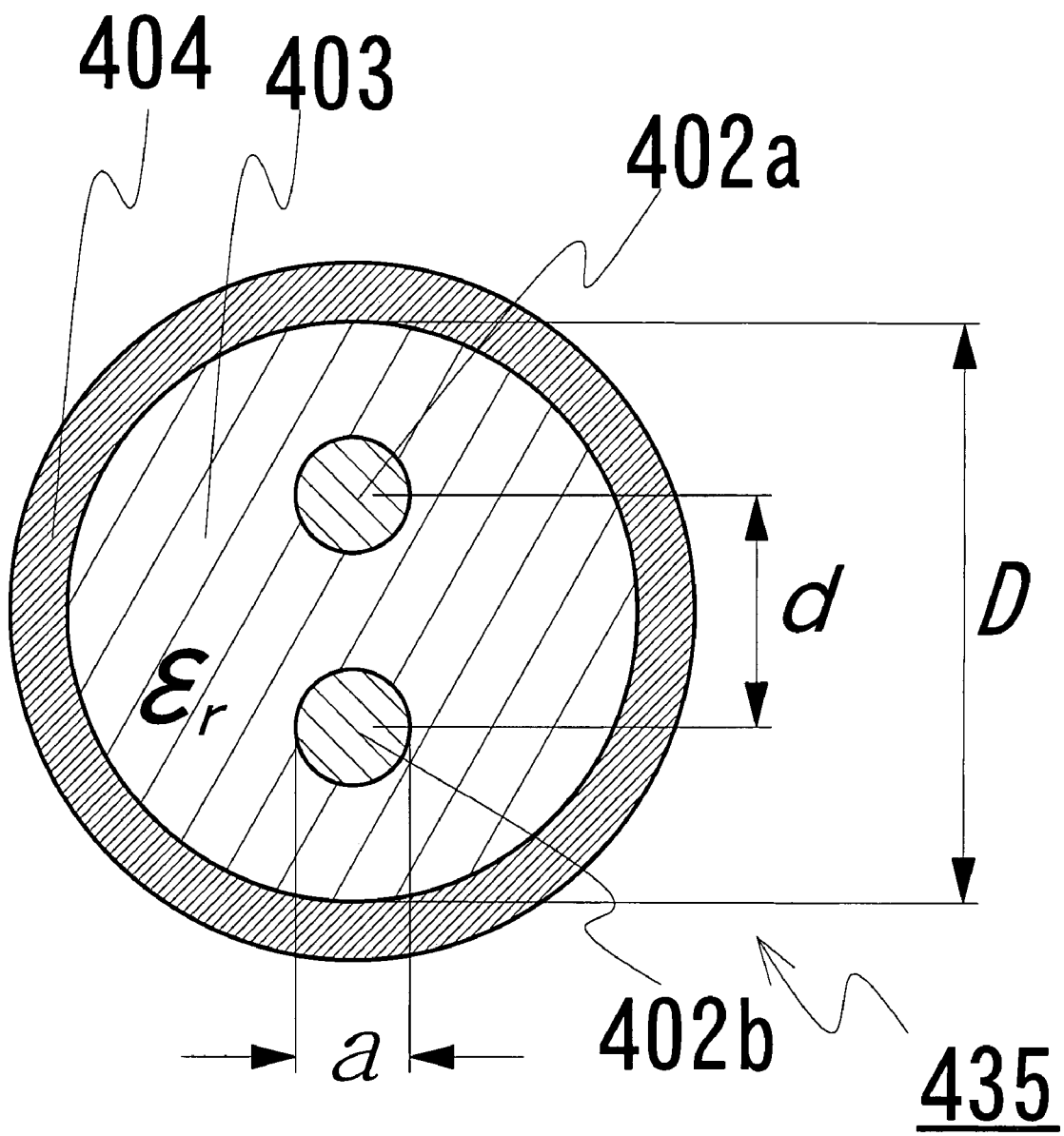

More concretely, the antenna assemblies 420 as illustrated in FIG. 20 and FIG. 21 have a configuration of the arrayed antenna assembly. They are made from a coupler-line 435 as illustrated in FIG. 22 and FIG. 23. More specifically a plurality pair of a first electrode 408 and a second electrode 409 is formed and the coupler-line 435 which is an RF power transmitting cable has a first and second central conductors 402*a* and 402*b* both of which are connected to the first electrodes 408 and the second electrodes 409 via power supplied points 434*a* and 434*b*, respectively in an arrangement that the first electrodes 408 and the second electrodes 409 are adjacently facing at the power supply points 434*a* and 434*b*, respectively. Each first electrode 408 and second electrode 409 is isolated by an electrically isolating gap 407.

Figure 24:
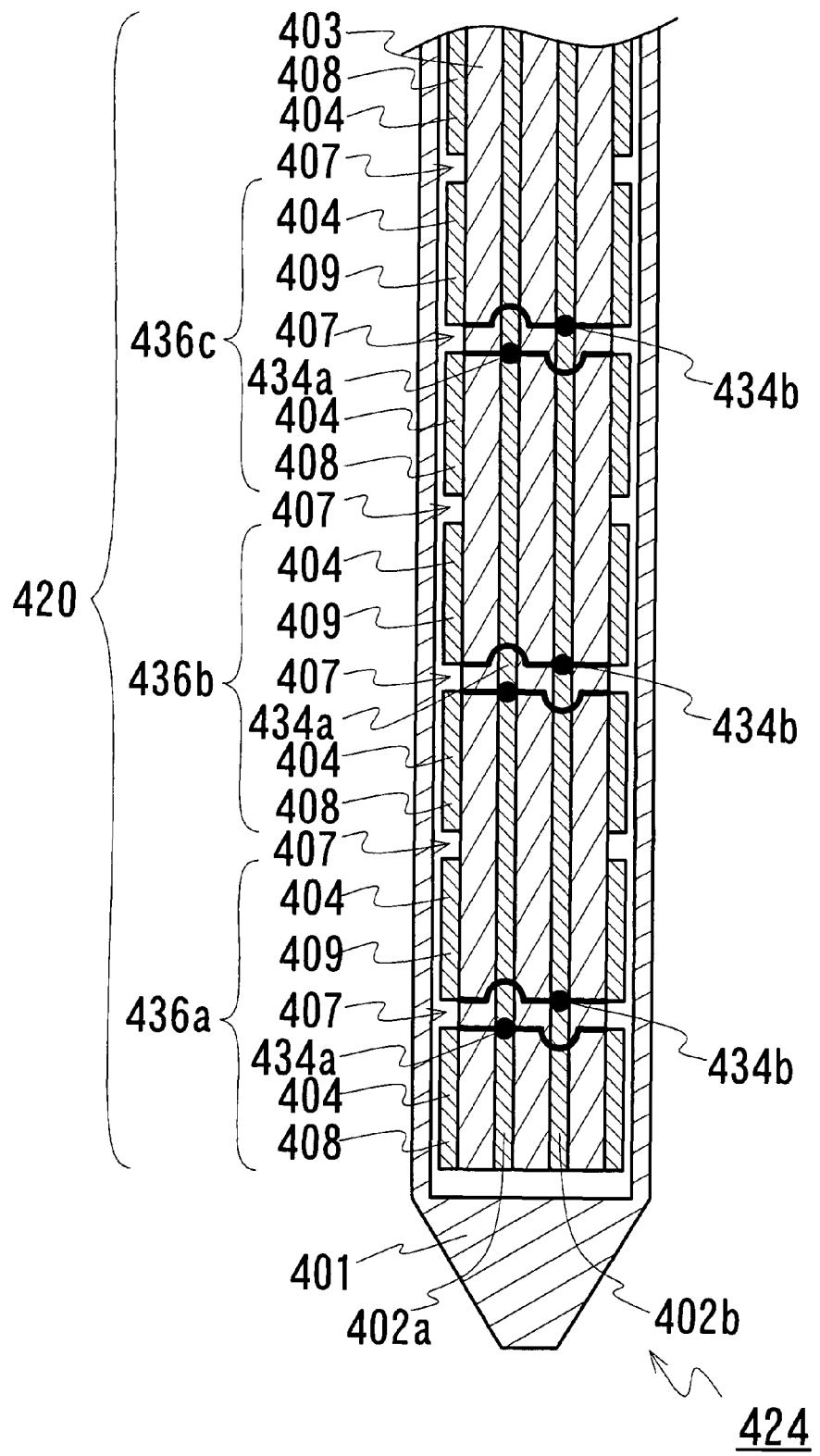
FIGS. 24 to 26 are cut views of the third object of the present invention.
Figure 25:
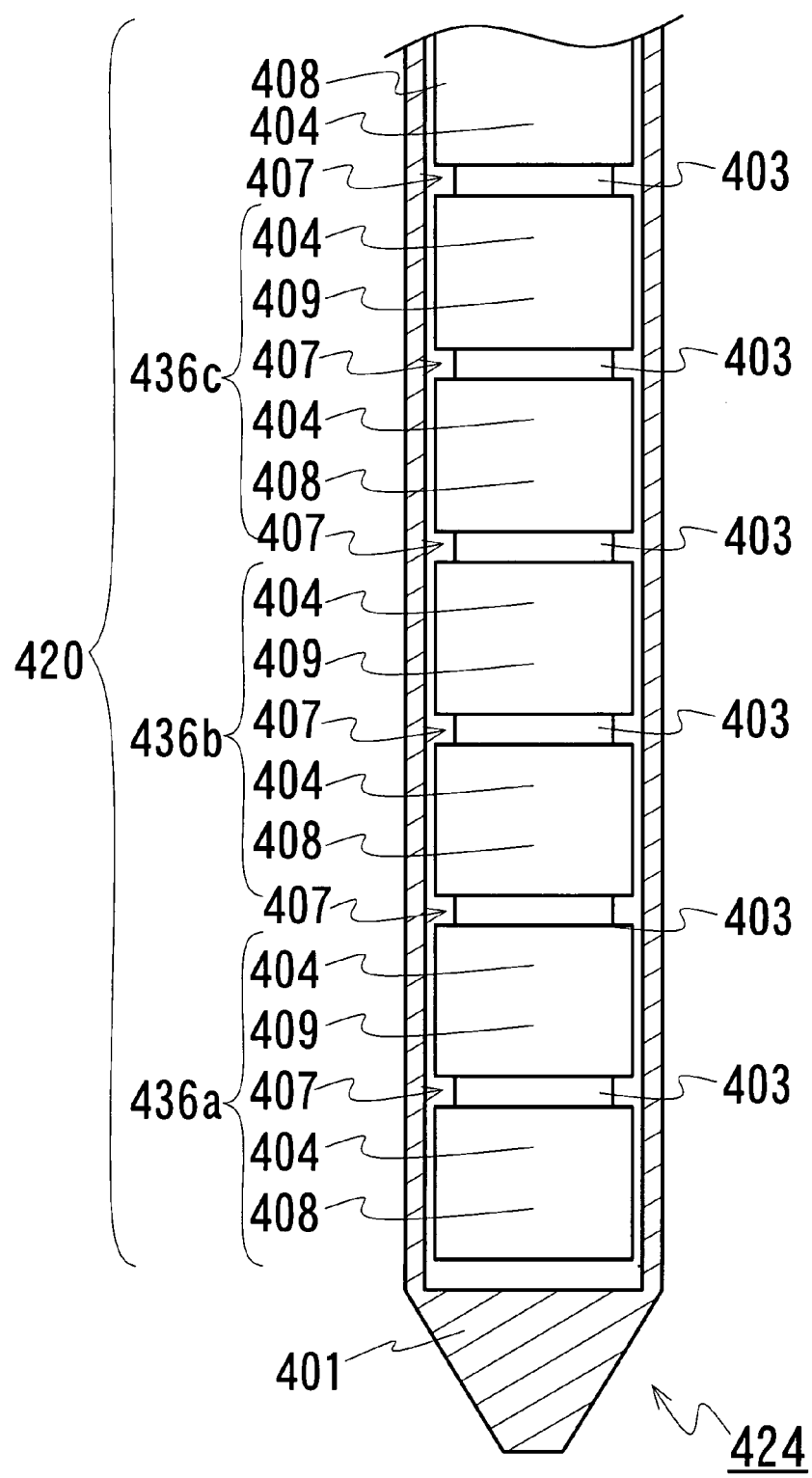
Figure 26:
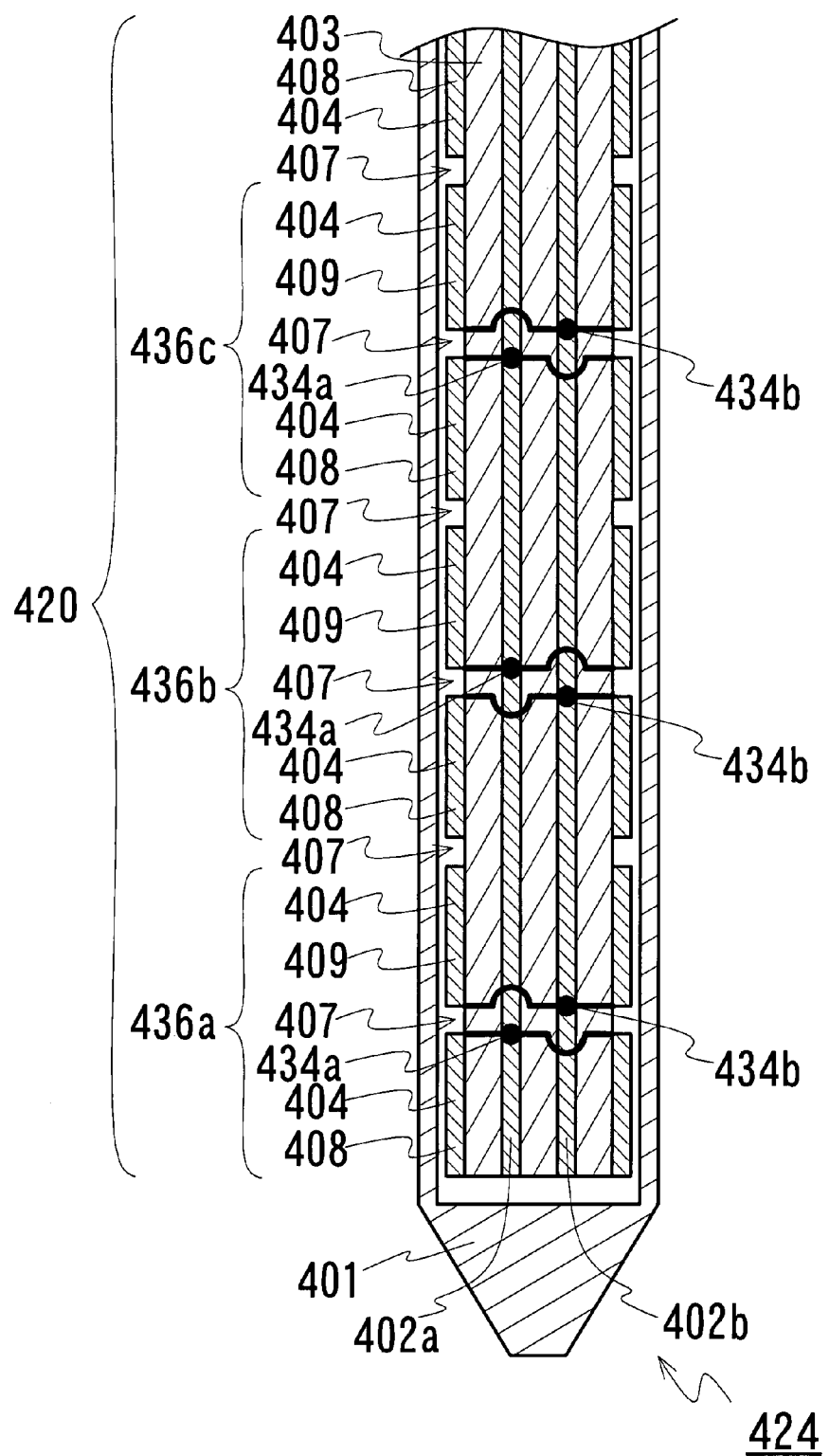

The TTDP 424 (as illustrated in FIGS. 24-26) of the present invention includes the antenna assembly 420 having plural central conductors as a first central conductor 402*a* and a second central conductor 402*b* (more than two central conductors are possible), a dielectric insulator 403 therearound, an outer conductor 404 formed on the surface of the dielectric insulator 403, a plurality of dipole antenna pairs 436*a* and 436*b* which are the members of the antenna assembly 420. The dipole antennas 436*a* and 436*b* have first electrodes 408 and second electrodes 409 both being formed from a part of the outer conductor 404 and isolated each other. The first electrodes 408 and the second electrodes 409 are connected to the first and second central conductors 402*a* and 402*b*, respectively. Each first electrode 408 and second electrode 409 is isolated by an electrically isolating gap 407. The outer conductor 404 has roughly cylindrical shape. The antenna assembly 420 having a plurality pair of dipole antennas 436*a*, 436*b*, 436*c*, etc. is enclosed in a single-body sheath 401. The combination of such antenna assembly 420 and the single-body sheath provides the TTDPs 424.

The difference of the antenna assemblies 420 between those illustrated in FIG. 20 and 21 or FIG. 24 and 26 is that of the power supply points 434*a* and 434*b* which are the connection between the central conductors 402*a* and 402*b* and the first and the second electrodes 408 and 409, respectively. The longitudinal lengths of the first electrodes 408 and the second electrodes 409 correspond to a quarter wave length of the RF wave which is radiated from the TTDP 424. Since a plurality of the dipole antenna pairs is physically arrayed in series, the first central conductors 402*a* and the second central conductors 402*b* are respectively connected to the first electrodes 408 and the second electrodes 409 in iteration. For this configuration, the electric fields and the electric currents of the RF power have the nodes and the anti-nodes at the power supply points 434*a* and 434*b*, respectively, since the RF wave has standing wave mode in the first and second electrodes 408 and 409 of which pair works as a dipole antenna. Since those power supply points 434*a* and 434*b* are the anti-nodes for the electric current, the maximum current can be supplied to the outer conductor 404. As the result, the antenna assembly 420 can support a plurality of dipole antennas as a first dipole antenna 436*a*, a second dipole antenna 436*b*, a third dipole antenna 436*c* and so on (three dipole antennas are entirely illustrated in FIGS. 24-26). Due to such plurality of dipole antennas, a homogeneous heating by RF power radiation is possible for the thermo-therapeutic operation of pathological tissues.

In the TTDP 424, the effective wave length in the coupler-line 435 for the RF wave which is radiated from these dipole antennas 436*a*, 436*b*, 436*c* and so on is rather short by means of the mutual coupling of the central conductors 402*a* and 402*b*. Therefore the physical length of the electrodes can be shortened in the axial direction of the coupler-line 435. For this shortening effect, the RF radiation sources which are the electrically isolating gaps can be closely arranged in a short interval per a unit length of the TTDP 424 and more homogeneously heating cauterizes pathological tissues, that allow quicker surgical operation.

For the conventional RF power transmission cable, coaxial cables are used where a central conductor, a dielectric insulator therearound and outer conductor are included. The axial lengths of the first electrode and the second electrode are the quarters of the effective wave lengths $\lambda_e$ of the conventional RF power transmission cables which have coaxial cable configuration. The effective wave length $\lambda_e$ is given by the equation (3).

$$\frac{\lambda_e}{4} = \frac{\frac{\lambda_0}{4}}{\sqrt{\varepsilon_r} \ln \frac{D}{a}} \quad (3)$$

Where, $\lambda_0$ is the wave length in vacuum, $\varepsilon_r$ the specific dielectric constant of the dielectric insulator, D the diameter of dielectric insulator and a the diameter of central conductors. As a numerical example, the length of the first and the second electrodes is 4.95 cm if the RF frequency is 2.45 GHz and the specific dielectric constant as 2.3 is assumed.

For the TTDP 424, a coupler-line 435, where two central conductors 402a and 402b, a dielectric insulator 403 and the outer conductor 404 are employed as illustrated in FIG. 22 and FIG. 23, is used as an RF power transmission cable. The effective wave length is further shortened by the coupling impedance between the central conductors 402a and 402b which is given by the equation (2).

$$\frac{\lambda_e}{4} = \frac{\frac{\lambda_0}{4}}{\sqrt{\varepsilon_r} \ln \frac{d}{a}} \quad (4)$$

Where, d is the separation distance (center to center distance) between the two central conductor 402a and 402b as illustrated in FIG. 23. Therefore the overall effective wave length is given by the equation (5).

$$\frac{\lambda_e}{4} = \frac{\frac{\lambda_0}{4}}{\sqrt{\varepsilon_r} \ln \frac{D}{a} \left(1 - k + \frac{k \ln \frac{D}{a}}{\ln \frac{d}{a}}\right)} \quad (5)$$

Where, k and $\alpha$ are given by $$k = \frac{\alpha}{2\pi - \alpha} \quad (6)$$

and $$\alpha = 2 \tan^{-1}\left(\frac{\frac{a}{2}}{d}\right) \quad (7)$$

The equation (6) represents a shield effect k of one central conductor to the other central conductors. The usual quantity of k is 0.3 to 0.5. Therefore the shortening effect of the coupler-line 435 is enhanced by a coefficient of given by the equation (8), as $$\frac{1}{1 - k + \frac{k \ln \frac{D}{a}}{\ln \frac{d}{a}}} \quad (8)$$

By applying the equation (8) to the equation (5), the shortening effect is 0.28 for the insulating case that D=1.1 mm, d/a=0.2 mm/0.18 mm. The lengths of the first electrodes and the second electrodes are 2.4 cm. The same shortening effect is obtained for the antenna assembly 420.

The shortening effect of the plural central conductors is enhanced with the quantity of the central conductors. For example when three central conductors are used, the quarter wavelength becomes $$\frac{\frac{\lambda_0}{4}}{\sqrt{\varepsilon_r} \ln \frac{D}{a} \left(1 - 2k + \frac{2k \ln \frac{D}{a}}{\ln \frac{d}{a}}\right)} \quad (9)$$

and the electrode lengths can be shortened by a factor of $$\frac{1}{1 - 2k + \frac{2k \ln \frac{D}{a}}{\ln \frac{d}{a}}} \quad (10)$$

The above shortening effects are not influenced to the position of the power supply points 434a and 434b. For the three central conducts, the usage of the central conductors is that two central conducts and the other conductor work as the first central conductor 434a and the second central conductor 402a and the second central conductor 402b, respectively. The two central conductors are selected from the three central conductors for each segment determined by two adjacent power supply points 434a.

The TTDP 424 of the present invention has many advantages other than explained above and further advantages will be explained in the description of the specific embodiments.

The fourth object of the present invention is to solve the lighthouse effect. For the fourth object of the present invention, the TTDP comprises an RF power transmitting means (such as a coupler-line) by which antenna assembly is formed and a sheath, being made of a hard material for at least a head portion which has a sharp edge, that includes the antenna assembly therein. The RF power transmitting means (such as a coupler-line) comprises two central conductors, a cylindrical dielectric insulator formed around the central conductors and an outer conductor all of which are formed to be the antenna assembly of which at least one dipole antenna is composed of a first electrode which is formed by a part of the outer conductor and electrically connected to the one central conductor, a second electrode which is formed by another part of the out conductor and an isolating means which is formed between the first electrode and the second electrode. Another dipole antenna formed at an end of the coupler-line has a pair of two half-annular electrodes surrounding the dielectric insulator. The dielectric insulator has such a structure that the two half-annular electrodes are isolated via electrically isolating gaps and the central conductors are electrically connected to the half-annular electrodes. The head portion is a head element comprising an edge portion and a flexible pipe that is coupled to a coupling portion formed in the head element. The sheath can be made of a hard material such as sapphire and formed in a single-body.

All of the dipole antennas arranged in the antenna assembly have RF power radiation from electrically isolating gaps that are formed between the first electrodes and the second electrodes. Such arrangement of the first and second electrodes constructs dipole antennas. The coupler-lines can supply RF power to front tip dipole antennas by means of the two central conductors and RF power transmitted to the front tip dipole antenna is radiated therefrom. This antenna configuration is added to a dipole antenna or a plurality of dipole antennas formed in the coupler-line.

Figure 27:
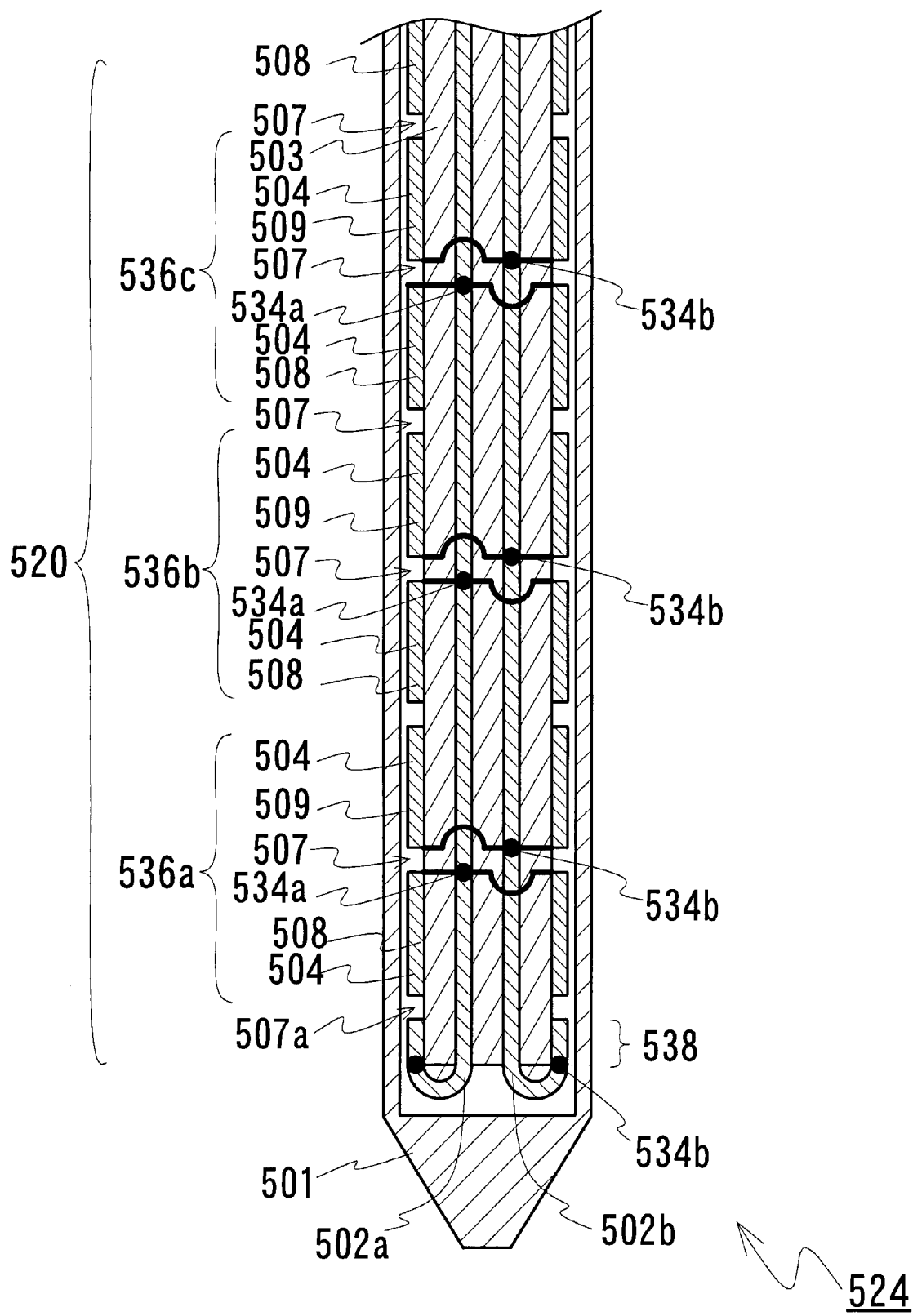
FIGS. 27 to 29 are cut views of the third object of the present invention.
Figure 28:
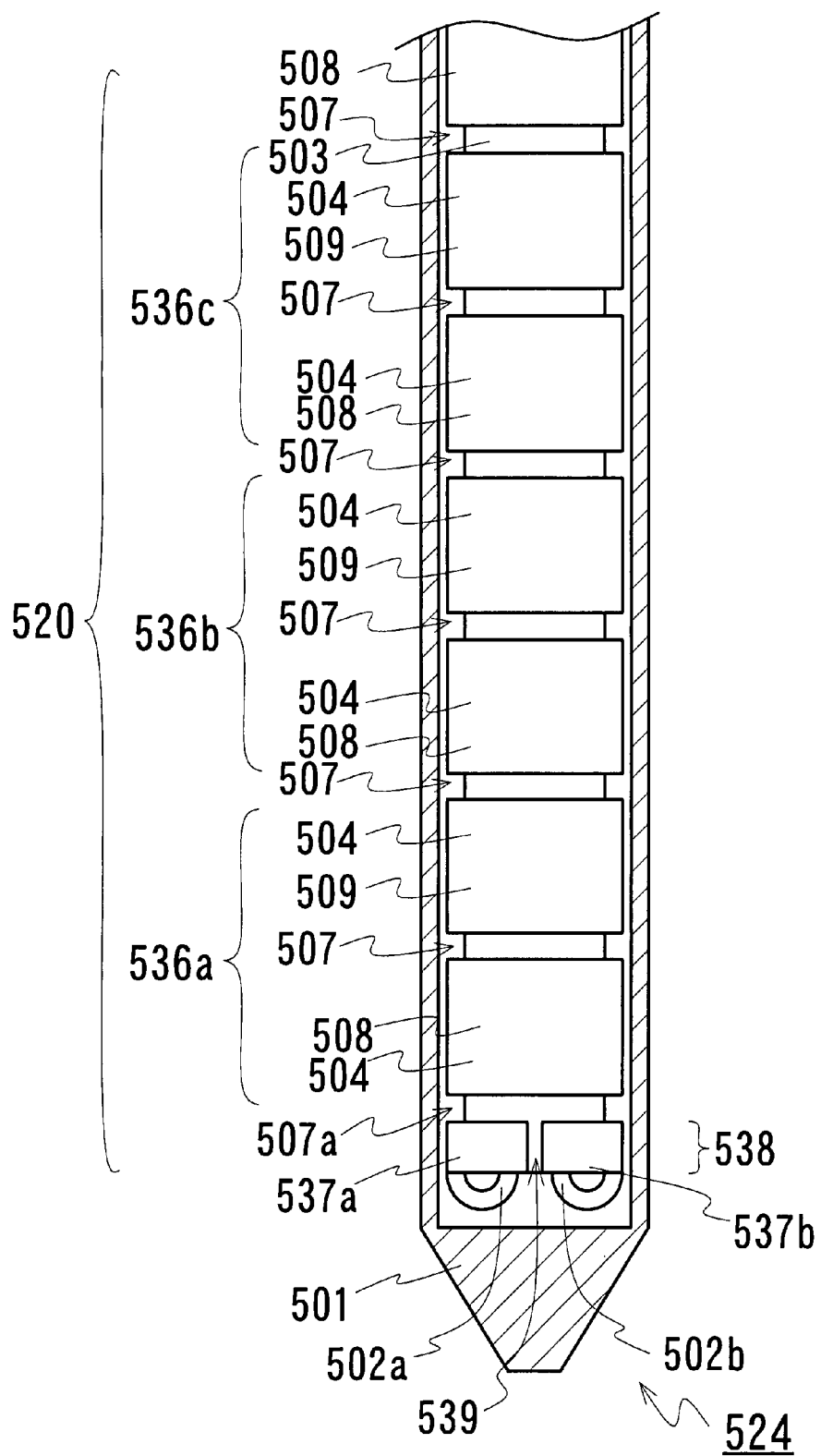
Figure 29:
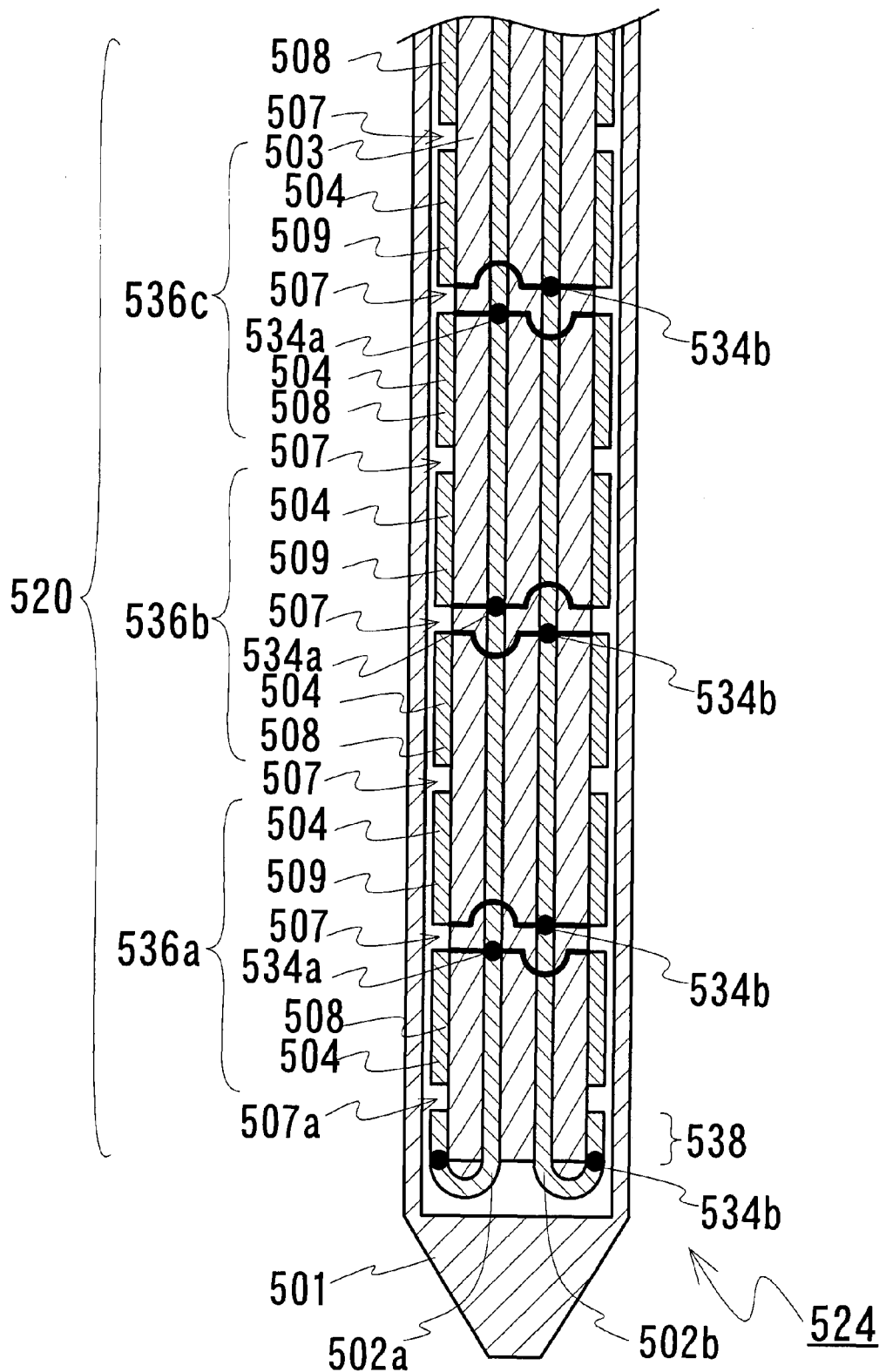

The configuration is illustrated in FIG. 27-29. The fundamental arrangement of the antenna assembly shown in FIGS. 27-29 is same as those shown in FIGS. 24-26. The detail structure for the antenna configuration is similar to those shown in FIGS. 24-26. Additional dipole antenna which is a member of the antenna assembly 520 is, however, installed to the front chip of the antenna assembly 520. A couple-line 435 illustrated in FIG. 22 is used to form the dipole antennas 536*a*, 526*b* and 536*c* by means of the outer conductor 504. Two central conductors 502*a* and 502*b* which transmit the RF power are terminated to the front chip dipole antenna 538 and can excite thereof in an even manner with the other dipole antennas 536*a*, 536*b*, 536*c*, etc which are members of the antenna assembly 520. The effective electric length of the front chip dipole antenna 538 seen at the last power supply points 534*a* and 534*b* to the nearest dipole antenna 536*a* is set to be a half-wave length. For this physical length, the reflection due to the termination by using the front chip dipole antenna 538 can be suppressed so that the RF power is transmitted to the front chip dipole antenna 538 and therefore the transmitted RF power ultimately radiates from the front chip dipole antenna 538 to the tissue regions.

The TTDP 524 of the present invention has many advantages other than explained above and further advantages will be explained in the description of the specific embodiments.

The first to fourth objects of the present invention is to realize preferable TTDPs that are much advanced from the conventional TTMPs. Further preferred TTDPs can be obtained by adding temperature control capability of the surface of TTDPs as discussed in the followings.

Figure 30:
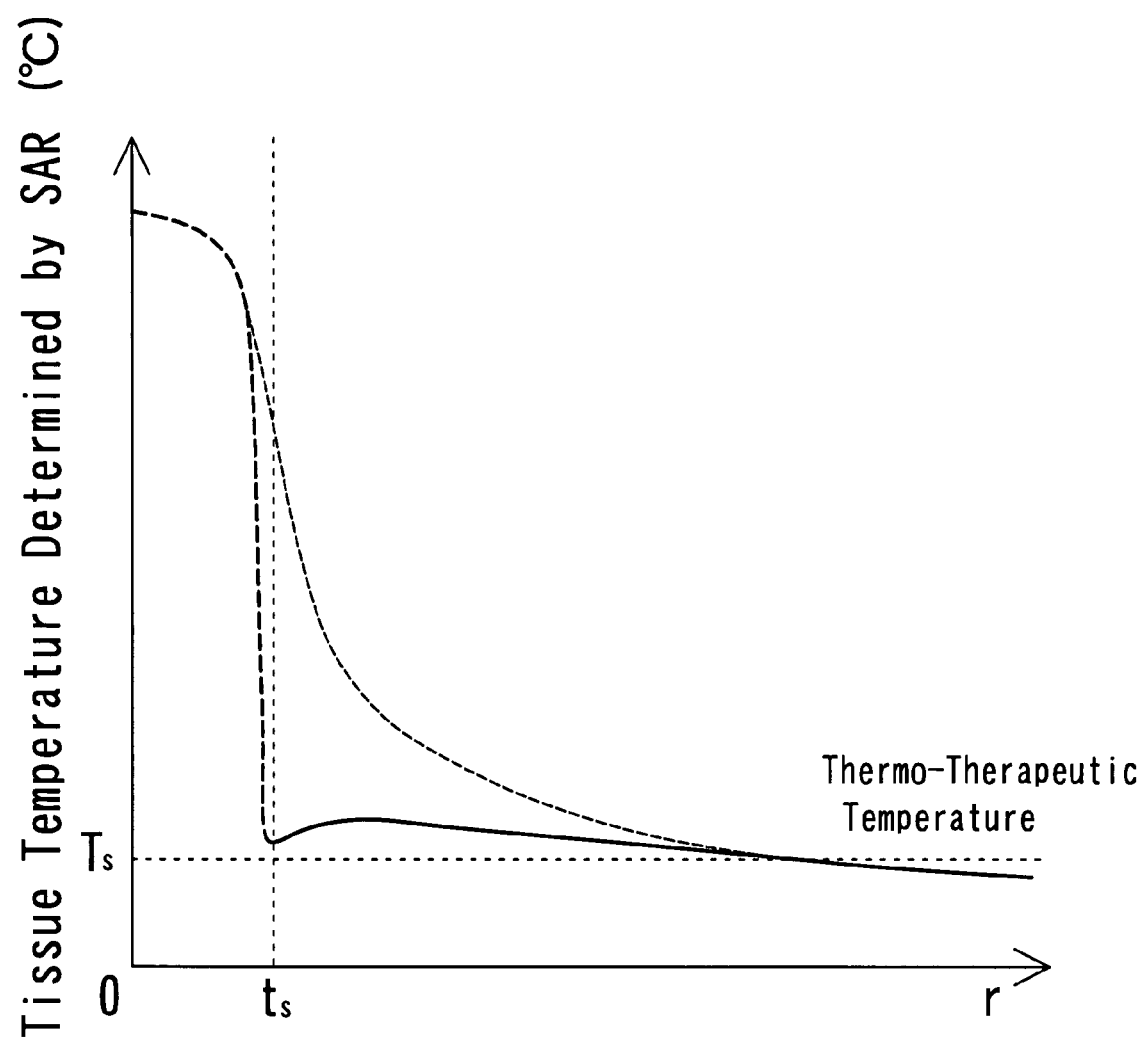
FIG. 30 is the temperature distribution determined by SAR in the tissues for the case when TTDPs regarding the first to third objects of the present invention equip a circulating structure of cooling liquid therein.

If the insulating cases of the TTDP 324, 424 and 524 comprise single-body sheath made of sapphire, temperature control of the single-body sheaths 301, 401 and 501 can be easily done by circulating cooling liquid therein. Then the surface temperature of the single-body sheaths 310, 401 and 501 can be kept low even the pathological tissues are heated by the RF radiation by the TTDPs 324, 424 and 524. Therefore the temperature of the pathological tissues can homogenously be controlled to be heated not much higher than the temperature that induces the pathological tissues to be necrotic like as shown in FIG. 30. The dotted line shows the temperature decrease in the pathological tissues and the dashed line the temperature variation to the distance from the surface of the TTDP. The temperature of the single-body sheaths 301, 401 and 501 can be extremely cooled down. Therefore the pathological tissues to which the TTDPs 324, 424 and 524 are inserted are less coagulated so that the necrosis of such tissues is not suppressed and the TTDPs 324, 424 and 524 are not stuck in the tissues. This temperature control can serve the surgeons to use high power RF but the therapeutic effects such as necrosis of the tissues and non-sticking of TTDPs to the tissues can provide the capability of heating wider region of the pathological tissues for the thermotherapy.

The fifth object of the present invention is to provide a drug delivery capability to the TTDP by which the drug is injected into the pathological tissues to which the TTDP is percutaneously inserted.

For the fifth object of the present invention, the TTDP as described in the first to fourth objects of the present invention has further a sheath that has a hole that opens from said sharp edge through a edge portion thereof or a hole that opens from the head portion of the single-body sheath. The sheath has a hole in cylindrical surface of said sheath from inside to outside thereof.

The advantages of the TTDP of the fifth object of the present invention are as follows. After injection, the drug can spread into tissues and/or be activated by heating by the RF power radiated from the TTDP 624 as illustrate in FIGS. 106-110, for examples. The TTDP has a physical channel for such drug delivery. The drug is encapsulated in thermal sensitive gel and the heating by RF radiation destroys the gel capsules and the drug is spread in the tumors or the drugs convert the receptiveness for cell protein of specific tumors by the heating so that the drug invades into the cells which are the members of such tumors. For the particular capsules or drugs, TTDPs can be effective for oncology therapy since a single action operation to percutaneously invade into tissues provides multiple tasks such as pathological tissue heating treatment, drug conversion and medicine injection.

The TTDP 624 of the present invention has many advantages other than explained above and further advantages will be explained in the description of the specific embodiments.

The sixth object of the present invention is to provide a control system for the surgeon to safely use the TTDPs disclosed in the first to fifth object of the present invention. The RF power is led to the TTDPs from an RF power source and the power reflection at the TTDPs should not return to the RF power source since the return power makes instability of the RF power generation in the RF power source. The control system has a circulator by which the RF power reflected at the TTDPs does not return to the RF power source. The control system controls the output level of the RF power to keep appropriate RF power level that the pathological tissues to which the TTDPs are inserted is not over heated.

For the sixth object of the present invention, a therapeutic antenna probe system comprising an RF power source, a circulator connected to said RF power source, said TTDPs, being selected from those regarding the first to the fifth object of the present invention, are connected to said circulator through an RF power transmitting means such as a coaxial cable or a coupler-line, an RF power meter connected to said RF power source via a power coupler. The RF power meter connected to a controller which controls RF power generated by said RF power source by an output signal of the said power meter.

The therapeutic antenna probe system may includes a thermal transducer wherein an output signal from said thermal transducer is input to said controller so that RF power generated by said RF power source is controlled by said output signal for better control of thermal therapy.

The therapeutic antenna probe system of the sixth object of the present invention has many advantages other than explained above and further advantages will be explained in the description of the specific embodiments.

The seventh object of the present invention is to provide a usage of the therapeutic antenna probe system as provided in the sixth object of the present invention with anti-cancer drugs, having one effect selected from a group of effects given by carcinostatic effect and cancer-fighting effect.

The usage of the therapeutic antenna probe system of the present invention with the anti-cancer drugs has many advantages other than explained above and further advantages will be explained in the description of the specific embodiments.

DESCRIPTION OF THE SPECIFIC EMBODIMENTS

Referring now to the drawings, a number of embodiments of TTDPs described as the first to the sixth objects of the present invention.

First of all, TTDPs for the first object of the present invention, employing sapphire heads and insulating flexible pipes, are described in the following.

FIGS. 13-15 are the preferred embodiments for this first object. The antenna assembly comprise a central conductor 202, a cylindrical dielectric insulator 203 formed around the central conductor 202 and an outer conductor 204 wherein a first electrode 208 formed from a part of the outer conductor 204 and electrically connected with the central conductor 202 and a second electrode 209 formed from the another part of the outer conductor 204 which is electrically isolated from the first electrode 208. The first electrode 208 and the second electrode 209 construct a dipole antenna to which RF power is supplied through a RF power transmission cable such as a coaxial cable. The central conductor 202, the cylindrical dielectric insulator 203 and the outer conductor 204 may be formed in a termination part of the coaxial cable. The TTDP comprises the antenna assembly 220 and a sheath 230 that comprises a sharp edge head 293 consisting of a edge portion 291 and a coupling portion 292 to which an isolating flexible pipe 294 tightly couples. The edge portion 291 of the sharp edge head 293 is, at the front edge, mechanically sharpened to be a blade to percutaneously cut and invade into the tissues.

The electrical isolation between the first electrode 208 and the second electrode 209 is provided by just an electrically isolating gap 207 formed in the outer conductor 204, wherein the electrically isolating gap 207 is cut off part of the outer conductor 204. The electrical connection between the central conductor 202 and the first electrode 208 is preferably via an electrical conducting disc 210 as illustrated in FIG. 13 and FIG. 14. FIG. 13 illustrates an outer view of the antenna assembly 220 and a cut view of the sheath 295. FIG. 14 further shows a cut view of the antenna assembly 220 illustrated in FIG. 13.

FIG. 15 further shows another preferred embodiment regarding the first object of the present invention. The electrical connection between the central conductor and the first electrode is made by the central conductor 202 extending and being bended to electrically contact to the first electrode 208. The electrical conducting disc 210 is not used for this embodiment. Therefore this embodiment is preferred when fewer components for the antenna assembly 220 are required.

Figure 31:
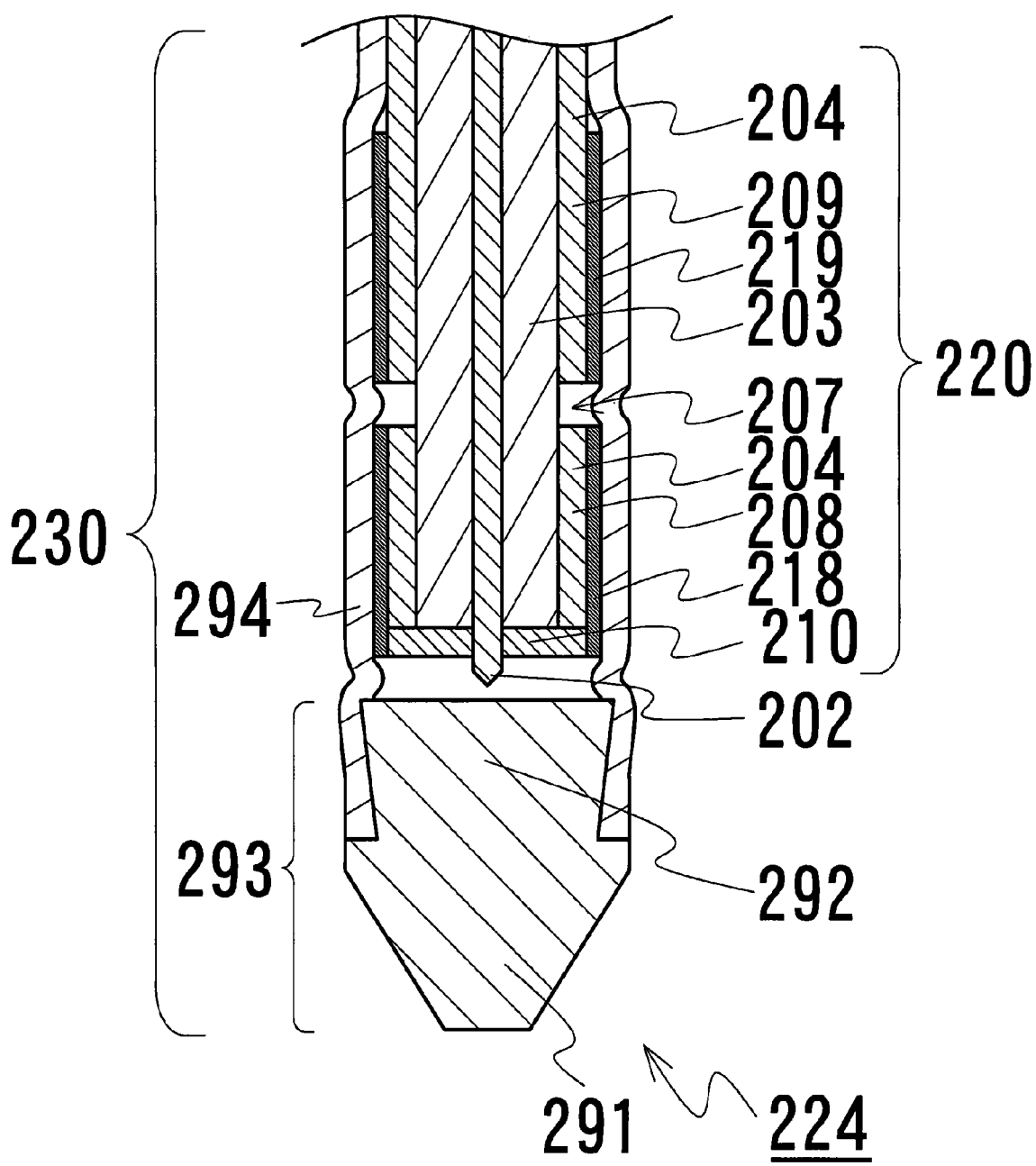
FIGS. 31 to 40 are the views of the TTDPs regarding the first object of the present invention.

FIG. 31 further illustrates another preferred embodiment regarding the present invention. The first and the second electrodes 208 and 209 have additional electrodes 218 and 219 which are made from metal pipes or metal plates rolled around the outer conductor 204 and electrically contacts to the first and second electrodes 208 and 209. For the case that the outer conductor 204 is made from a metal mesh (which is used for flexible coaxial cables) or a metal mesh being stiffed by tin or solder (which is used for semi-rigid coaxial cables), the electrodes 208 and 209 are too soft to be formed in a mechanical preciseness so that structure of the electrodes insures clear cut-lines or physical preciseness for the electrically isolating gap 207. Then the additional electrodes 218 and 219 provide clear cut-lines instead of the first and the second electrodes 208 and 209 to electrically determine the electrically isolating gap 207 by their peripheral lines.

Figure 32:
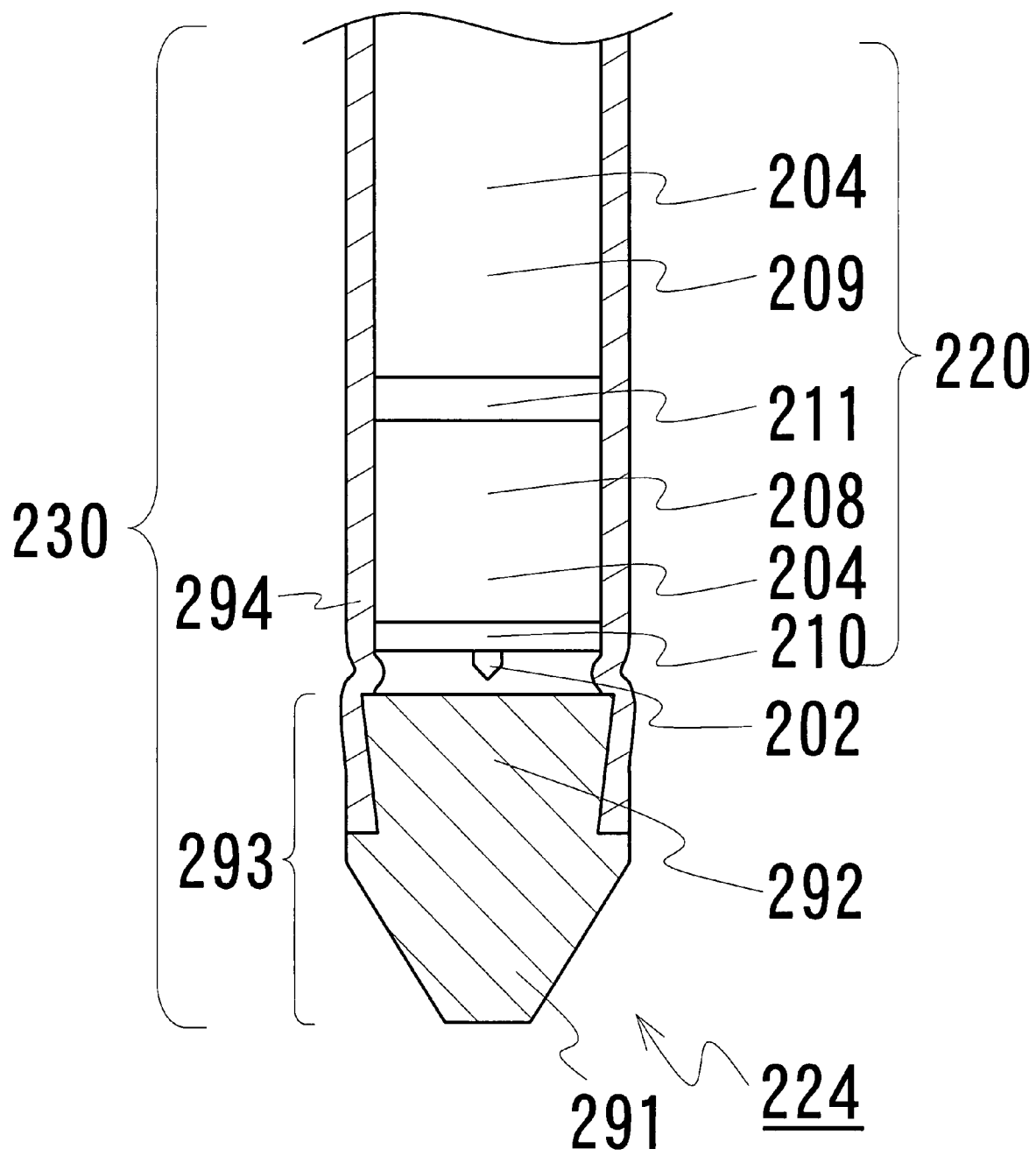
Figure 33:
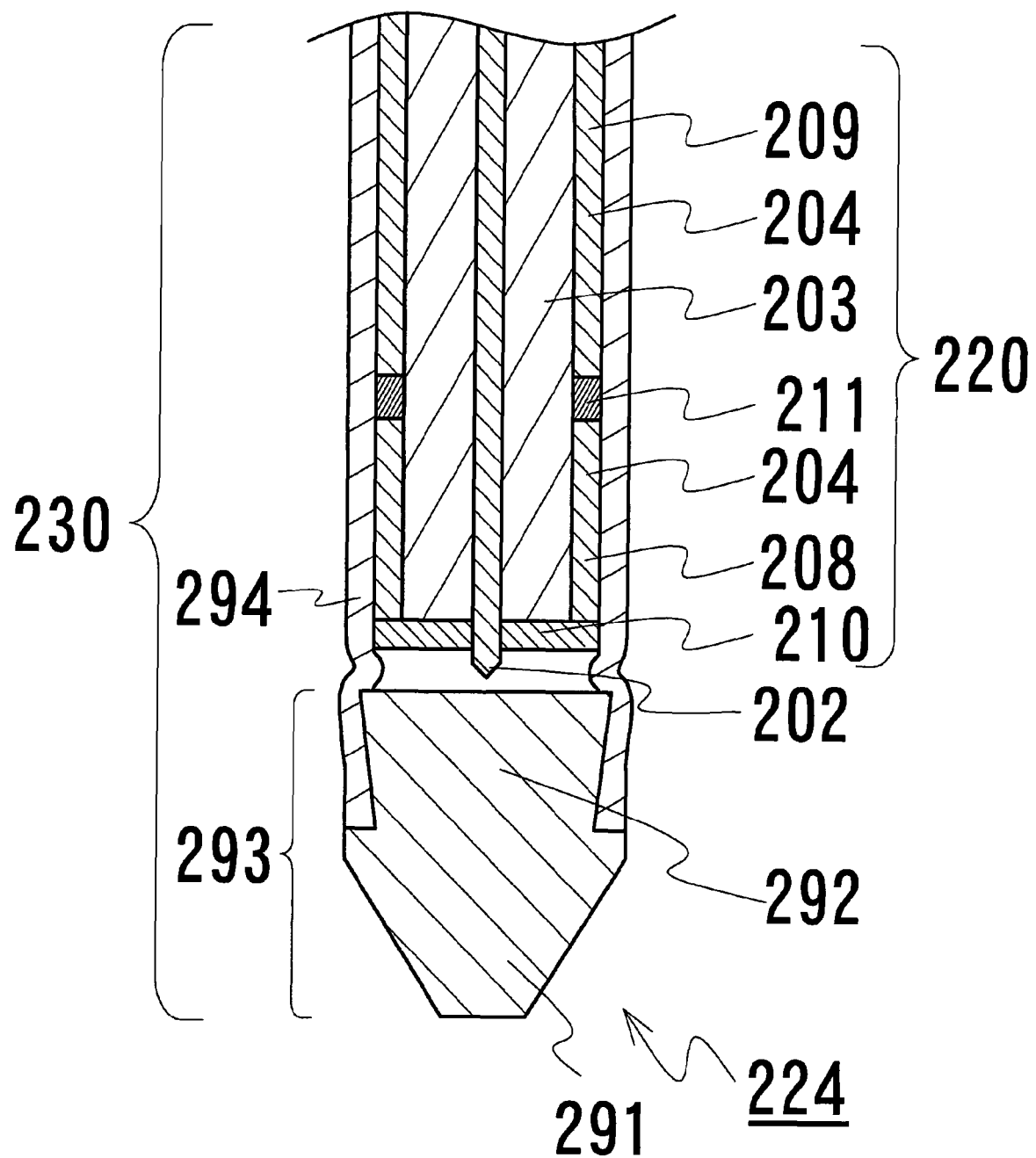
Figure 34:
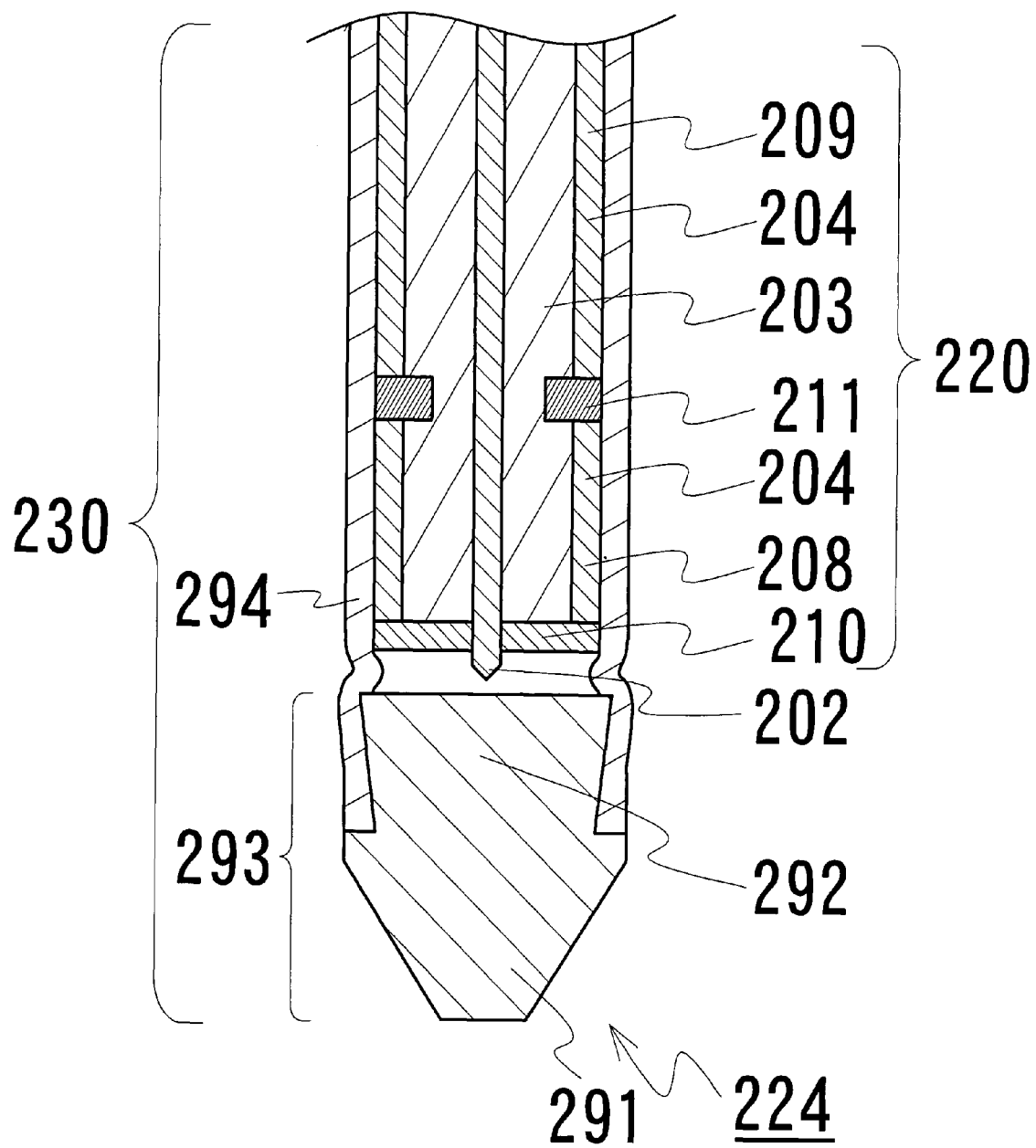

FIGS. 32-34 illustrate other preferred embodiments regarding the first object of the present invention. An electrically isolating gap made for the electrical isolation between the first electrode 208 and the second electrode 209 is filled with an insulating collar 211 which works as an electrical insulator therebetween and is preferably made from the same material as the cylindrical dielectric insulator 203 or similar material. The breakdown voltage between the first electrode 208 and the second electrode 209 can be increased by using this insulating collar 211 in comparison with just an electrically isolating gap 207 as cut. Therefore, more RF power can be supplied so that more RF power radiation is possible. The distortion of the electrically isolating gap by bending force can be suppressed due to the existence of mechanical stiffness of this insulating collar 211. The insulating collar 211 shown in FIG. 34 is buried in a gap recessed in the cylindrical dielectric insulator 203 and therefore the edge of the outer conductor 204 at the electrically isolating gap can be clear so that the debris at the edge liness of the first and second electrodes 208 and 209 are removed.

Figure 35:
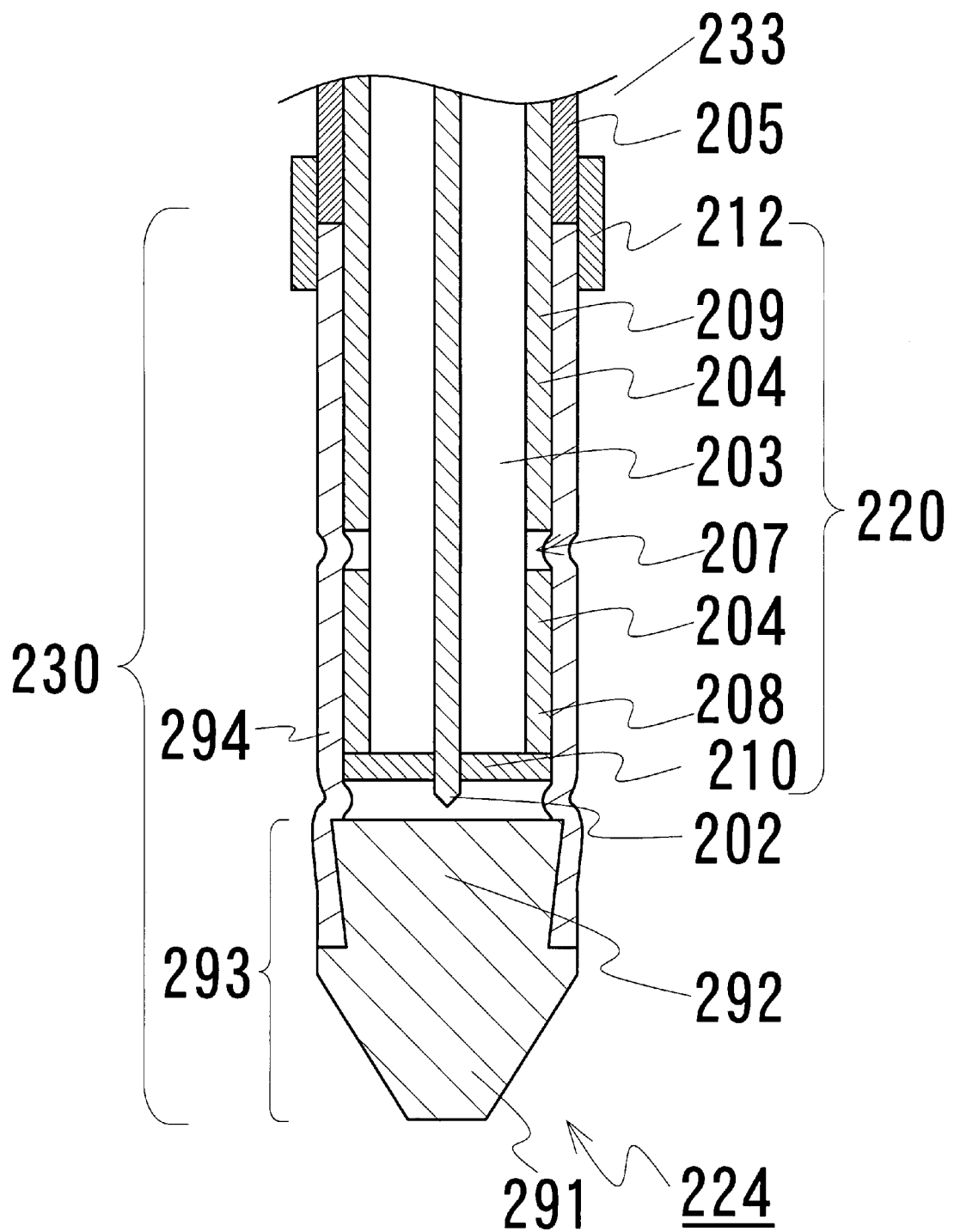
Figure 36:
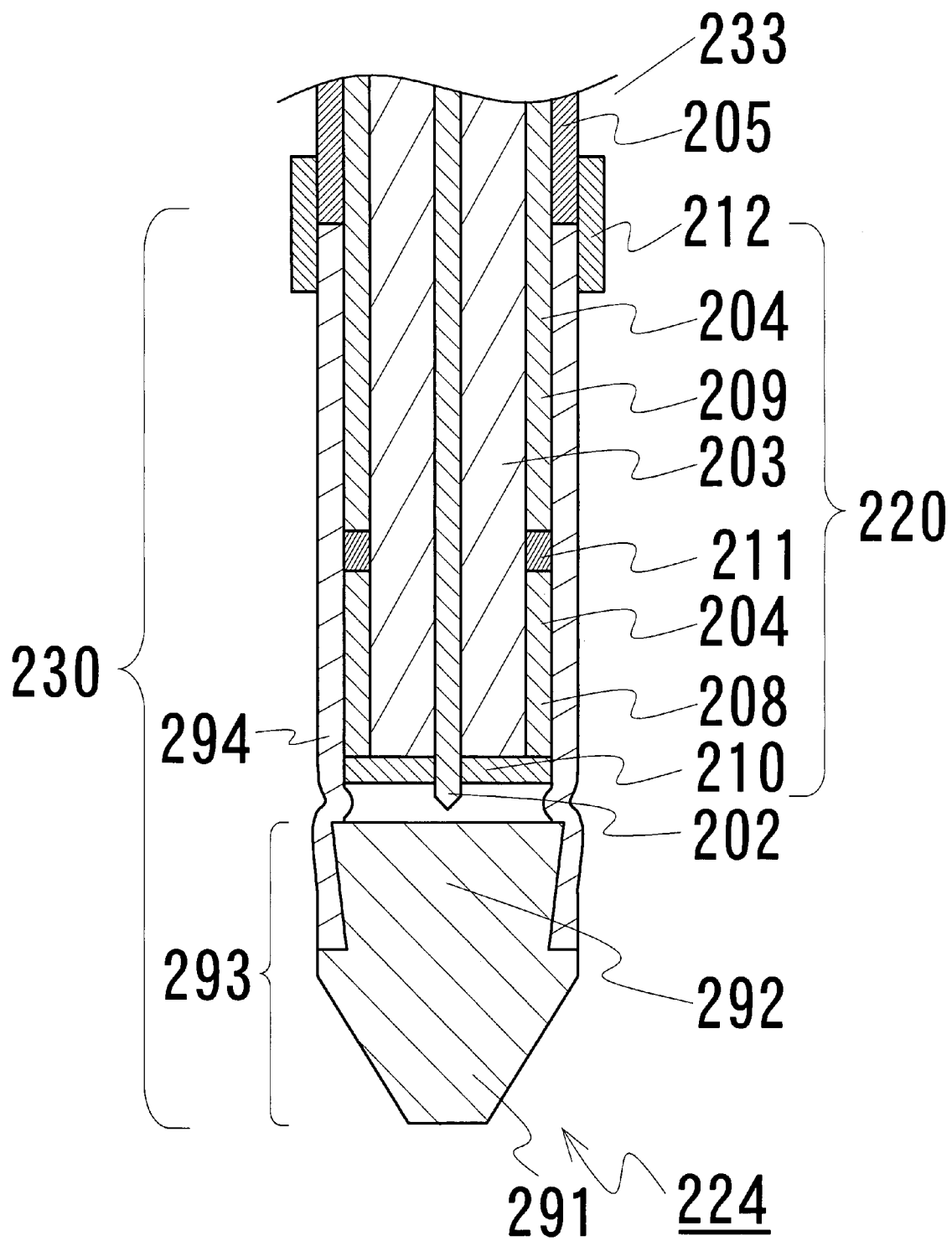

FIGS. 35 and 36 illustrate other preferred embodiments regarding the first object of the present invention, where the TTDPs 224 have linkages with jackets 205 which cover and protect the coaxial cables 233 from which TTDP antenna assemblies 220 illustrated in FIG. 14 and FIG. 33 are formed at the front ends, respectively. Additional thermal shrinkable tube 212 is added to make airtight between inside of the shrinkable tubes 294 and outside air to suppress out-coming of germs in order to form the antenna assemblies 220. Of cause the thermal shrinkable tubes 294 covering the TTDP antenna assemblies 220 can directly cover the jackets 205, by which configuration no additional thermal shrinkable tube 212 are required.

Figure 37:
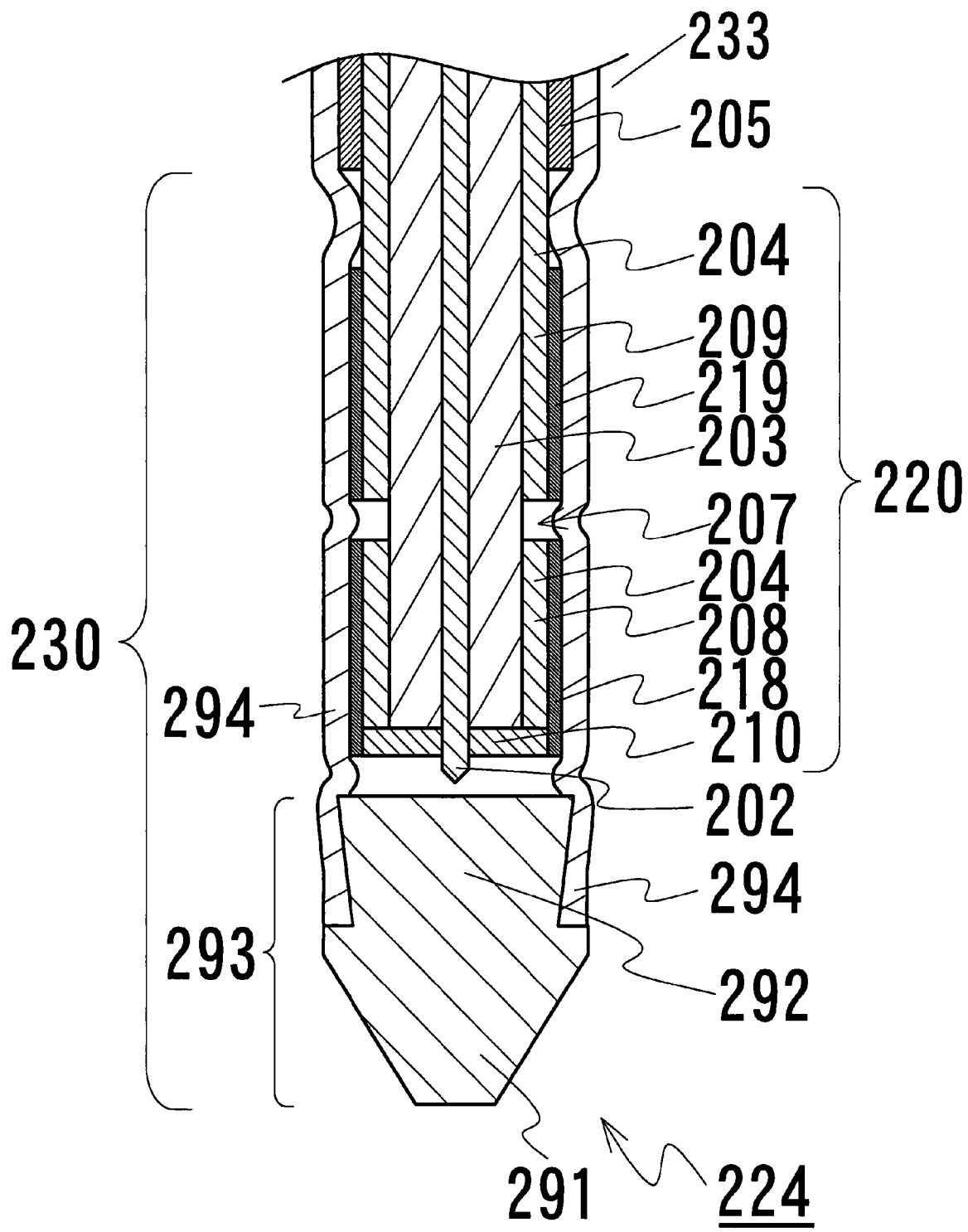

FIG. 37 illustrates another preferred embodiment regarding the first object of the present invention, where the thermal shrinkable tube 294 is extended to cover the bare coaxial cable in stead of using additional shrinkable tubes 212 as illustrated in FIGS. 35 and 36. Then thermal shrinkable tube 294 works as a protection jacket of the bared coaxial cable and can effectively suppress out-coming of germs from the antenna assembly 220.

Figure 38:
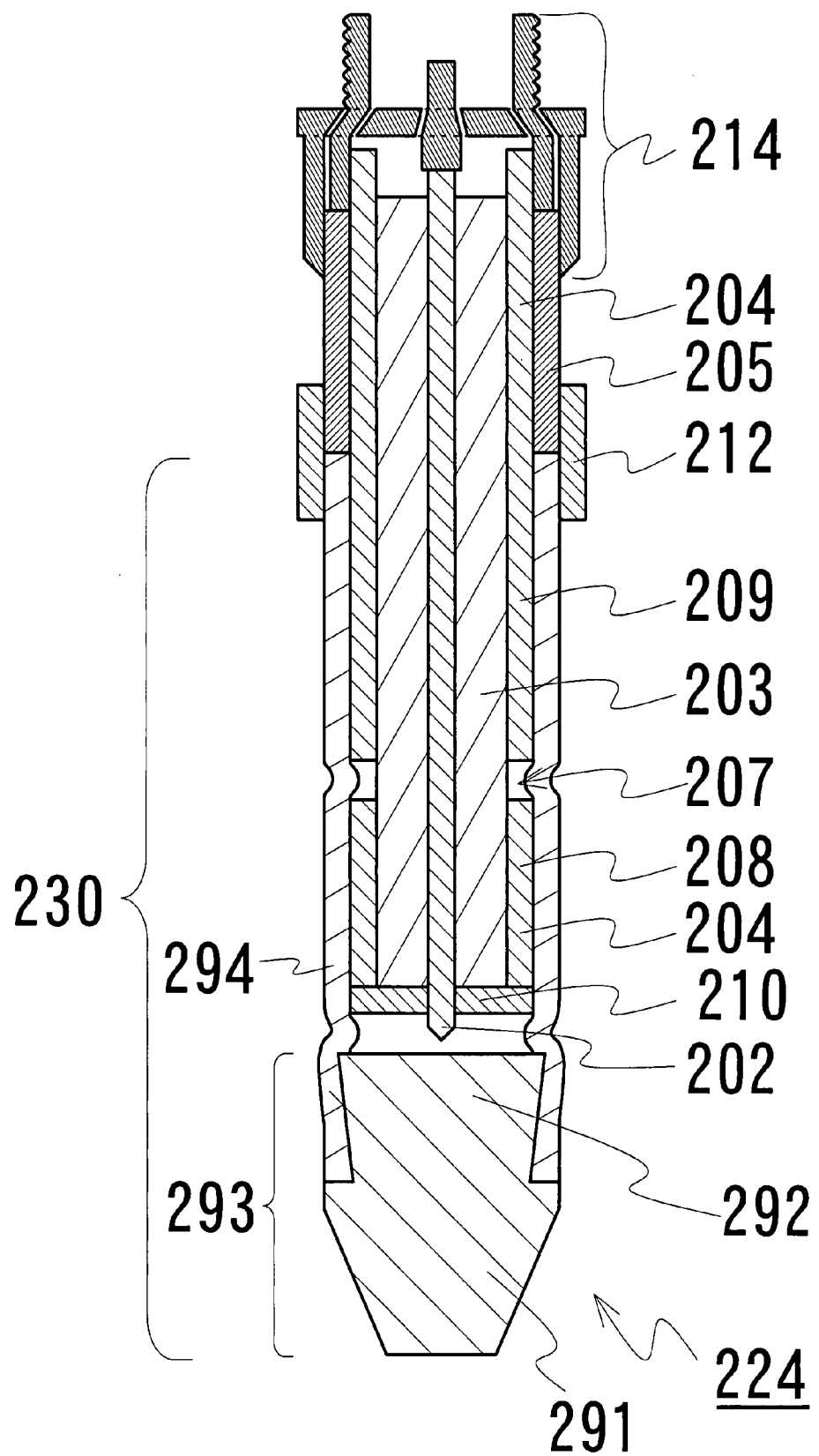

For the purpose of easily handling of the TTDPs, separated configuration of TTDPs from the semi-rigid coaxial cables or flexible coaxial cables is sometimes preferred for power transmission from an RF power source to the TTDPs. As illustrated in FIG. 38, the antenna assembly 220 is separated from such cables but has a connector 214 that couples thereto. The RF power is supplied to the connector 214 via a RF power transmission line. This TTDP 224 can be sterilized in a box of sterilizer since such cables are disconnected. Infection trouble after operation can be reduced.

Figure 39:
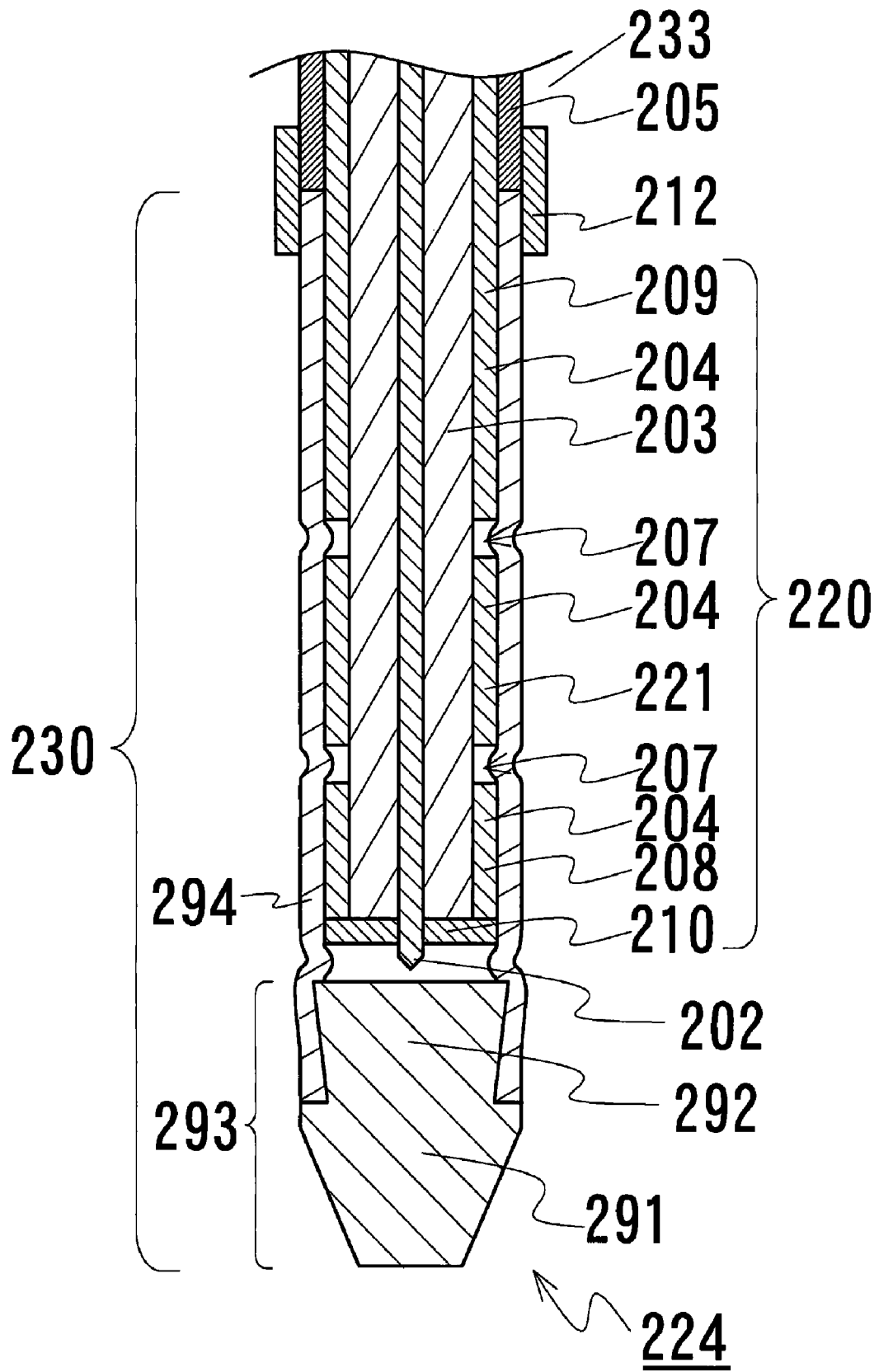
Figure 40:
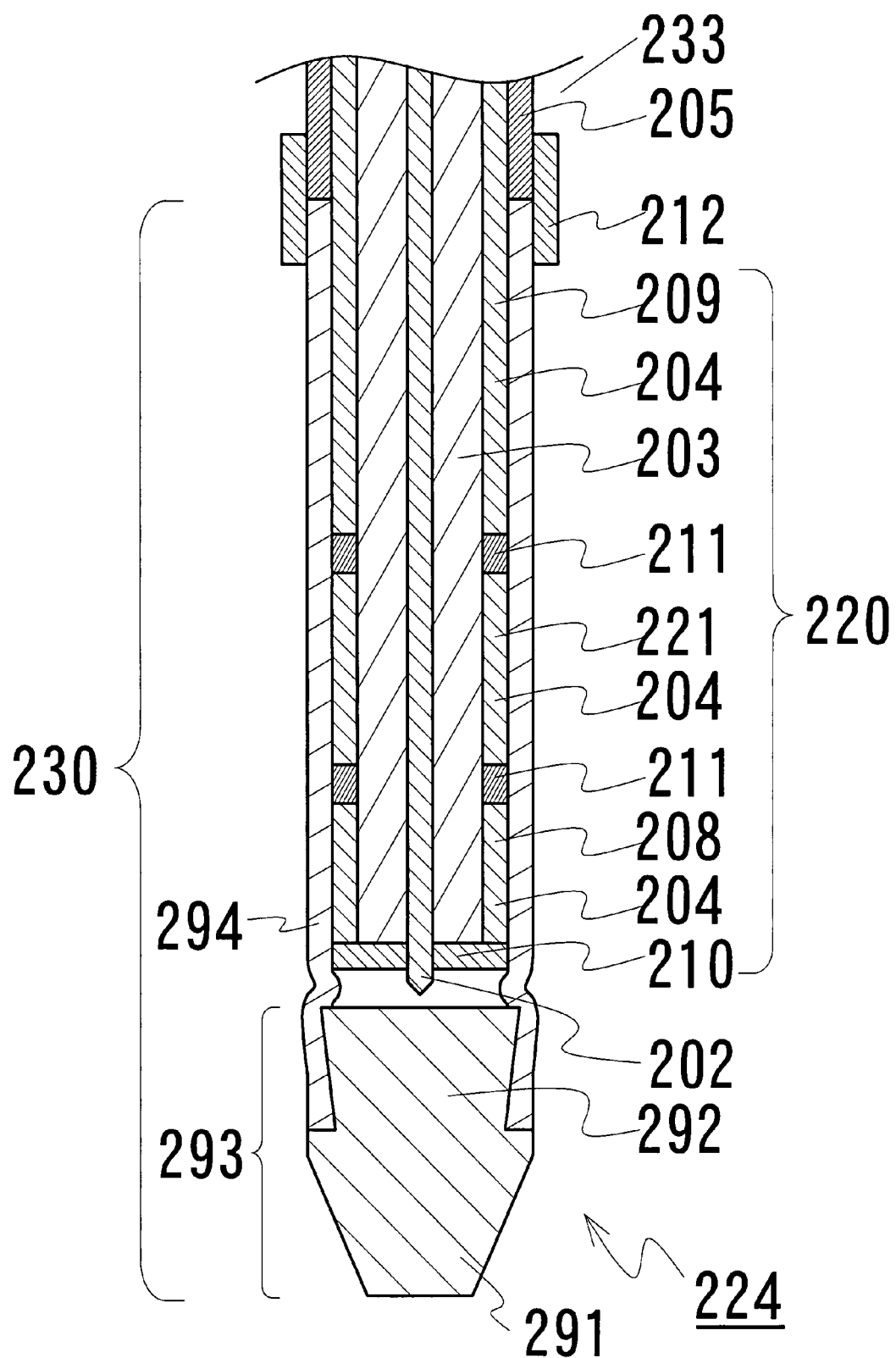

FIG. 39 and FIG. 40 illustrate other preferred embodiments regarding the first object of the present invention, where additional electrodes 221 are added between the first electrodes 208 and the second electrodes 204. The SAR distribution elongates at additional electrodes so that long cauterization along the TTDP 224 is possible, by which a single therapy can be operated instead of multiple cauterization in the depths of percutaneous insertion of TTDP 224 to the pathological tissues.

Figure 41:
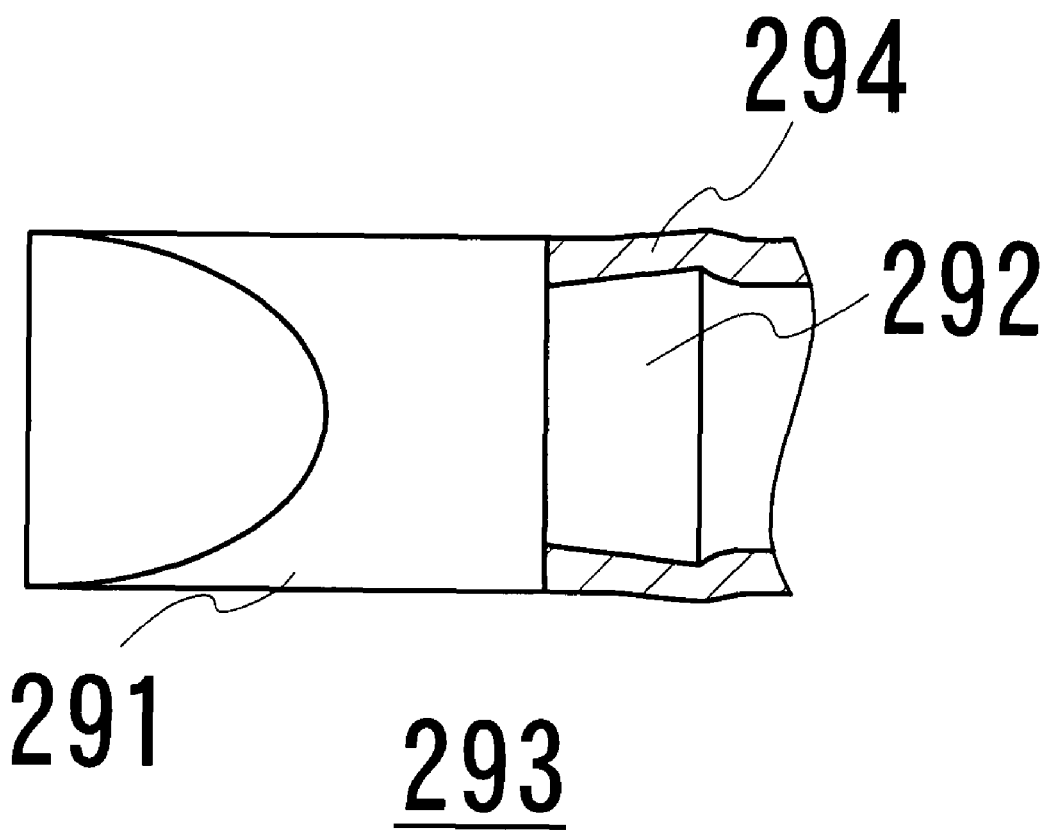
FIGS. 41 to 48 are the views of the head portions of the TTDPs regarding the first object of the present invention.
Figure 42:
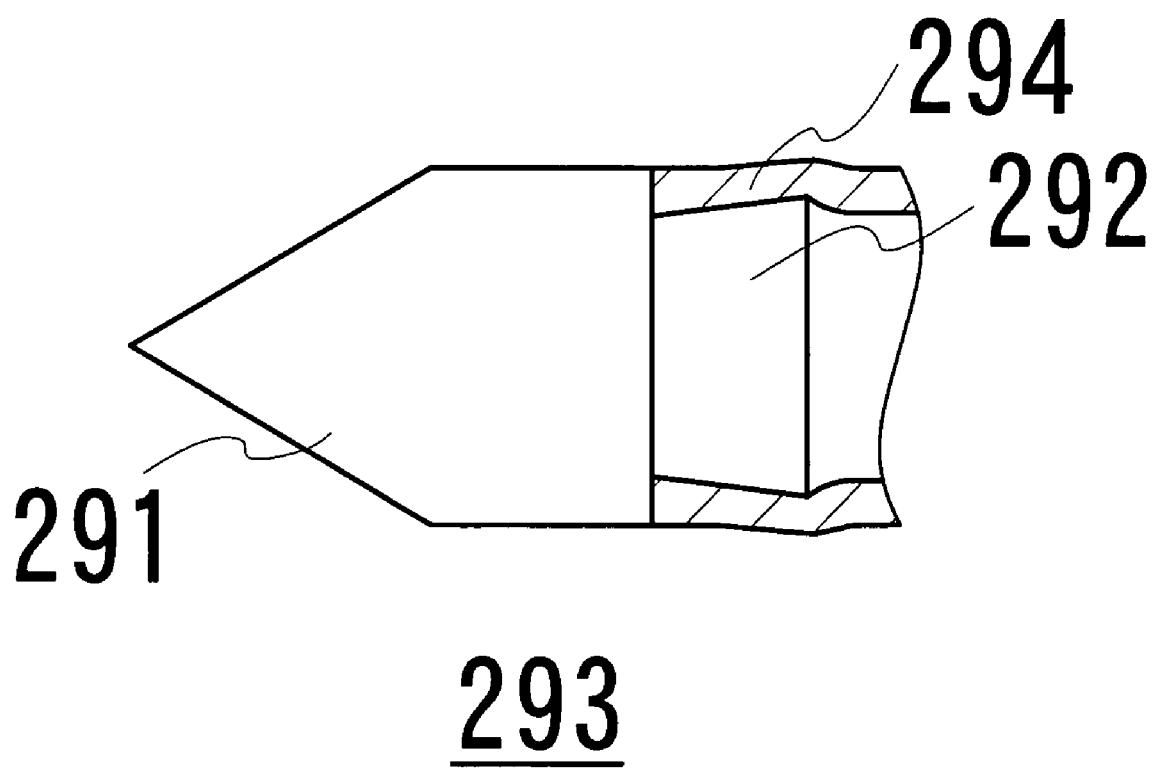
Figure 43:
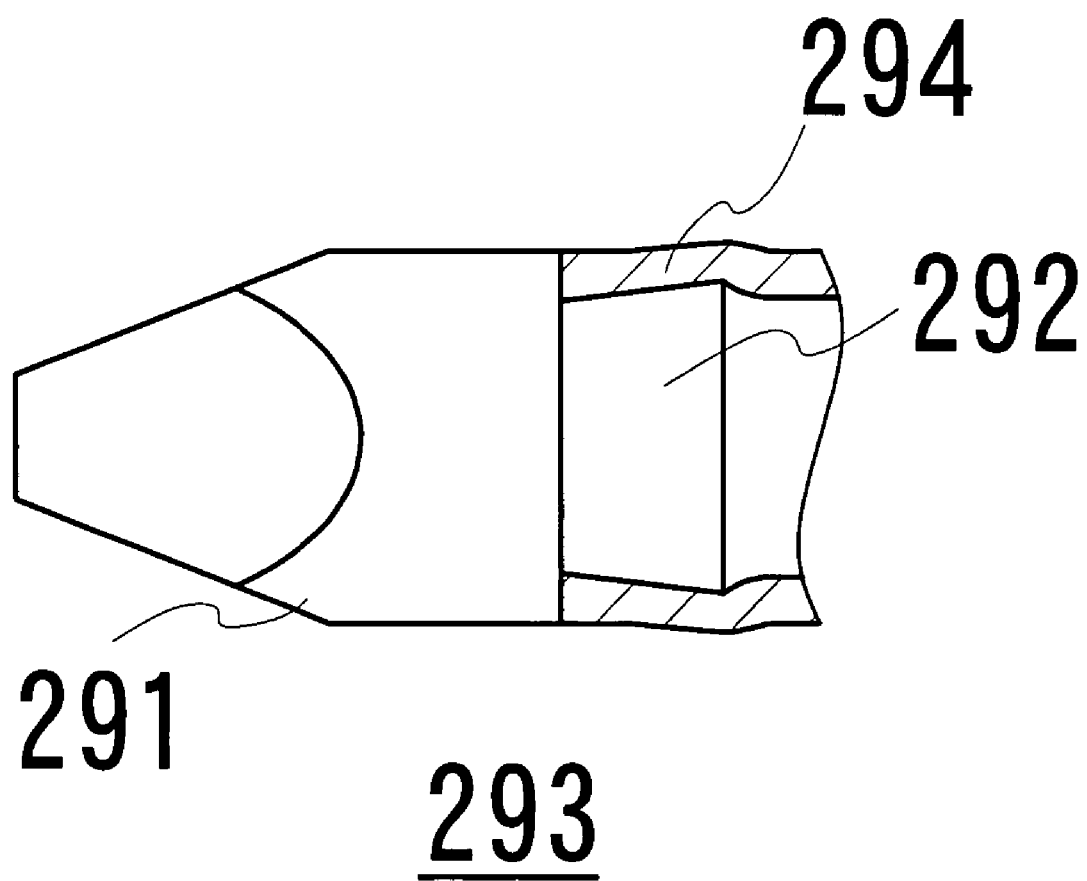
Figure 44:
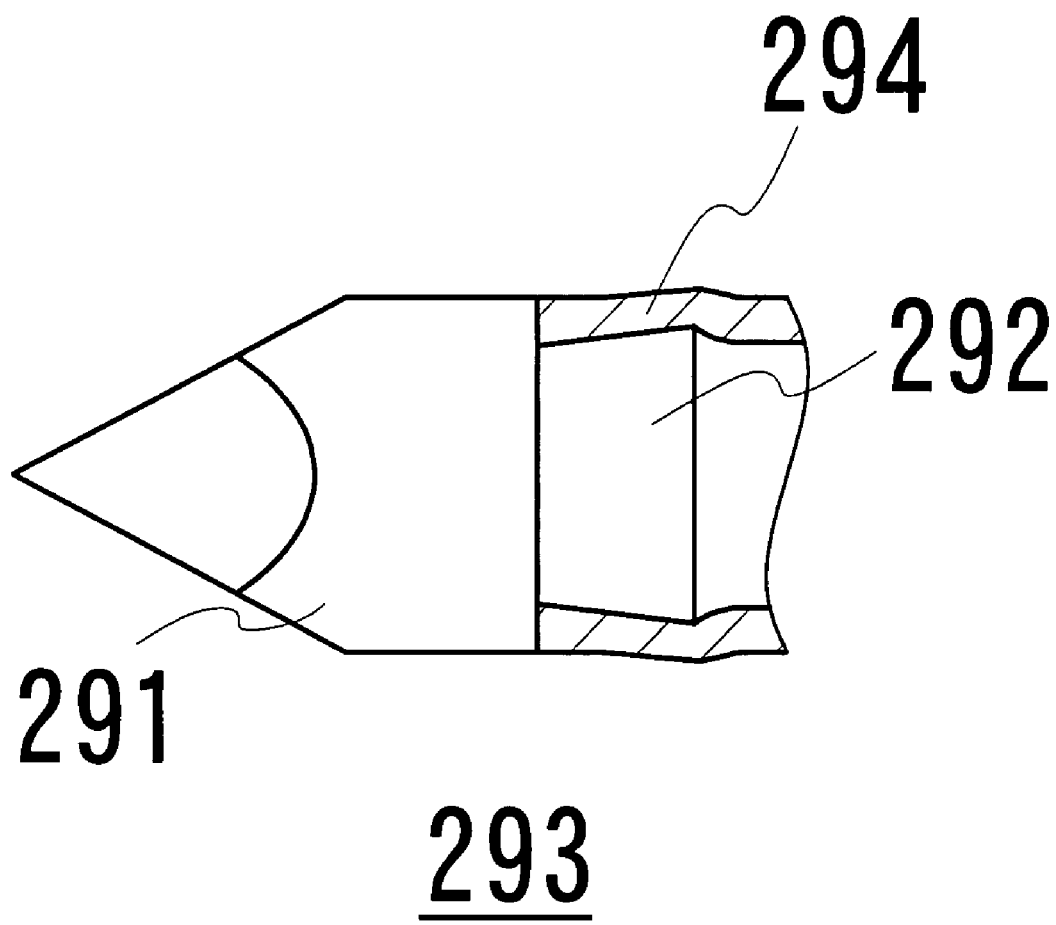
Figure 45:
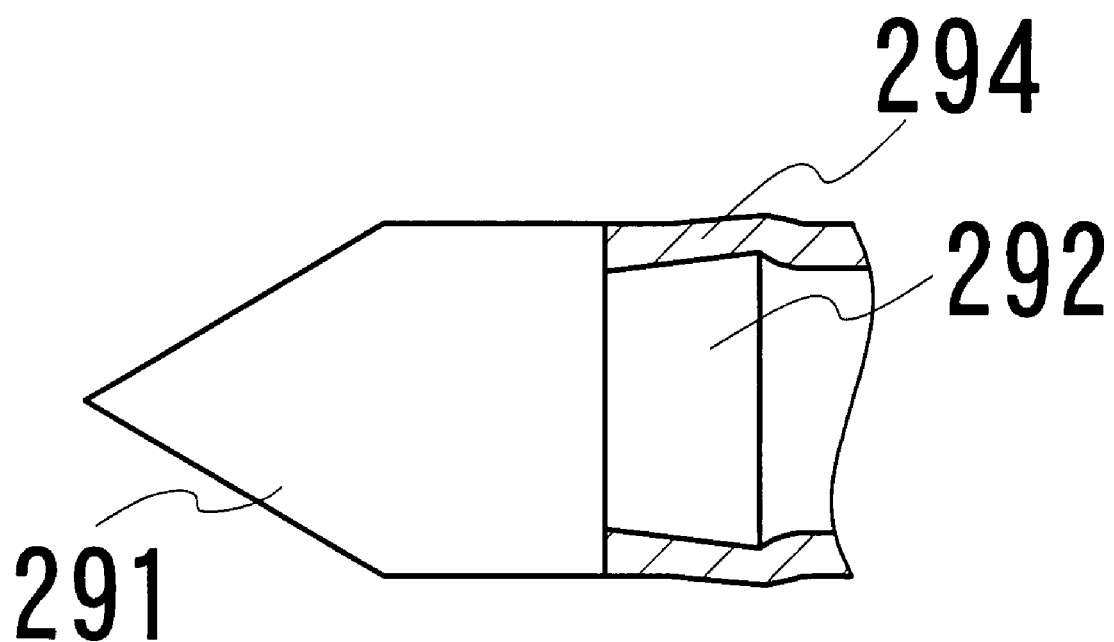
Figure 46:
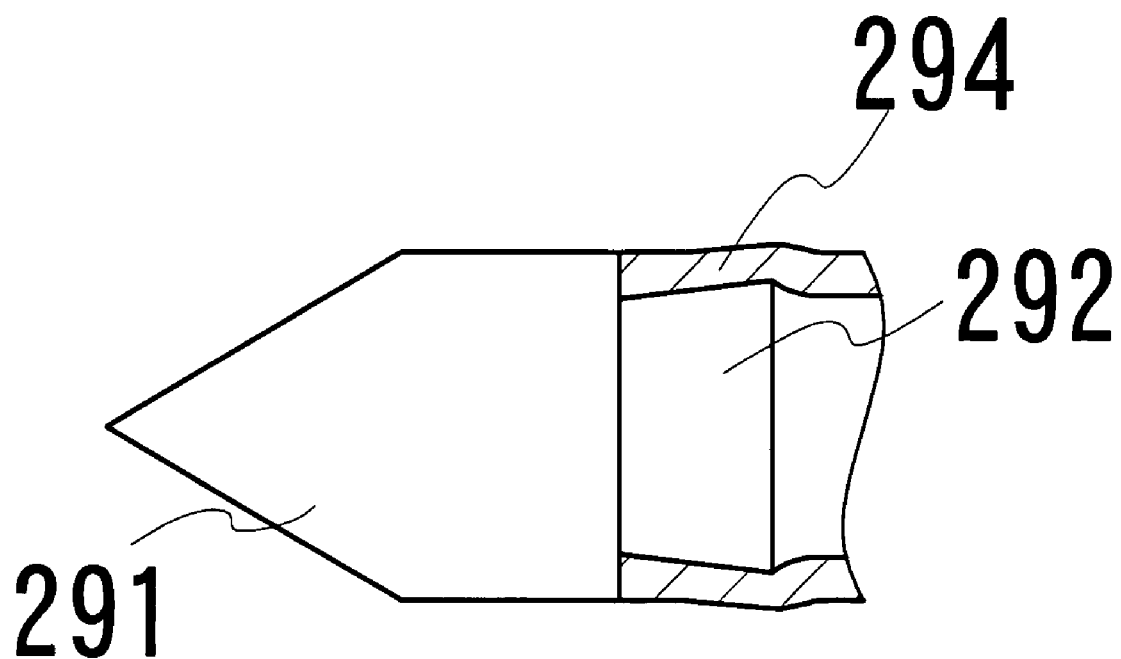
Figure 47:
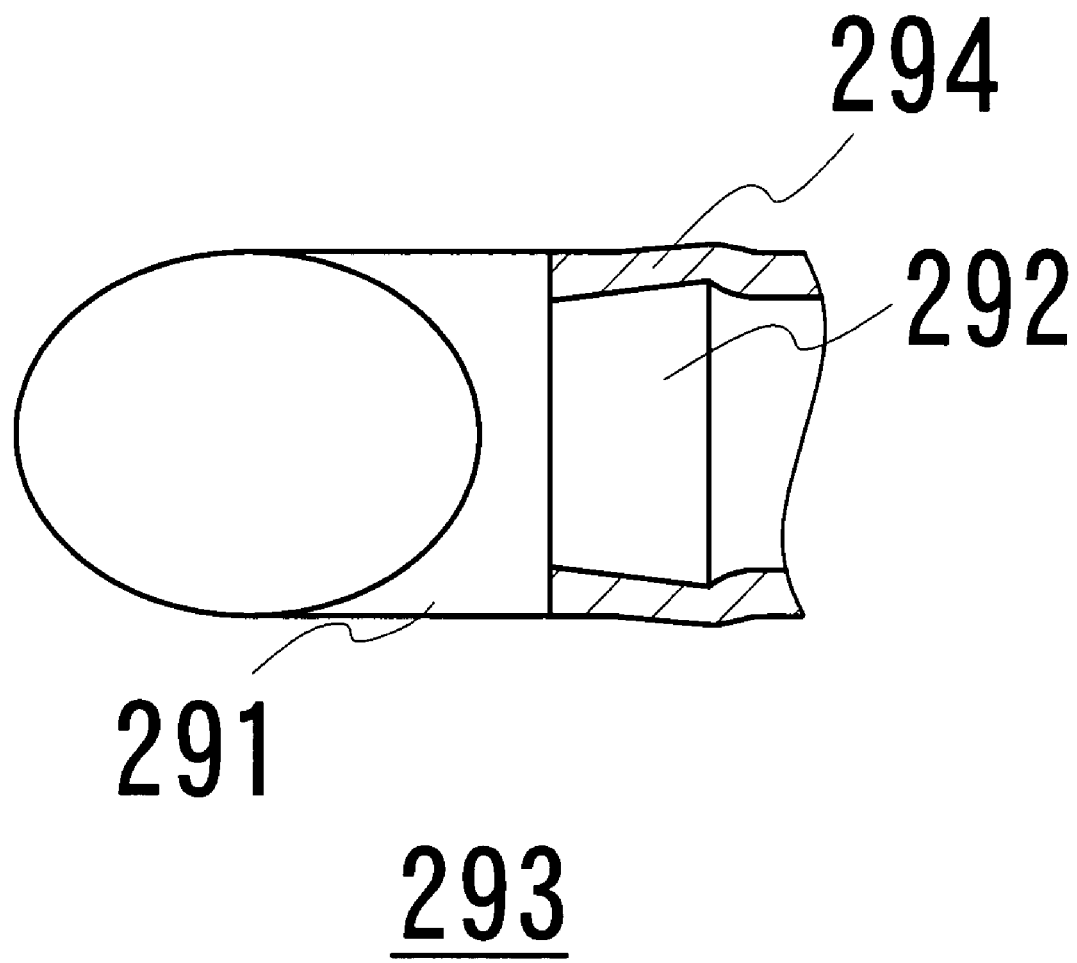
Figure 48:
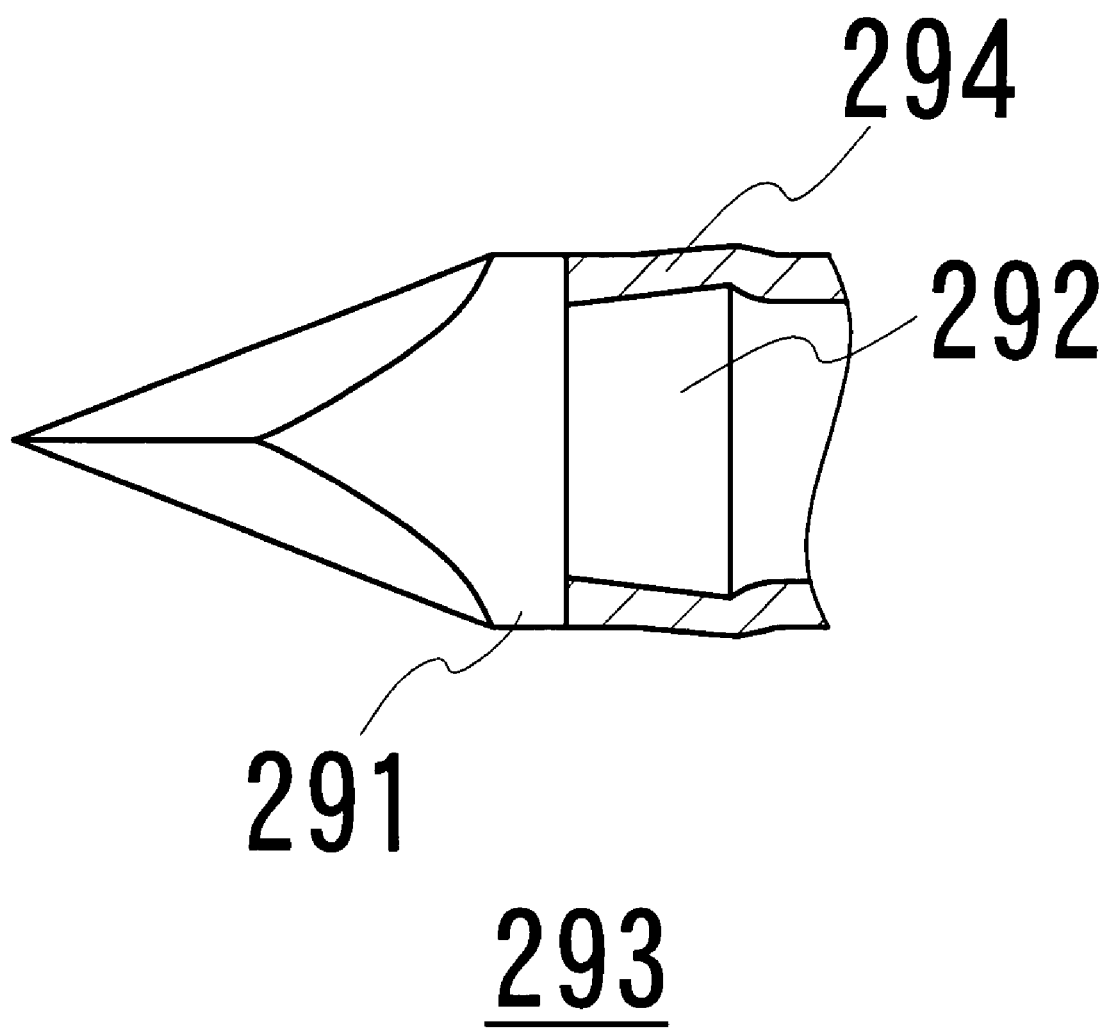

FIGS. 41-48 illustrate other preferred embodiments regarding the first object of the present invention, where cutting edge shapes of a sharp edge head 293 consisting of a edge portion 291 and a coupling portion 292 to which a thermal shrinkable tube 294 tightly fits to form a sheath 230 in a shape of a single bladed probe. The thermal shrinkable tubes 294 are illustrated in cut-views in order to easily see how the coupling portions 292 engraft into thermal shrinkable tubes 294. The are slightly tapered such that the diameters in the right-hand side are slightly larger than those in the left side. Therefore the sapphire heads 293 can tightly engraft into thermal shrinkable tube 294 at the coupling portions 292 and TTDPs 224 can be pulled out without an accident such that the thermal shrinkable tubes 294 are pulled out and the sapphire heads 293 are left in the tissues. The edge portion 291 and the coupling portion 292 are made from a single block of sapphire or a sapphire ore by cutting and ablating. The cutting edge shape illustrated in FIGS. 41 and 42 shows a straight blade. The cutting edge shape illustrated in FIGS. 43 and 44 shows a tapered blade. The cutting edge shape illustrated in FIGS. 45 and 46 shows a corn tip. The cutting edge shape illustrated in FIGS. 47 and 48 shows a spearhead blade.

Figure 49:
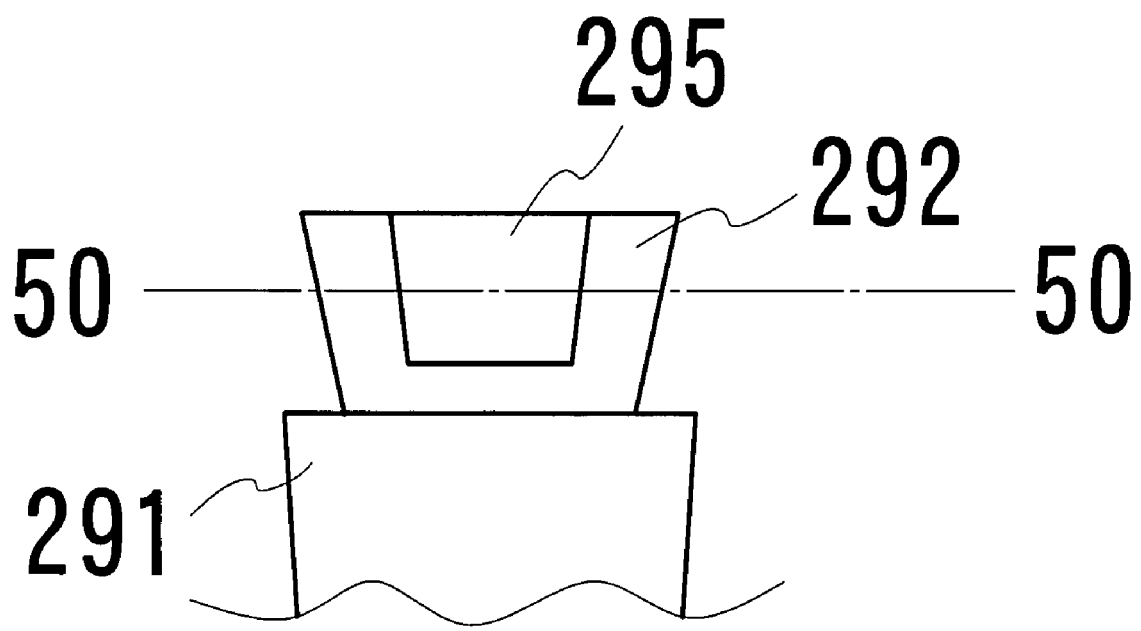
FIG. 49 is the cut surface formed in coupling portions of the head elements of TTDPs
Figure 50:
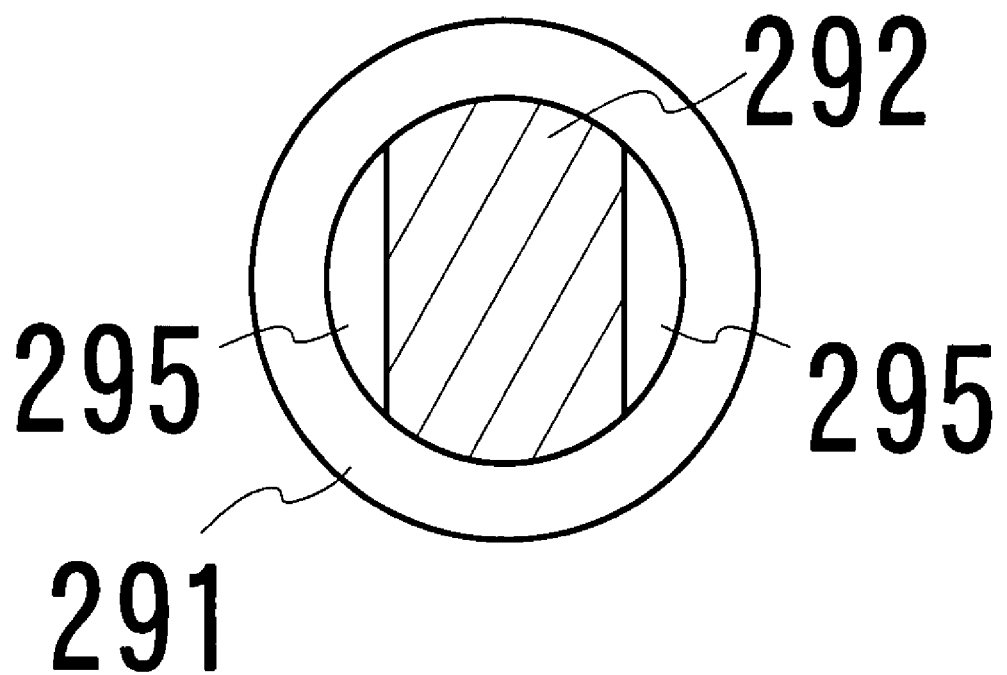
FIGS. 50 and 51 are the view of the notches and cut formed in coupling portions of the head elements of TTDPs
Figure 51:
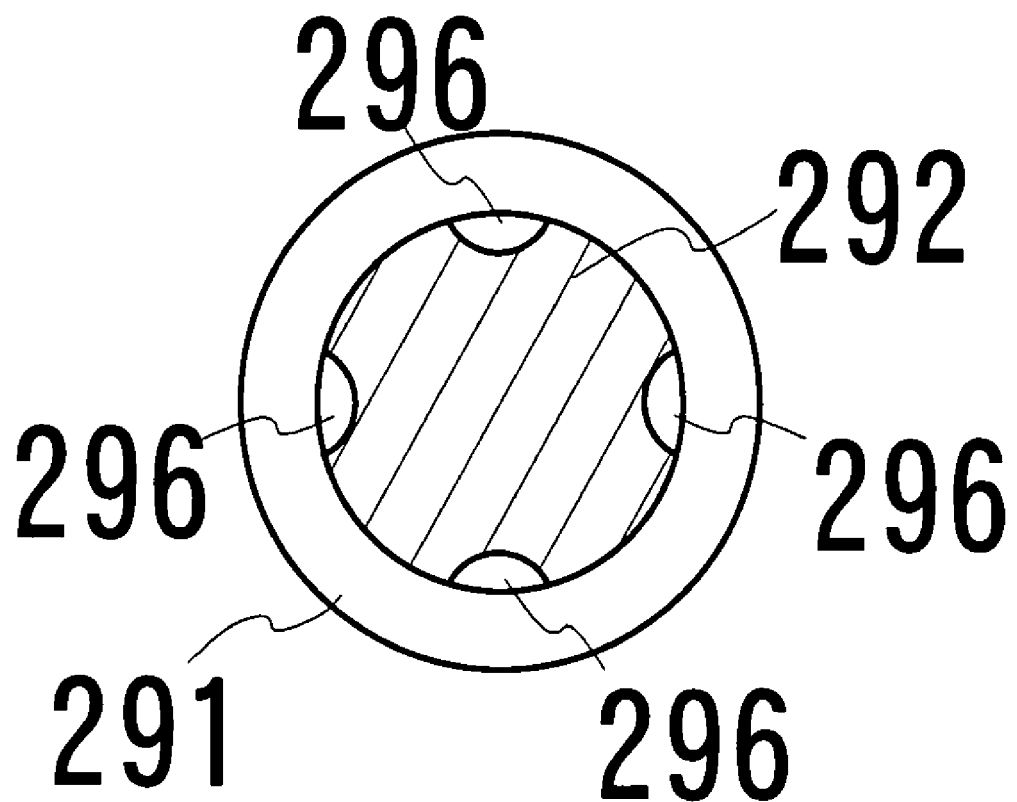

FIGS. 49-51 illustrate other preferred embodiments regarding the first object of the present invention, where the coupling portions 292 have cut surfaces 295 to which thermal shrinkable tubes tightly fit so that the edge portions 291 do not rotate therein. FIGS. 50 and 51 illustrate cross sectional cut-views of the coupling portions 292 with the edge portions 291. The notches 296 illustrated in FIG. 51 are also preferred to the first object of the present invention as well as cut surfaces 295 as illustrated in FIGS. 49-50.

The second object of the present invention is to reduce the temperature localization. The TTDPs. for the second object of the present invention, employing sapphire sheath to cover the antenna assemblies, are described as follows with FIGS. 16-18.

The TTDP for the second object of the present invention has a configuration as illustrated in FIGS. 16-18. The antenna assembly 320 comprises a central conductor 302, a cylindrical dielectric insulator 303 formed around the central conductor 302 and an outer conductor 304 wherein a first electrode 308 formed from a part of the outer conductor 304 and electrically connected with the central conductor 302 and a second electrode 309 formed from the another part of the outer conductor 304 which is electrically isolated from the first electrode 308. The first electrode 308 and the second electrode 309 construct a dipole antenna to which RF power is supplied through the coaxial cable. The central conductor 302, the cylindrical dielectric insulator 303 and the outer conductor 304 may be formed in a termination part of the coaxial cable. The TTDP 324 comprises the antenna assembly 320 and a sheath 301 that is made of sapphire. The head of the sheath 301 is mechanically sharpened to be blade to percutaneously cut and invade into the tissues.

The electrical isolation between the first electrode 308 and the second electrode 309 is provided by just an electrically isolating gap 307 formed in the outer conductor 304, wherein the electrically isolating gap 307 is cut off part of the outer conductor 304. The electrical connection between the central conductor 302 and the first electrode 308 is via an electrical conducting disc 310 as illustrated in FIG. 16 and FIG. 17. FIG. 16 illustrates an outer view of the antenna assembly 320 and a cut view of the sheath 301. FIG. 17 further shows a cut view of the antenna assembly 320 illustrated in FIG. 16.

FIG. 18 further shows another preferred embodiment regarding the second object of the present invention. The electrical connection between the central conductor and the first electrode is made by the central conductor 302 extending and being bended to contact to the first electrode 308. The electrical conducting disc 310 is not used. Therefore this embodiment is preferred when fewer components for the antenna assembly 320 are required.

Figure 52:
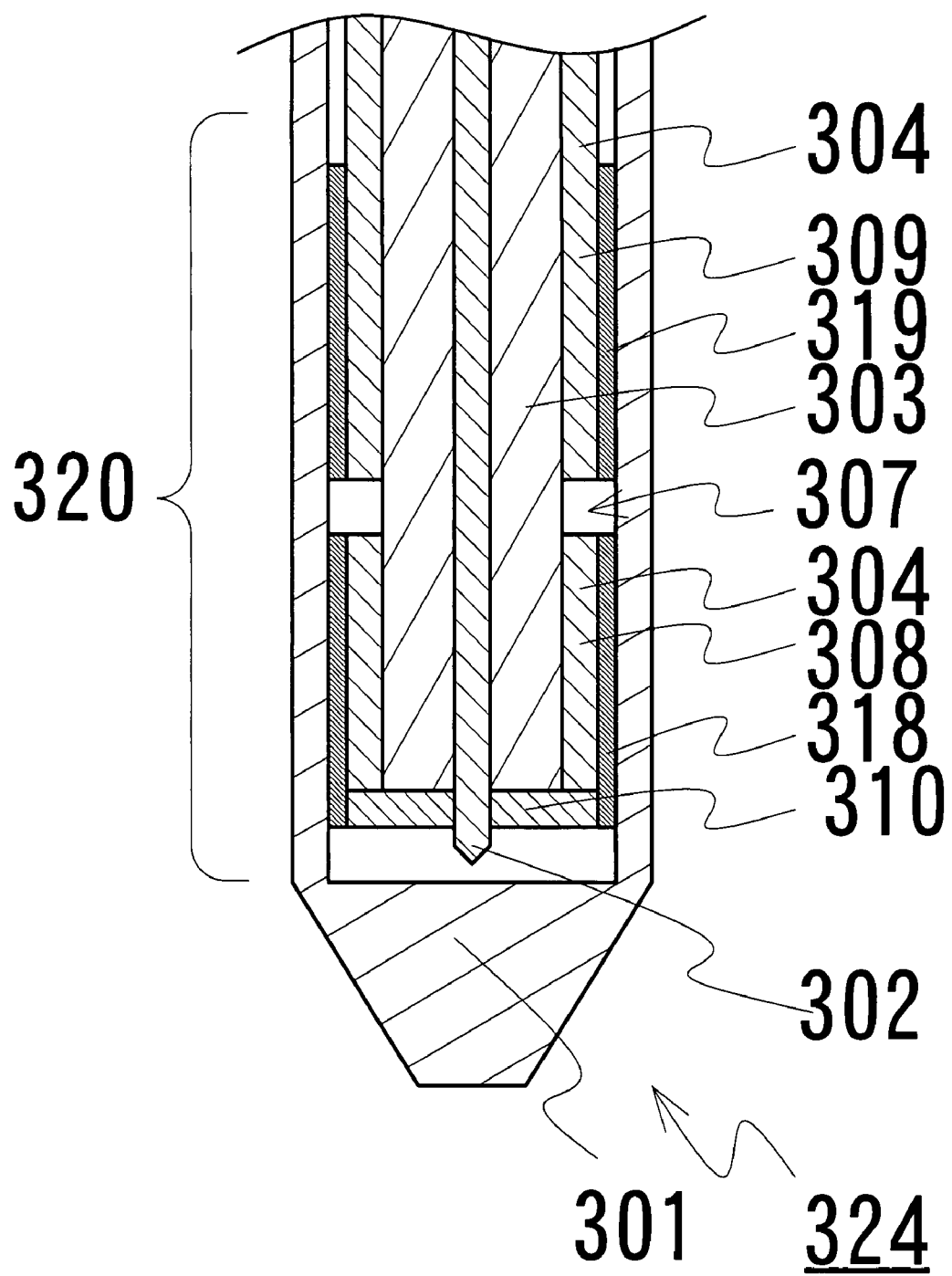
FIGS. 52 to 61 are the views of the variation of the TTPD of the second object of the present invention, which have modification in the antenna assemblies.

FIG. 52 further illustrates another preferred embodiment regarding the second object of the present invention. The first and the second electrodes 308 and 309 have additional electrodes 318 and 319 which are made from metal pipes or metal plates rolled around the outer conductor 304. For the insulating case of the outer conductor 304 is made from a metal mesh pipe (which is used for flexible coaxial cables) or a metal mesh being stiffed by tin or solder (which is used for semi-rigid coaxial cables), the electrodes 308 and 309 are too soft to be formed in a mechanical preciseness so that structure of the electrodes insures clear cut-lines or physical preciseness for the electrically isolating gap 307. Then the additional electrodes 318 and 319 provide clear cut-lines instead of the first and the second electrodes 308 and 309 to electrically determine the electrically isolating gap 307 by their peripheral lines.

Figure 53:
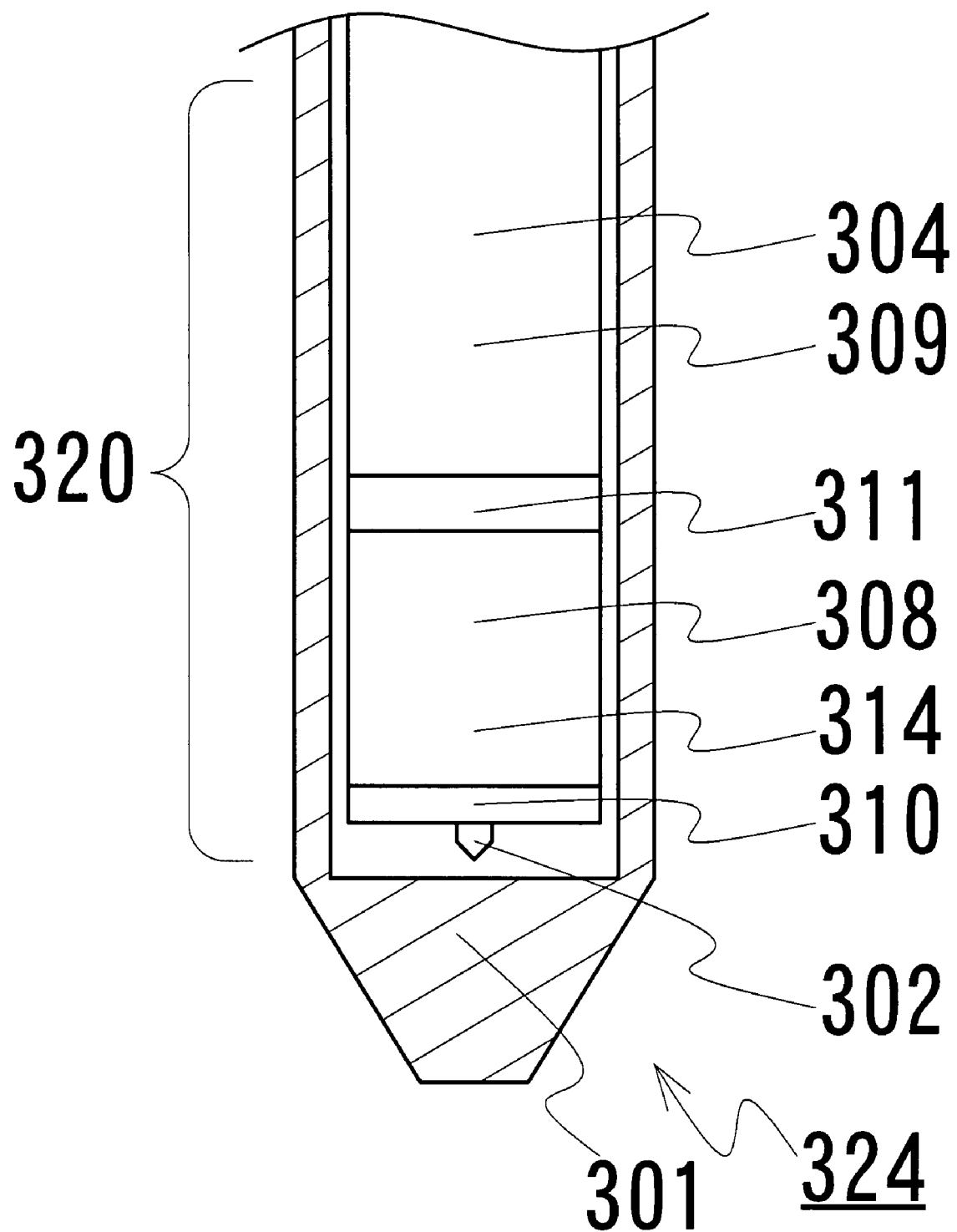
Figure 54:
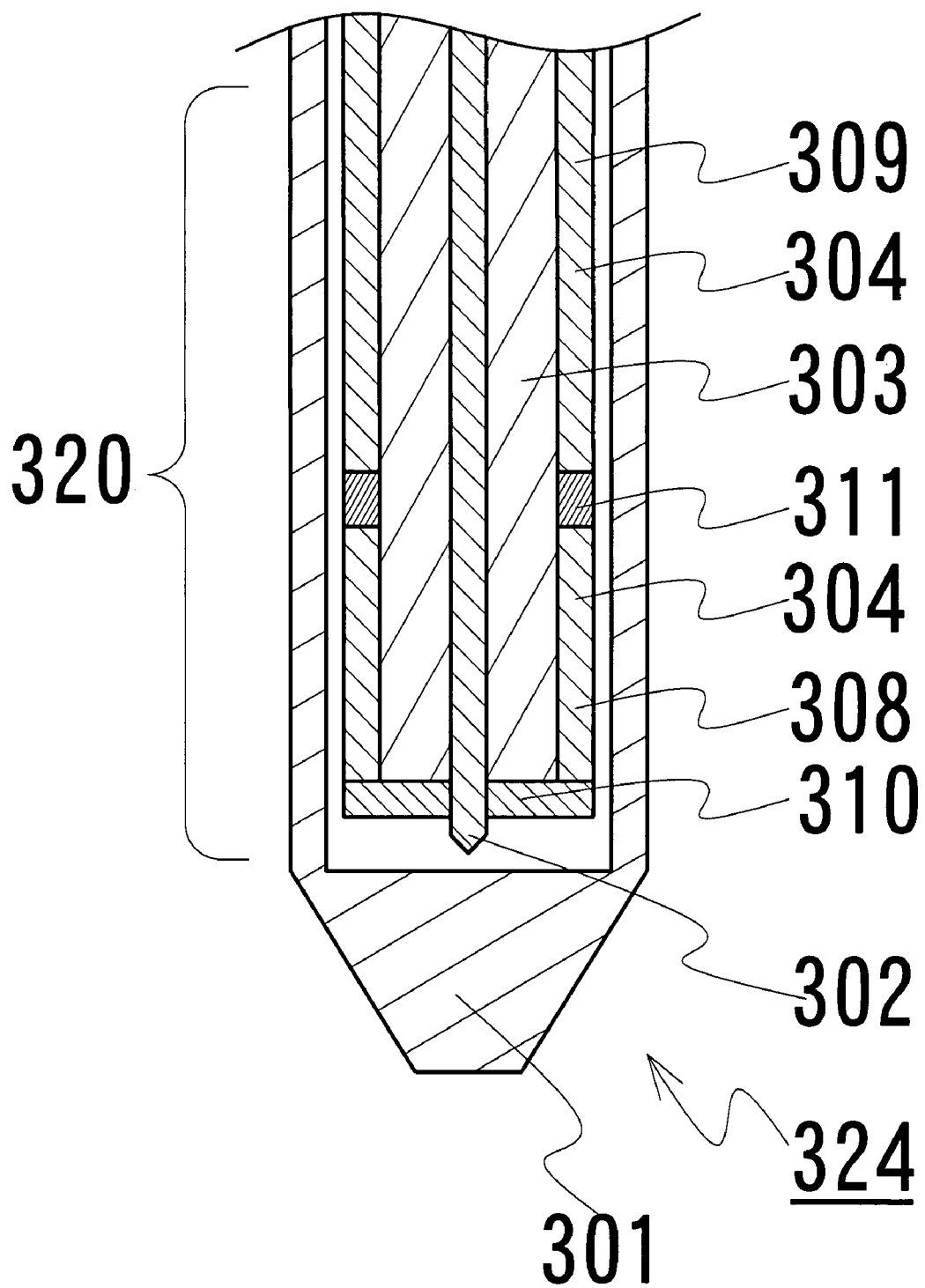
Figure 55:
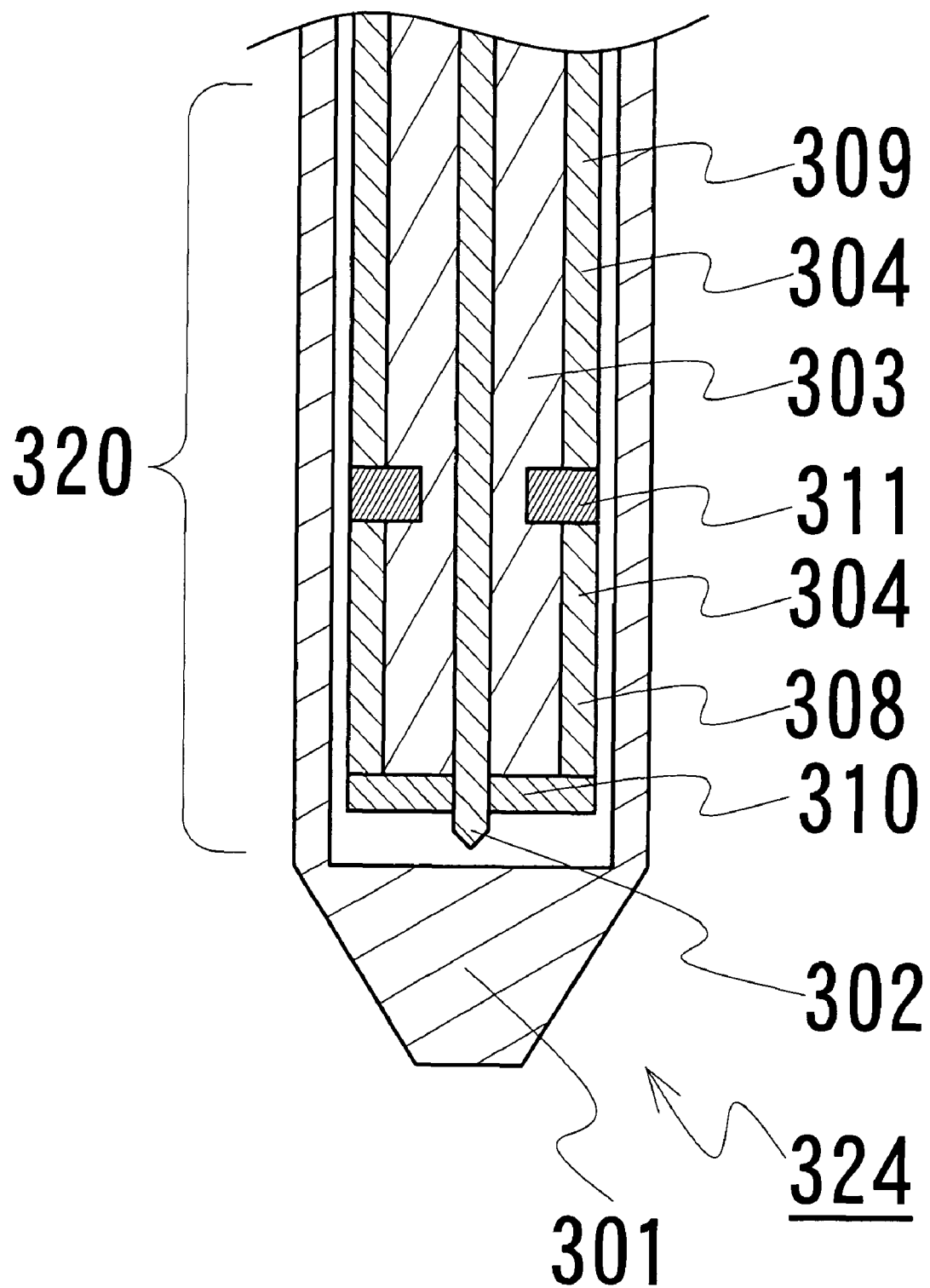

FIGS. 53-55 illustrate other preferred embodiments regarding the second object of the present invention. An electrically isolating gap made for the electrical isolation between the first electrode 308 and the second electrode 309 is filled with an insulating collar 311 which is made from the same material as or similar material to the cylindrical dielectric insulator 303. The breakdown voltage between the first electrode 308 and the second electrode 309 can be increased by using this insulating collar 311 in comparison with just an electrically isolating gap 307 as cut. Therefore, more RF power can be supplied so that more RF power radiation is possible. The distortion of the electrically isolating gap by bending force can be suppressed due to mechanical stiffness of this insulating collar 311. The insulating collar 311 shown in FIG. 55 is buried in a gap recessed in the cylindrical dielectric insulator 303 and therefore the edge of the outer conductor 304 at the electrically isolating gap can be clear so that the debris at the edge lines of the first and second electrodes 308 and 309 are removed.

Figure 56:
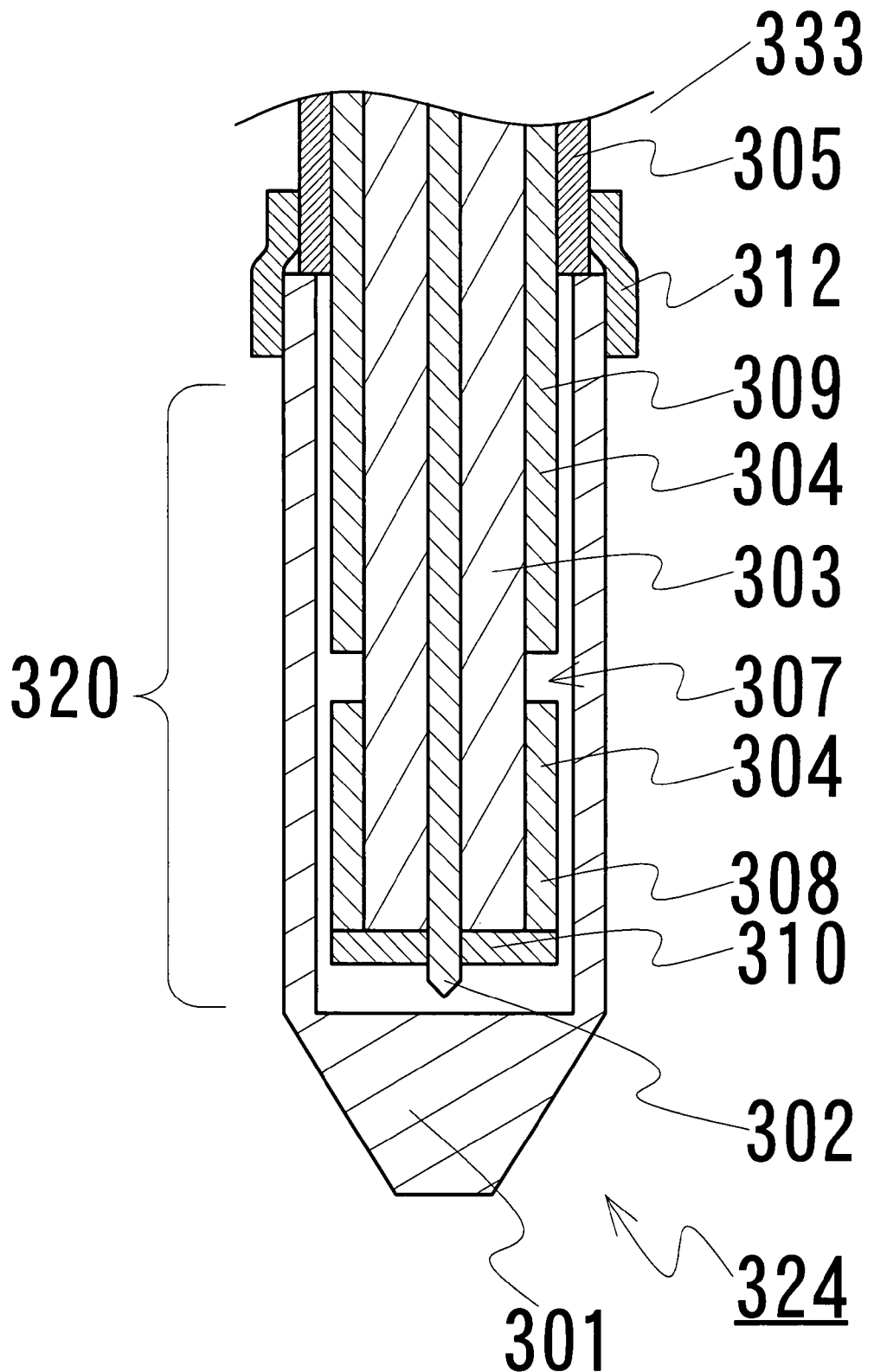
Figure 57:
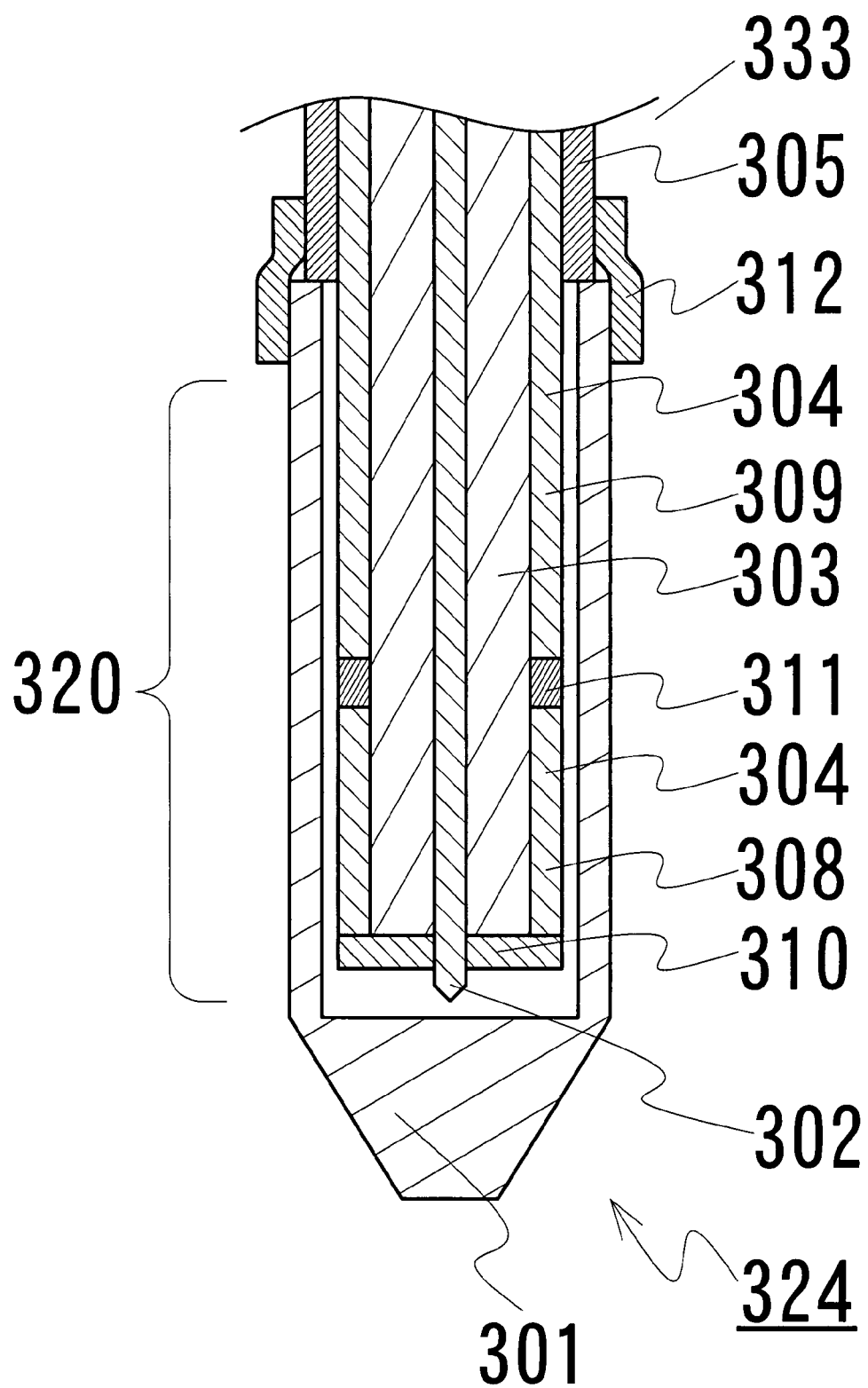

FIGS. 56 and 57 illustrate other preferred embodiments regarding the second object of the present invention, where the TTDPs 324 have linkages with jackets 305 which cover and protect the coaxial cables 333 from which TTDP antenna assemblies 320 illustrated in FIG. 17 and FIG. 54 are formed at the front ends, respectively. Additional thermal shrinkable tube 312 is added to make airtight between inside of the single-body sheath 301 and outside air to suppress out-coming of germs from the antenna assemblies 320. Of cause the single-body sheath 301 enclosing the TTDP antenna assemblies 320 is covered by the thermal shrinkable tube 312 with the jackets 305 as illustrated in FIG. 56 and 57.

Figure 58:
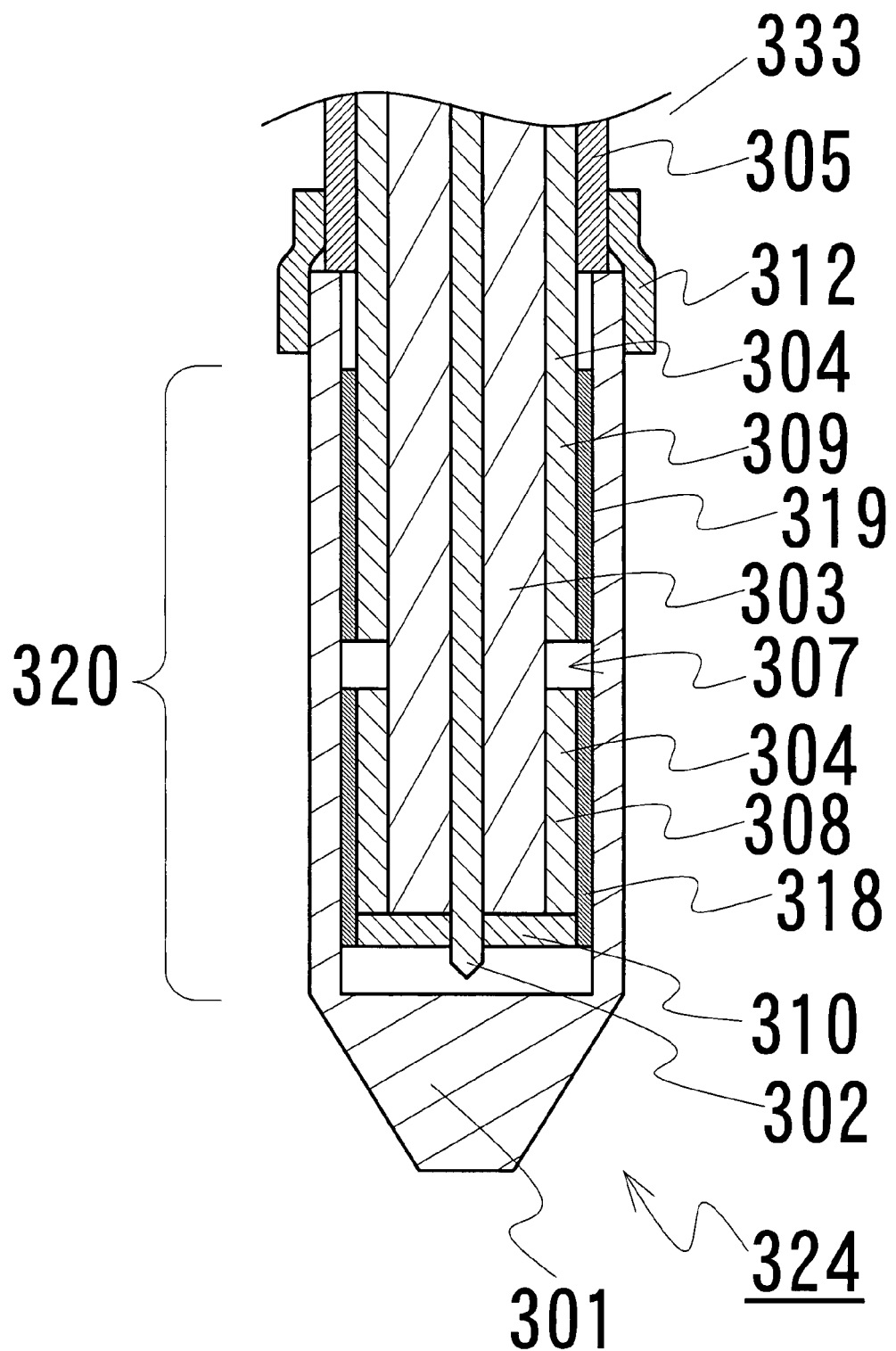

FIG. 58 illustrates another preferred embodiment regarding the second object of the present invention, where a first and a second electrodes 308 and 309 have additional electrodes 318 and 319 which are made from metal pipes or metal plates rolled around the outer conductor 304 and electrically contacts to the first and second electrodes 308 and 309, as illustrated in FIG. 52. The thermal shrinkable tube 312 works as a protection jacket of the coaxial cable 333 and can effectively suppress out-coming of germs from the antenna assembly 320.

Figure 59:
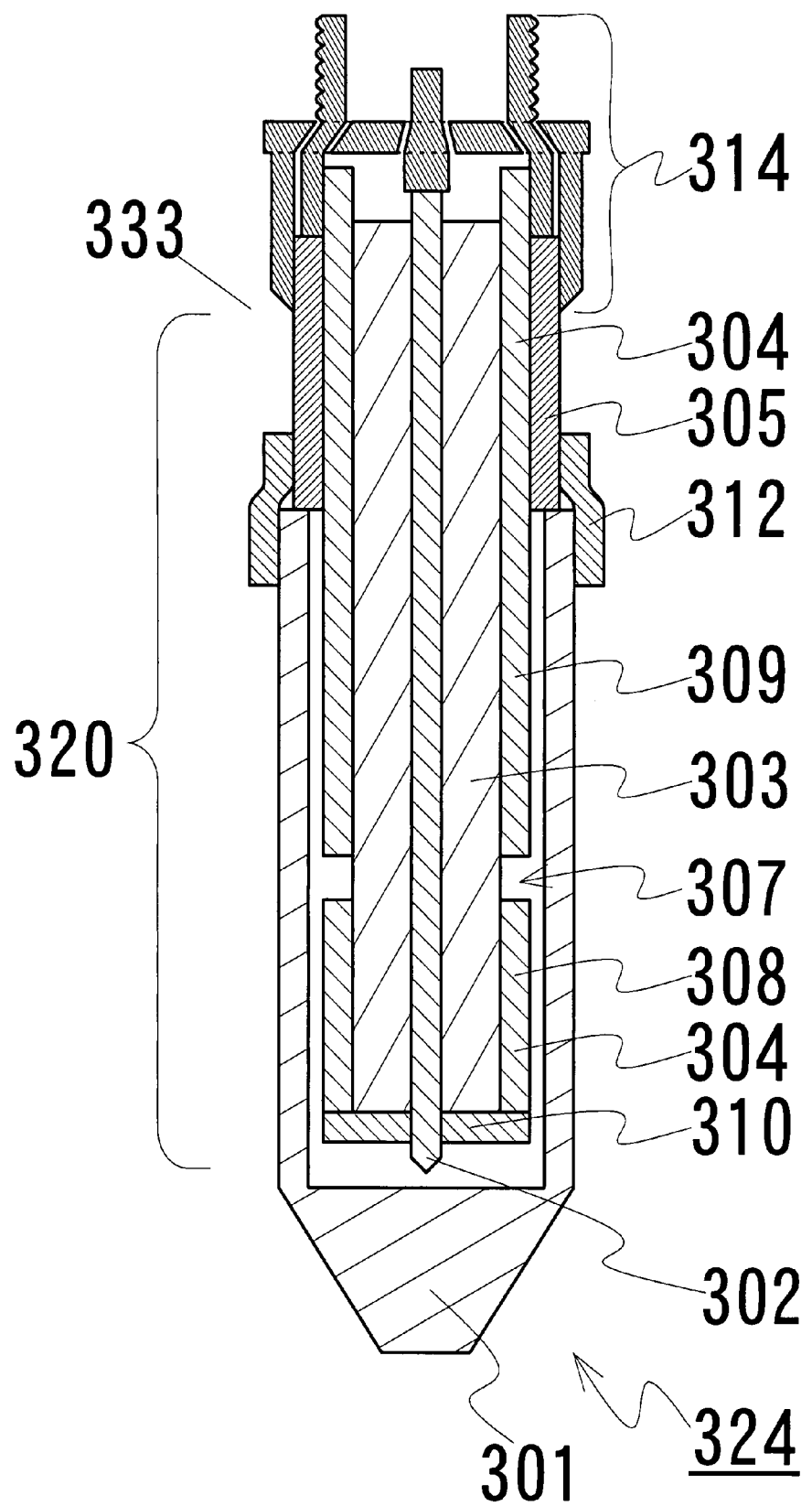

For the purpose of easily handling of the TTDPs, separated configuration of TTDPs from the semi-rigid coaxial cables or flexible coaxial cables are sometime preferred. As illustrated in FIG. 59, the antenna assembly 320 is separated from such cables but has a connector 314 that couples thereto. The RF power is supplied to the connector 314 via a RF power transmission line. This TTDP 324 can be sterilized in a box of sterilizer since such cables are disconnected. Infection trouble after operation can be reduced.

Figure 60:
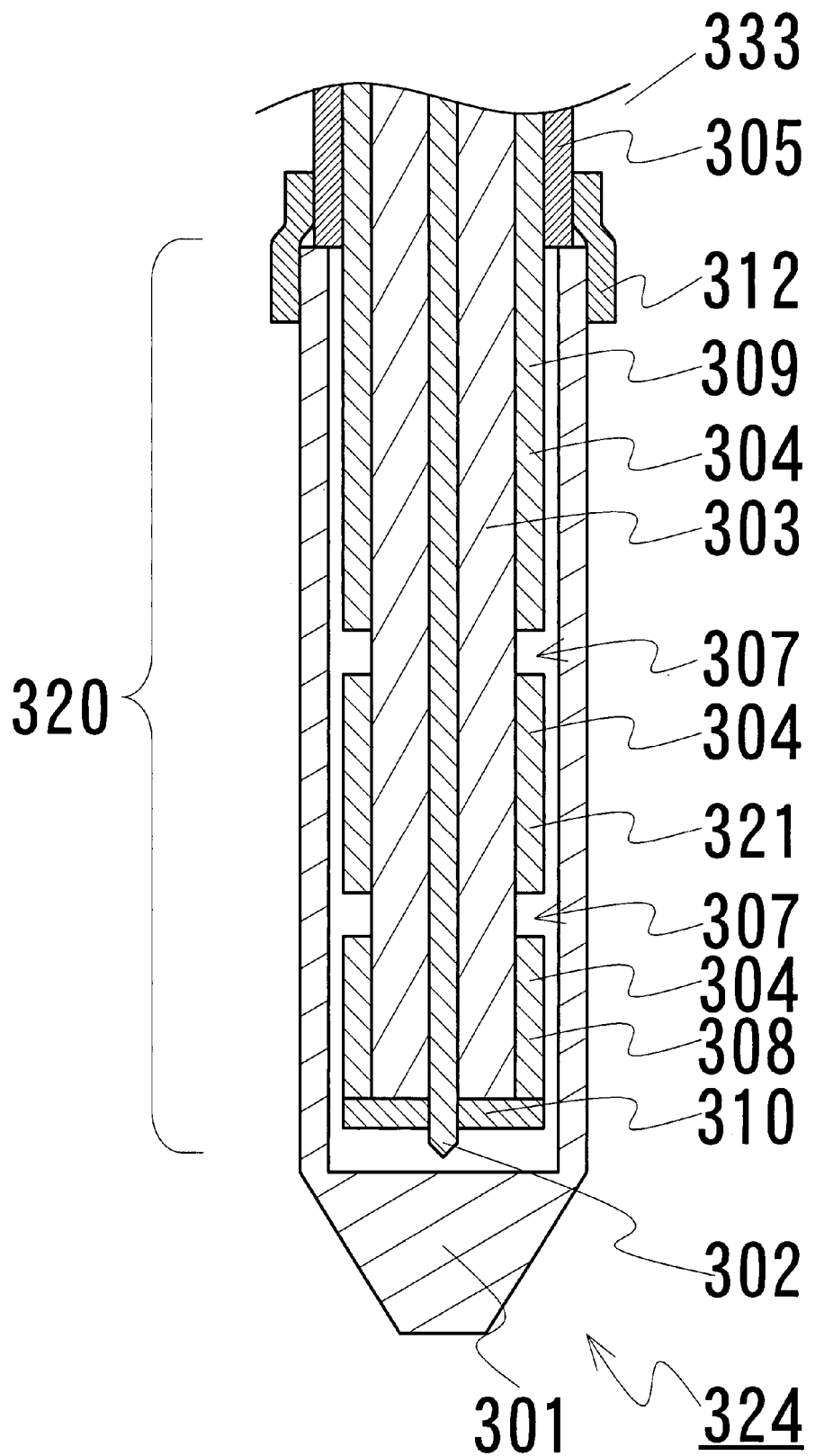
Figure 61:
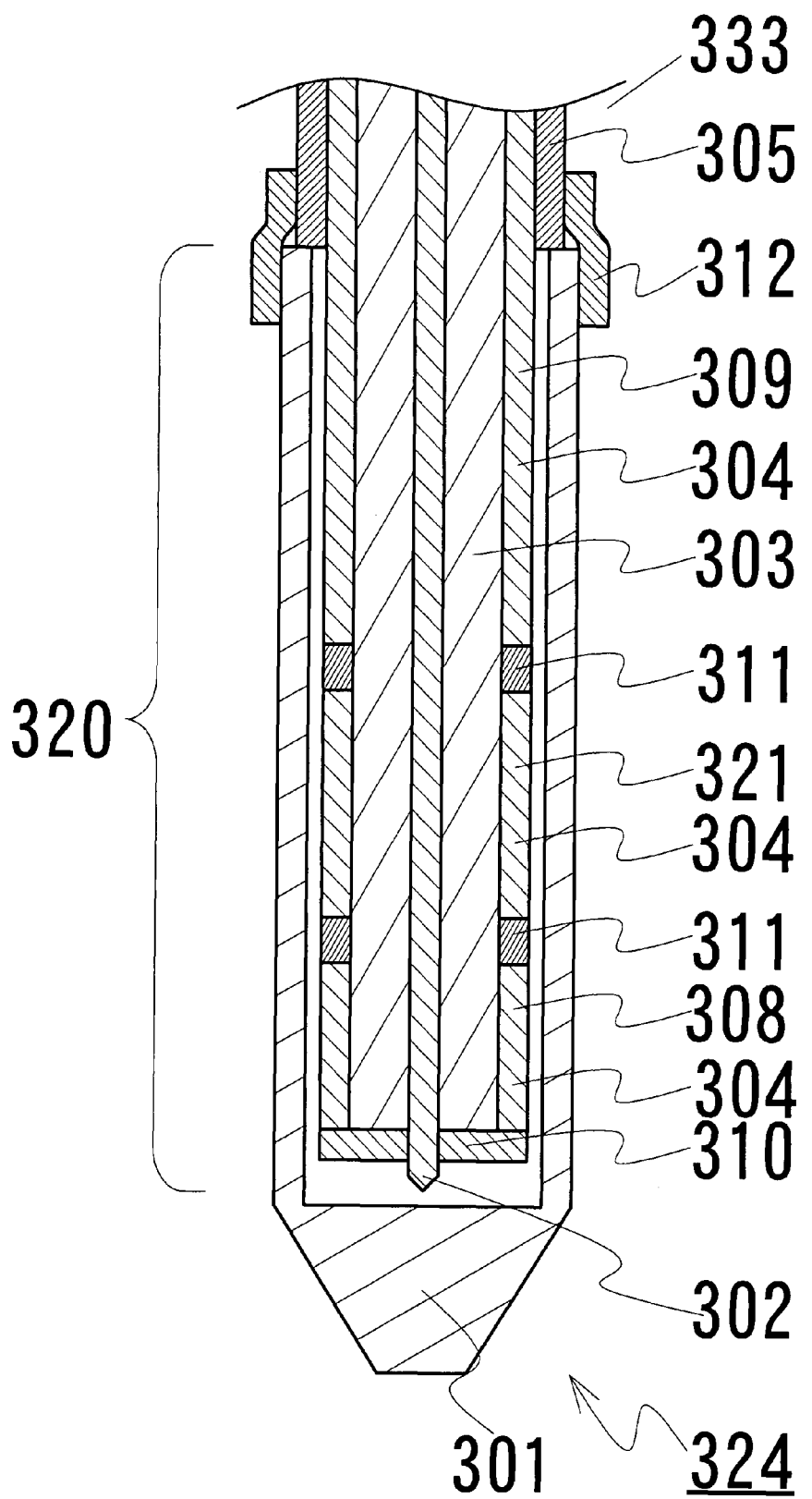

FIG. 60 and FIG. 61 illustrate other preferred embodiments regarding the second object of the present invention, where third electrodes 321 are added between the first electrodes 308 and the second electrodes 304. The SAR distribution elongates at additional electrodes so that long cauterization along the TTDP 324 is possible, by which a single therapy can be operated instead of multiple cauterization in the depths of TTDP 324 percutaneous insertion to the pathological tissues (see Ref. 2)

Figure 62:
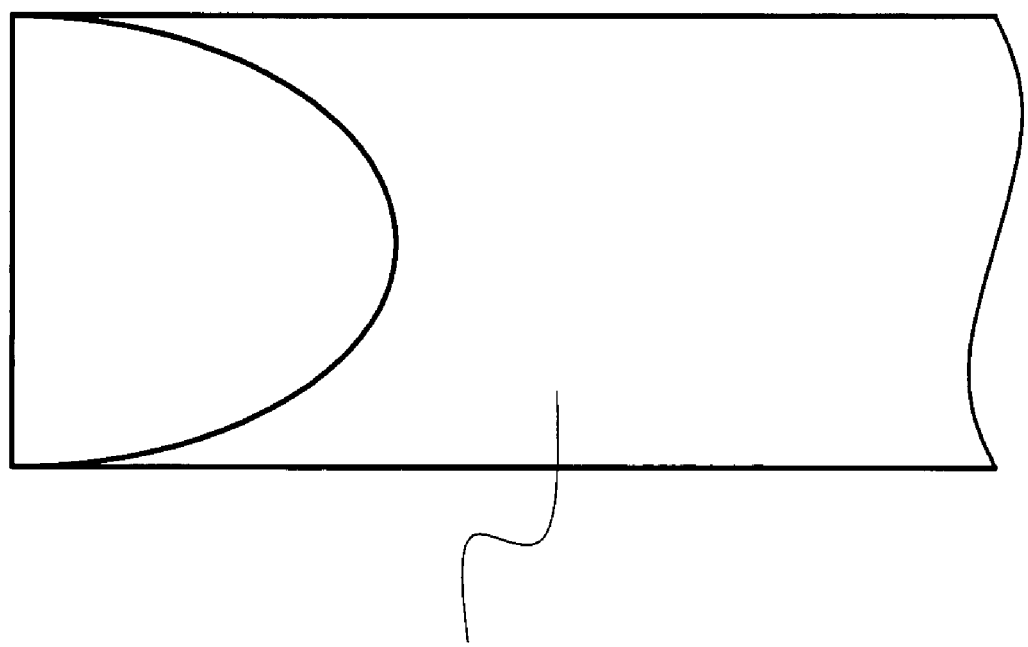
FIGS. 62 to 69 are the views of the shapes of the head portions of the TTDPs regarding the third object of the present invention.
Figure 63:
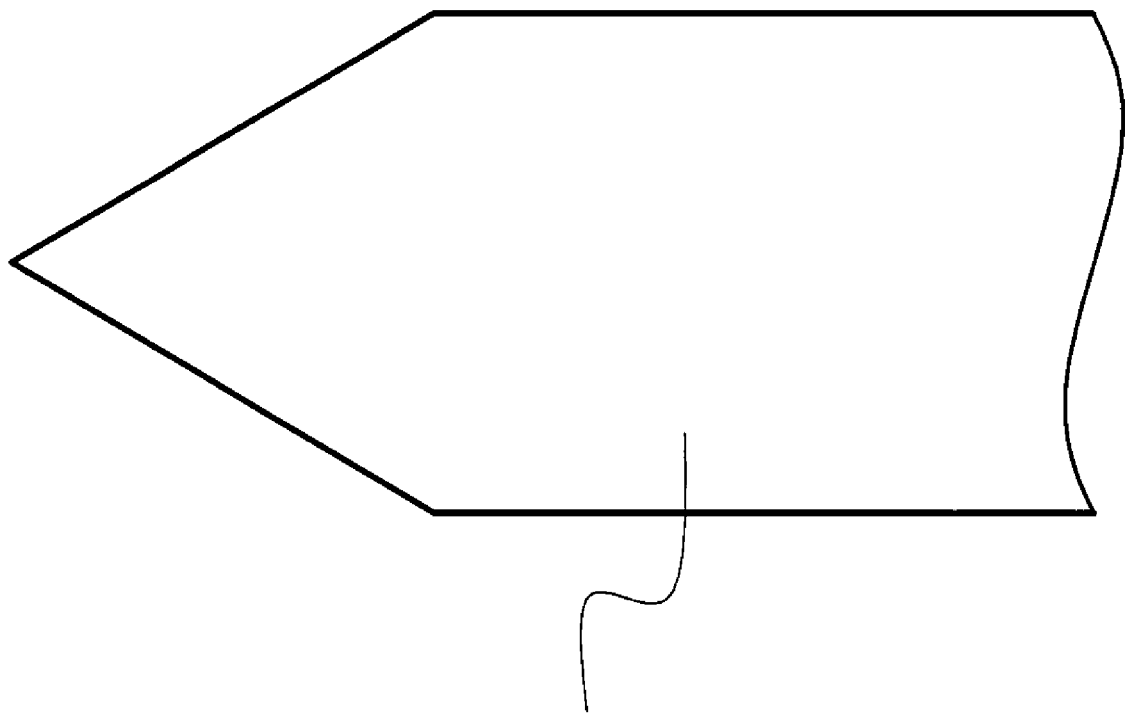
Figure 64:
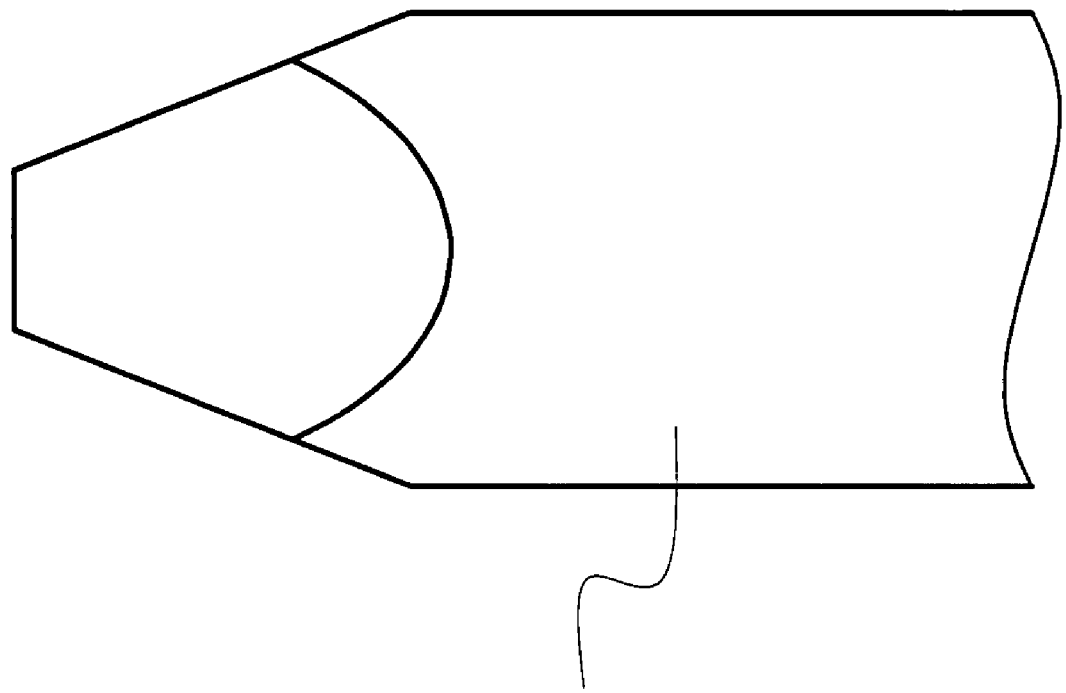
Figure 65:
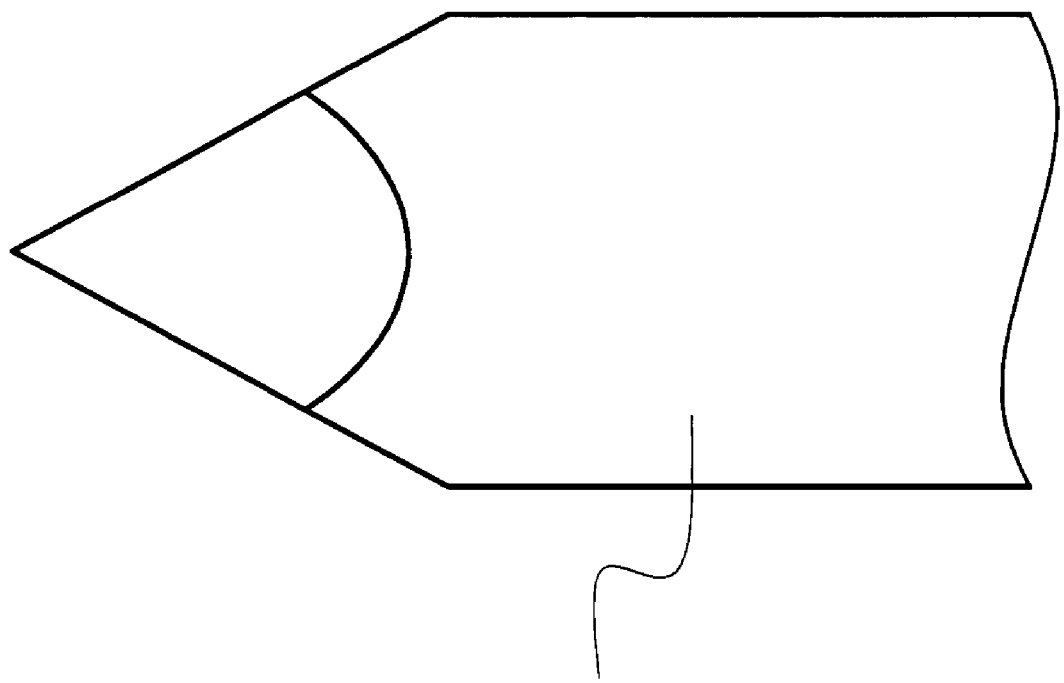
Figure 66:
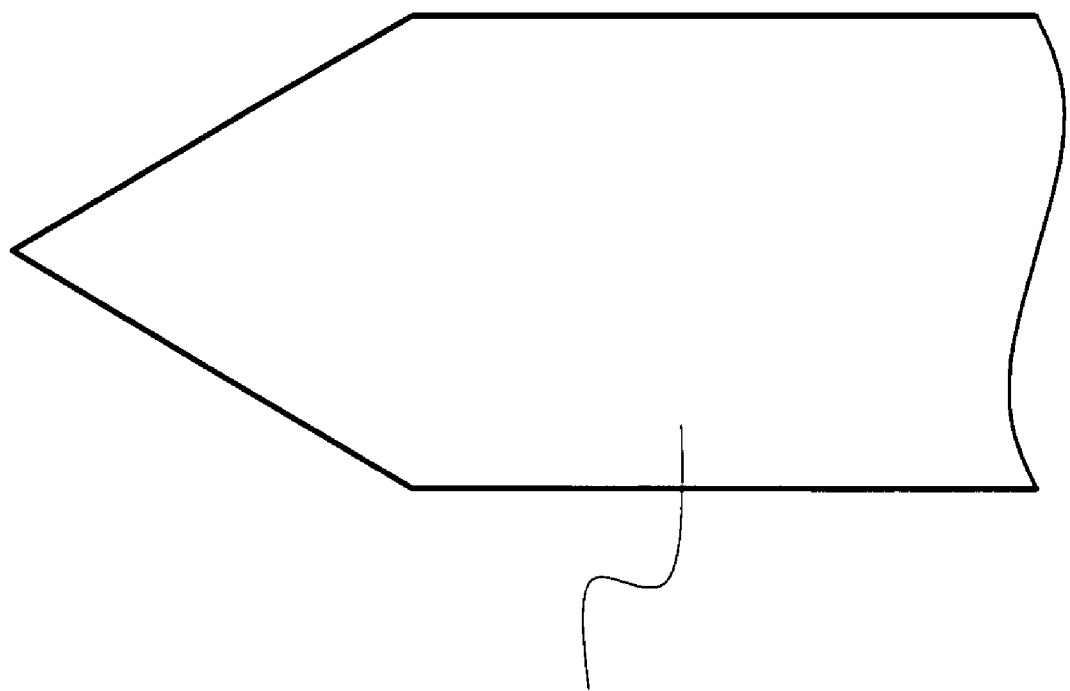
Figure 67:
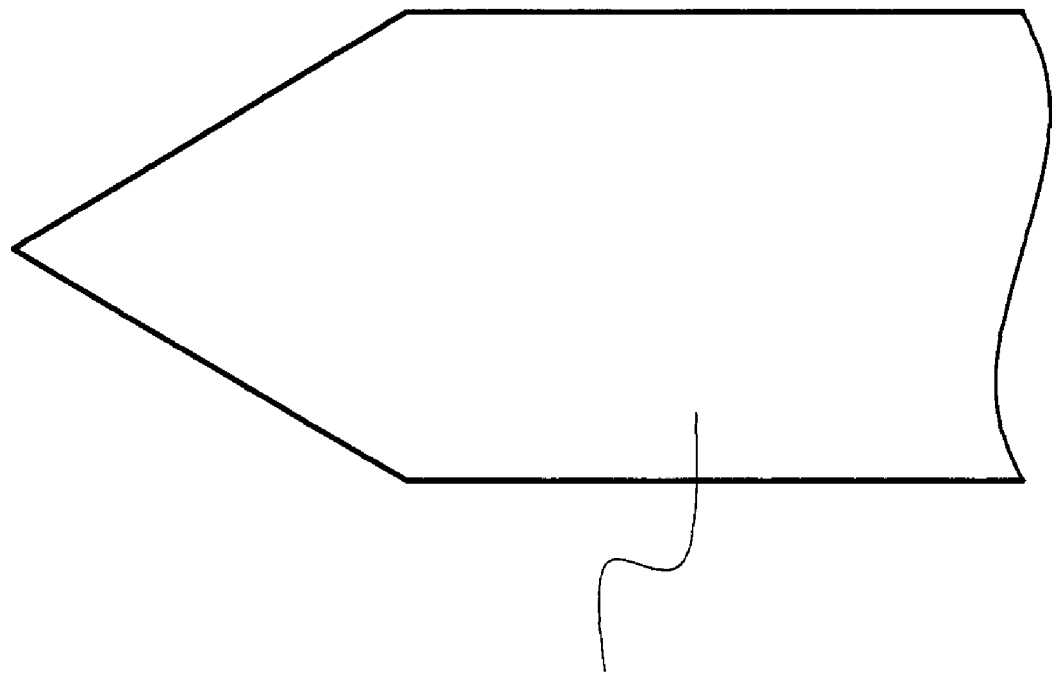
Figure 68:
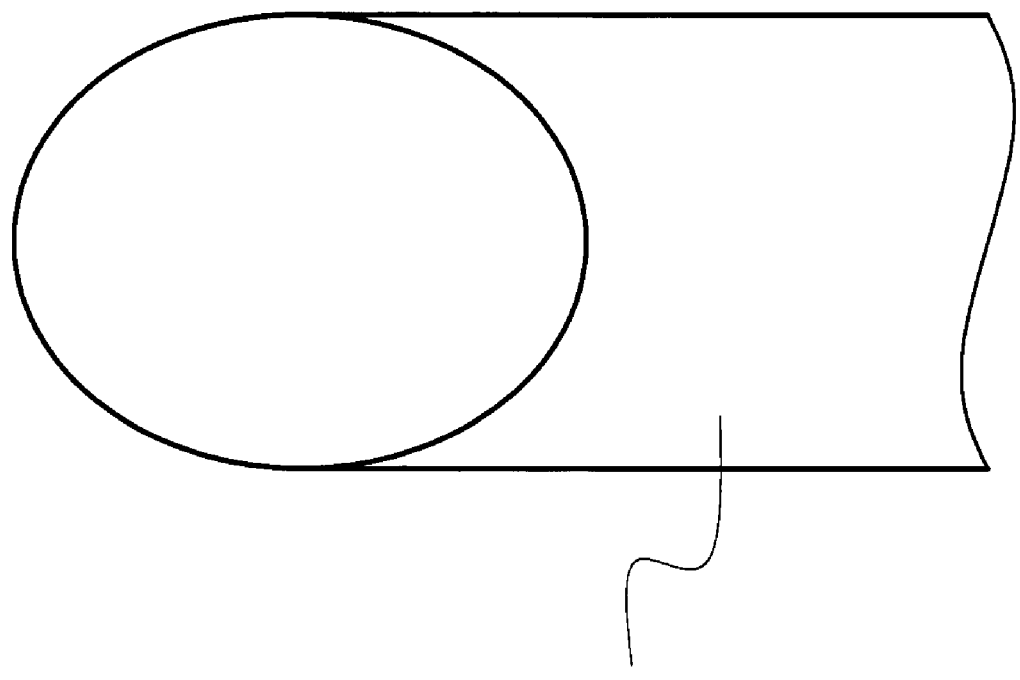
Figure 69:
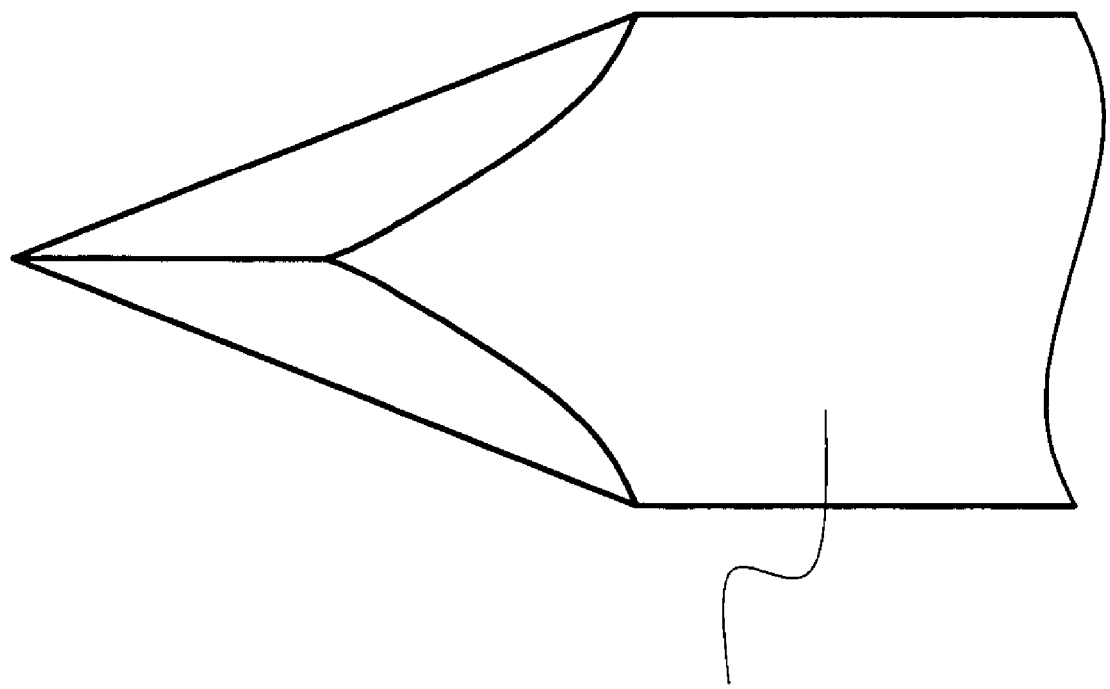

FIGS. 62-69 illustrate other preferred embodiments regarding the second object of the present invention, where the head of the sapphire sheath 301 is mechanically sharpened to be blade to percutaneously cut and invade into the tissues. The cutting edge shapes of the sapphire head 301 illustrated in FIGS. 62 and 63 shows a straight blade. The cutting edge shapes of the sapphire head 301 illustrated in FIGS. 64 and 65 shows a tapered blade. The cutting edge shape of the sapphire head 301 illustrated in FIGS. 66 and 67 shows a corn tip. The cutting edge shape of the sapphire head 301 illustrated in FIGS. 68 and 69 shows a spearhead blade.

The third object of the present invention is to solve single radiation gap problem, that is, RF radiation source to tissues is from a single gap so that homogeneous cauterization is difficult. We provide such antenna configuration that plurality of electrically isolating gaps is formed onto the antennas used for TTDPs.

FIGS. 24-26 show a set of preferred embodiments regarding the third object of the present invention. Each electrode pair consisting of a first electrode 408 and a second electrode 409 has an electrically isolating gap 407 by partly stripping the outer conductor 404 of the coupler-line. FIG. 25 illustrates a front view of the antenna assembly. The first electrodes 408, the second electrodes 409 and the central conductors 402a and 402b are electrically connected in the structure of the coupler-line 333 as illustrated in FIGS. 24-26 which illustrate the different electrical connection between the first and the second central conductors 402a and 402b and the first and the second electrodes 408 and 409. The pairs of the first electrodes 408 and the second electrodes 409 form dipole antennas as 436a, 436b and 436c. The TTDP 424 comprises the antenna assembly 420 consisting of the dipole antennas 436a, 436b and 426c and a single-body sheath 401 which is made of sapphire. It is possible to use a sheath consisting of an insulating material such as either a combination of a sapphire head and a polymer pipe.

The embodiment illustrated in FIG. 24 is given by a coupler-line that has a first central conductor 402a and second central conductors 402b. The first and the second electrodes 408 and 409 are respectively connected to the first the second central conductors 402a and 402b via power supplied points 434a and 434b so that the first electrodes 408 and the second electrodes 409 are adjacently facing at the power supply points 434a and 434b, respectively. The embodiment illustrated in FIG. 26 is given by a coupler-line that has a first and a second central conductor 402a and 402b. The first and second central conductors are respectively connected to a first electrode pair consisting of the first electrodes 408 and the second electrodes 409 via power supplied points 403a and 403b so that the first electrodes 408 and the second electrodes 409 are adjacently facing at the power supply points, 403a and 403b, respectively. The first and second central conductors are respectively connected to a second electrode pair consisting of the second electrodes 409 and the first electrodes 408 via power supplied points 403b and 403a so that the first electrodes 408 and the second electrodes 409 are adjacently facing at the power supply points 403b and 403a, respectively. The first electrode pair and the second electrode pare are alternatively formed in the antenna assembly 420.

In addition, the single-body sheath 301 can be made of sapphire. In addition the sheath is formed by a sheath that comprises a sapphire head consisting of a edge portion and a coupling portion to which an isolating flexible pipe (made of TEFLON (a trade mark) or Polyethylene other than PTFE) tightly couples. The edge portion of the sapphire head is, at the front edge, mechanically sharpened to be a blade to percutaneously cut and invade into the tissues.

Figure 70:
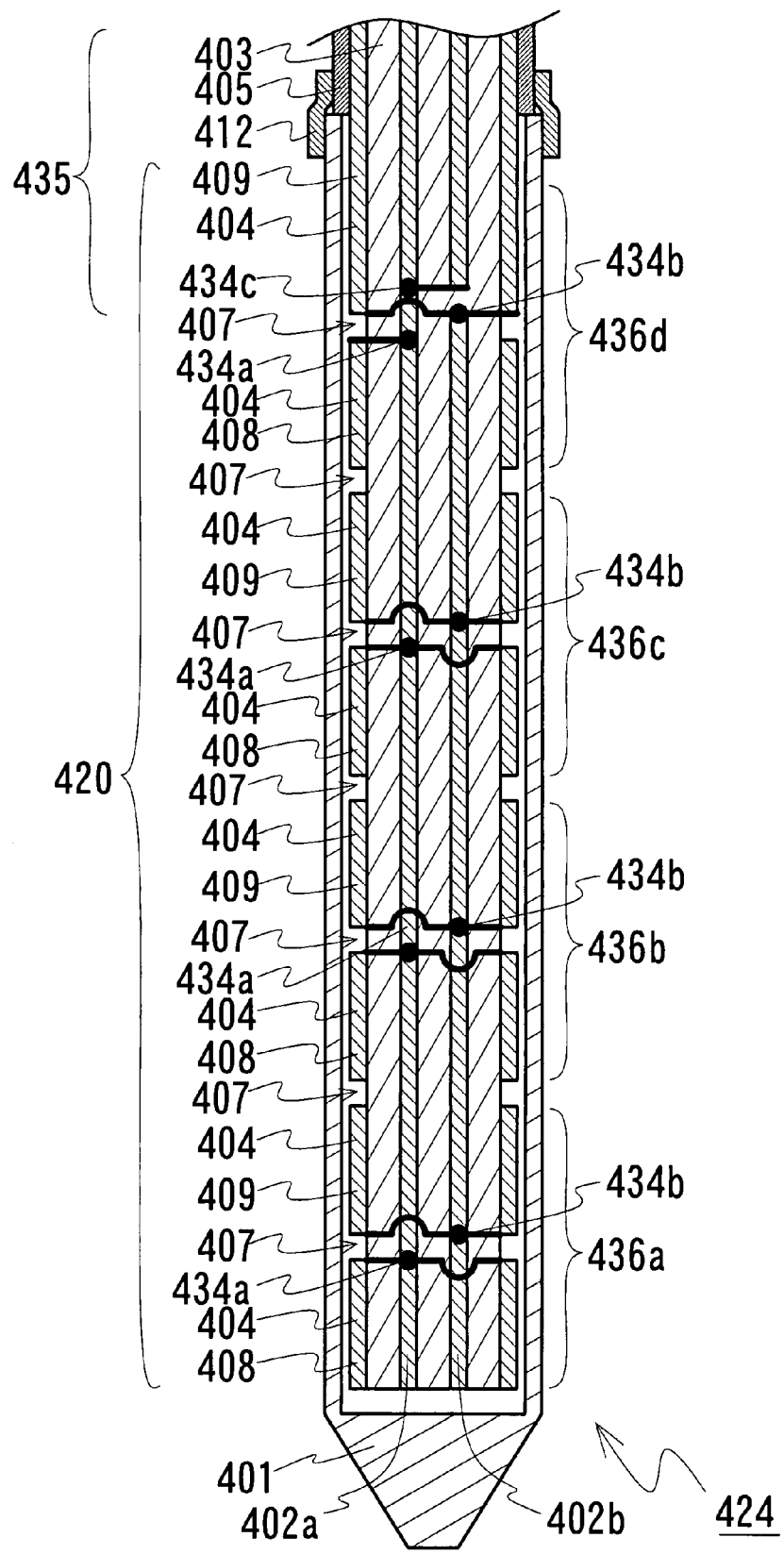
FIGS. 70 to 85 are the cut views and the perspective part views of the TTDPs regarding the third object of the present invention.
Figure 71:
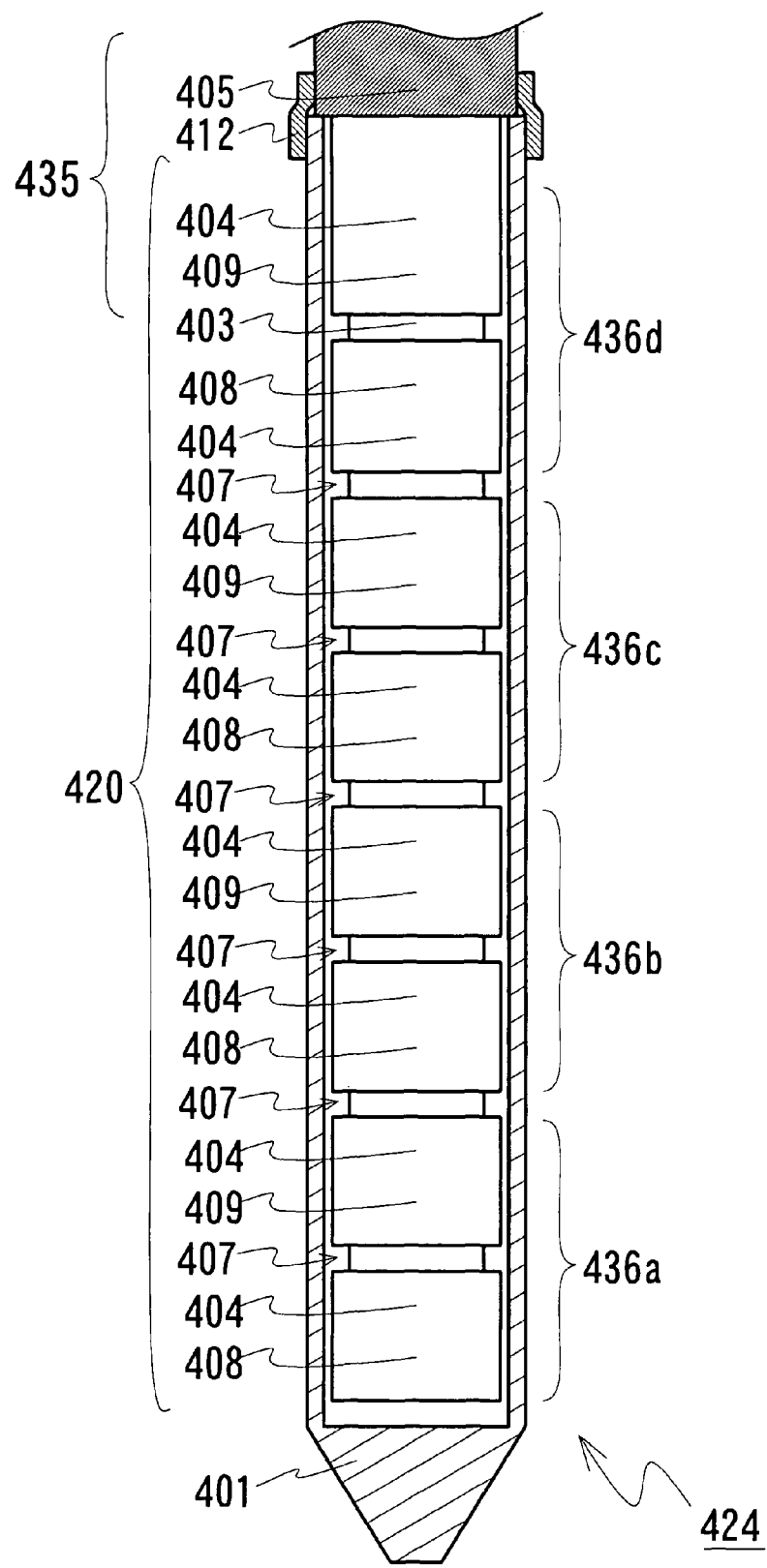
Figure 72:
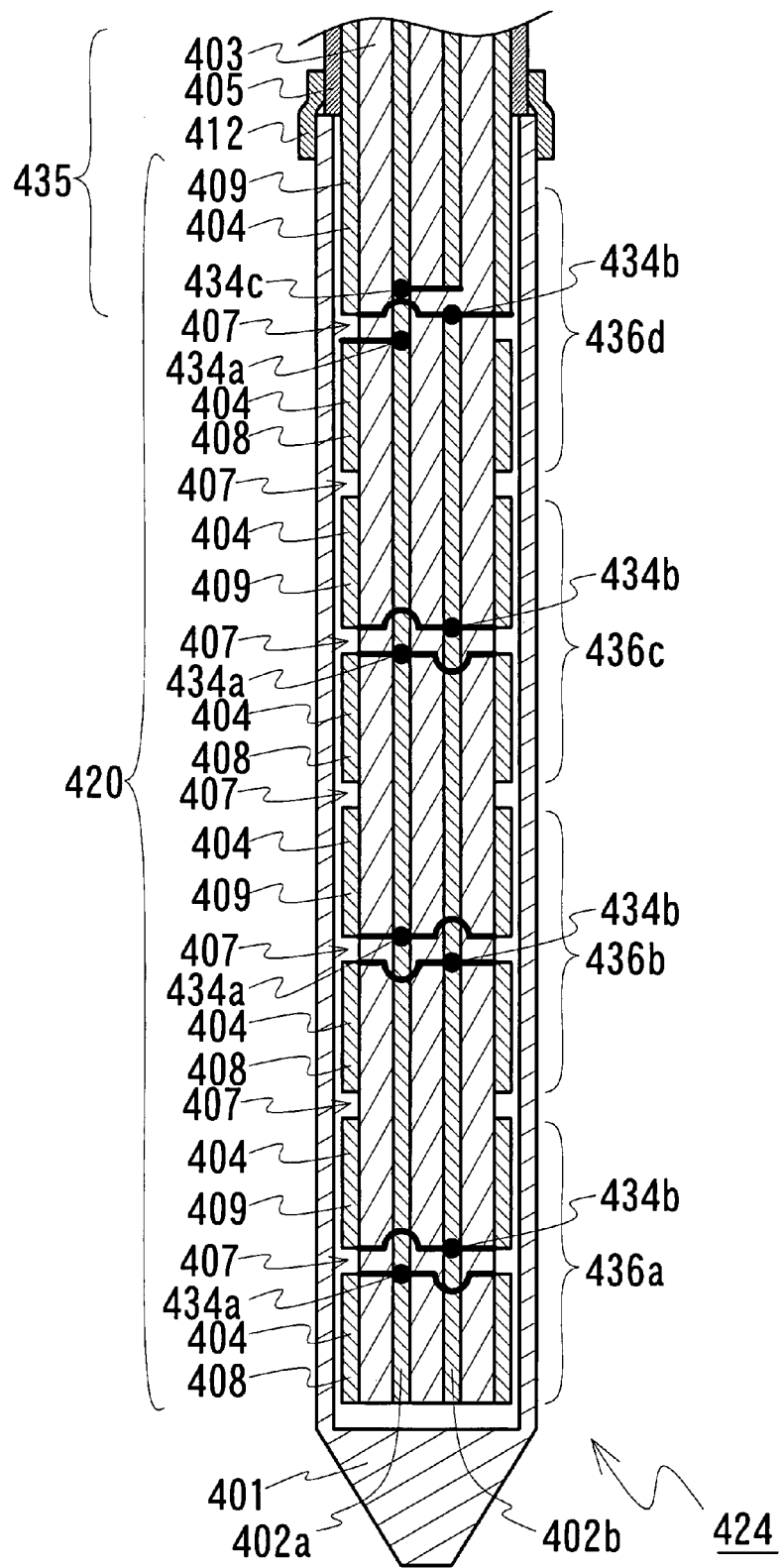

FIGS. 70-72 show another set of preferred embodiments regarding the third object of the present invention. A couple-line 435 connected to RF power source works as a RF power transmission cable to which the two central conductors 402a and 402b are electrically connected. The antenna assembly 420 consisting of a plural pair of dipole antennas has the same configuration of electrical connection between the first and second electrodes and the central conductors 402a and 402b as that of those illustrated in FIG. 24 and 26 which illustrates the different electrical connection between the first and the second central conductors 402a and 402b and the first and the second electrodes 408 and 409. On the other hand, the couple-line 435, which works as a power transmission cables, as illustrated in FIGS. 70 and 72 (both are cross sections of this set of preferred embodiments) and FIG. 71 (a front view of this set of preferred embodiments) has an outer jacket 405 thereof. Additional shrinkable tube 412 is added to make airtight between the jacket 405 and the single-body sheath 401. This airtight configuration suppresses out-coming germs from the TTDP antenna assembly in the operation. Whichever electrical connection between the first and the second electrodes and the central conductors can be possible as that illustrated in FIG. 70 or FIG. 72. The shrinkable tube 412 can be thermal shrinkable one and the outer jacket 405 can be non-shrinkable one.

Figure 73:
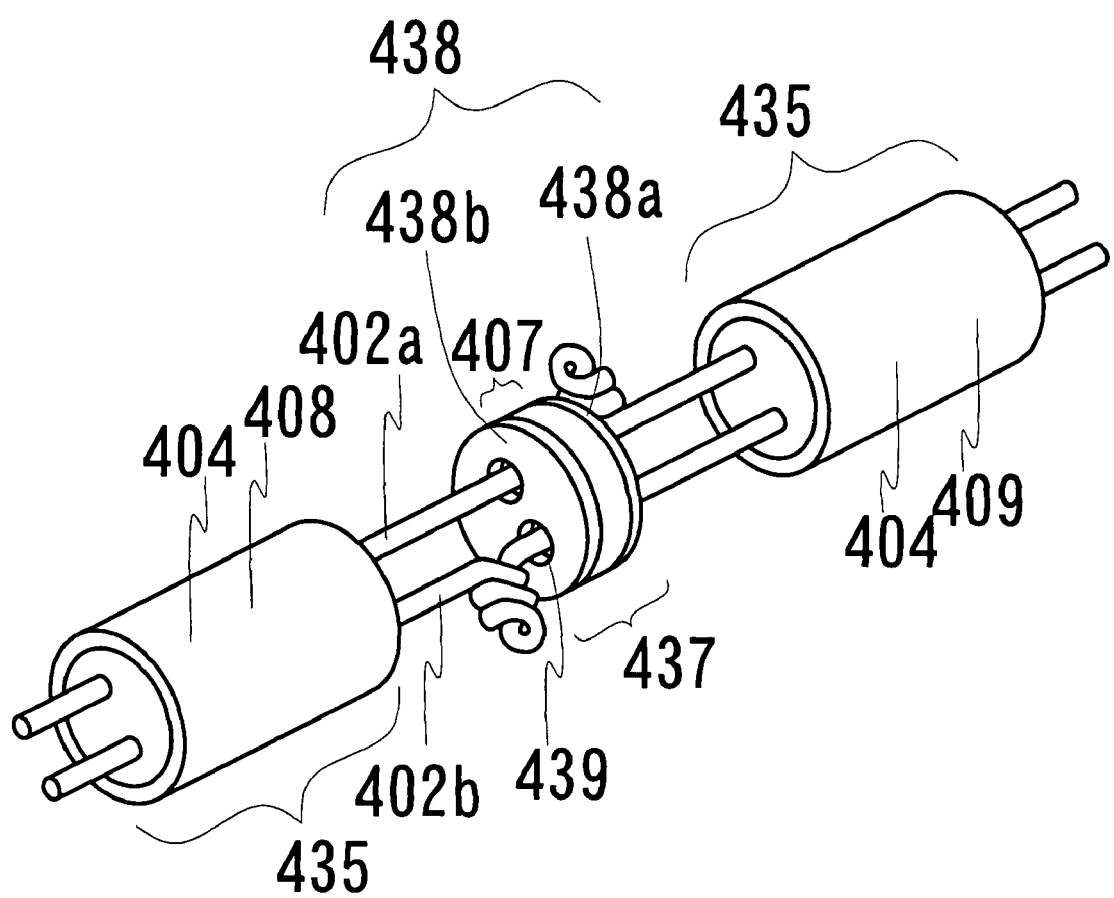
Figure 74:
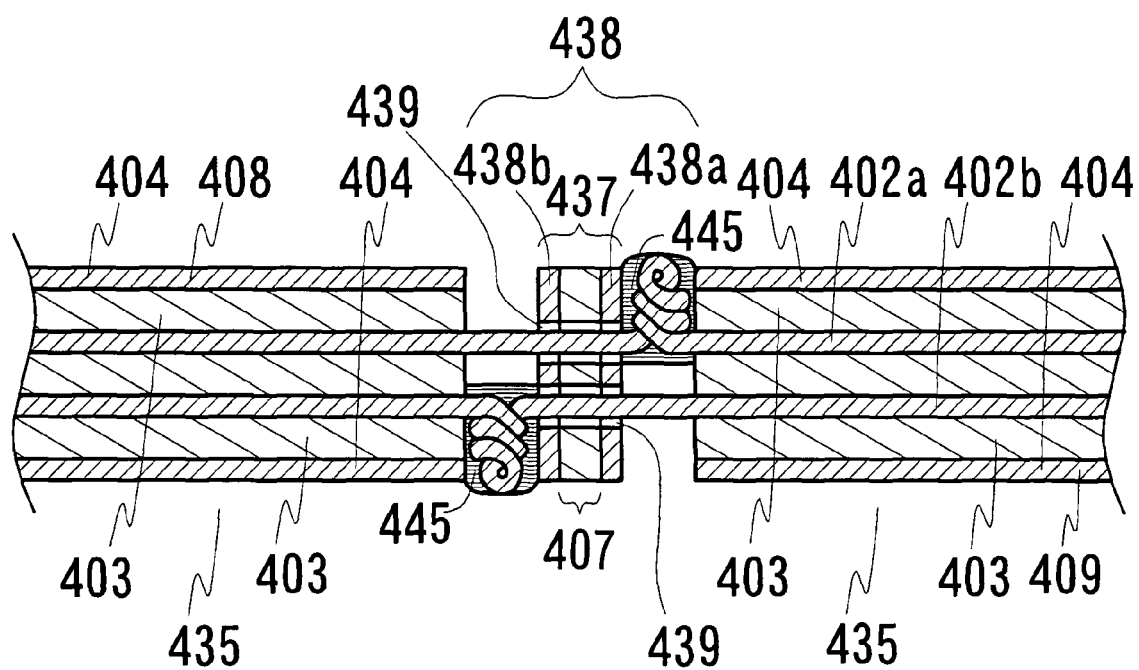
Figure 75:
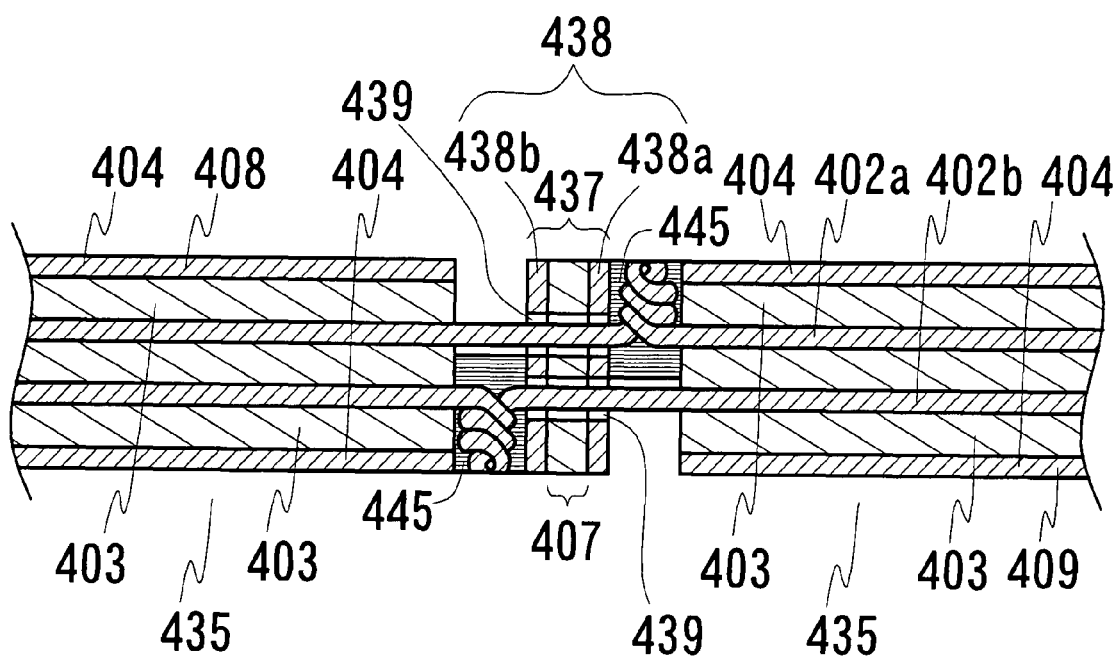
Figure 76:
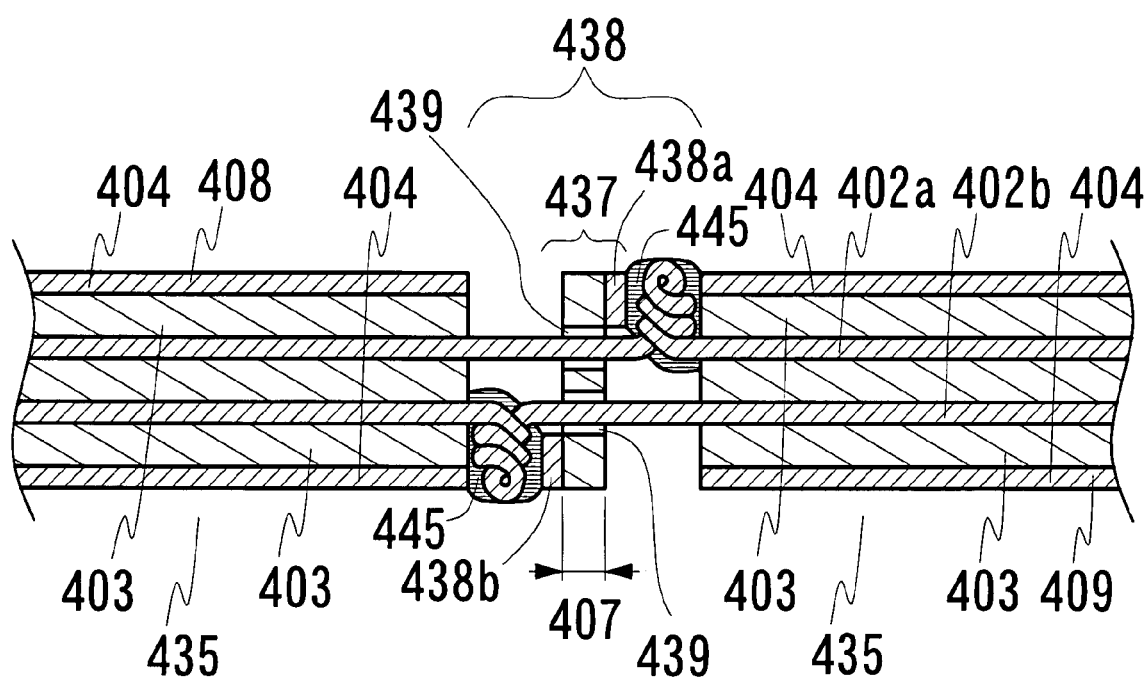
Figure 77:
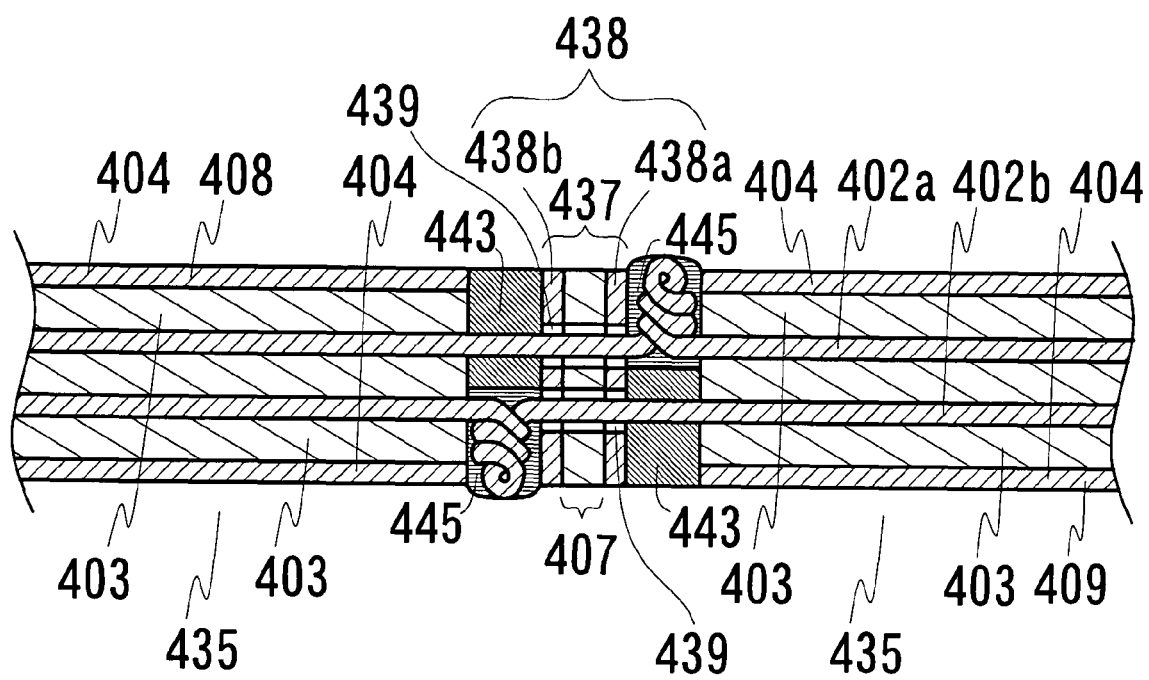

FIGS. 73-79 show another set of preferred embodiments regarding the third object of the present invention, especially, those regarding to the connection of the two central conductors 402a and 402b with the outer conductor 404. The structure, that is, the first electrode 408 and the second electrode 409 are isolated via an electrically isolating gap 407 further has an electrical connection such that the first electrode 408 and the second electrode 409 are connected to the central conductors 402a and 402b. The first and the second electrodes are made from a coupler-line 435 by cutting into pieces. The central conductors 402a and 402b are led out from the terminal faces of the first electrode 408 and the second electrode 409 of the pieces which are facing each other. As illustrated in FIGS. 73 and 74, an electrically insulating gap 407 is provided by an insulating gap piece 437 which can be made from a printed circuit board (called as PCB for abbreviation) having conductive surfaces 438a and 438b. The insulating gap piece 437 is formed into a disc shape which is similar to the cross section shape of the couple-line 435 and has two through-holes 439 through which the central conductors 402a and 402b are led therethrough. The electrically conductive layers 438a and 438b of the insulating gap piece 437 are largely removed in comparison to the diameter of the through-holes 439 so that the central conductors 402a and 402b do not contact with the conductive layer 438a and 438b in the through-holes 439. To an electrically conductive layer 438a of insulating gap piece 437 which contacts with the first electrode 408, the first central conductor 402a being in the side of the second electrode 409 is led out. To the other electrically conductive layer 438b of insulating gap piece 437 which contacts with the second electrode 409, the second central conductor 402b being in the side of the first electrode 408 is led out. The first and second central conductors 402a and 402b are respectively brazed to the second electrode 409 and the first electrode 408 by using solder 445 as illustrated in FIGS. 73 and 74 (FIG. 73 is a perspective drawing and FIG. 74 a cross section drawing). To shorten the longitudinal length of the electrically isolating gap 407 along the couple-line 435 for assembling into a dipole antenna constructed with the first and the second electrodes 48 and 409, the twisted part of the first central conductor 402a and the second central conductor 402b is pulled out from the outer conductor 404. The twisted part of the first central conductor 302a and the second central conductor 402b, which comes out from the surface of the outer conductor 404 is removed after being braded, as illustrated in FIG. 75. In order to avoid unnecessary contact of the central conductors 402a and 402b to conductive surfaces 438a and 438b on the insulating gap piece 437, respectively, the conductive surface s 438a and 438b are partly left for the portion of the insulating gap piece 437 where the second electrode 409 and the first electrode 408 are braded and the unnecessary portions are removed, as illustrated in FIG. 76 (a cross sectional drawing). When the central conductors 402a and 402b, insulating gap piece 437 and the first electrode 408 and the second electrode 409 are braded, it is possible to fill the gaps around the central conductor 402a and 402b with another insulating piece 443 made of dielectric insulating material (such as a resin) which is different from the dielectric insulator 403 of the couple-line 435 as illustrated in FIG. 77.

Figure 78:
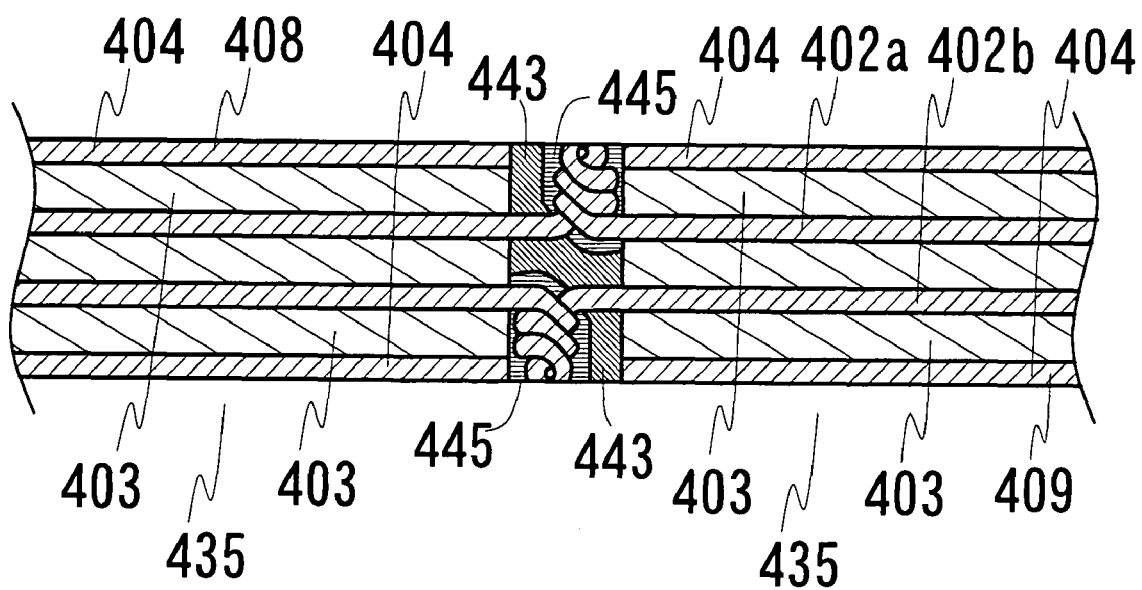

In stead of using the insulating gap piece 437, the twisted portions of the central conductors 402a and 402b are led out to the outer conductor 404 and brazed to the outer conductor 404 and then the twisted portions protruding form the surface of the couple-line is removed so that the above mentioned insulating piece 443 is inserted or filled into the slot which is between the first electrode 408 and the second electrode 409 and has the twisted portions therein, as illustrated in FIG. 78.

Figure 79:
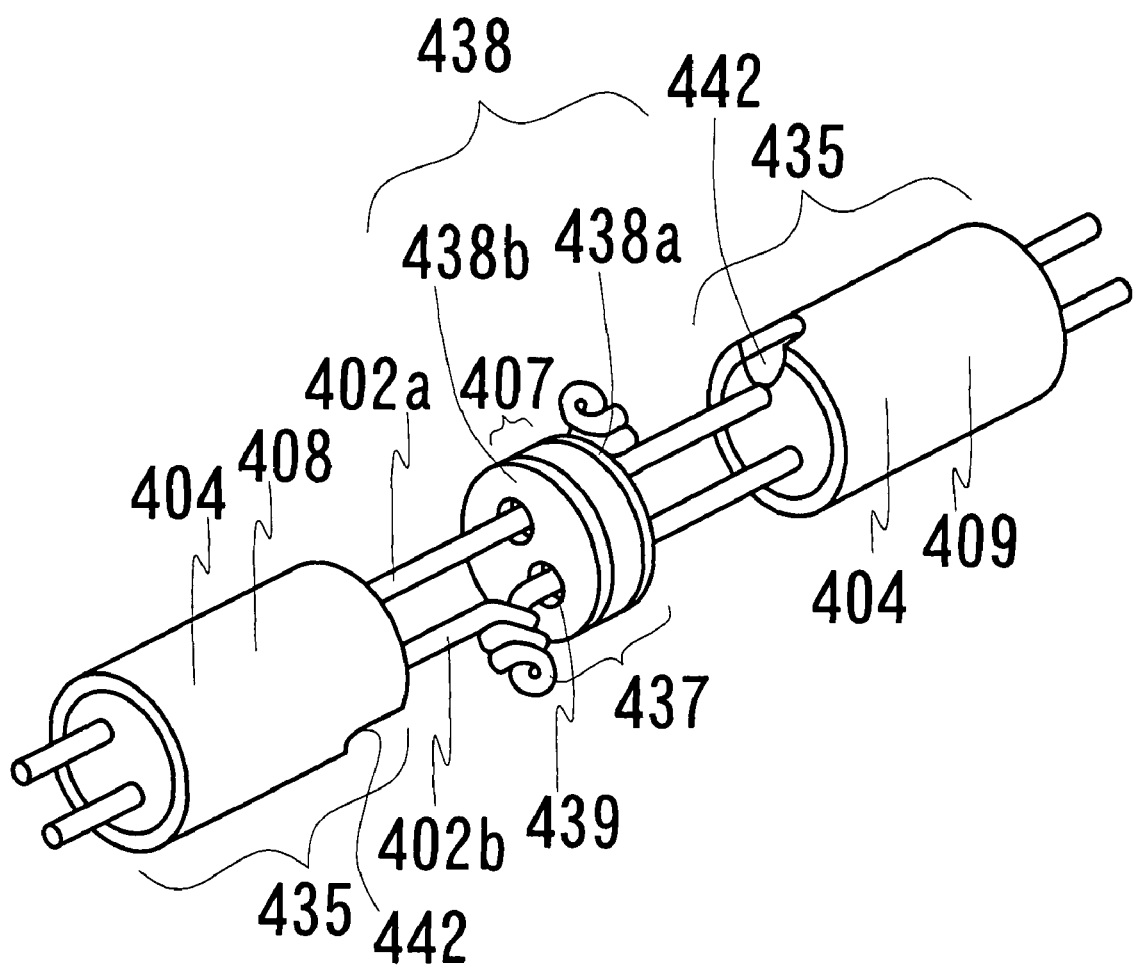

The 407 between the first electrode 408 and the second electrode 409 is formed by removing the outer conductor 404. Therefore, the electrical connection 434a and 434b between the central conductors 402a and 402b need a spatial volume in the antenna assembly 420. For the better electrical connection 434a and 434b, the outer conductor 404 may have a slot 442 on the surface so that the central conductors 402a and 402b, the first and second electrodes 408 and 409 can be surely brazed as illustrated in FIG. 79.

Figure 80:
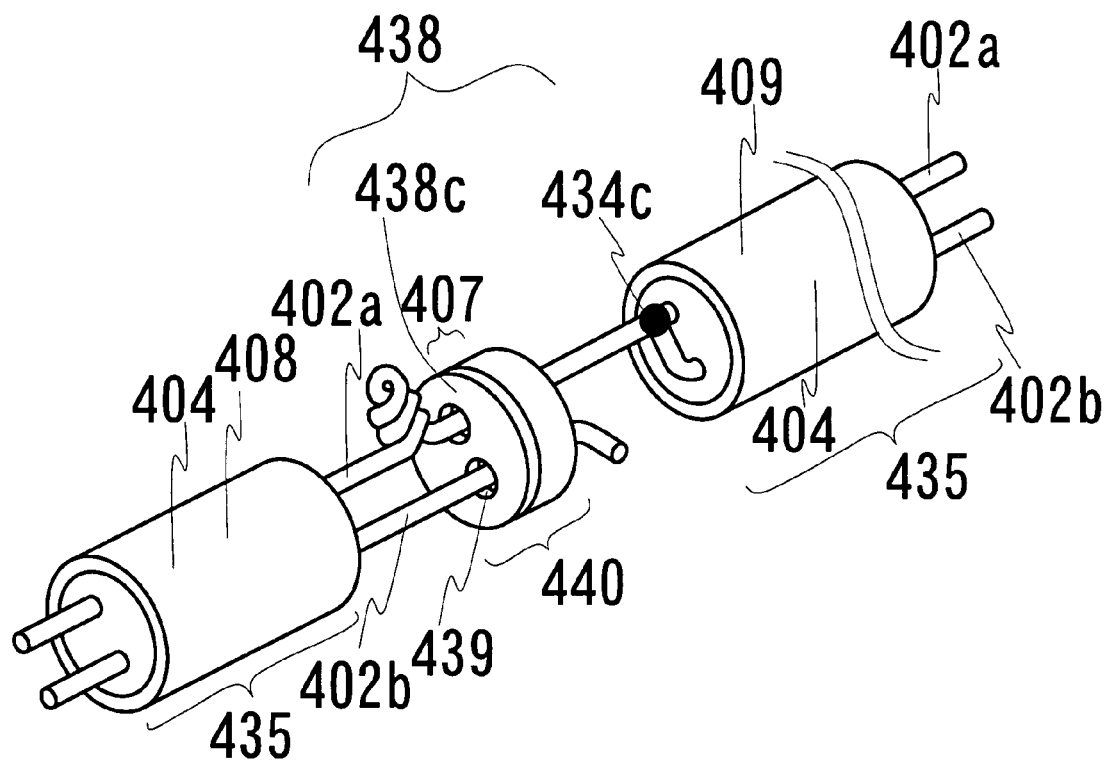
Figure 81:
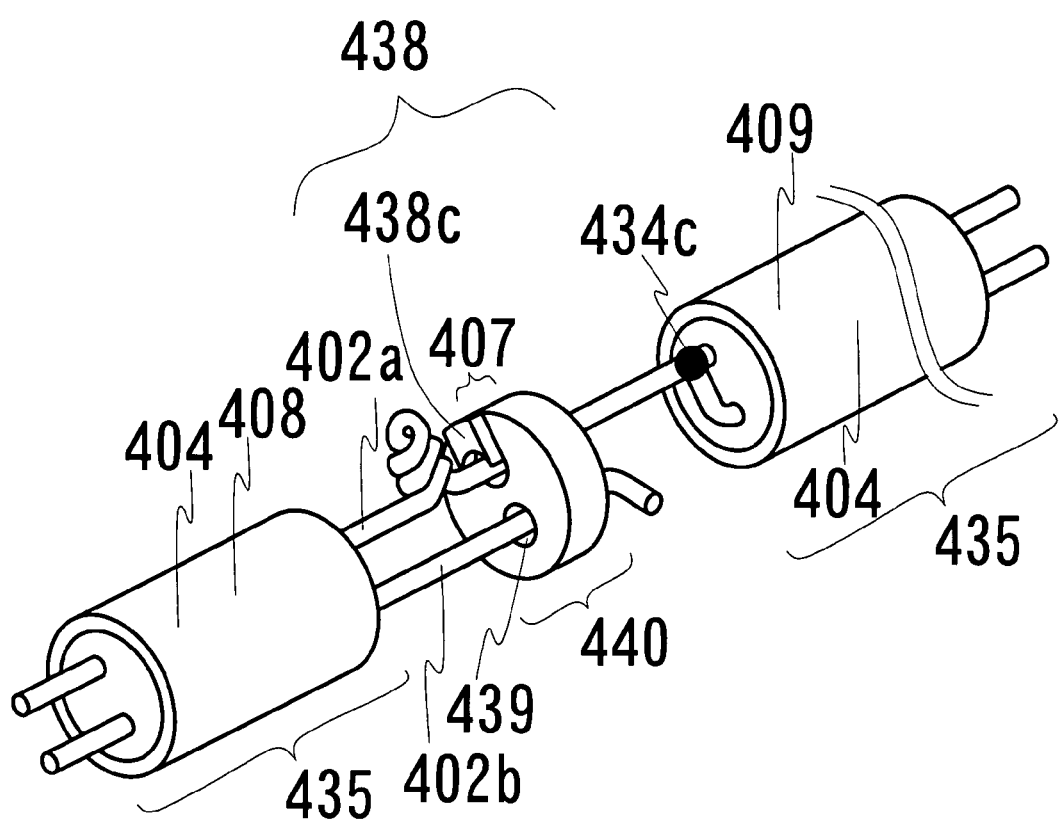
Figure 82:
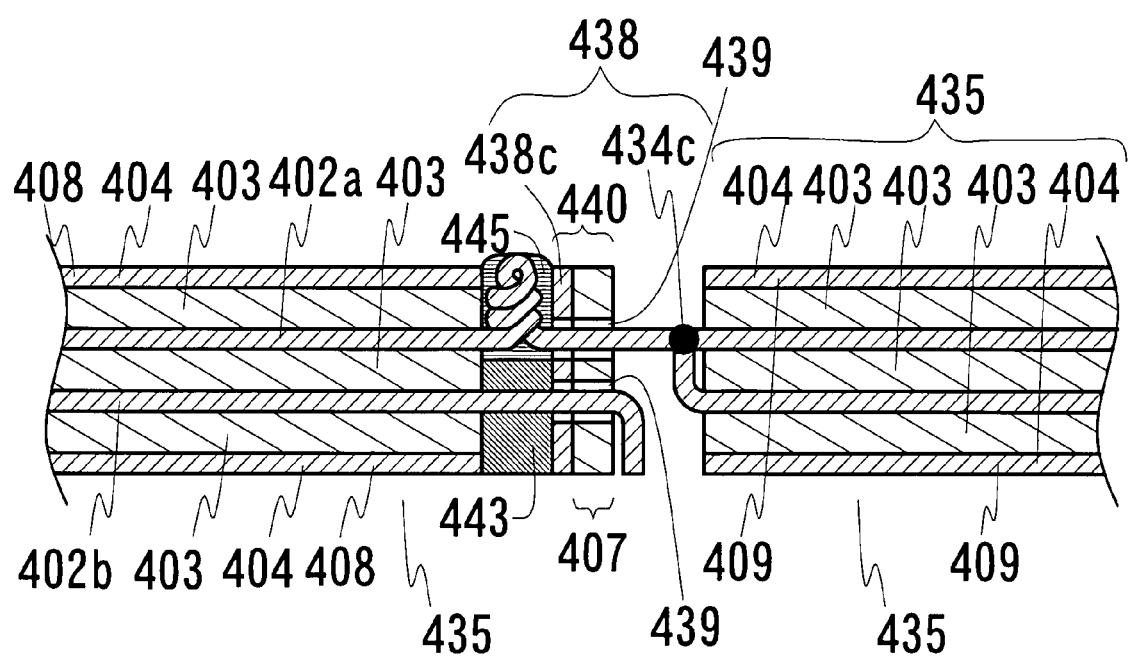

FIGS. 80-82 show another set of preferred embodiments regarding the second object of the present invention, especially, those regarding to the connection of the antenna assembly 420 and the coupler-line 435 which works as a power transmission cable. The coupler-line 435 comprises two central conductors 402a and 402b, dielectric insulator 403 and the outer conductor 404 and an antenna assembly 420 is made in the end therefrom. The coupler-line 435 can be same as the conventional RF power transmission cable. In the present embodiments, the first and the second central conductors 402a and 402b are connected each other. An insulating gap piece 440 which has a conductive layer 438c in only one side is used for an electrically isolating gap 407. The insulating gap piece 440 is formed into a disc shape which is similar to the cross section shape of the couple-line 435 and has two through-holes 439 through which the central conductors 402a and 402b are led. The central conductor 402a in the first electrode 408 is led and brazed to the outer conductor 404 of the coupler-line 435 with solder. The central conductor 402a of the couple-line 435 which works as a power transmission cable and the central conductor 402a in the antenna assembly 420 (as shown in FIGS. 70 to 73) are connected in the side facing to the conductive layer 438c of the insulating gap piece 440 and brazed to the first electrode with solder 445, as illustrated in FIG. 80.

In order to avoid unnecessary contact between the central conductors 402a and 402b and the 438c of the insulating gap piece 440 and to surely make electrical connection between the outer conductor 404 and the central conductor 402b of the first electrode 408, a larger a portion of the conductive layer 438c, which faces against the first electrode 308, is left to be brazed to the first electrode 408 as shown in FIG. 81 wherein the other portion of the conductive layer 438c is removed instead of removing the electrically conductive layers 438c largely in comparison to the diameter of the through-holes 439, as illustrated in FIG. 81 (perspective drawing a major view). In order to fill the space around the central conductor 402b which is generated in brazing the central conductor 402b, the insulating gap piece 440 and the first electrode 408, the above insulating piece 443 is used in the space between the insulating gap piece 440 and the first electrode 408, as illustrated in FIG. 82. The two central conductors of the coupler-line 435 is terminated at 434c, therefore, it is possible to use the two central conductors as a single central conductor in RF power supply from an RF power source.

Figure 83:
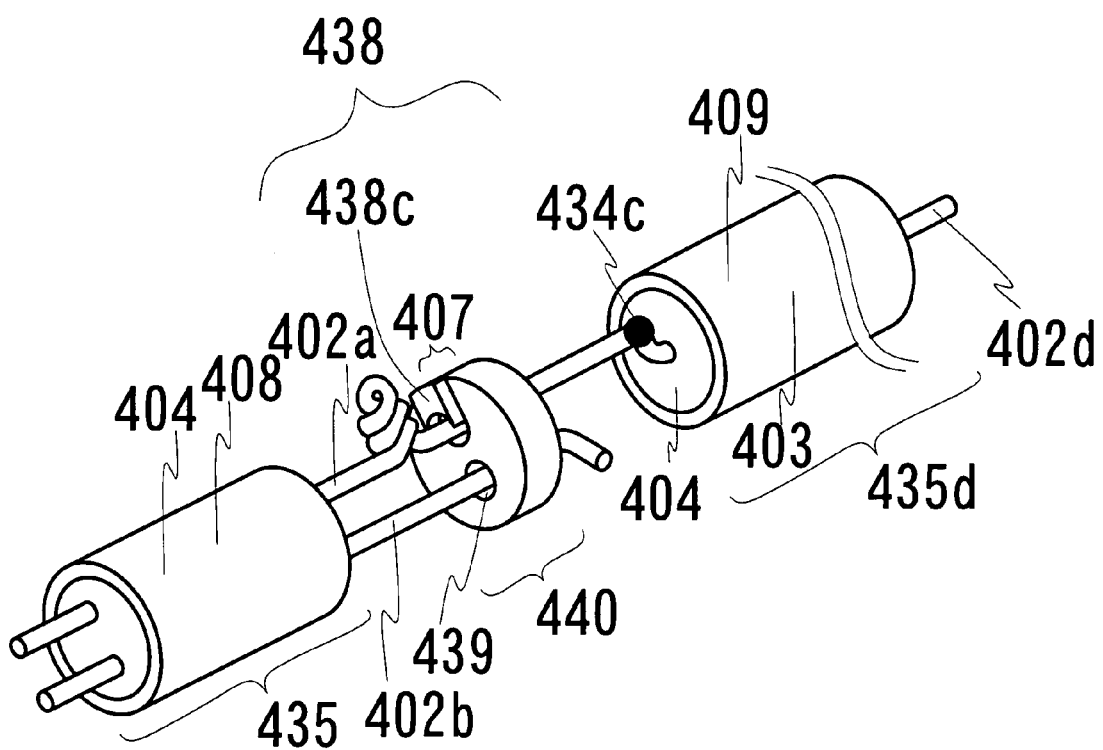

A conventional RF power transmission cable, which is a coaxial cable 435d, comprising a single central conductor 402d, a cylindrical dielectric insulator 403 formed around the central conductor 402d and an outer conductor 404 therearound, can be used for a power transmission cable wherein the central conductor 402d is electrically connected with the first central conductor 402a and the outer conductor 404 of the with the second conductor 402b, as illustrated in FIG. 83.

Figure 84:
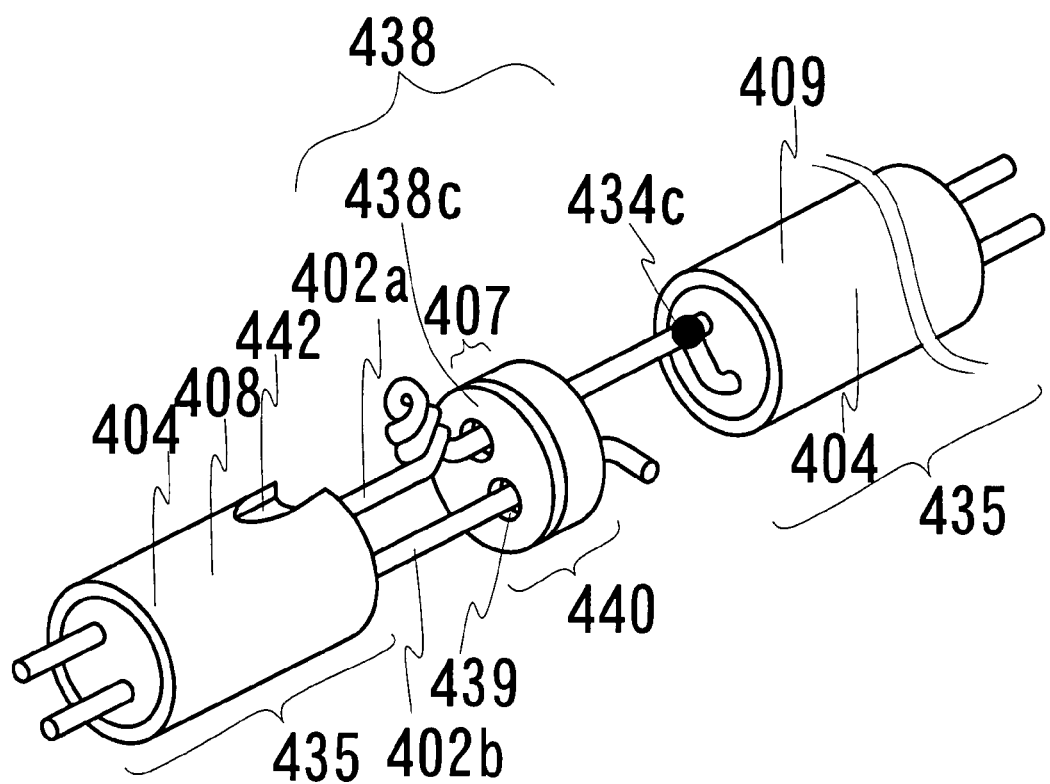

An insulating gap piece 440 may have a conductive layer 438a at a portion which contact to the first and second electrodes 408 and 409 with solder brazing. More specifically, the twisted portion of the conductors 402a and 402b needs a spatial volume to be accommodated in the antenna assembly 420. For the purpose of better electrical connection, the outer conductor 404 may have a slot 442 on the surface so that the central conductors 402a and 402b, and the first and second electrodes 408 and 409 can be surely brazed as illustrated in FIG. 84.

Figure 85:
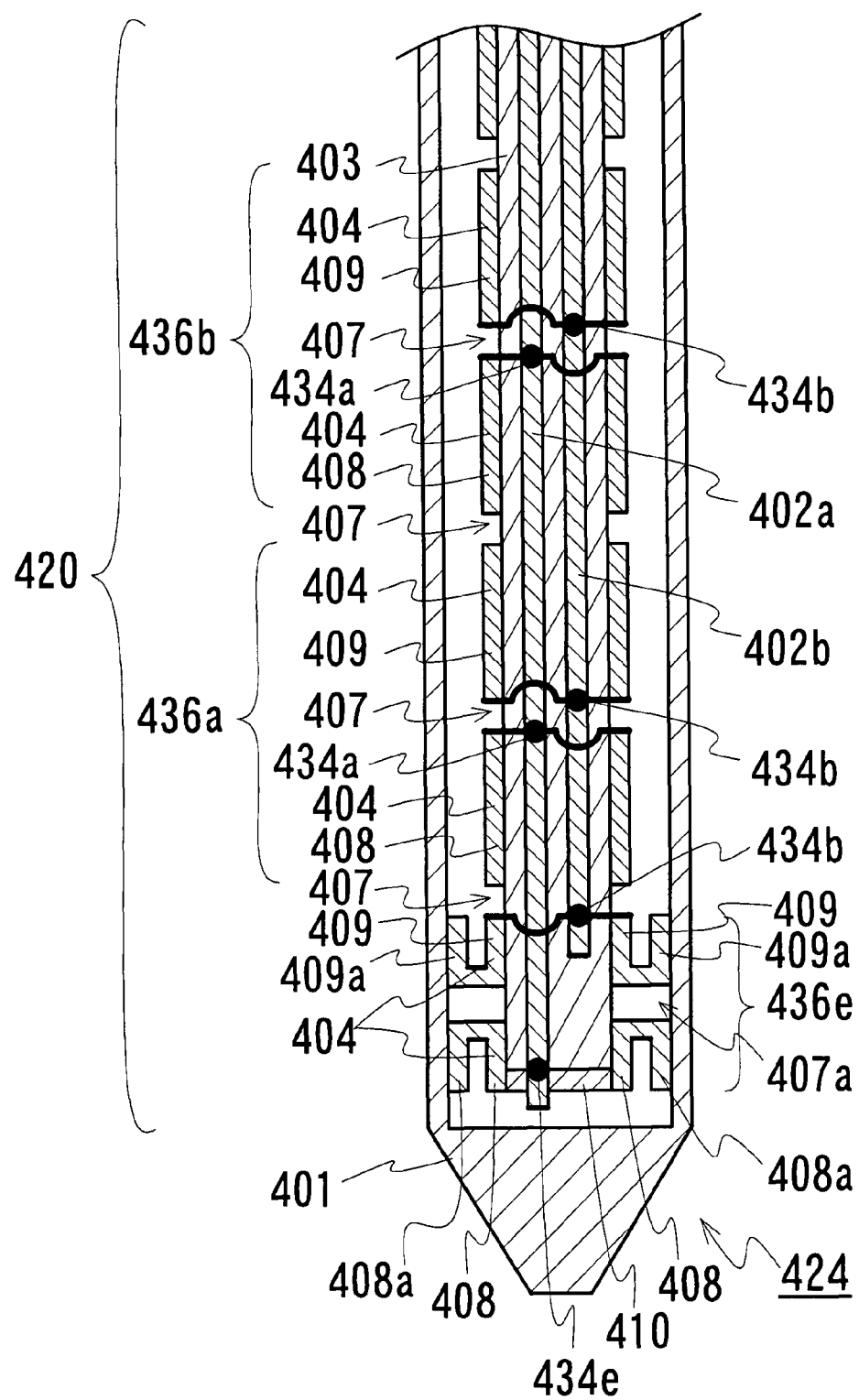
Figure 86:
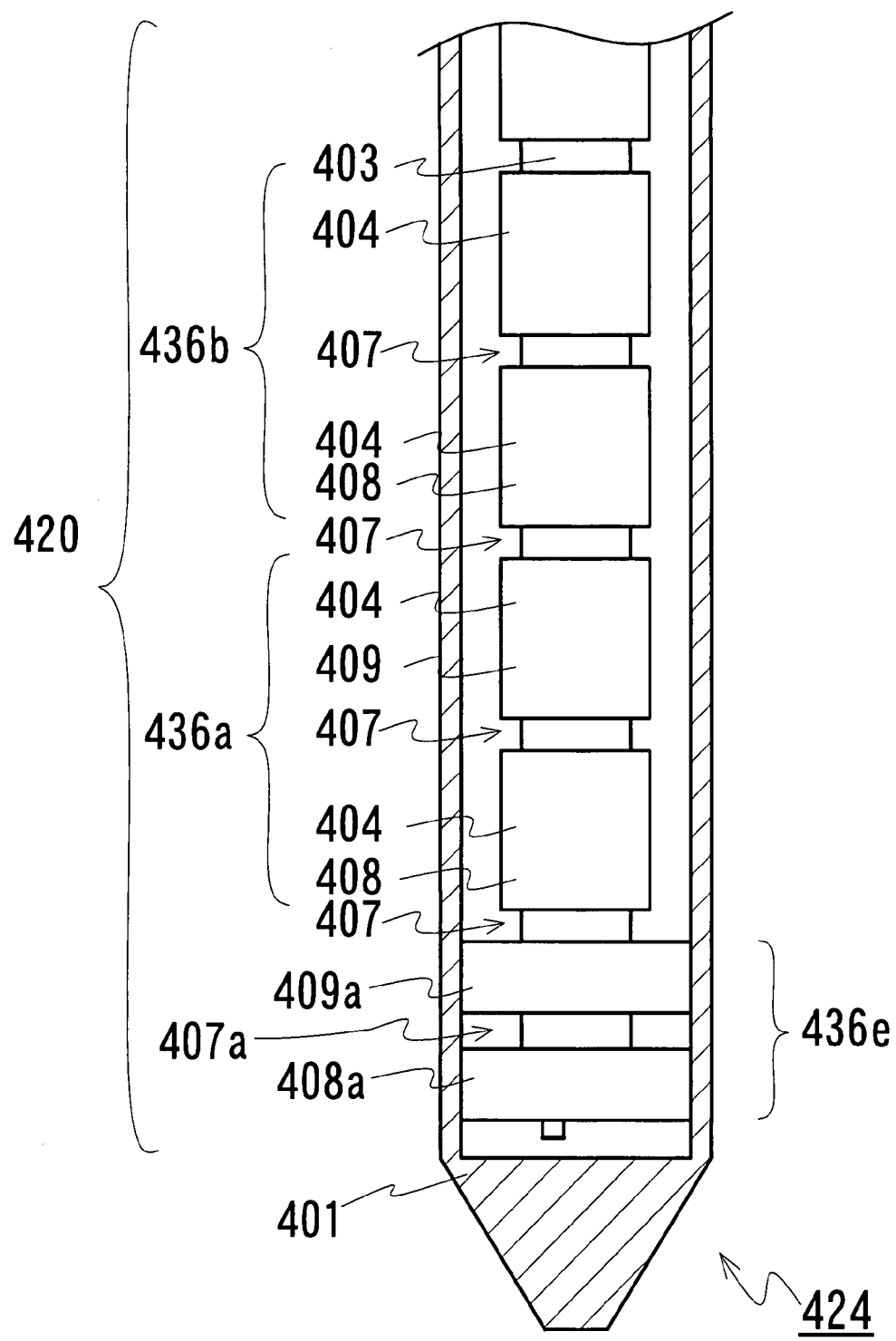
FIGS. 86 to 90 are the cut views of the modification of the TTDPs regarding the third object of the present invention.
Figure 87:
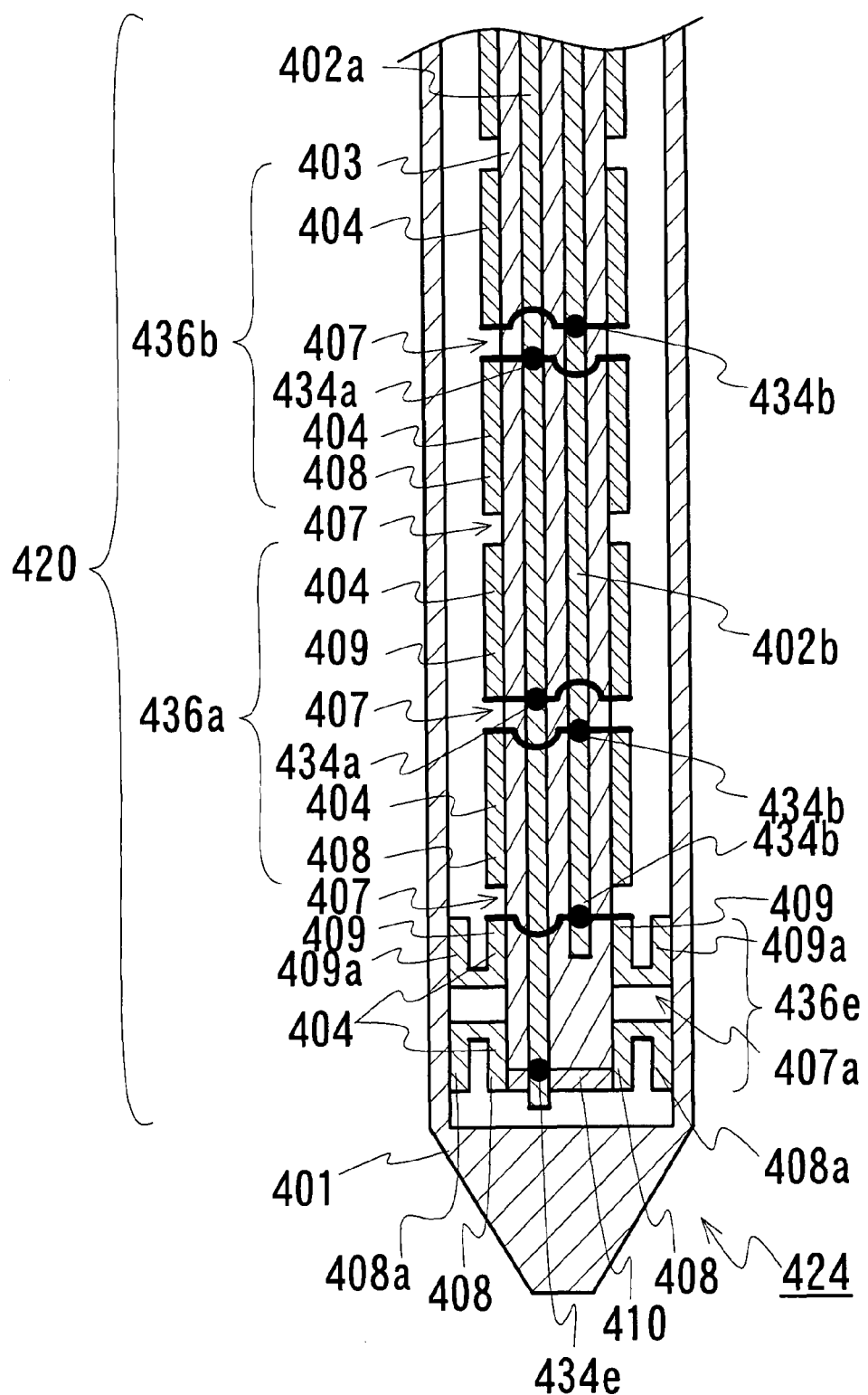

FIGS. 85 to 87 show another set of preferred embodiments regarding the third object of the present invention. The antenna assembly 420 includes dipole antennas 436a and 436b both consisting of the first electrodes 408 and the second electrodes 409 and the other electrode pair 436e wherein the electrodes are folded in the longitudinal direction with reverse orientation each other. The first and second electrodes 408 and 409 are formed from the outer conductor 404. The other outer electrodes 408a and 409a are electrically connected to the first and second electrodes 408 and 409, respectively so that these electrodes are in a shape of being folded in the cut-views as illustrated inn FIG. 85 and 87. The configuration of dipole antennas 436a and 436b shown in FIGS. 85 and 87 is same as that of dipole antennas 436a and 436b as illustrated in FIG. 24 and electrode pairs 436b and 436c as FIG. 26, respectively. The power supply points 434b and 434e are determined in a rule such that the electrically isolating gap 407a is the point where relatively large RF power, in comparison to the other place on the electrodes of the antenna assembly 420, radiates to the outer tissue region where the TTDP 424 is inserted. The electrode pair 436e works as a dipole antenna. The electrically isolating gap 407a is formed by partly stripping the outer conductor 404 of the coupler-line 435 and two folded electrodes 408a and 409a are formed on the outer conductor 404 which is formed partly into the first electrode 408 and partly into the second electrode 409, respectively. The electrical connection between the second central conductor 402b and the folded electrode 409a has the same configuration as that of the second conductor 402a and the outer conductor 404 as illustrated in FIGS. 73-79. The electric connection between the first central conductor 402a and another folded electrode 408a is made via an electrical conducting disc 410 similar to the electrical conducting disc 210 as illustrated in FIG. 13. FIG. 86 illustrates a front view of the antenna assembly. The first electrodes 408, the second electrodes 409 and the central conductors are electrically connected in the coupler-line 435 (not particularly shown in FIGS. 85 to 87) as illustrated in FIG. 85 and FIG. 87 which illustrates the different electrical connection between the first and the second central conductors 402a and 402b and the first and the second electrodes 408 and 409. The pairs of the first electrodes 408 and the second electrodes 409 forms dipole antennas as 436a and 436b and another pair of the folded electrodes 409a and 408a do a dipole antenna 436d. The TTDP 424 comprises the antenna assembly 420 consisting of the dipole antennas 436a, 436b and 426d and a sheath 401, which is made of an insulating material.

Figure 88:
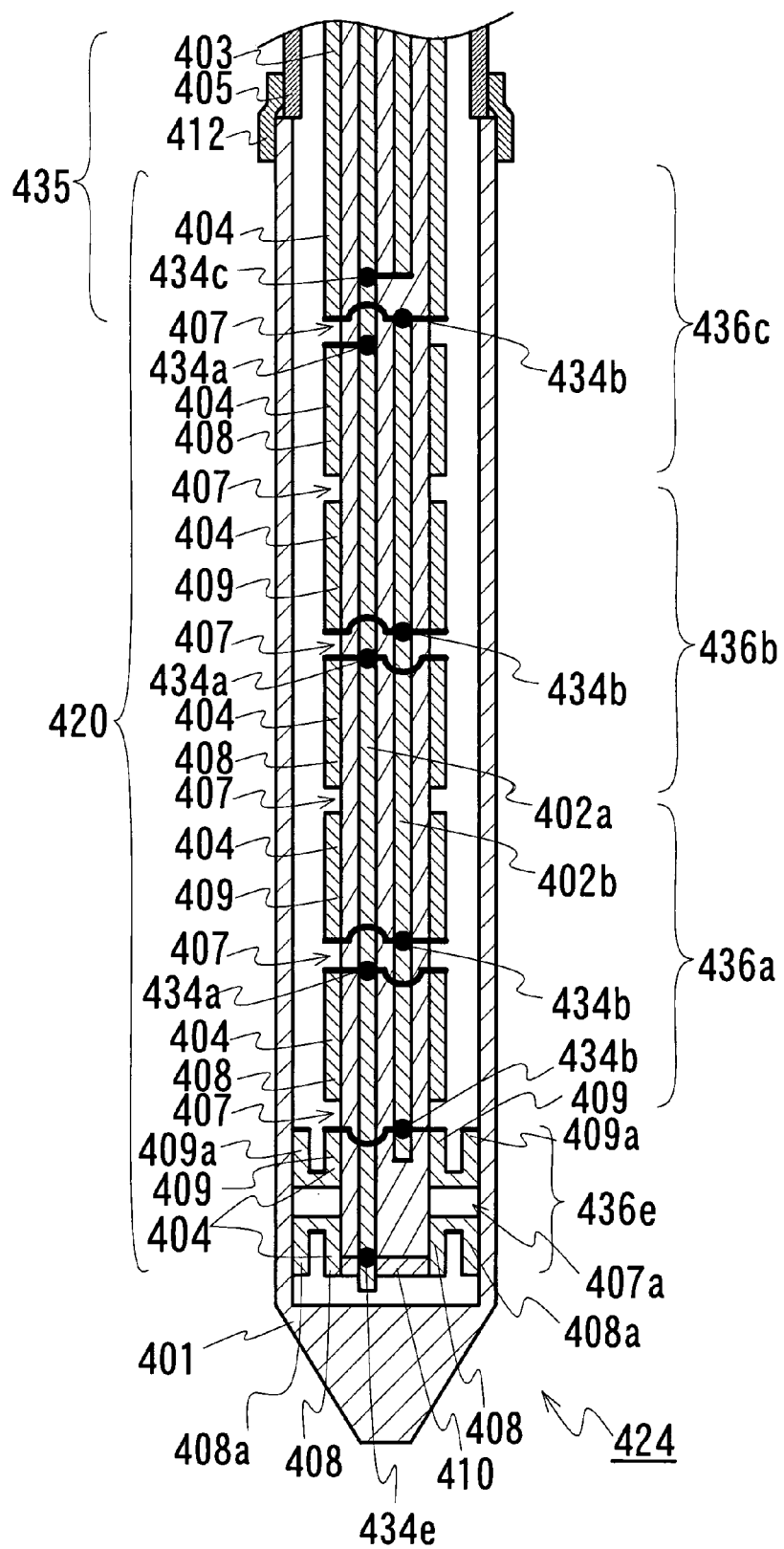
Figure 89:
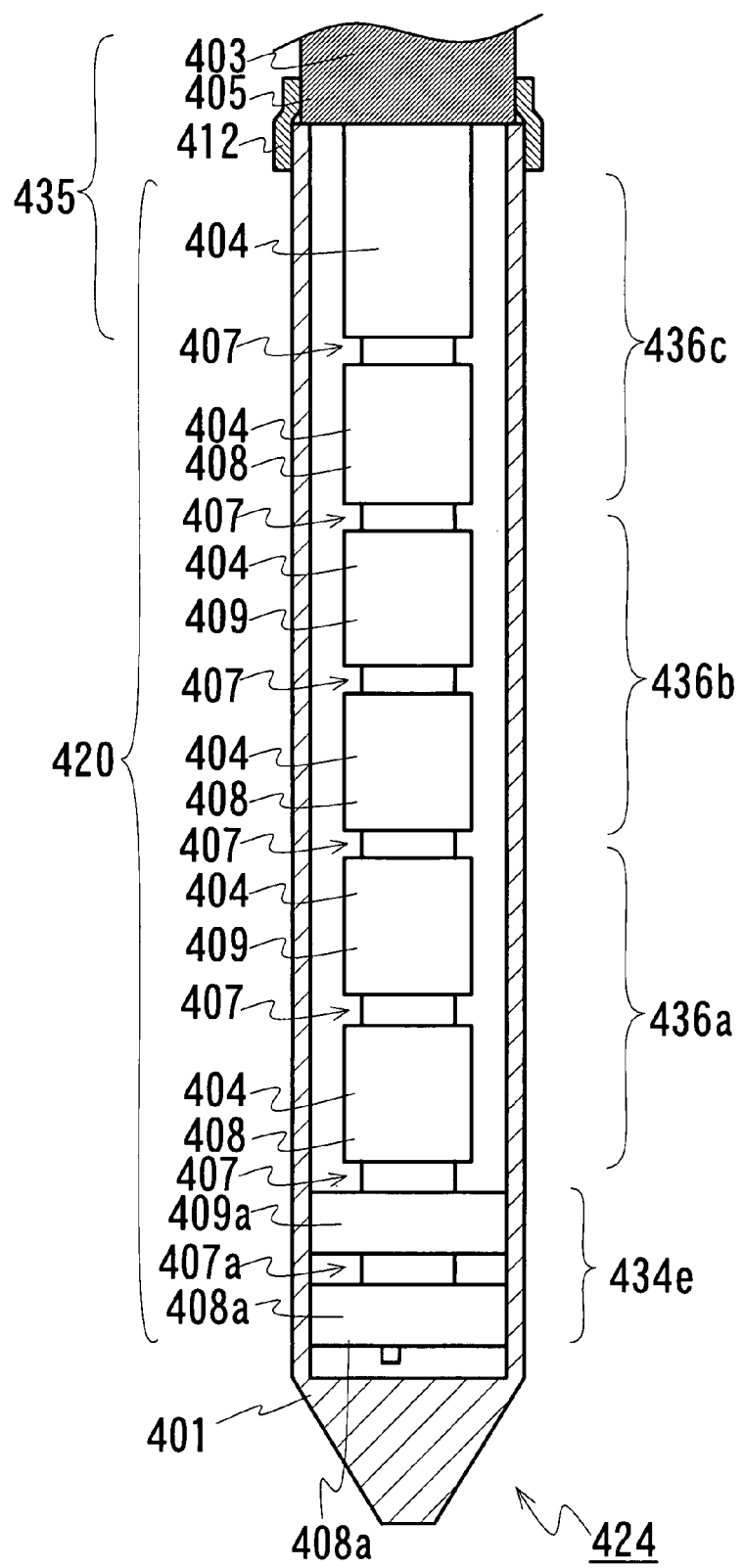
Figure 90:
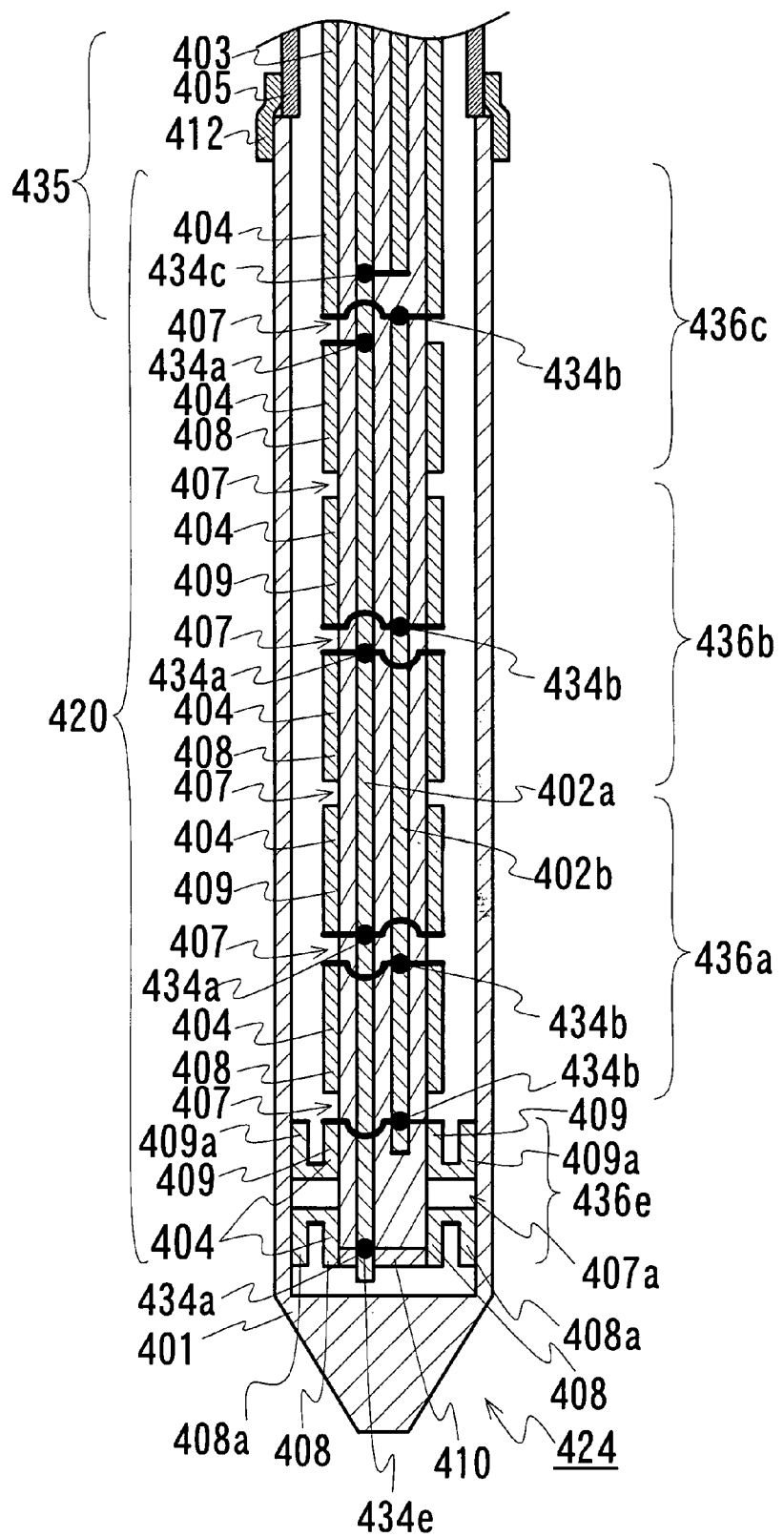

FIGS. 88-90 show another set of preferred embodiments regarding the third object of the present invention. A couple-line 435 connected to an RF power source works as a RF power transmission cable to which the two central conductors 402a and 402b are electrically connected. The antenna assembly 420 consisting of a plural pair of dipole antennas 536a, 536b, 536c and 536d has the same configuration of electrical connection between the first and second electrodes 408 and 409 and the central conductors 402a and 402b as that of those illustrated in FIG. 24 and 26. On the other hand, couple-line 435, which works as a power transmission cables, as illustrated in FIGS. 70 and 72 (both are cross sections of this set of preferred embodiments) and FIG. 71 (a front view of this set of preferred embodiments) has outer jacket 405 thereof. FIG. 89 is a front view of this set of preferred embodiment, as well. Additional shrinkable tube 412 is added to make airtight between the jacket 405 and the sheath 401. This airtight configuration suppresses out-coming germs from the antenna assembly 420 in the operation. Whichever electrical connection between the first and the second electrodes 408 and 409 and the central conductors 402a and 402b can be possible as that illustrated in FIG. 88 or FIG. 90 that is same as illustrated in FIG. 70 or FIG. 72. The shrinkable tube 412 can be thermal shrinkable one and the outer jacket 405 can be non-shrinkable one.

The sheath 401 of the third object of the present invention can be, instead of a single-body structure as illustrated in FIG. 24 et. al., same as the sheath 230 used for the TTDP 224, such as the sheath comprising a sharp edge head 293 which consists of a sharp edge portion and a thermal.

Figure 91:
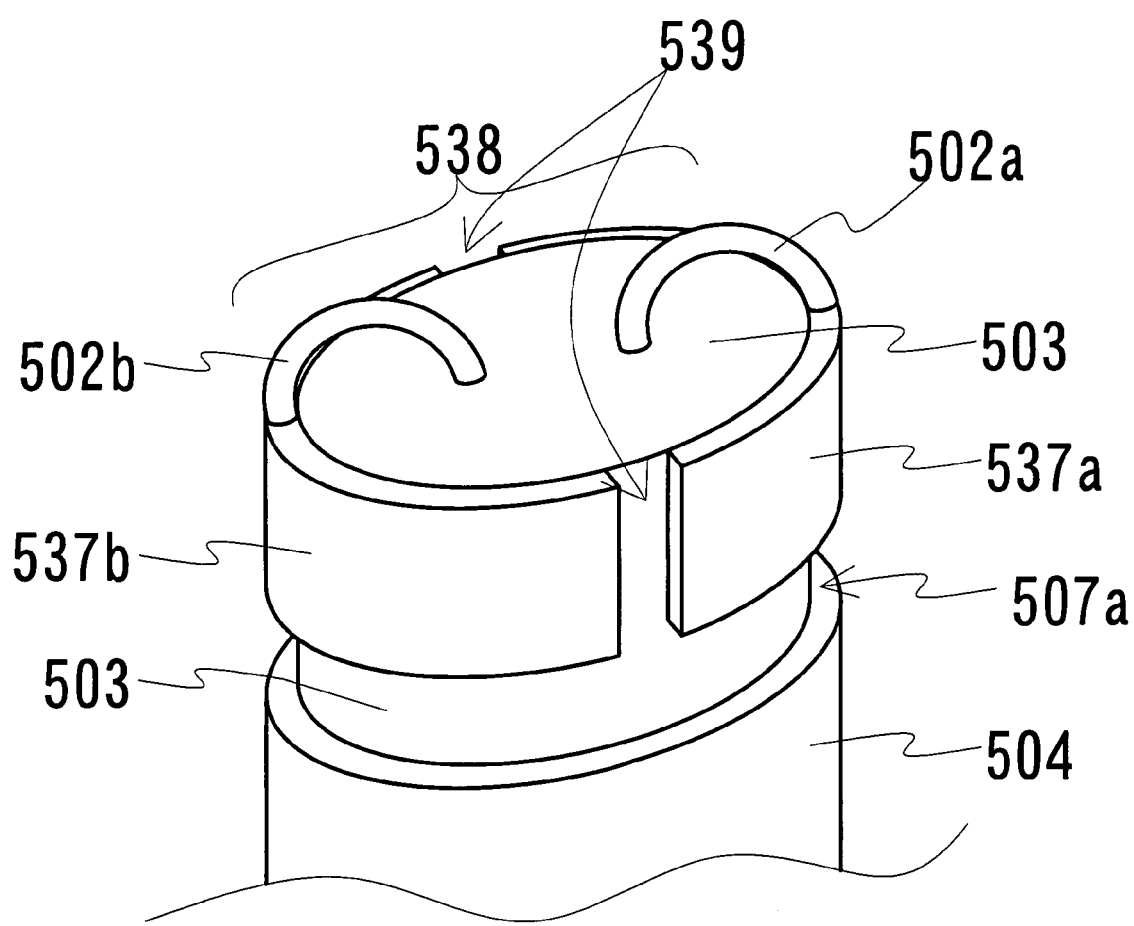
FIG. 91 is the perspective view of the additional dipole antenna of the TTDP regarding the fourth object of the present invention.

FIGS. 27 to 29 show a set of preferred embodiments regarding the fourth object of the present invention. The antenna assembly 520 includes an electrode pair 537a and 537b constructing a front dipole antenna 538 at the front tip of antenna assembly 520. The central conductors 502a and 502b are connected to the electrodes 537a and 537b, respectively. The electrodes 537a and 537b have two electrically isolation gaps 507a and 539 so that each electrode is isolated each other. The RF power is radiated from the gaps 539 to outside. The gaps are determined in a rule such that the electrically isolating gap 507a and gaps 539 are formed to the same impedance of the dipole antennas 536a, 536b and 536c. Then the RF power radiates to the outer tissue regions through the dipole antennas 536a, 536b and 536c such that a part of the RF power horizontally radiates to the peripherally cylindrical tissue region and through the front dipole antenna 538 such that the other part of the RF power vertically radiates to the front tissue region where the TTDP 524 is inserted. FIG. 91 illustrates a zoom-in view of the front dipole antenna 538. The electrically isolating gap 507a is formed by partly stripping the outer conductor 504 of the coupler-line 535. A pair of two half-annular electrodes 537a and 537b are formed in a form such that they surround the dielectric insulator 503. Two electrically isolating gaps 539 are formed between the pair of the two half-annular electrodes 537a and 537b. The central conductors 502a and 502b are electrically connected to the half-annular electrodes 537a and 537b, respectively. The length of the half-annular electrode s 537a and 537b along the axis of the coupler-line 535 is determined such that the effective length of the central conductors 502a and 502b from the nearest power supply points 534a and 534b to the gaps 539 is a half-wave length of the RF wave. Then the largest current is induced at the gap 539 and a certain level of current induced in the gap 507a so that other RF power is radiated from the gap 539 and the gap 507a. The pair of the half-annular electrodes 537a and 537b is formed to a dipole antenna particularly a front dipole antenna 538. The radiation from the gaps 539 especially reduces the lighthouse effect. FIG. 28 illustrates a front view of the antenna assembly with a cut view of the single-body sheath 501. The first electrodes 508, the second electrodes 509 and the central conductors 502a and 502b are electrically connected in the coupler-line 535 as illustrated in FIG. 27 and FIG. 29 which illustrates the different electrical connection between the first and the second central conductors 502a and 502b and the first and the second electrodes 508 and 509. The pairs of the first electrodes 508 and the second electrodes 509 are formed to dipole antennas as 536a, 536b and 536c and a pair of half-annular electrodes 537a and 537b are formed to a dipole antenna 538. The TTDP 524 comprises the antenna assembly 520 consisting of the dipole antennas 536a, 536b, 536c, and 538 and a single-body sheath 501 which is made of an insulating material such as sapphire.

Figure 92:
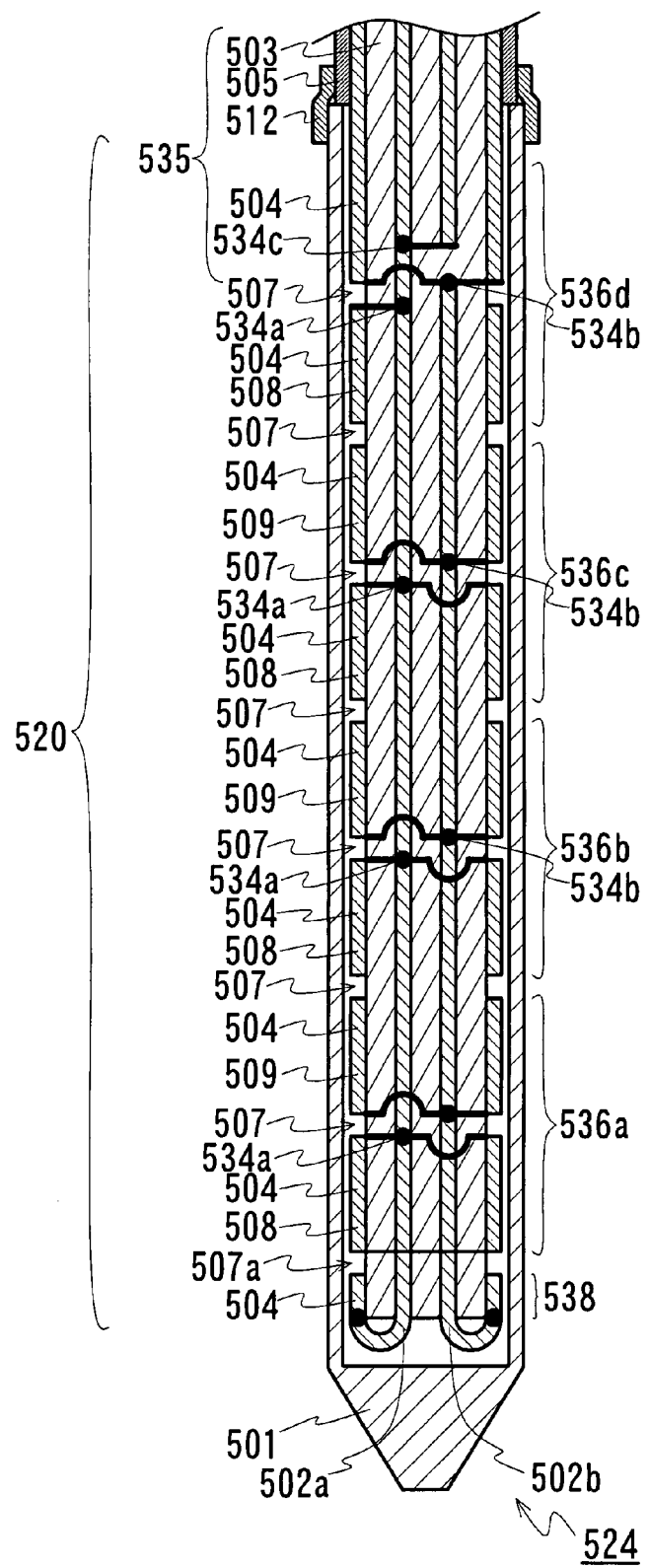
FIGS. 92 to 97 are the cut views of the TTDPs regarding the fourth object of the present invention.
Figure 93:
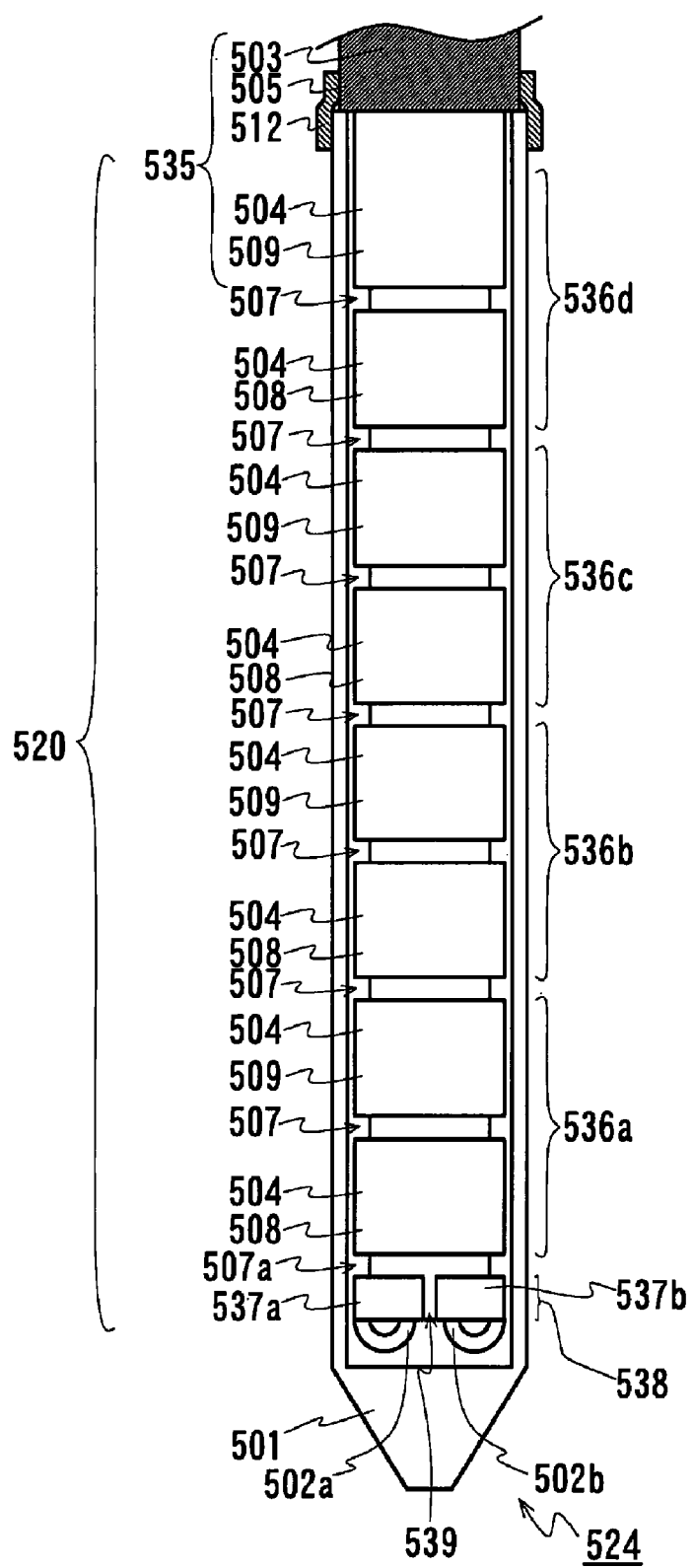
Figure 94:
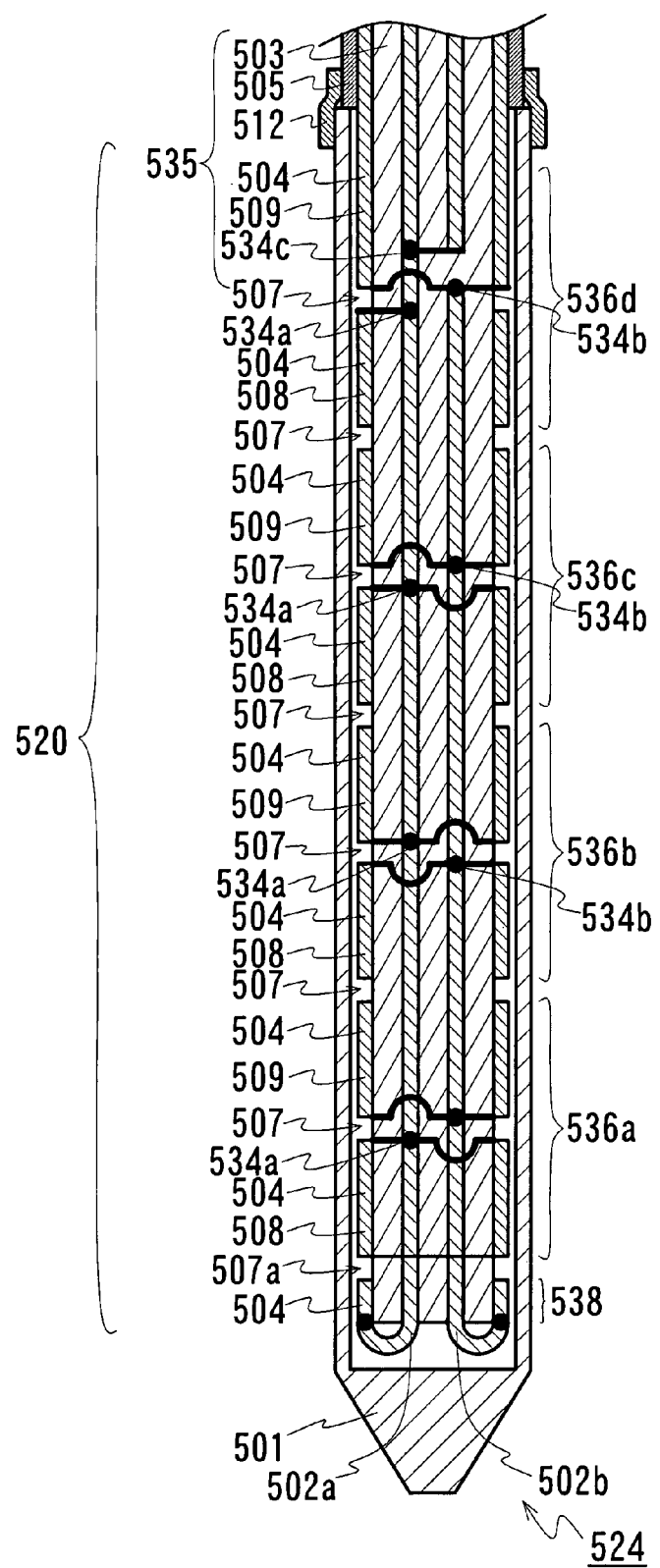

FIGS. 92 to 94 show another set of preferred embodiments regarding the fourth object of the present invention. A couple-line 535 connected to an RF power source (not shown in these figures) works as a RF power transmission cable to which the two central conductors 502a and 502b are electrically connected. The antenna assembly 520 consisting of a plural pair of dipole antennas has the same configuration of electrical connection between the first and second electrodes and the central conductors 502a and 502b as that of those illustrated in FIGS. 27 and 29. On the other hand, the couple-line 535, which works as a power transmission cables, as illustrated in FIGS. 92 and 94 (both are cross sections of this set of preferred embodiments) and FIG. 93 (a front view of this set of preferred embodiments with a cut view of a single-body sheath 501) has outer jacket 505 thereof. Additional shrinkable tube 512 is added to make airtight between the jacket 505 and the sheath 501. This airtight configuration suppresses out-coming germs from the antenna assembly 520 in the operation. Whichever electrical connection between the first and the second electrodes 508 and 509 and the central conductors 502a and 502b can be possible as that illustrated in FIG. 92 or FIG. 94 that is same as illustrated in FIG. 70 or FIG. 72. The shrinkable tube 512 can be thermal shrinkable one and the outer jacket 505 can be non-shrinkable one.

Figure 95:
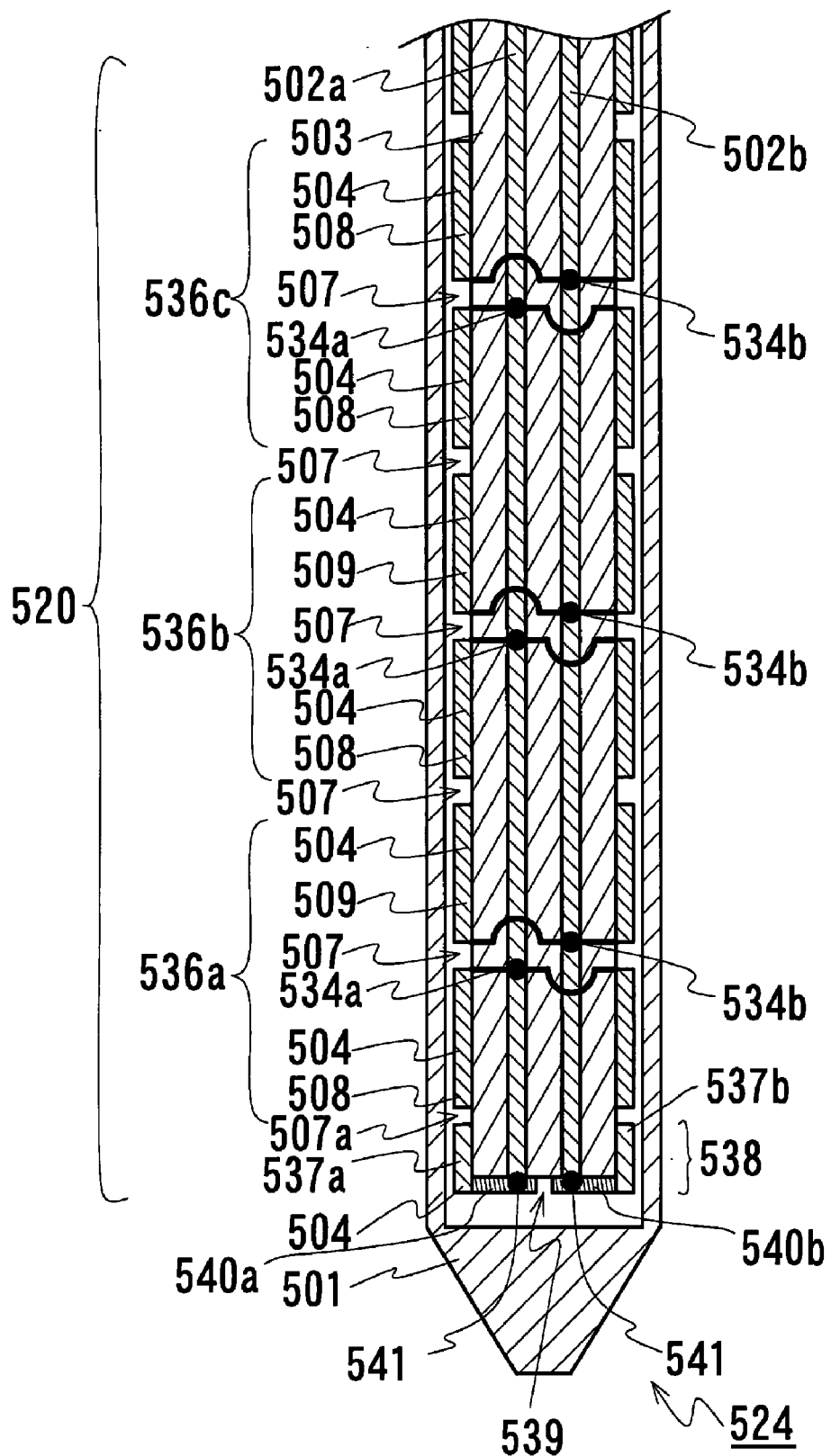
Figure 96:
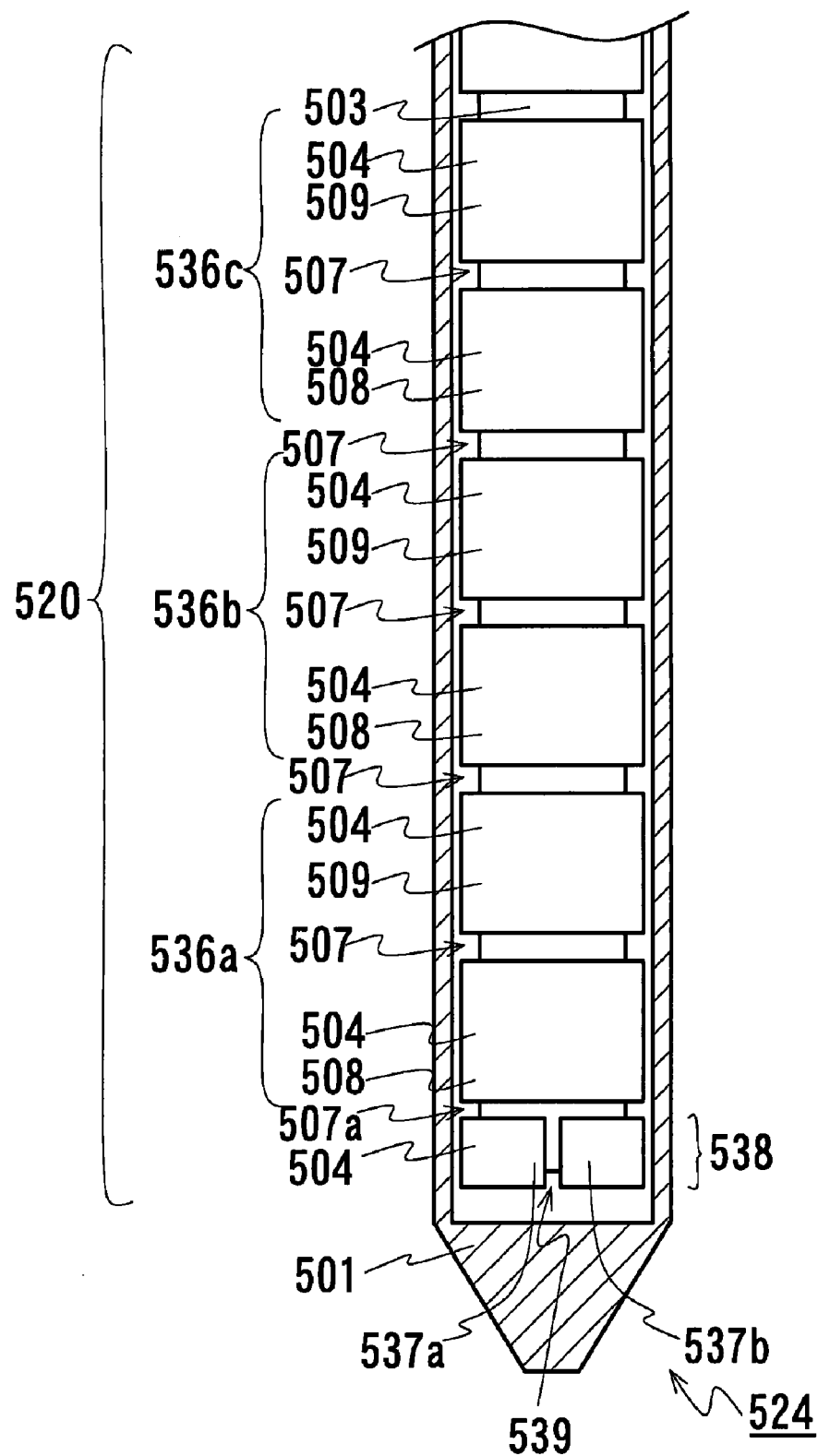
Figure 97:
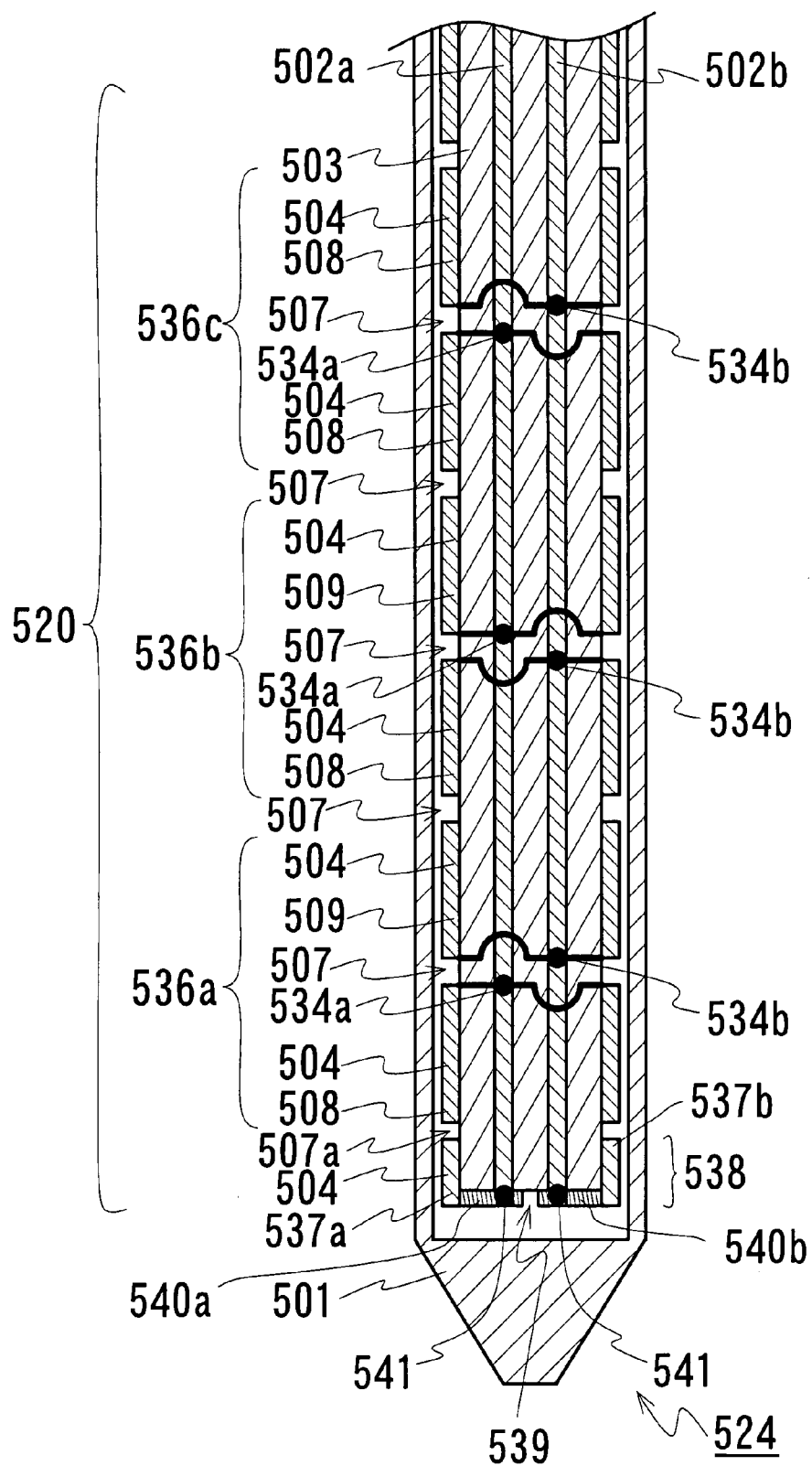
Figure 98:
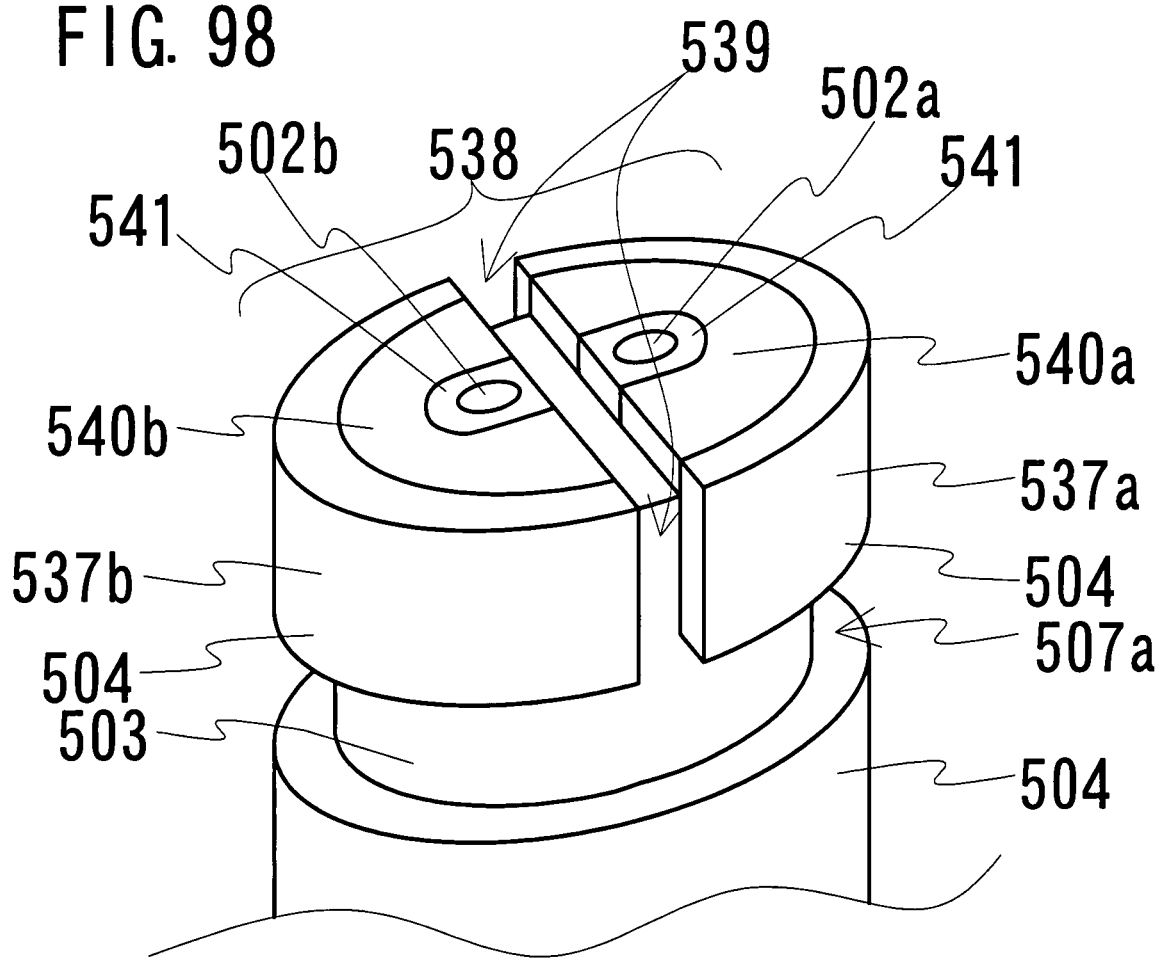
FIG. 98 is the perspective view of the additional dipole antenna of the TTDP regarding the fourth object of the present invention.

FIG. 95 to FIG. 97 show another set of preferred embodiments regarding the fourth object of the present invention. The antenna assembly 520 includes an electrode pair 537a and 537b constructing a front dipole antenna 538 at the front tip of antenna assembly 520. The central conductors 502a and 502b are connected to the electrodes 537a and 537b, respectively. The electrodes 537a and 537b have a structure of a half-cut cup as illustrated in FIG. 98. They comprise a front dipole antenna 538. The electrodes 537a and 537b having a shape of two half-annular are formed in a form such that they surround the dielectric insulator 503. The central conductors 502a and 502b are, respectively, electrically connected to the electrodes 537a and 537b through electrically conductive tops 540a and 540b and buried soldering 541. The electrodes 537a and 537b have two electrically isolation gaps 539 so that each electrode is isolated each other. The RF power is radiated from the gaps to outside. The gap 539 is determined in a rule such that the electrically isolating gap 507a and gaps 539 are formed to the same impedance of the dipole antennas 536a, 536b, 536c and 536d. Then the RF power radiates to the outer tissue regions through the dipole antenna 538 such that a part of the RF power horizontally radiates to the peripherally cylindrical tissue region and the other part of the RF power vertically to the front tissue region where the TTDP 524 is inserted. FIG. 98 illustrates a zoom-in view of the front dipole antenna 538. The electrically isolating gap 507a is formed by partly stripping the outer conductor 504 of the coupler-line 533. The length of the electrodes 537a and 537b along the axis of the coupler-line 535 is determined such that the effective length of the central conductors 502a and 502b from the nearest power supply points 534a and 534b to the gaps 539 is a half-wave length of the RF wave of the RF power. Then the largest current induced at the gaps 539 and a certain level of current induced in the gap 507a are obtained so that another RF power is radiated from the gaps 539 and the gap 507a than that radiated form gaps 507. The radiation from the gap 539 especially reduces the lighthouse effect. FIG. 96 illustrates a front view of the antenna assembly with a cur view of a single-body sheath. The first electrodes 508, the second electrodes 509 and the central conductors 502a and 502b are electrically connected in the coupler-line 535 as illustrated in FIG. 95 and FIG. 97 which illustrate the different electrical connection between the first and the second central conductors 502a and 502b and the first and the second electrodes 508 and 509, respectively. The pairs of the first electrodes 508 and the second electrodes 509 as 536a, 536b, 536c, and 536d comprise dipole antennas and a pair of half-annular electrodes 537a and 537b does. The TTDP 524 comprises the antenna assembly 520 consisting of the dipole antennas 536a, 536b, 536c, 536d and 538 and a sheath 501 which is made of an insulating material such as sapphire.

Figure 99:
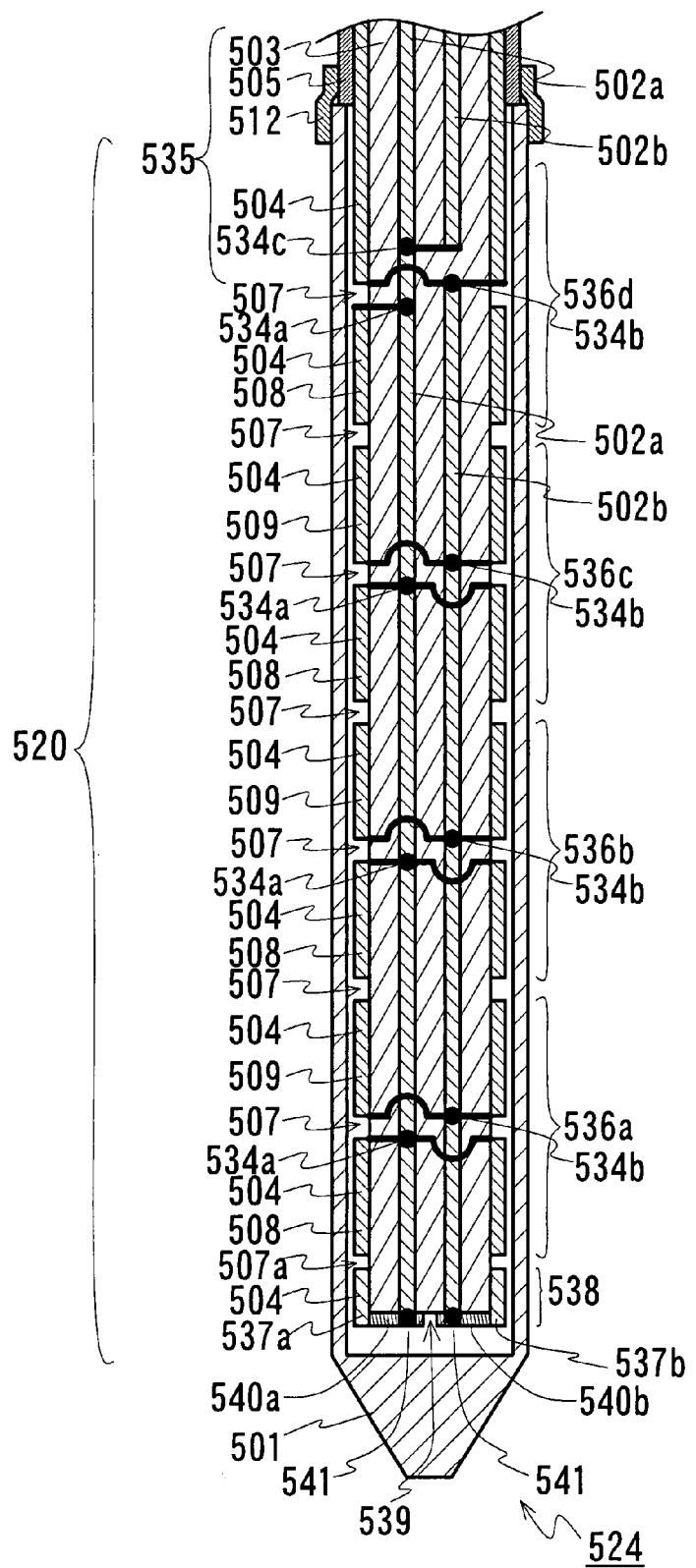
FIG. 99 to 101 are the cut views of the TTDPs regarding the fourth object of the present invention.
Figure 100:
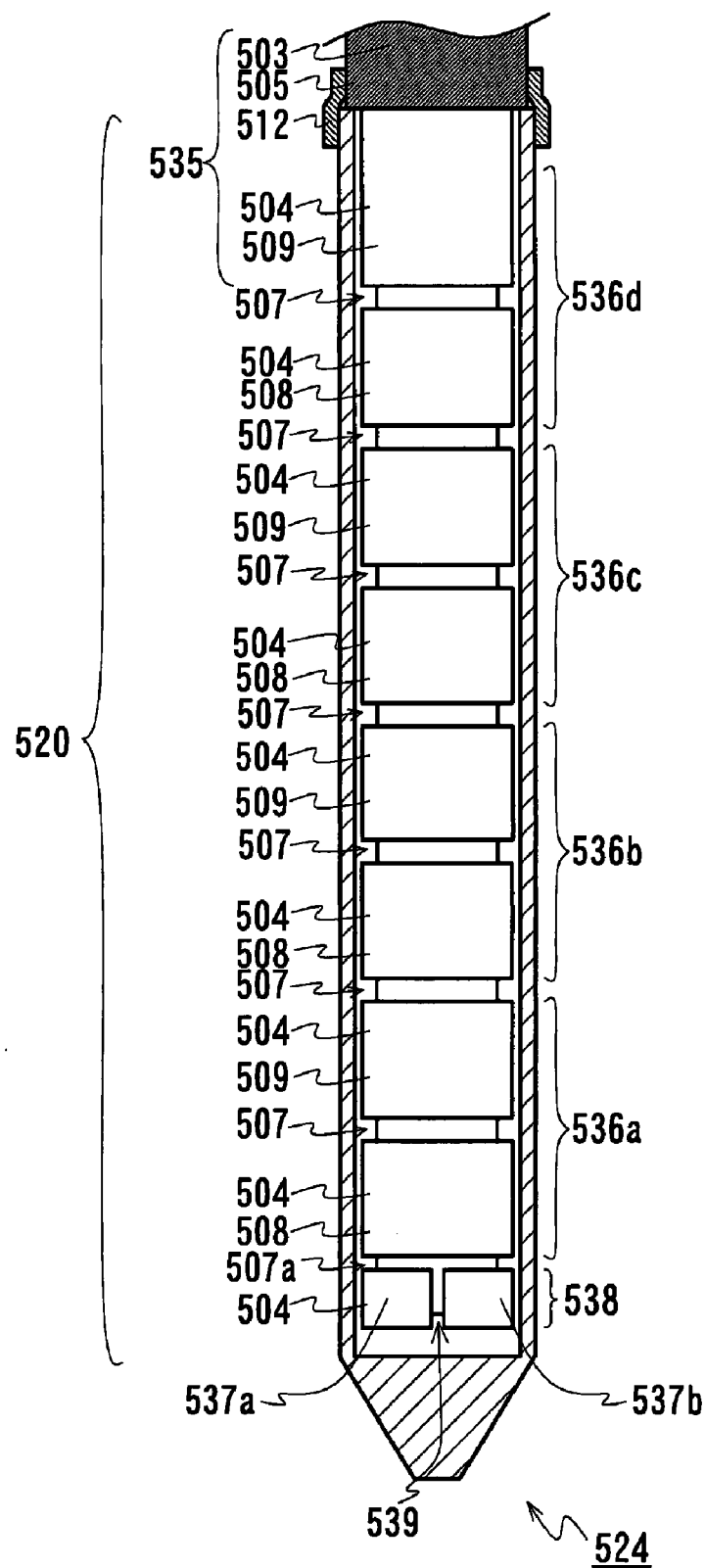
Figure 101:
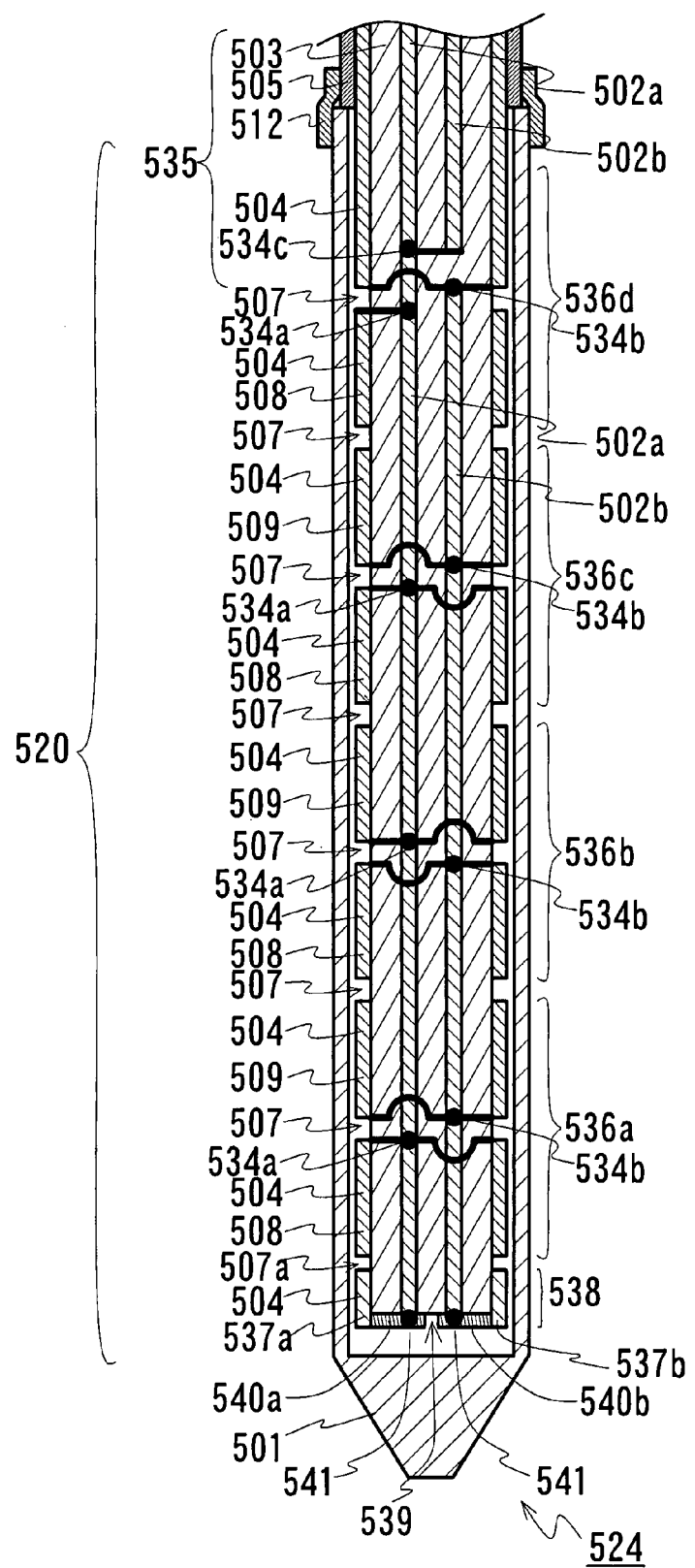

FIGS. 99-101 show another set of preferred embodiments regarding the fourth object of the present invention. A couple-line 535 which works as a RF power transmission cable is connected to an RF power source to which the two central conductors 502a and 502b are electrically connected. The antenna assembly 520 consisting of a plural pair of dipole antennas has the same configuration of electrical connection between the first and second electrodes and the central conductors 502a and 502b as that of those illustrated in FIG. 70 and 72. On the other hand, the couple-line 535, which works as a power transmission cable, as illustrated in FIGS. 70 and 72 (both are cross sections of this set of preferred embodiments) and FIG. 71 (a front view of this set of preferred embodiments with a cut view of a single-body sheath 501) has outer jacket 505 thereof. Additional shrinkable tube 512 is added to make airtight between the jacket 505 and the sheath 501. This airtight configuration suppresses out-coming germs from the Antenna assembly in the operation. Whichever electrical connection between the first and the second electrodes and the central conductors can be possible as that illustrated in FIG. 88 or FIG. 90 that is same as illustrated in FIG. 70 or FIG. 72. The shrinkable tube 512 can be thermal shrinkable one and the outer jacket 505 can be non-shrinkable one.

Figure 102:
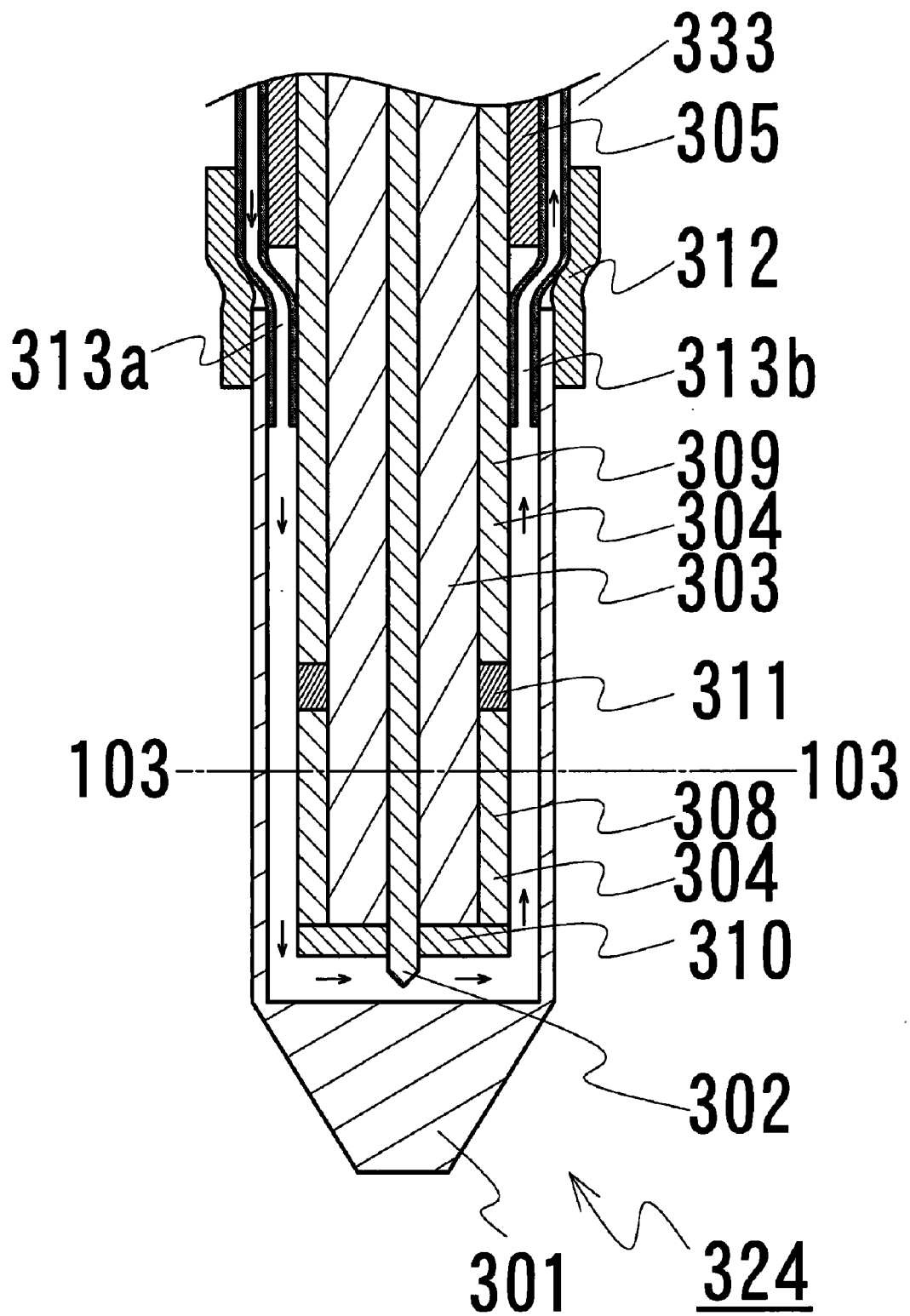
FIG. 102 is the cut view of the TTDP regarding the first object of the present invention that equips a circulating structure of cooling liquid therein.
Figure 103:
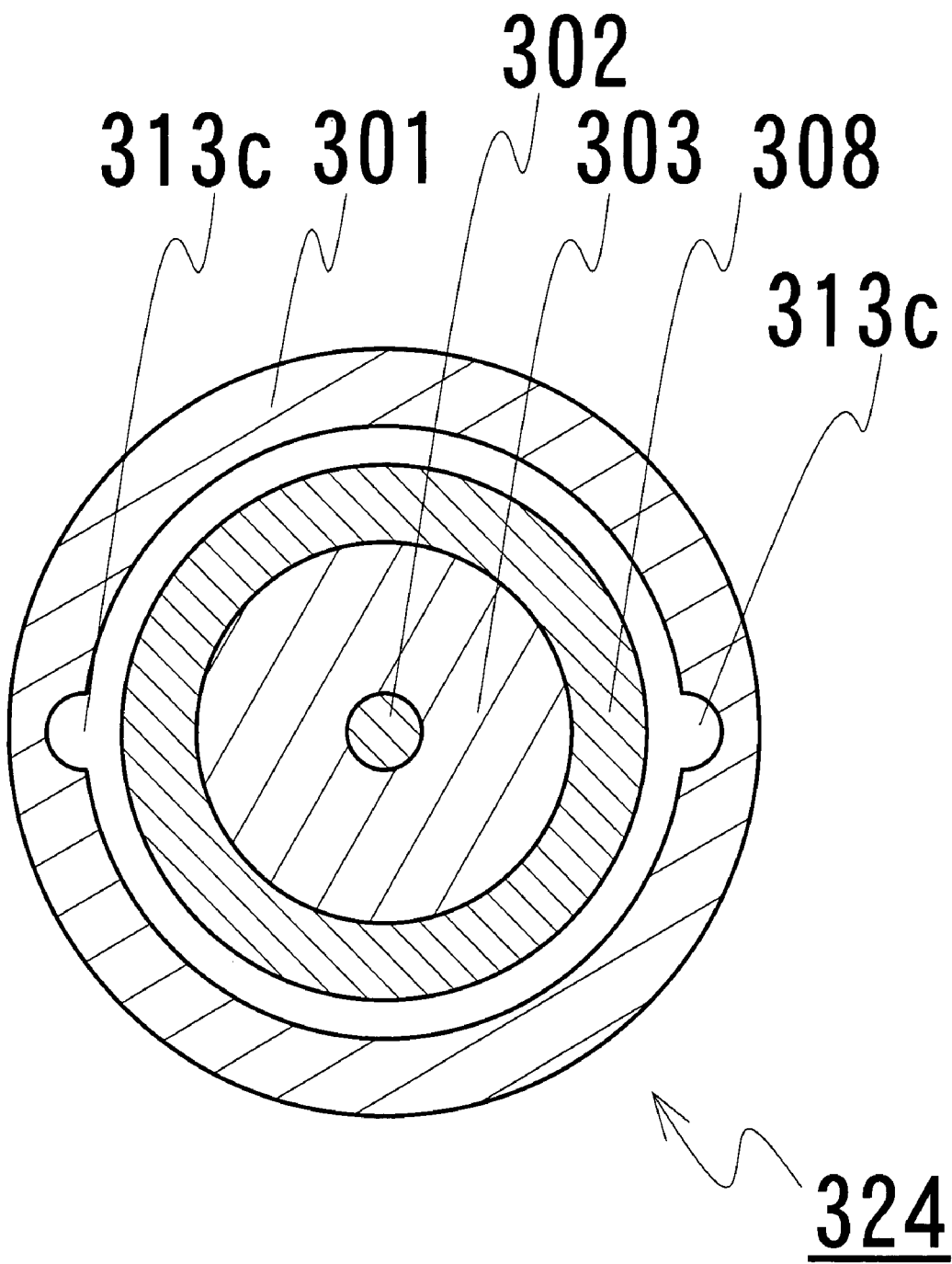
FIG. 103 is a cross-sectional view of the TTDP regarding the second object of the present invention that equips a circulating structure of cooling liquid therein.

When the insulating case of the TTDPs comprises a single-body sheath that is made of sapphire, temperature control of the sapphire can be easily done by circulating cooling liquid in the sapphire. FIGS. 102 and 103 illustrate further preferred embodiments regarding the second object of the present invention. FIG. 103 illustrates a cut view of the TTDP 324 at the line 103. The TTDP 324 has a tube 313a to let cooling liquid flow into and flow out from the inside of TTDP 324, especially a spatial gap between the inner surface of the single-body sheath 301 and the antenna assembly 320. Slabs 313c are made on the inner surface of the single-body sheath 301 for the purpose of the channels that allow the liquid flow to easily flow inside of the TTDP 324. The surface temperature of the sheath 301 can be made low even the pathological tissues are heated by the RF radiation by using the TTDP 324. Therefore the temperature of the pathological tissues can homogenously be controlled to be heated not much more than the temperature that induces the pathological tissues to be necrotic like as shown in FIG. 30. Therefore the pathological tissues to which the TTDP 324 is inserted are less coagulated so that the necrosis of such tissues is not suppressed and the TTDP 324 is not stuck in the tissues. This temperature control can serve the surgeon to use high power RF but the therapeutic effects such as necrosis of the tissues and no sticking of TTDP 324 to the tissues can provide the capability of heating wider region of the pathological tissues. The same cooling means such as tubes 313a and 313b and slabs 313c in single sapphire sheath 301 can be applied to the other TTDPs 224 and the TTDPs 424 and TTDPs 524 which are the second, third and fourth objects of the present invention, respectively. The particular embodiments that can be obtained from the second, third and fourth objects of the present inventions after being modified to have such cooling means are not illustrated since the modification to add such tubes 313a and 313b and the slabs 313c that allow the cooling liquid flowing inside the single-body sheaths 301, 401 and 501 are easily understood. The TTDPs 324 as illustrated in FIGS. 56, 57, 58, 60, and 61, TTDPs 424 as illustrated in FIGS. 70, 72, 88, and 90 and TTDPs 524 as illustrated in FIGS. 92, 94, 99 and 101 can be modified to have circulation capability of cooling flow.

The sheath 501 of the fourth object of the present invention can be, instead of a single-body structure as illustrated in FIG. 92 et. al., same as the sheath 230 used for the TTDP 224, such as the sheath comprising a sharp edge head 293 which consists of a sharp edge portion and a thermal.

Figure 104:
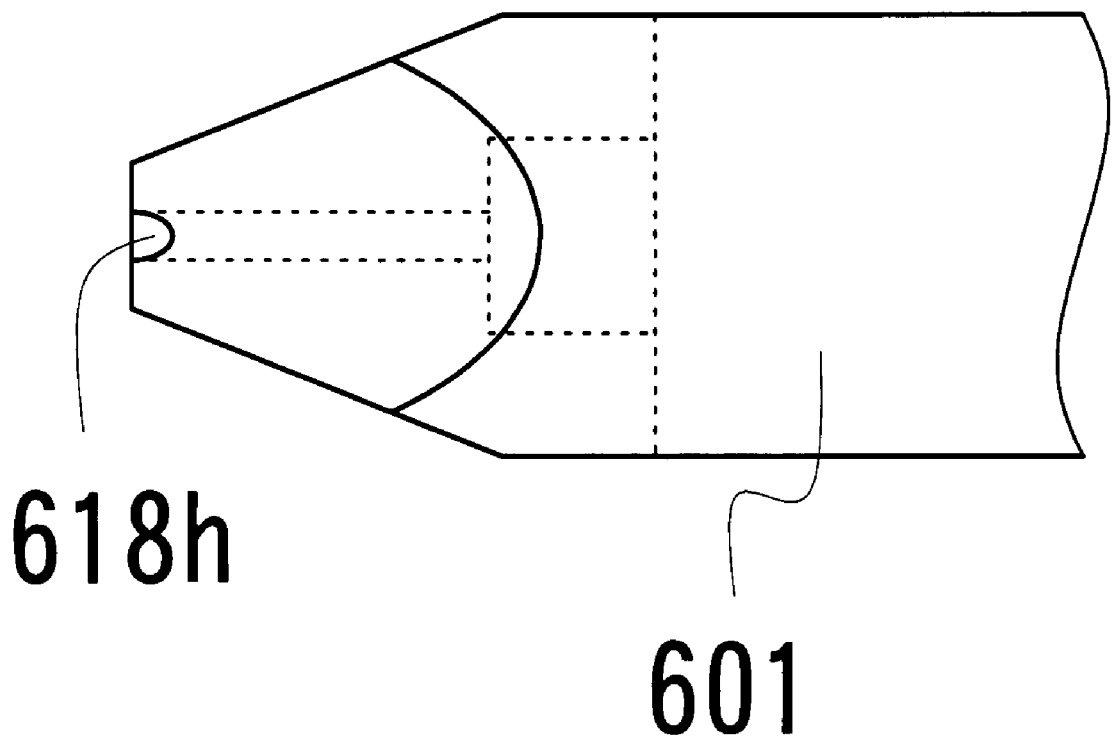
FIGS. 104 and 105 are the views of the head portion of the TTDPs regarding the fifth object of the present invention.
Figure 105:
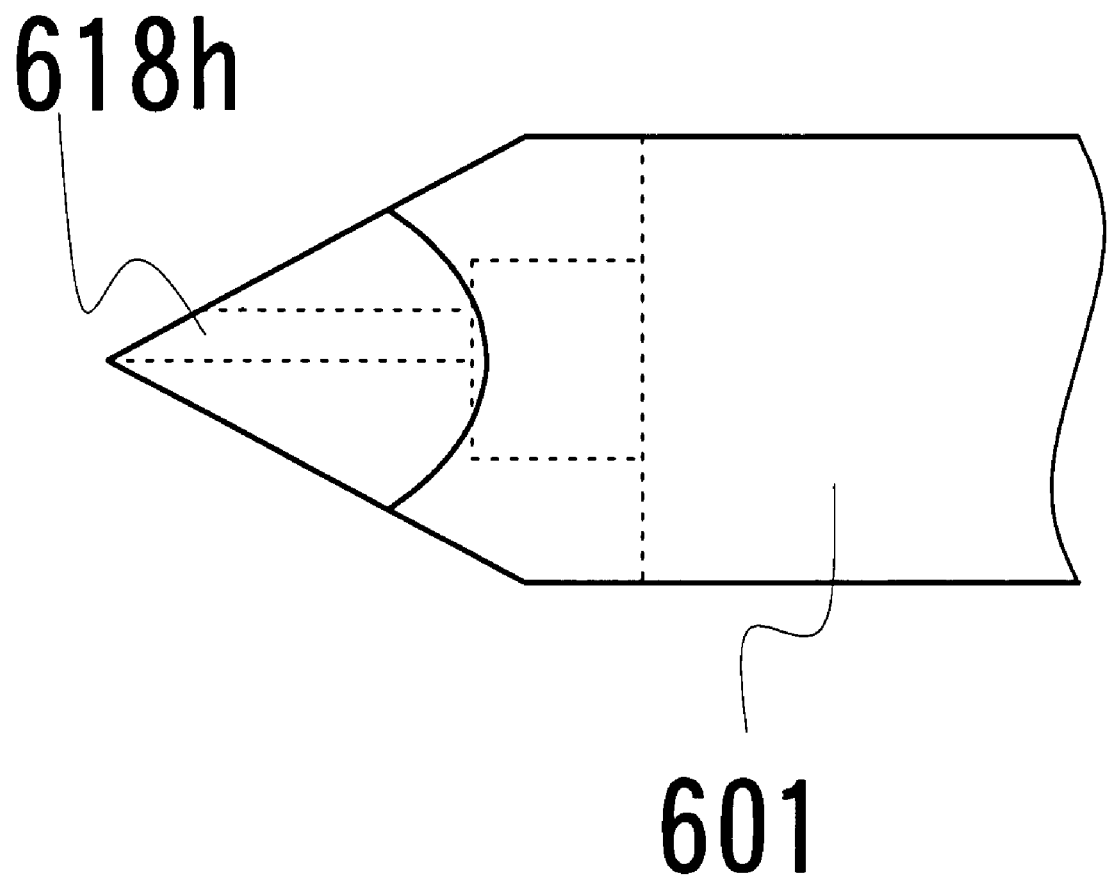
Figure 106:
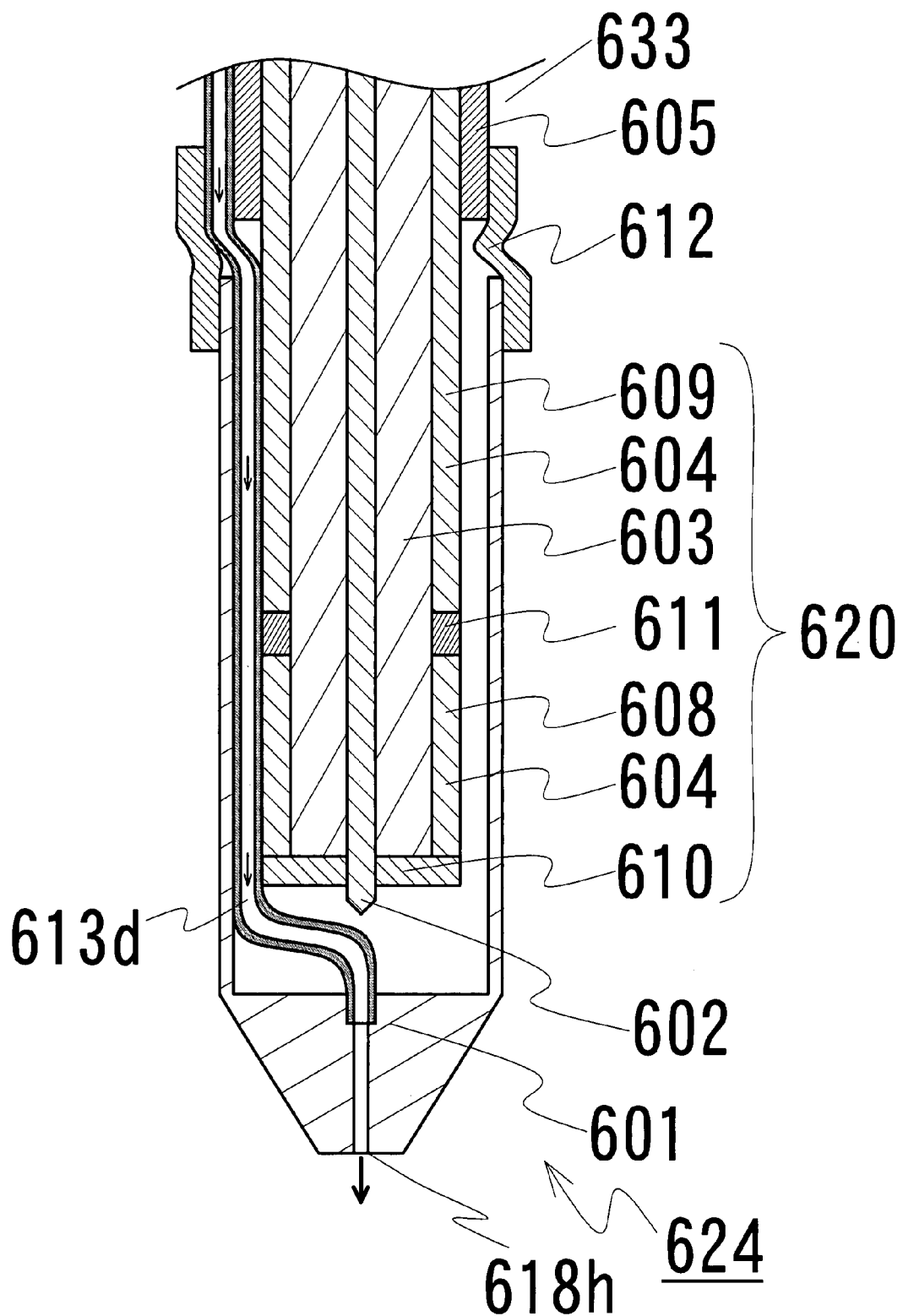
FIGS. 106 to 110 are the cut views of the TTDPs regarding the fifth object of the present invention.
Figure 107:
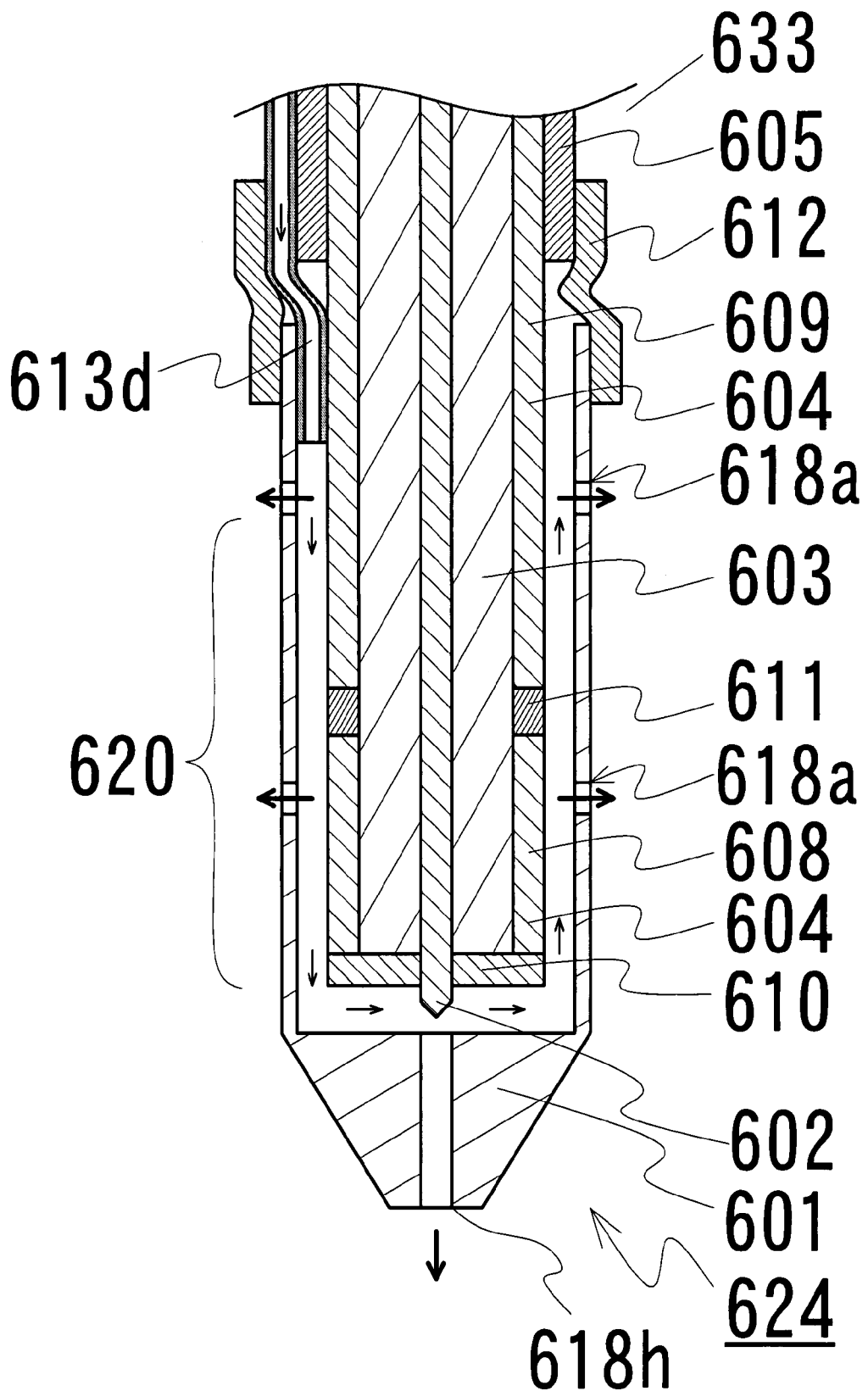

FIGS. 104 to 107 show a set of preferred embodiments regarding the fifth object of the present invention, particularly TTDPs 624 that have sapphire heads 693 or single-body sheaths 301 which are made of sapphire can equip flow channels to allow the drugs delivery therethrough. FIGS. 104 and 105 show a cutting edge of the single-body sheath 301 which has a hole that opens from the sharp edge through the edge portion thereof. The hole is called a drug injecting side hole 618h that allows injection of the drugs to the pathological tissues to which the TTDPs 624 are inserted. FIG. 106 illustrates a TTDP 624 that has a drug delivery capability. The flow channel comprises a tube 613d installed in the gap between the single-body sheath 601 and the antenna assembly 620 as well as the drug injecting side hole 618h. The other parts of structure is same as TTDP 324 as illustrated in FIG. 57. The drugs are carried through a tube 613d which works as a flow channel and injected to the pathological tissues by supplying from a syringe means such as a syringe pump that contains the drugs. FIG. 107 illustrates a TTDP 624 that has another type of drug delivery capability, especially drugs are horizontally injected into the pathological tissues. Holes are additionally formed in the cylindrical surface of the single-body sheath 601 from the inside to the outside as well as the drug injecting side hole 618h formed in the cutting edge of the single-body sheath 601. The holes are called drug injecting side holes 618a that allows the drugs to flow out from the inside of the single-body sheath to the tissues to which the TTDP 624 is inserted. The tube 613d is short so that the drugs can flow out through the drug injecting side holes 618a. The other parts of structures are same as TTDP 324 as illustrated in FIG. 57. In order to avoid the contamination of the drugs by contacting to the surface of the antenna assembly 620, the surface of the antenna assembly 620 may be coated by photo resin or polymer to avoid ion elution from the metal surface of the antenna assembly 620 to the drugs. This drug delivery has a feature such that the drug delivery is quickly and uniformly carried out than that carried out by the TTDP shown in FIG. 106. The difference does not mean the superior of drug delivery capability but the variety of selection for the various kinds of capsules that contain drugs.

Figure 108:
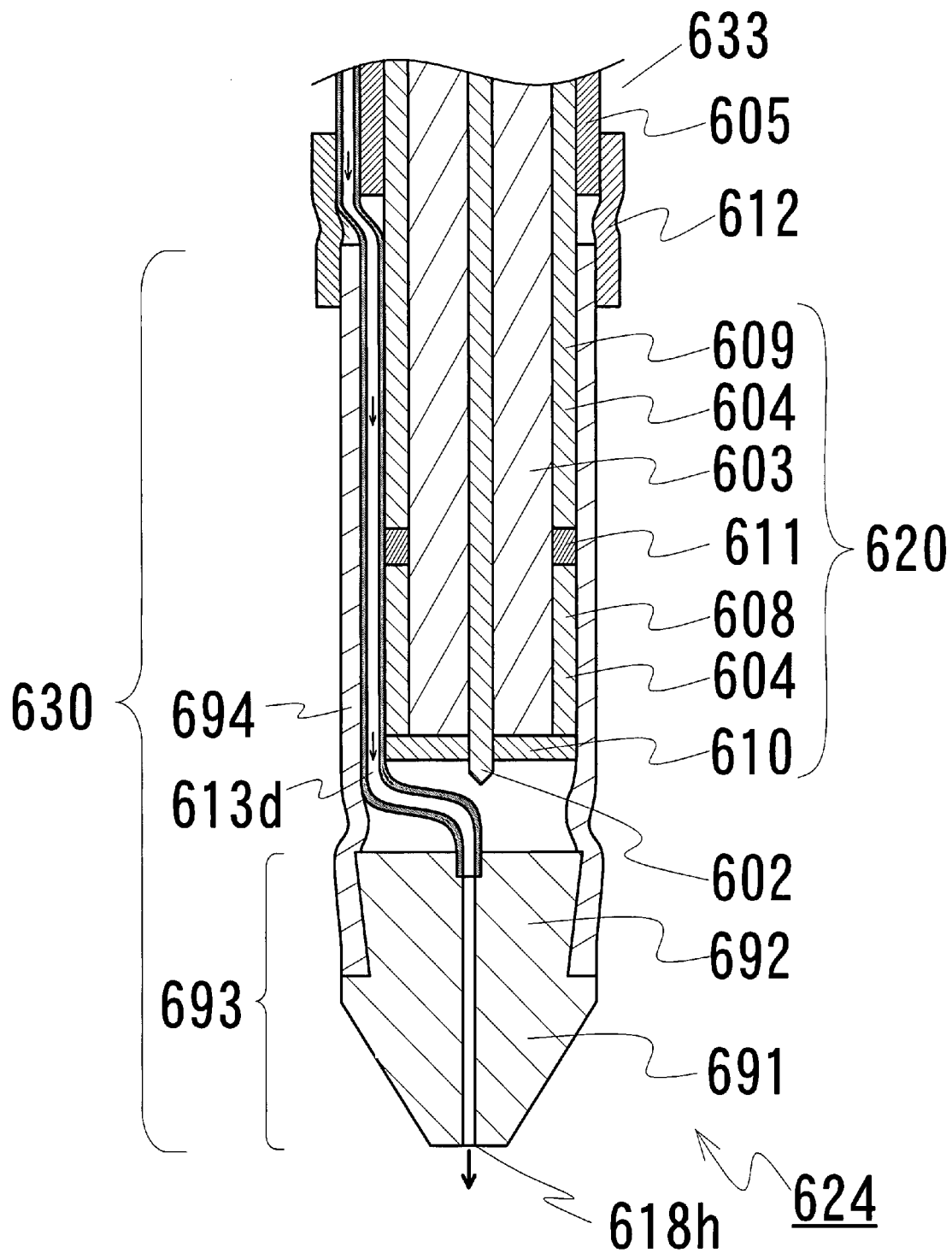

FIG. 108 illustrates another preferred embodiment regarding the fifth object of the present invention. The same flow channel formed for the TTDP 624 that has shrinkable tube 694 in the sheath 630 in stead of a single-body sheath 601. The drug delivery can be performed in the same manner as that using TTDP 624 illustrated in FIG. 106.

Figure 109:
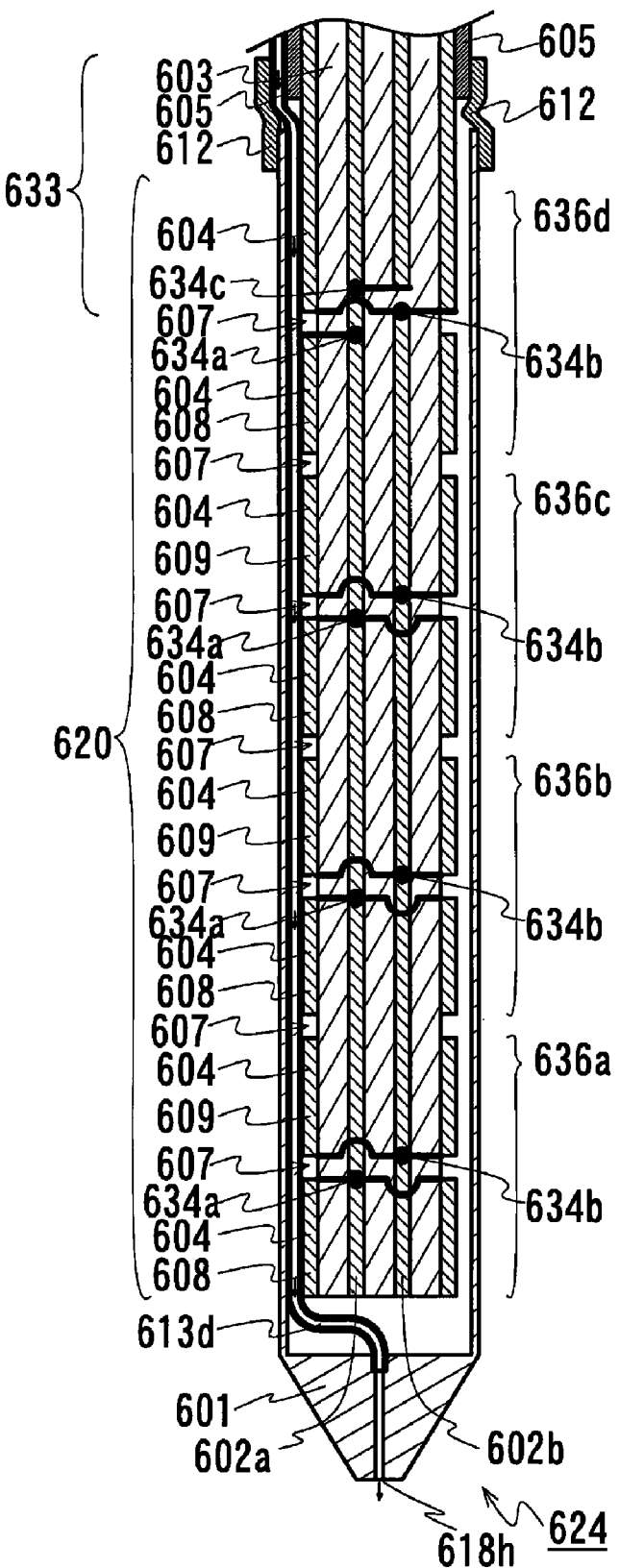
Figure 110:
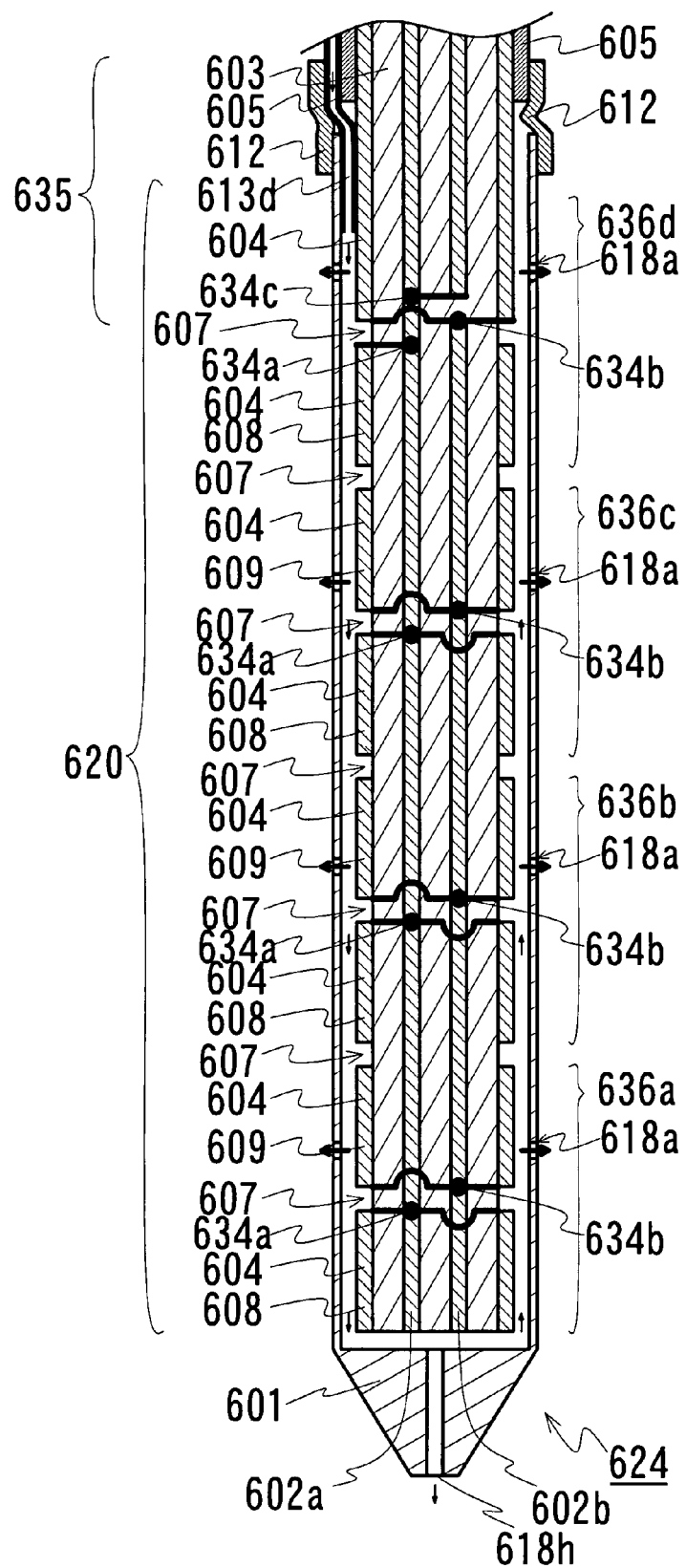

FIGS. 109 and 110 illustrate another set of preferred embodiments regarding the fifth object of the present invention. The flow channel for the drug delivery is additionally formed in the TTDPs 424 embodied for the third object of the present invention. The flow channel includes a tube 613d running in the sapphire sheath 601 and a drug injecting side hole 618h formed in the cutting edge of the single-body sheath 601.

The same embodiments of the drug delivery capability to be applied the fourth object of the present inventions after being modified to have such flow channels are obviously obtained. But they are not illustrated since modification to add such flow channels that allow the drugs are carried to pathological tissues are easily understood. The TTDPs 224 as illustrated in FIGS. 35, 37, 39 and 40, the TTDPs 324 as illustrated in FIGS. 56, 58, 60, and 61, the TTDPs 424 as illustrated in FIGS. 70, 72, 88, and 90 and the TTDPs 524 as illustrated in FIGS. 92, 94, 99 and 101 can be modified to have circulation capability of cooling flow.

Anti-cancer drugs, that has carcinostatic effect or cancer-fighting effect, such as mitomycin C, adriamycin, epirubicin, pirarubicin, cisplatin, methotrexate, 5-FU(FU, 5-FU, tegafur, UFT, carmofur, doxifluridine, TS-1, irinotecan, docetaxel, leucovorin (all are trade marks), etc. are injected into pathological tissues as in liquid phase or drug carrier, or drug transporter having thermal sensitivity for self-distraction, polymeric micelle, thermo-sensitive nano micelle, thermo-sensitive hydrophobic/hydrophilic micro-hydrogel particle, new polymeric micelle like drug carrier having reactive PEG (Polyethelene Glycol) chains that encapsulates cisdichlorodiammineplatinum therein, or block copolymeric micelle including cisdichlorodiammineplatinum. The anti-cancer drugs do not directly attack the sound cells. After the drugs are injected, heating of the tissues by means of the TTDPs 624 ignites decomposition of the carriers or transporters including the anti-cancer drugs. Then the anti-cancer drugs stay in the tumors so that the thermal necrosis by the TTDPs 624 and accelerated apoptosis by the drugs locally and simultaneously break out over the thermal therapeutic region. Therefore cancer therapy is performed with less burden to the human bodies. Other anticancer drugs such as anticancer drug-DNA complexes, chemopreventive agents, macromolecular anti-cancer drugs can be used with above encapsulation technology. Applying this TTDPs 624 to cancer therapies, high effectiveness and long-term effect of drug activity can be obtained. It is concluded the combination of RF heating of cell water and the drug injection capability to the specific pathological cells.

Figure 111:
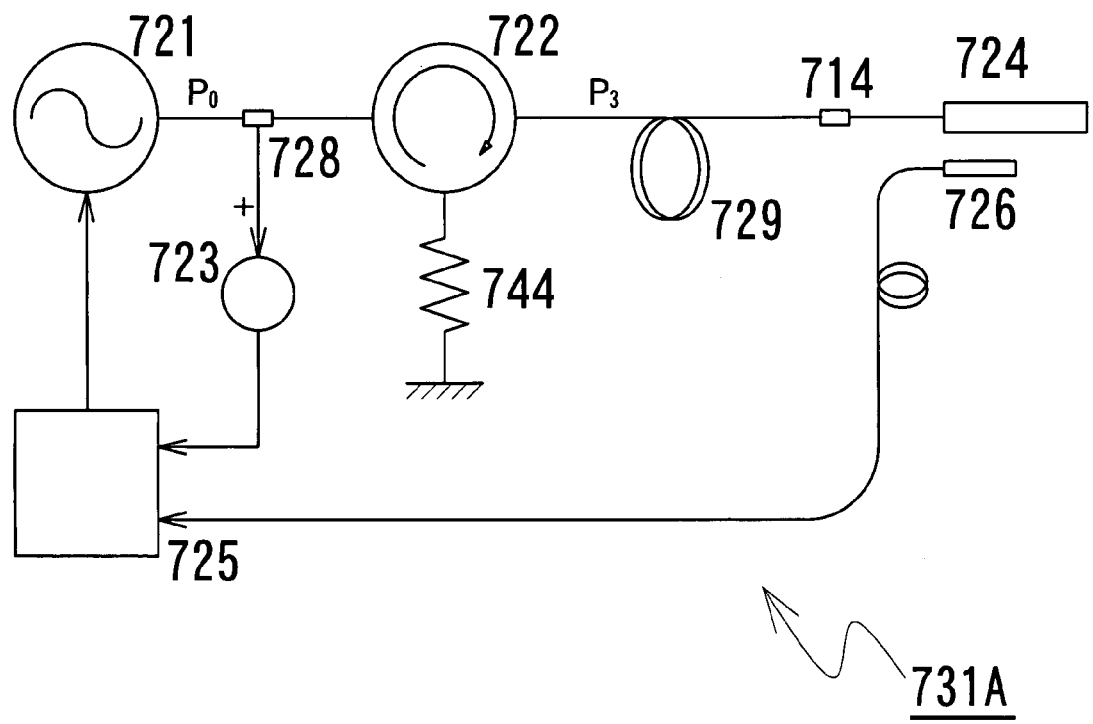
FIGS. 111 and 112 are the diagrams of the therapeutic antenna probe systems regarding the sixth objection of the present invention.

FIG. 111 shows a preferred embodiment regarding the sixth object of the present invention. The therapeutic antenna probe system 731A comprises an RF power source 721 (or called as a microwave power source when the microwave power which has microwave frequencies is used), a circulator 722 connected to the RF power source 721, a power guide cable 729 which is an RF power transmitting means such as a coaxial cable 233 and 333 or a coupler-line 435, 535 and 635, a power meter 723 connected to the RF power source 721 via a power coupler 728 and a controller 725 which controls the RF power generated by the RF power source 721 by virtue of the output signal of the power meter 723 that measures the RF power. The power coupler 728 is to monitor the intensity level of the RF power output from the RF power source 721 and a little quantity of the RF power shared from the RF power output by the power coupler 728 is enough since it is used for monitoring, provided keeping proportionality to the RF power output. The circulator 722 has a load 744 connected thereto so that the reflected power from the TTDPs 724 is absorbed and no reflection returns back to the RF power source 721 so that the therapeutic antenna probe system 731 can stably operate.

In this therapeutic antenna probe system 731A, the power guide cable 729 is connected to the TTDPs 724 via a connector and a coaxial cable 233 and 333 and a coupler-line 435 and 535 depending on the kinds of TTDPs as TTDP 224, 324, 424, 524 and 624, respectively. The outer conductor of the power guide cable 729 is connected to the outer conductor of the coaxial cable 233 or 333 or the coupler-line 435, 535 or 635 and ultimately to the first electrode 208, 308, 408, 508 or 608 and the second electrode 209, 309, 409, 509 or 609.

The therapeutic antenna probe system 731A is further preferred to have a thermal transducer 726, which is a separated device from the TTDPs 724, such as a thermo-coupler or a platinum temperature sensor, with the TTDPs 724 so that the output power from the RF power source 721 is controlled to prevent coagulation due to over heating of the pathological tissues by the RF power. The control is also to maintain an appropriate level of the RF power from the RF power source 721 in the therapeutic operation by monitoring the temperature of the pathological tissues which are heated by TTDPs 724.

The RF power source 721 generates microwave power of 2.45 GHz or so-called UHV of 945 MHz. For the frequency difference of the RF power, the gap 207, 307, 407, 407a, 507, 507a, 539, 607 has to be modified as 2.6 times larger in 945 MHz than in 2.45 GHz.

Figure 112:
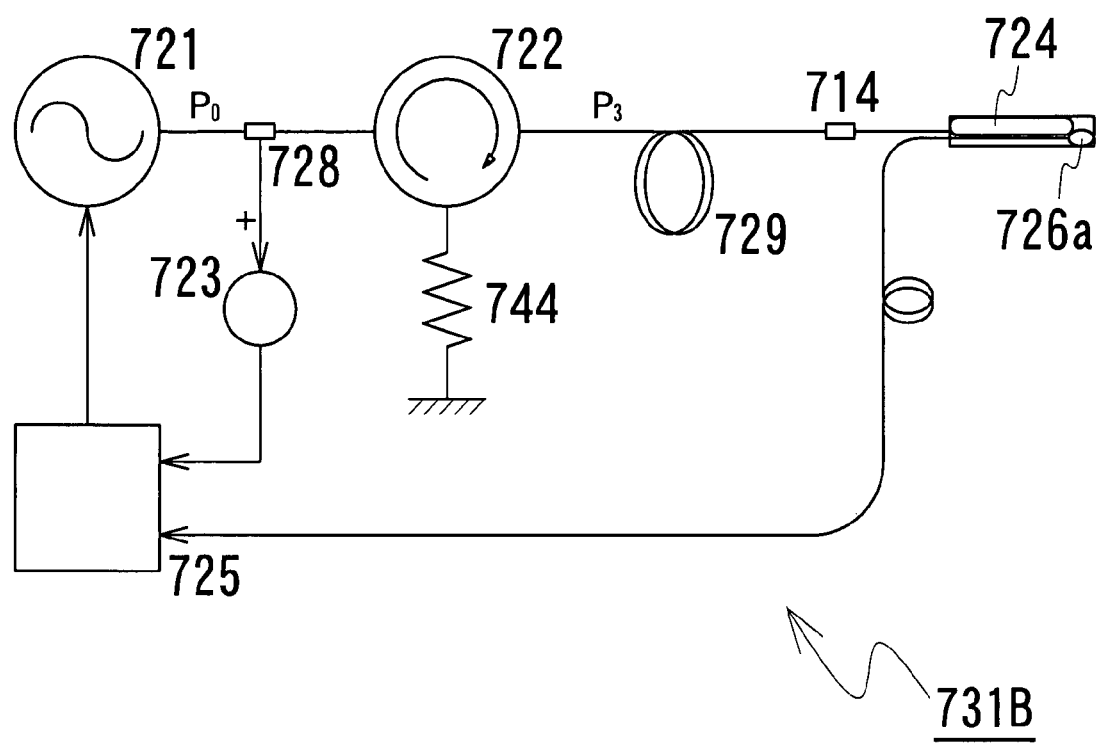
Figure 113:
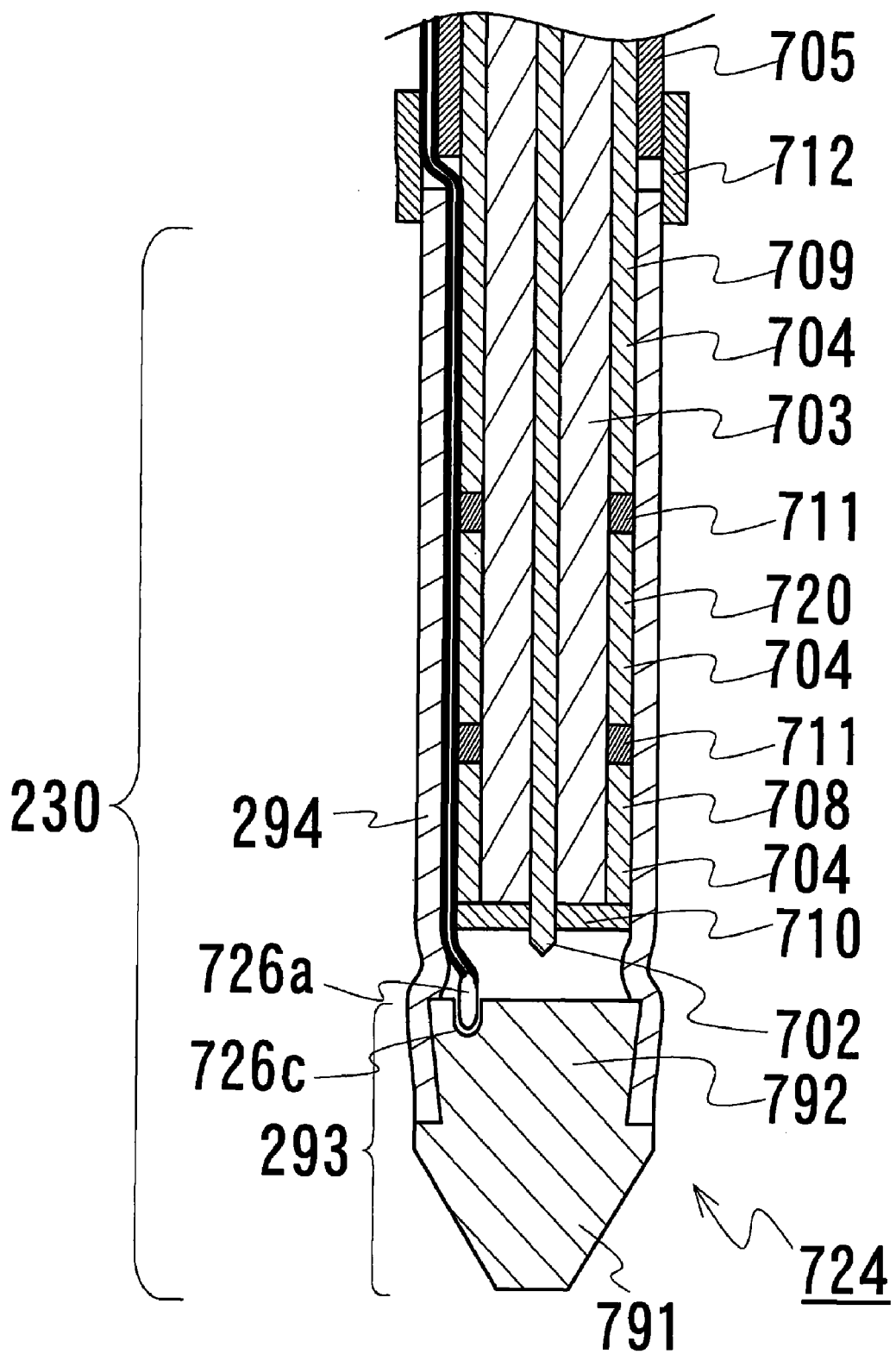
FIGS. 113 and 116 are the cut views of the TTDP used for the therapeutic antenna probe system regarding the sixth object of the present invention.
Figure 114:
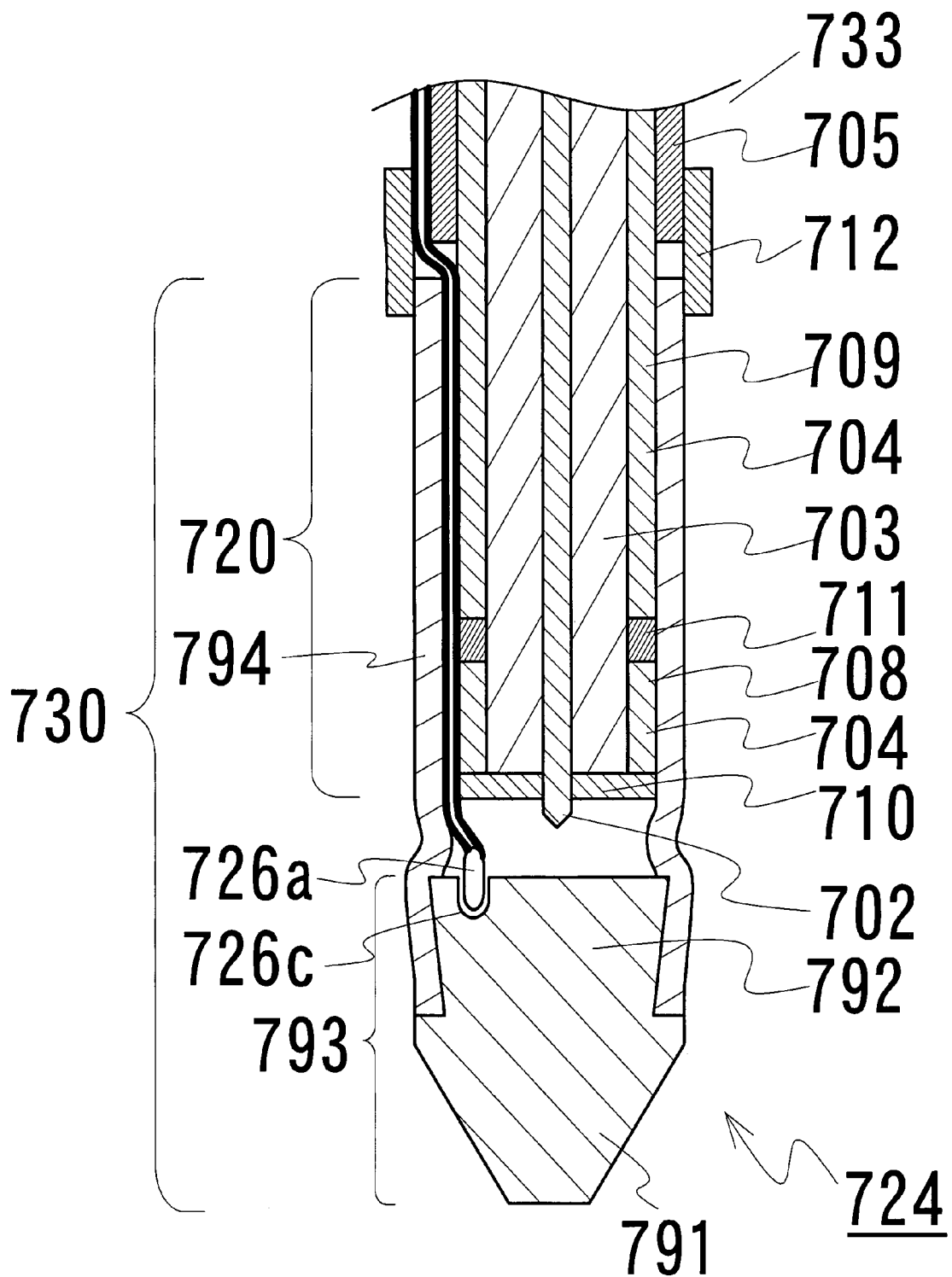
Figure 115:
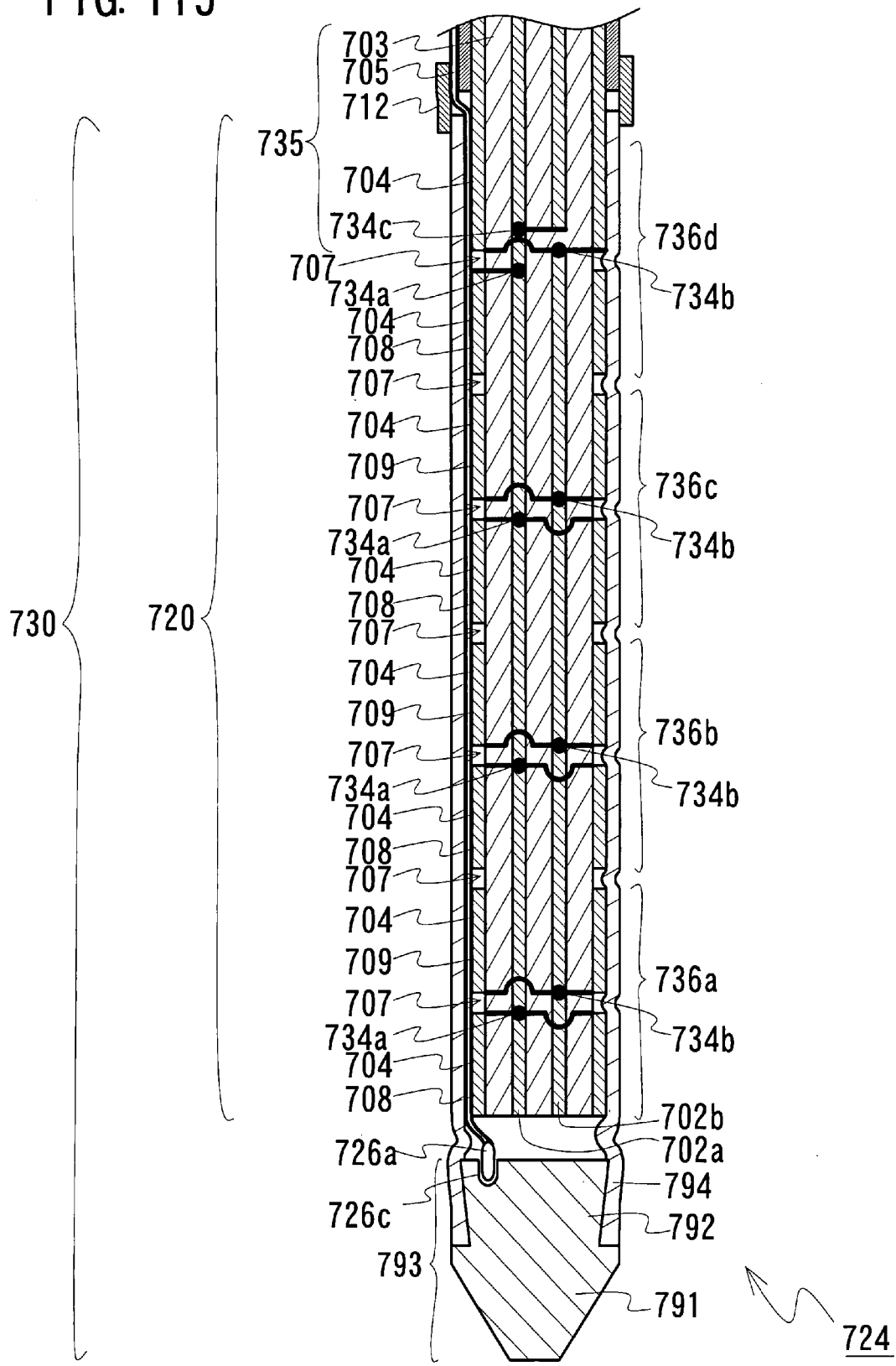
Figure 116:
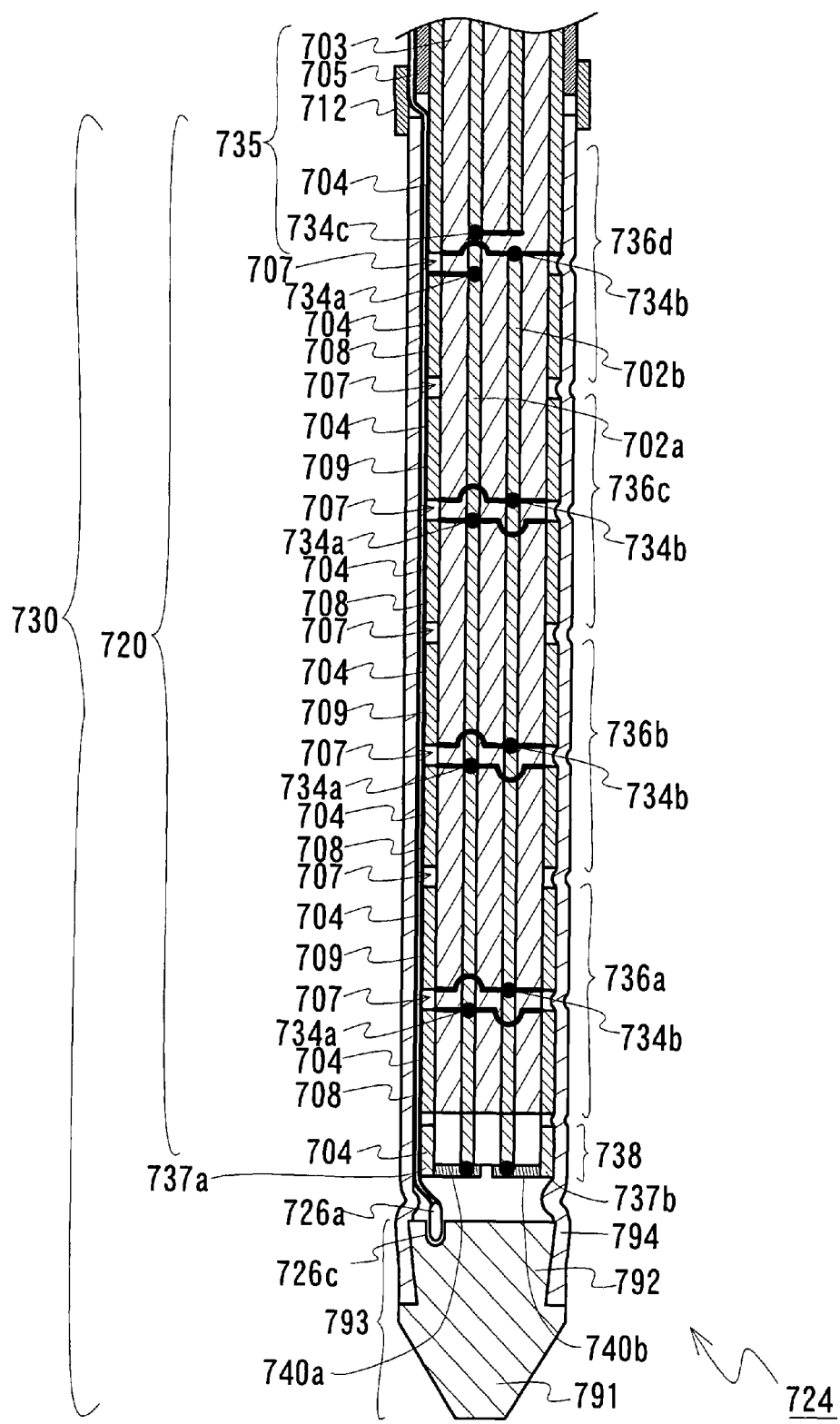

FIG. 112 shows another preferred embodiment regarding the sixth object of the present invention. The therapeutic antenna probe system 731B equips with a TTDP 724 has a thermal transducer 726a which is built the sheath of the TTDP 724. The thermal transducer 726a is preferred to be a thermo-coupler or a platinum temperature sensor. FIG. 113 to 116 illustrate cut views of each kind of the TTDPs of the first, third and fourth objects of the present invention where the thermal transducers 726a is put in holes 726c recessed in the edge portion 793 or the tip of the sheath 730. The contact of the thermal transducer 726a to the portion 793 is done with thermally conductive cement or heat sink oil. The other TTDPs can preferably have the thermal transducer 726a built-in their single-body sheaths 301, 401, 501 and 601 as well.

Figure 117:
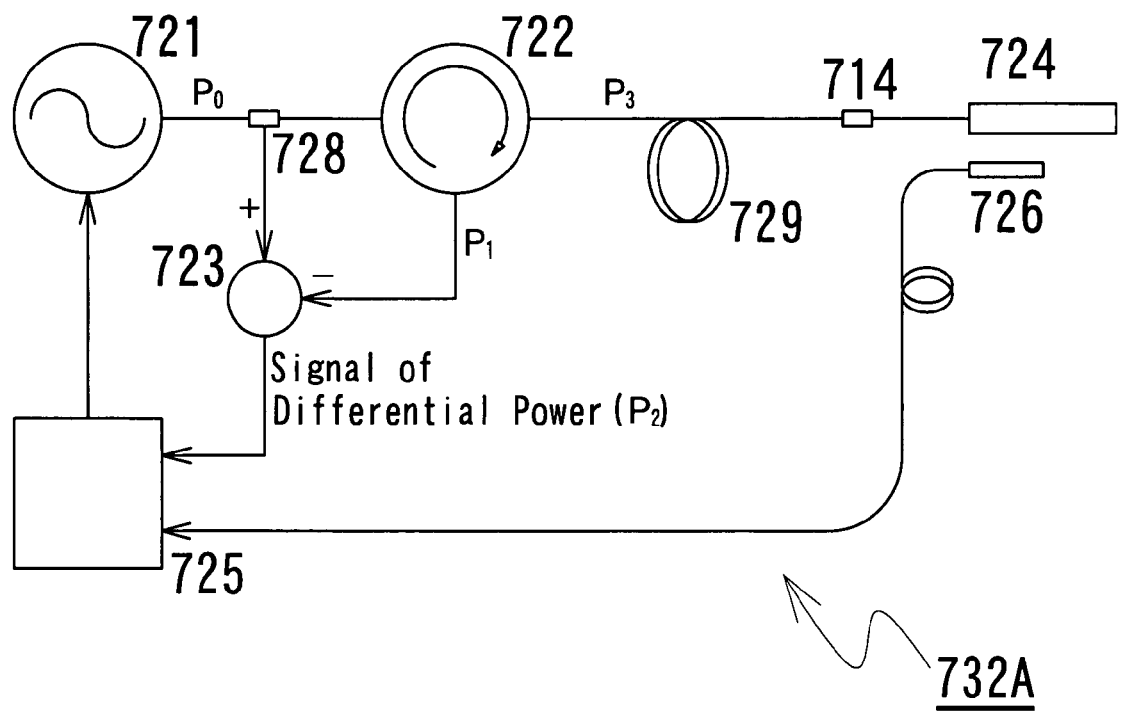
FIGS. 117 and 118 are the diagrams of the therapeutic antenna probe systems regarding the sixth objection of the present invention.
Figure 118:
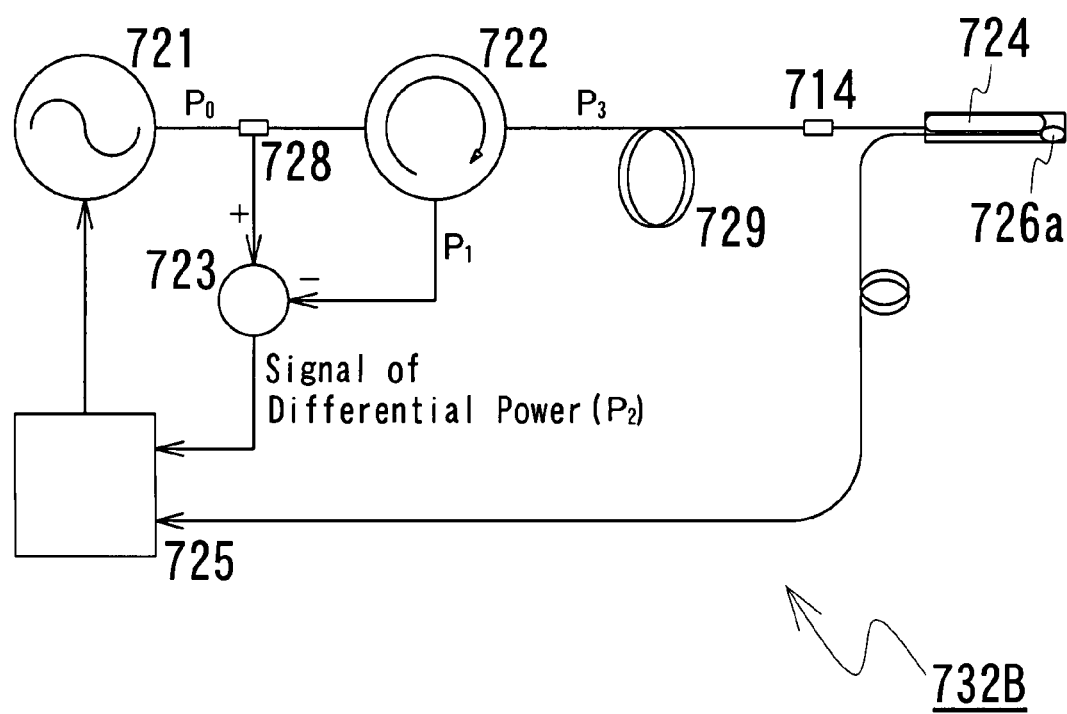

FIGS. 117 and 118 show other preferred embodiments regarding the sixth object of the present invention. Especially the input signal to the power meter 723 is given by the output power from the RF power source 721 and by the power given by the remaining port of the circulator 722. It is possible to measure the reflected power (P1) from the TTDP 724 by monitoring the power from this remaining port. The differential power between the output power from the RF power source 721 and the reflected power (P1) can be measured. The output power (P0) of the RF power source 721 can be controlled by the controller 725 so that the input to the tissues (P0-P1) is appropriately controlled.

As the result, the signal of the differential power (P2) between the output power (P0) of the RF power source 721 and the reflected power from the TTDP 724 is measured as the differential power (P2). The differential power (P2) is regarded as actual input power into the tissues to which the TTPD 724 is inserted. Therefore, it is possible for the RF power source 721 to output the appropriate RF power to the tissues by controlling the controller 725 with the signal of the differential power (P2).

Figure 119:
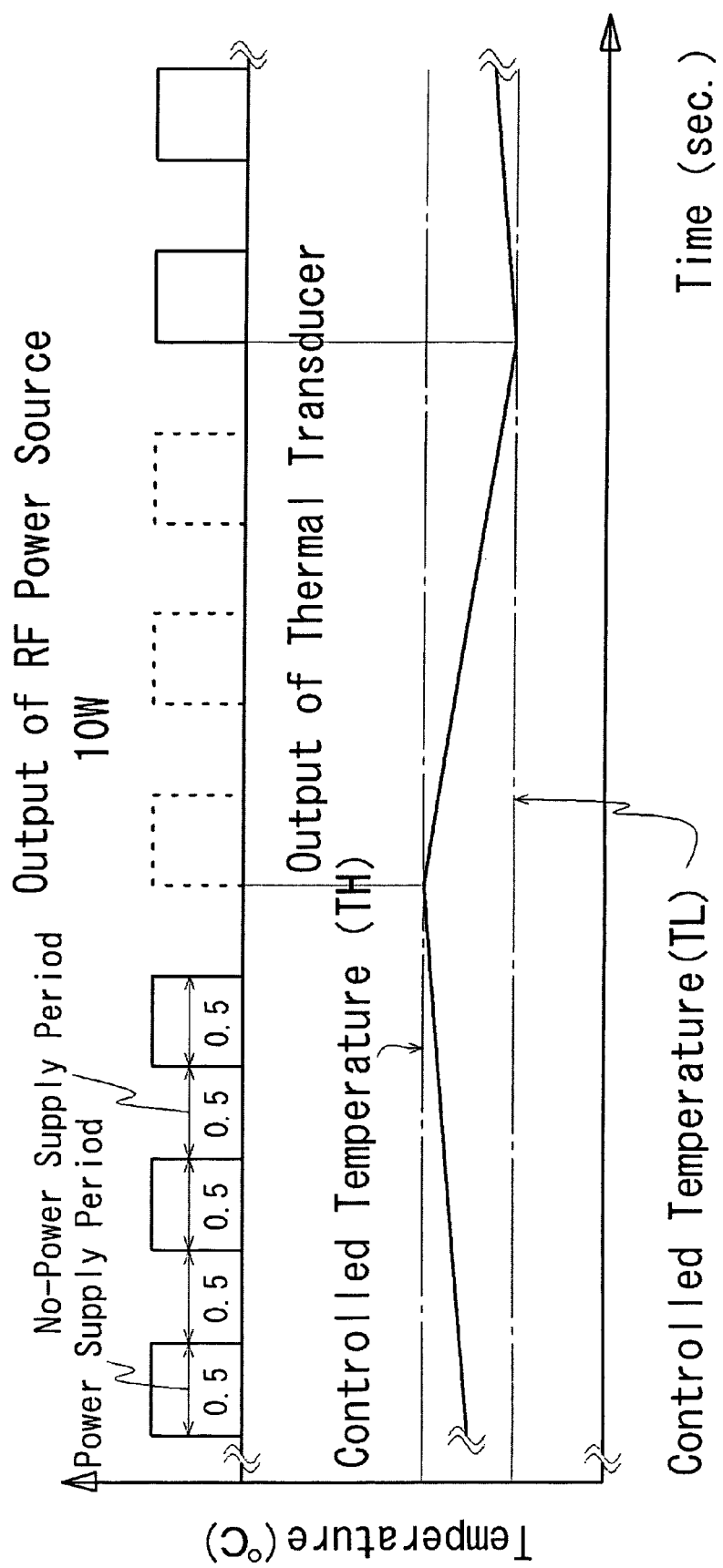
FIG. 119 is a control sequence of the method of the control sequence regarding the therapeutic antenna probe system regarding the sixth object of the present invention.

FIG. 119 illustrates another preferred embodiment regarding the sixth object of the present invention, especially a control sequence of the RF power from the RF power source 721, where a signal of the thermal transducer 726 or 726a is input to the controller 725 which control the RF power source 721 in a fashion of ON and OFF thereof. Particularly, the output power from the RF power source 721 is given in an intermittent fashion of power supply period and no-power supply period. The RF power level in the power supply period is constant or cut off when the RF power level is exceed to the level of overheating of the tissues by monitoring the differential power (P2). The power supply period is monitored and controlled by the output signal of the thermal transducer 726 or 726a. By this control method, it is possible to maintain appropriate temperature of the tissues to which the TTDP 724 is inserted within the range of the pathological region to which the thermal therapy provides necrosis without local coagulation.

The lower limit of the controlled temperature TL set in the controller 725 is the temperature close to the temperature of the protein degradation (42.5 deg C.) that induces cell necrosis. When the output signal of the thermal transducer 726 has indicated that the temperature is bellower than the lower limit of the controlled temperature TL, the output from the RF power source 721 is resumed. The output power from the RF power source 721 is 10 Watt in average, the duty cycle 50% (a power supply period and no-power supply period are both 50% of the one repetitive period) and the total RF power supply (under 50% duty) term 600 seconds as one unit of cauterization of this thermal therapeutic operation. When the temperature of the tissues to which the TTDP 724 is inserted becomes to be higher than 44 deg C., the controller 721 controls the RF power source 721 and the output therefrom has been shut-off.

The higher limit of the controlled temperature TH is set in the controller 725. By the controlled temperatures TL and TH, the output signals of the thermal transducers 726 or 726a are assessed. As described above, the output power from the RF power source 721 is shut-off when the output signal from thermal transducers 726 or 726a once indicates to be TH. Then the temperature of the pathological tissues to which the TTDP is inserted has started to be cooled down to the temperature of the normal cells that surround the pathological tissues. When the temperature of the pathological tissues has come down to TL, the controller 725 restarts the RF power source 721 to provide the output power. The controller 725 controls the power ON and OFF in such a hysteretic sequence.

FIG. 119 illustrates a sequence of the operation of the controller 725 which controls the RF power source 721. The output power level of the RF power is kept to be constant and the ON and OFF of the RF power output from the TTDP is controlled in a 50% duration. When the temperature of the tissues has become to be more than TH (44 deg C.), the power output is shut off and is resumed when the temperature of the tissues has come down to TL (42.5 deg C.).

Figure 120:
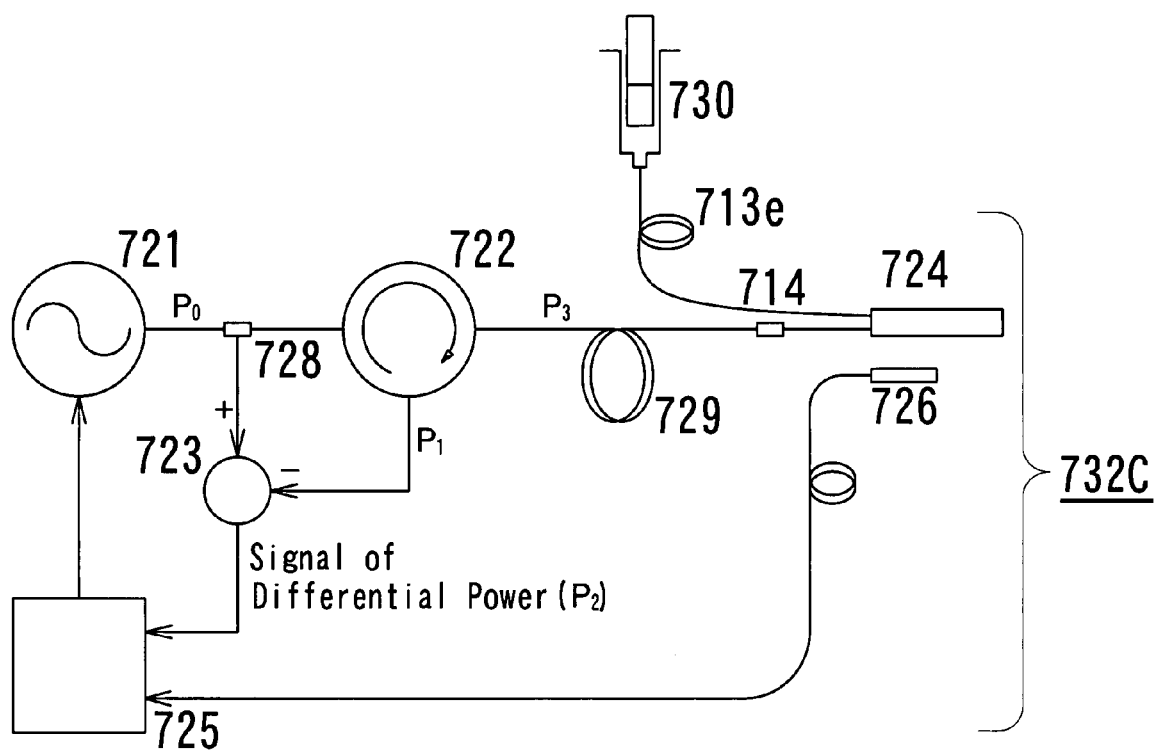
FIG. 120 is the block diagram of the g the therapeutic antenna probe system regarding the sixth object of the present invention.

FIG. 120 illustrates another preferred embodiment regarding the sixth object of the present invention. The therapeutic antenna probe system 732C includes a drug delivery system that comprises a syringe unit 730 including a syringe pump for drug injection through a feeding tube 713e which is an extension and connected to a tube 613a of the TTPD 624.

The syringe unit 730 supplies drugs to the pathological tissues to which the above TTDPs 724 that have drug injecting side holes 618h and 618a are inserted, respectively. The syringe unit 730 is preferred to manually operate or automatically operate with electric motors. The other parts of this therapeutic antenna probe system 731C are same as the therapeutic antenna probe system 731A or 731B. The drug injection to the TTDPs 724 is carried out before, while or after the cauterization by the TTDPs 724 is performed to activate the drugs injected in to the pathological tissues is performed depending on the efficacy of the drugs such as anticancer drugs.

Figure 121:
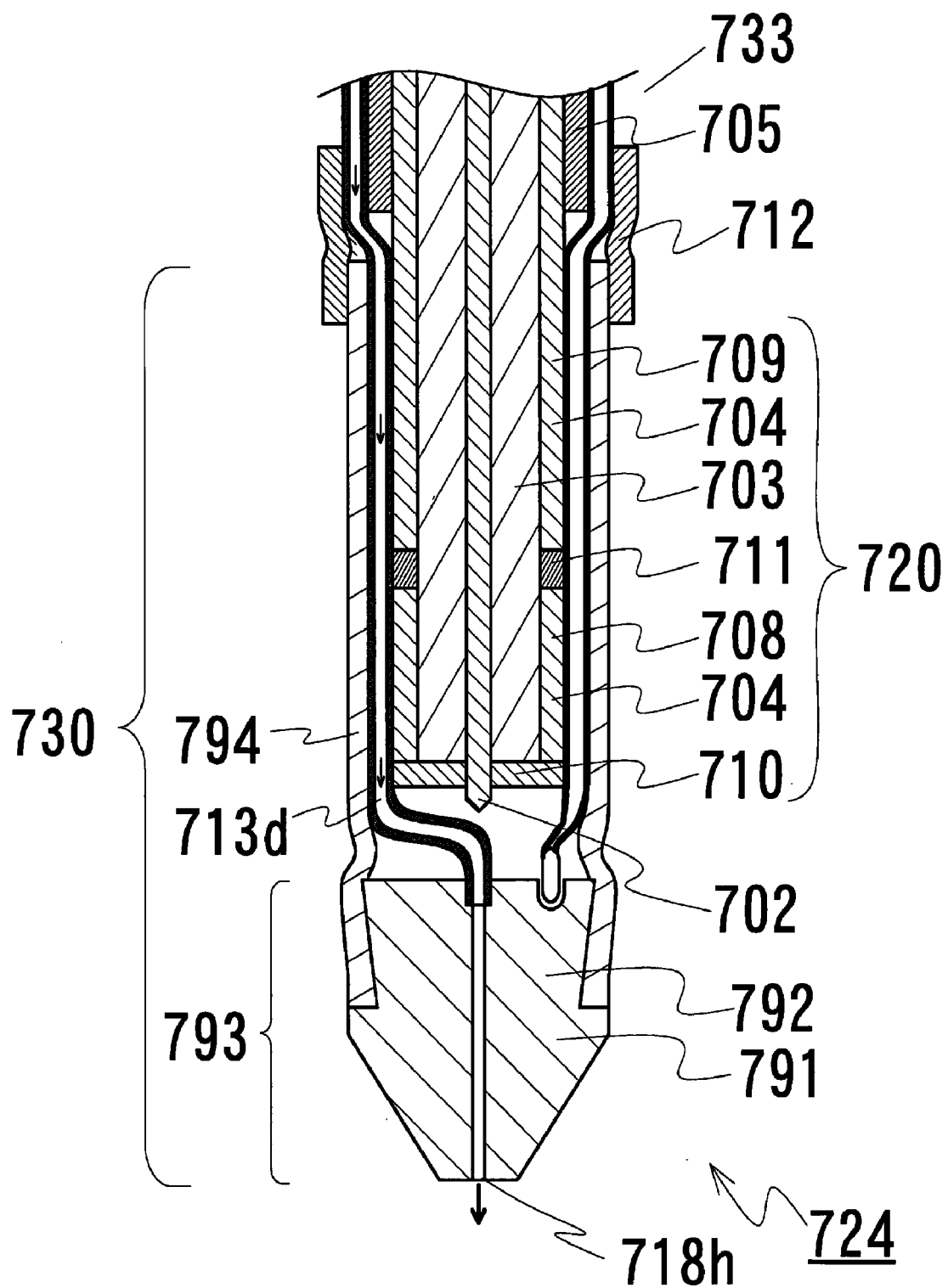
FIG. 121 is the cut view of the TTDP used for the therapeutic antenna probe system regarding the sixth object of the present invention.

FIG. 121 illustrates another preferred embodiment regarding the sixth object of the present invention. This TTDP 724 has the same configuration of the first object of the present invention where the thermal transducers 726a is put in holes 726c recessed in the edge portion 793 or the tip of the sheath 730. The contact of the thermal transducer 726a to the portion 793 is done with thermally conductive cement or heat sink oil. The TTDP 724 has additionally the drug delivery capability which is same as that illustrated in FIG. 106. This TTDP 724 enables to monitor the temperature of the tissues to which the TTDP 724 is inserted and to deliver the anti-cancer drugs at an appropriate temperature condition of the tissues.

The other TTDPs can preferably have the thermal transducer 726a built-in their single-body sheaths 301, 401, 501 and 601 as well.

The single-body sheaths 301, 401, 501, 601 and 701 have a monocoque structure so that mechanical durability against bending and pressing is high.

The thermal shrinkable tubes 294 and sheaths 301 can be colorized partly or in a whole. By visually confirm the color of the TTDPs, it is possible to control the therapeutic processes and surgical operation methods.

The present invention is not limited within the embodiments as illustrated in the above drawings. The modification in the range of the same concept of the present invention is included as a same or an equivalent invention thereto.

What is claimed is:

1. A therapeutic antenna probe comprising:
an RF power transmitting means by which a dipole antenna assembly is formed, and
a sheath, being made of a hard material for including at least a head element having a hard material and a sharp edge, wherein said dipole antenna assembly is disposed in the sheath.

2. A therapeutic antenna probe as set forth in claim 1, wherein
said RF power transmitting means comprises at least one central conductor, a cylindrical dielectric insulator formed around said central conductor and an outer conductor all of which are formed to be said dipole antenna assembly of which at least one dipole antenna is composed of a first electrode which is formed by a part of said outer conductor and electrically connected to said at least one central conductor, a second electrode which is formed by another part of said outer conductor and an isolating means which is formed between said first electrode and said second electrode.

3. A therapeutic antenna probe as set forth in claim 2, wherein said insulating means is formed by removing said out conductor.

4. A therapeutic antenna probe as set forth in claim 2, wherein said insulator is formed by an insulating collar filled between said first electrode and said second electrode.

5. A therapeutic antenna probe as set forth in claim 2, wherein said head element comprising an edge portion and a flexible pipe that is coupled to a coupling portion are included in a head portion thereof.

6. A therapeutic antenna probe as set forth in claim 5, wherein said head element is made of sapphire and said flexible pipe is thermal shrinkable tube.

7. A therapeutic antenna probe as set forth in claim 5, wherein said coupling portion has notches or cut surfaces therearound.

8. A therapeutic antenna probe as set forth in claim 2, wherein said sheath is formed in a single-body and said hard material is sapphire.

9. A therapeutic antenna probe system as set forth in claim 8, wherein longitudinal length L of said first electrode along said power transmission means is given as in a following equation under an assumption that shortening effect be k, dielectric constant of said single sapphire $\in_s$, wave length of RF power supplied thereto $\lambda$, length of said insulating means a, diameter of a dielectric insulator d, $$\left(\frac{1}{k} + \sqrt{\varepsilon_s}\right) \cdot L \geq \frac{\lambda}{4} - a - \frac{d}{2} \geq \frac{2}{k}L.$$

10. A therapeutic antenna probe as set forth in claim 8, wherein said sheath has a groove made on inner surface of said sheath.

11. A therapeutic antenna probe as set forth in claim 8, wherein said sheath has a hole in cylindrical surface of said sheath from inside to outside thereof.

12. A therapeutic antenna probe as set forth in claim 2, wherein all of said at least one central conductor are electrically connected in a section of said first electrode which is in said dipole antenna assembly at a reverse side of said head element.

13. A therapeutic antenna probe system as set forth in claim 2, wherein a shrinkable tube is attached over a jacket covering said power transmitting means and said sheath.

14. A therapeutic antenna probe as set forth in claim 2, wherein said insulating means is a insulating gap piece which has a disc shape of which diameter is same as that of said outer conductor and holes through which said central conductor penetrates therethrough.

15. A therapeutic antenna probe as set forth in claim 14, wherein said insulating gap piece has a conductive layer in at least one side thereof and one of said first and second electrodes contacts to said conductive layer.

16. A therapeutic antenna probe as set forth in claim 14, wherein said insulating means is an insulating gap piece which has a conductive layer at a portion which contacts said first electrode with solder brazing and another conductive layer at a portion which contacts a second electrode with solder brazing.

17. A therapeutic antenna probe as set forth in claim 2, wherein a third electrode is formed between said first electrode and said second electrode.

18. A therapeutic antenna probe as set forth in claim 2, wherein said first electrode is electrically connected to said central conductor via a electrically conductive disc.

19. A therapeutic antenna probe as set forth in claim 2, wherein additional electrodes that electrically contact to said first and second electrodes are attached on surfaces thereof.

20. A therapeutic antenna probe as set forth in claim 2, wherein a connector through which RF power is supplied, connected to said dipole antenna assembly.

21. A therapeutic antenna probe as set forth in claim 2, wherein said RF power transmitting means is a coupler-line which comprises at least a first and a second central conductors, a dielectric insulator formed around said at least a first and a second central conductors and an outer conductor from which at least a pair of a first electrode and a second electrode is formed with an insulating means therebetween so that at least one dipole antenna is constructed, and
a dipole antenna is formed in such a structure that said first and second central conductors are respectively connected to said first electrodes and said second electrodes via power supplied points in an arrangement that said first electrodes and said second electrodes are adjacently facing at said power supply points, respectively.

22. A therapeutic antenna probe as set forth in claim 2, wherein said RF power transmitting means is a coupler-line which comprises at least a first and a second central conductors, a dielectric insulator formed around said at least a first and a second central conductors and an outer conductor from which at least two pairs of a first electrode and a second electrode are formed with an insulating means therebetween so that a first dipole antenna and a second dipole antenna are constructed in such a manner that said first dipole antenna is formed in such a structure that said first and second central conductors are respectively connected to said first electrodes and said second electrodes via power supplied points in an arrangement that said first electrodes and said second electrodes are adjacently facing at said power supply points,
a second dipole antenna is formed in such a structure that said first and second central conductors are respectively connected to said second electrodes and said first electrodes via power supplied points in an arrangement that said first electrodes and said second electrodes are adjacently facing at said power supply points,
and said first electrode pair and said second electrode pair are alternatively formed therein.

23. A therapeutic antenna probe selected from a group of those set forth in claim 21 and claim 22, wherein a dipole antenna formed at an end of said coupler-line has a folded first electrode and a folded second electrode which have outer electrodes electrically connected to said first and second electrodes formed from said outer conductor, respectively.

24. A therapeutic antenna probe selected from a group of those set forth in claim 21 and in claim 22, wherein a dipole antenna formed at an end of said coupler-line has a pair of two half-annular electrodes surrounding said dielectric insulator in a structure that said two half-annular electrodes are isolated via an electrically isolating gaps and said central conductors are electrically connected to said half-annular electrodes.

25. A therapeutic antenna probe as set forth in claim 2, wherein said sheath is at least partly colored.

26. A therapeutic antenna probe as set forth in claim 2, wherein said sheath has a hole that opens from said sharp edge through an edge portion thereof.

27. A therapeutic antenna probe as set forth in claim 2, wherein a thermal transducer is attached to a edge portion of said sheath.

28. A therapeutic antenna probe system comprising an RF power source, a circulator connected to said RF power source, said therapeutic antenna probe selected from a group of those set forth in claims 2, 5, 8 and 20 that are connected to said circulator through an RF power transmitting means and an RF power meter connected to said RF power source via a power coupler and a controller which controls RF power generated by said RF power source by an output signal of said power meter.

29. A therapeutic antenna probe system as set forth in claim 28, wherein said output signal of said RF power meter is controlled by a differential power between said RF power generated by said RF power source and a reflected power obtained via said circulator of which reflection is from said therapeutic antenna probe.

30. A therapeutic antenna probe system selected from a group of those set forth in claim 28, further including a thermal transducer wherein an output signal from said thermal transducer is input to said controller so that RF power generated by said RF power source is controlled by said output signal.

31. A therapeutic antenna probe system selected from a group of those set forth in claim 28, wherein said RF power generated by said RF power source is given in an intermittent pulse shape such that RF power and no RF power are alternatively and repetitively given with certain terms, said RF power is set by said controller and said certain terms when said RF power is given is controlled by said output signal from said thermal transducer.

32. A therapeutic antenna probe system selected from a group of those set forth in claim 28, further including a syringe means for drug injection through said therapeutic antenna probe selected from a group of those set forth in claim 18 and 19.

33. Usage method of said therapeutic antenna probe system as set forth in claim 32 with one or two more anti-cancer drugs, having one effect selected from a group of effects given by carcinostatic effect and cancer-fighting effect, which are selected from a group of MITOMYCIN C ((1aS,8S,8aR, 8bR)-6-Amino-4,7-dioxo-1,1a,2,8,8a,8b-hexahydro-8a-methoxy-5-methylazirino[2,3:3,4]pyrrolo[1,2-α]indol-8-yl-methylcarbamate), ADRIAMYCIN ((8S,10S)-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione), EPIRUBICIN (10-(4-amino-5-hydroxy-6-methyl-oxan-2-yl)oxy-6,8,11-trihydroxy-8-(2-hydroxyacetyl)-1-methoxy-9,10-dihydro-7H-tetracene-5,12-dione), PIRARUBICIN ((3S)-3-gly-coloyl-3,5,12-trihydroxy-10-methoxy-6,11-dioxo-1,2,3,4,6, 11-hexahydrotetracen-1-yl 3-amino-2,3,6-trideoxy-4-O-[(2R)-tetrahydro-2H-pyran-2-yl]-α-L-lyxo-hexopyranoside), CISPLATIN ((SP-4-2)-diamminedichloridoplatinum), METHOTREXATE ((2S)-2-[(4-{[(2,4-diaminopteridin-6-yl)methyl](methyl) amino}phenyl)formamido]pentanedioic acid), 5-FU (5-Fluoropyrimidine-2,4(1H,3H)-dione), TEGAFUR (5-fluoro-1-(tetrahydrofuran-2-yl)pyrimidine-2,4(1H,3H)-dione), UFT (Tegarfur Fluorouracil Prodrug; a compound of 5-fluoro-1-(tetrahydrofuran-2-yl)pyrimidine-2,4(1H,3H)-dione and pyrimidine-2,4(1H,3H)-dione), CARMOFUR (5-fluoro-N-hexyl-2,4-dioxo-pyrimidine-1-carboxamide), DOXIFLURIDINE (5'-deoxy-5-fluorouridine), TS-1 (tegafur gimeracil oteracil potassium), IRINOTECAN ((S)-4,11-diethyl-3,4,12,14-tetrahydro-4-hydroxy-3,14-dioxo1H-pyrano[3',':6,7]-indolizino[1,2-b]quinolin-9-yl-[1, 4'bipiperidine]-1'-carboxylate), DOCETAXEL ((2R,3S)— N-carboxy-3-phenylisoserine, N-tert-butyl ester, 13-ester with 5,20-epoxy-1,2,4,7,10,13-hexahydroxytax-11-en-9-one 4-acetate 2-benzoate, trihydrate), LEUCOVORIN ((S)-2-[4-[(2-amino-5-formyl-4-oxo-5,6,7,8-tetrahydro-1H-pteridin-6-yl)methylamino]benzoyl]aminopentanedioic acid), etc. are injected into pathological tissues as in liquid phase or drug carrier, or drug transporter having thermal sensitivity for self-distraction, polymeric micelle, thermo-sensitive nano micelle, thermo-sensitive hydrophobic/hydrophilic micro-hydrogel particle, new polymeric micelle like drug carrier having reactive PEG (Polyethelene Glycol) chains that encapsulates cisdichlorodiammineplatinum therein, or block copolymeric micelle including cisdichlorodiammineplatinum.

34. Usage method as set forth in claim 33, wherein said anti-cancer drugs are supplied to said therapeutic antenna probe by said syringe means in conjunction with said RF power supplied from said RF power source.

35. A therapeutic antenna probe system selected from a group of those set forth in claim 29, further including a thermal transducer wherein an output signal from said thermal transducer is input to said controller so that RF power generated by said RF power source is controlled by said output signal.

36. A therapeutic antenna probe system selected from a group of those set forth in claim 29, wherein said RF power generated by said RF power source is given in an intermittent pulse shape such that RF power and no RF power are alternatively and repetitively given with certain terms, said RF power is set by said controller and said certain terms when said RF power is given is controlled by said output signal from said thermal transducer.

37. A therapeutic antenna probe system selected from a group of those set forth in claim 29, further including a syringe means for drug injection through a therapeutic antenna probe selected from a group of those set forth in claim 18 and 19.

\* \* \* \* \*